United States Patent
Furlong et al.

(10) Patent No.: US 11,076,840 B2
(45) Date of Patent: Aug. 3, 2021

(54) SURGICAL CONSOLE, SPECIMEN RECEIVER, AND INSERTABLE ENDOSCOPIC INSTRUMENT FOR TISSUE REMOVAL

(71) Applicant: Interscope, Inc., Whitinsville, MA (US)

(72) Inventors: Cosme Furlong, Worcester, MA (US); Michael W. Marcoux, Jamaica Plain, MA (US); Richard Stephen Wisdom, Hyde Park, MA (US); William R. Rebh, Jr., Shrewsbury, MA (US); Evan Costa, Waltham, MA (US); Stephen C. Evans, Westford, MA (US)

(73) Assignee: INTERSCOPE, INC., Northbridge, MA (US)

( * ) Notice: Subject to any disclaimer, the term of this patent is extended or adjusted under 35 U.S.C. 154(b) by 744 days.

(21) Appl. No.: 15/459,870

(22) Filed: Mar. 15, 2017

(65) Prior Publication Data

US 2017/0319188 A1     Nov. 9, 2017

Related U.S. Application Data

(63) Continuation-in-part of application No. 14/792,369, filed on Jul. 6, 2015, now Pat. No. 10,265,055, which
(Continued)

(51) Int. Cl.
*A61B 10/04*     (2006.01)
*A61B 10/02*     (2006.01)
(Continued)

(52) U.S. Cl.
CPC .......... *A61B 10/04* (2013.01); *A61B 1/00091* (2013.01); *A61B 1/05* (2013.01);
(Continued)

(58) Field of Classification Search
CPC . A61B 10/04; A61B 10/0283; A61B 10/0096; A61B 17/320016;
(Continued)

(56) References Cited

U.S. PATENT DOCUMENTS 3,760,810 A    9/1973   Van Hoorn
3,834,392 A    9/1974   Lampman et al.
(Continued)

FOREIGN PATENT DOCUMENTS

CN    202051784    11/2011
DE    33 39 322 A1    5/1984
(Continued)

OTHER PUBLICATIONS

Canadian Examination Report on CA Application No. 2911545 dated Nov. 20, 2015.
(Continued)

*Primary Examiner* — Devin B Henson
(74) *Attorney, Agent, or Firm* — Foley & Lardner LLP

(57) ABSTRACT

A surgical console includes a drive assembly, vacuum interface, fluid transfer device, user interface, and control circuit. The drive assembly is configured to be coupled to an endoscopic tool and to be rotated by a motor. The vacuum interface is configured to apply a vacuum to the endoscopic tool. The fluid transfer device is configured to flow fluid through the endoscopic tool. The user interface is configured to receive a user input indicating at least one of instructions to rotate the endoscopic tool while applying the vacuum, or to flow fluid through the endoscopic tool. The control circuit controls at least one of the drive assembly, the vacuum interface, or the fluid transfer device based on the instructions, and is configured to cause the drive assembly to rotate
(Continued)

the endoscopic tool while the vacuum interface applies the vacuum responsive to the user input indicating instructions to rotate the endoscopic tool.

18 Claims, 99 Drawing Sheets

Related U.S. Application Data is a continuation of application No. 14/537,362, filed on Nov. 10, 2014, now Pat. No. 9,072,505, which is a continuation of application No. 14/280,202, filed on May 16, 2014, now Pat. No. 8,882,680, which is a continuation-in-part of application No. 13/336,491, filed on Dec. 23, 2011, now Pat. No. 9,808,146.

(60) Provisional application No. 62/308,829, filed on Mar. 15, 2016, provisional application No. 61/824,760, filed on May 17, 2013, provisional application No. 61/566,472, filed on Dec. 2, 2011.

(51) Int. Cl.
*A61B 17/00* (2006.01)
*A61B 17/32* (2006.01)
*A61B 1/00* (2006.01)
*A61B 1/05* (2006.01)
*A61B 90/30* (2016.01)

(52) U.S. Cl.
CPC .. *A61B 10/0283* (2013.01); *A61B 17/320016* (2013.01); *A61B 90/30* (2016.02); *A61B 2017/0034* (2013.01); *A61B 2017/00973* (2013.01); *A61B 2017/320064* (2013.01); *A61B 2217/005* (2013.01)

(58) Field of Classification Search
CPC .. A61B 2017/320064; A61B 2217/005; B01L 3/50; B01L 2300/0681; B01D 2201/204
See application file for complete search history.

(56) References Cited

U.S. PATENT DOCUMENTS

| | | | |
|---|---|---|---|
| 3,911,923 A | 10/1975 | Yoon | |
| 4,222,380 A | 9/1980 | Terayama | |
| 4,226,239 A | 10/1980 | Polk et al. | |
| 4,257,419 A | 3/1981 | Goltner et al. | |
| 4,548,201 A | 10/1985 | Yoon | |
| 4,646,738 A | 3/1987 | Trott | |
| 4,756,309 A | 7/1988 | Sachse et al. | |
| 4,763,667 A | 8/1988 | Manzo | |
| 4,834,729 A | 5/1989 | Sjostrom | |
| 4,850,957 A | 7/1989 | Summers | |
| 4,950,278 A | 8/1990 | Sachse et al. | |
| 4,966,162 A | 10/1990 | Wang | |
| 5,108,381 A * | 4/1992 | Kolozsi | A61M 1/0056 |
| | | | 210/406 |
| 5,269,789 A | 12/1993 | Chin et al. | |
| 5,320,630 A | 6/1994 | Ahmed | |
| 5,320,635 A | 6/1994 | Smith | |
| 5,349,940 A | 9/1994 | Takahashi et al. | |
| 5,417,697 A | 5/1995 | Wilk et al. | |
| 5,423,834 A | 6/1995 | Ahmed | |
| 5,462,559 A | 10/1995 | Ahmed | |
| 5,507,797 A | 4/1996 | Suzuki et al. | |
| 5,529,580 A | 6/1996 | Kusunoki et al. | |
| 5,662,671 A | 9/1997 | Barbut et al. | |
| 5,782,748 A | 7/1998 | Palmer et al. | |
| 5,871,453 A | 2/1999 | Banik et al. | |
| 5,906,615 A | 5/1999 | Thompson | |
| 5,938,680 A | 8/1999 | Ginn | |
| 5,961,534 A | 10/1999 | Banik et al. | |
| 6,059,719 A | 5/2000 | Yamamoto et al. | |
| 6,068,603 A | 5/2000 | Suzuki | |
| 6,193,672 B1 | 2/2001 | Clement | |
| 6,245,011 B1 | 6/2001 | Dudda et al. | |
| 6,299,763 B1 * | 10/2001 | Ashman | A61C 1/0076 |
| | | | 210/448 |
| 6,517,560 B1 | 2/2003 | Toth et al. | |
| 6,572,578 B1 | 6/2003 | Blanchard | |
| 6,585,694 B1 | 7/2003 | Smith et al. | |
| 6,645,218 B1 | 11/2003 | Cassidy et al. | |
| 6,666,854 B1 | 12/2003 | Lange | |
| 6,689,146 B1 | 2/2004 | Himes | |
| 7,247,161 B2 | 7/2007 | Johnston et al. | |
| 7,276,074 B2 | 10/2007 | Adams et al. | |
| 7,625,347 B2 | 12/2009 | Burbank et al. | |
| 7,691,110 B2 | 4/2010 | Secrest et al. | |
| 7,857,784 B2 | 12/2010 | Schmidberger et al. | |
| 8,070,756 B2 | 12/2011 | Secrest et al. | |
| 8,070,762 B2 | 12/2011 | Escudero et al. | |
| 8,123,750 B2 | 2/2012 | Norton et al. | |
| 8,277,474 B2 | 10/2012 | Norman et al. | |
| 8,435,259 B2 | 5/2013 | Dierck | |
| 8,475,484 B2 | 7/2013 | Wulfman et al. | |
| 8,528,563 B2 | 9/2013 | Gruber | |
| 8,574,254 B2 | 11/2013 | Hedstrom et al. | |
| 8,622,997 B2 * | 1/2014 | Shippert | A61M 1/0056 |
| | | | 604/542 |
| 8,696,621 B2 | 4/2014 | Gunday et al. | |
| 9,095,367 B2 | 8/2015 | Olson et al. | |
| 2001/0013487 A1 | 8/2001 | Kaendler | |
| 2002/0013570 A1 | 1/2002 | Ruegg et al. | |
| 2002/0058857 A1 | 5/2002 | Smith | |
| 2003/0055315 A1 | 3/2003 | Gatto et al. | |
| 2003/0097146 A1 | 5/2003 | Montalvo et al. | |
| 2004/0147934 A1 | 7/2004 | Kiester | |
| 2004/0162572 A1 | 8/2004 | Sauer | |
| 2005/0090848 A1 | 4/2005 | Adams | |
| 2005/0159767 A1 | 7/2005 | Adams et al. | |
| 2005/0272976 A1 | 12/2005 | Tanaka et al. | |
| 2007/0038022 A1 | 2/2007 | Nakao | |
| 2007/0197871 A1 | 8/2007 | Geitz et al. | |
| 2008/0082021 A1 | 4/2008 | Ichikawa et al. | |
| 2008/0183201 A1 | 7/2008 | Berberich | |
| 2008/0194910 A1 | 8/2008 | Miyamoto et al. | |
| 2008/0234602 A1 | 9/2008 | Oostman et al. | |
| 2008/0249553 A1 | 10/2008 | Gruber et al. | |
| 2008/0290040 A1 | 11/2008 | Kane et al. | |
| 2009/0069806 A1 | 3/2009 | De La Mora Levy et al. | |
| 2009/0234378 A1 | 9/2009 | Escudero et al. | |
| 2009/0240261 A1 | 9/2009 | Drews et al. | |
| 2010/0010525 A1 | 1/2010 | Lockard et al. | |
| 2010/0016757 A1 | 1/2010 | Greenburg et al. | |
| 2010/0036375 A1 | 2/2010 | Regadas | |
| 2010/0048992 A1 | 2/2010 | Okada et al. | |
| 2010/0049225 A1 | 2/2010 | To et al. | |
| 2010/0081874 A1 | 4/2010 | Miyamoto et al. | |
| 2010/0121141 A1 | 5/2010 | Rontal | |
| 2010/0168512 A1 | 7/2010 | Rahmani | |
| 2010/0217245 A1 | 8/2010 | Prescott | |
| 2010/0291536 A1 * | 11/2010 | Viljoen | A61B 10/0051 |
| | | | 435/4 |
| 2010/0298855 A1 | 11/2010 | Dierck | |
| 2011/0106029 A1 * | 5/2011 | Garren | A61B 1/00131 |
| | | | 604/319 |
| 2011/0112364 A1 | 5/2011 | Rone et al. | |
| 2011/0270126 A1 | 11/2011 | Gunday et al. | |
| 2012/0109130 A1 | 5/2012 | Casey et al. | |
| 2012/0226101 A1 | 9/2012 | Tinkham et al. | |
| 2012/0226103 A1 | 9/2012 | Gunday et al. | |
| 2013/0016316 A1 | 1/2013 | Cheng et al. | |
| 2013/0046313 A1 | 2/2013 | Sullivan et al. | |
| 2013/0046316 A1 | 2/2013 | Sullivan et al. | |
| 2013/0103067 A1 | 4/2013 | Fabro et al. | |
| 2013/0190561 A1 | 7/2013 | Oskin et al. | |
| 2013/0317529 A1 | 11/2013 | Golden et al. | |
| 2014/0100567 A1 | 4/2014 | Edwards et al. | |
| 2014/0155923 A1 | 6/2014 | Edwards et al. | |

(56) References Cited

U.S. PATENT DOCUMENTS

| | | |
|---|---|---|
| 2014/0236165 A1 | 8/2014 | Ries et al. |
| 2014/0249448 A1 | 9/2014 | Furlong et al. |

FOREIGN PATENT DOCUMENTS

| | | |
|---|---|---|
| DE | 33 20 076 A1 | 12/1984 |
| DE | 19522403 A1 | 9/1997 |
| EP | 0 609 084 A2 | 8/1994 |
| EP | 1 031 371 | 8/2000 |
| EP | 1 586 275 | 10/2005 |
| EP | 1 875 871 A2 | 1/2008 |
| JP | 2000-354708 | 12/2000 |
| JP | 2002-503132 | 1/2002 |
| JP | 2003-524479 | 8/2003 |
| WO | WO-95/30377 | 11/1995 |
| WO | WO-98/20352 A2 | 5/1998 |
| WO | WO-01/22889 | 4/2001 |
| WO | WO-2006/122279 | 11/2006 |
| WO | WO-2012/075409 A1 | 6/2012 |
| WO | WO-2013/022525 | 2/2013 |
| WO | WO-2016/037132 A1 | 3/2016 |

OTHER PUBLICATIONS

International Preliminary Report on Patentability and Written Opinion of the International Searching Authority for Application No. PCT/US2015/052979 dated Apr. 4, 2017.
Office Action for CN2014800030452 dated Aug. 22, 2016.
Declaration of Non-Establishment of International Search Report dated Jan. 8, 2016 in PCT Application No. PCT/US2015/052980.
Examination Report for EP 12809398.6 dated Jul. 19, 2016.
Examination Report for EP 14731875.2 dated Aug. 17, 2016.
Examination Report No. 1 for Standard patent application for Application No. 2016201686, dated Mar. 1, 2017, 4 pages.
Examination report No. 2 for Standard Patent Application for Application No. 2012345609 dated Jun. 4, 2017.
First Office Action dated Feb. 3, 2016 in Chinese Patent Application No. 201280068003.8.
International Preliminary Report and Written Opinion of the International Searching Authority for application No. PCT/US2015/052977 dated Apr. 4, 2017.
International Preliminary Report on Patentability (Chapter 1 of the Patent Cooperation Treaty) and Written Opinion of the International Searching Authority for Application No. PCT/US2015/052978 dated Apr. 4, 2017.
International Preliminary Report on Patentability dated Nov. 26, 2015 in PCT Application No. PCT/US2014/038443.
International Preliminary Report on Patentability dated Jun. 12, 2014 in PCT Application No. PCT/US2012/067614.
International Search Report and Written Opinion dated May 28, 2013 in PCT App. No. PCT/US2012/067614.
International Search Report and Written Opinion for International Patent Application No. PCT/US2014/038443 dated Sep. 1, 2014.
International Search Report and Written Opinion for PCT/US2017/022536 dated Aug. 10, 2017.
International Search Report and Written Opinion of the International Searching Authority for International Application No. PCT/US2015/052977 dated Dec. 18, 2015.
International Search Report and Written Opinion of the International Searching Authority for International Application No. PCT/US2015/052979 dated Dec. 17, 2015.
International Search Report and Written Opinion of the International Searching Authority on International Application No. PCT/US2015/052978 dated Dec. 17, 2015.
Office Action for JP 2016-114249 dated Jun. 6, 2017.
Office Action for JP2008/0249553 dated Nov. 8, 2016.
Office Action in European Patent Application No. 14731875.2 dated Feb. 12, 2016.
Office Action on U.S. Appl. No. 13/336,491 dated Jan. 19, 2017.
Office Action on U.S. Appl. No. 13/336,491 dated Oct. 26, 2016.
Patent Examination Report for AU 2012345690 dated Jul. 22, 2016.
Search Report for CN2012800680038 dated Oct. 18, 2016.
Search Report for CN2014800030452 dated Aug. 22, 2016.
Second Office Action for CN2012800680038 dated Oct. 18, 2016.
Third Office Action for Application No. 201280068003.8 dated Apr. 17, 2017, 6 pages.
U.S. Notice of Allowance for U.S. Appl. No. 14/280,202 dated Oct. 7, 2014.
U.S. Notice of Allowance for U.S. Appl. No. 14/501,865 dated Feb. 20, 2015.
U.S. Notice of Allowance for U.S. Appl. No. 14/501,942 dated Mar. 18, 2015.
U.S. Notice of Allowance for U.S. Appl. No. 14/537,362 dated May 26, 2015.
U.S. Notice of Allowance in U.S. Appl. No. 14/501,957 dated Oct. 21, 2015.
U.S. Notice of Allowance on U.S. Appl. No. 13/336,491 dated Jul. 6, 2017.
U.S. Notice of Allowance on U.S. Appl. No. 13/336,491 dated Aug. 7, 2017.
U.S. Notice of Allowance on U.S. Appl. No. 14/316,203 dated Jun. 23, 2016.
U.S. Office Action for U.S. Appl. No. 13/336,491 dated Mar. 2, 2016.
U.S. Office Action for U.S. Appl. No. 13/336,491 dated Sep. 18, 2015.
U.S. Office Action for U.S. Appl. No. 14/280,202 dated Aug. 20, 2014.
U.S. Office Action for U.S. Appl. No. 14/316,203 dated Mar. 15, 2016.
U.S. Office Action for U.S. Appl. No. 14/501,865 dated Dec. 4, 2014.
U.S. Office Action for U.S. Appl. No. 14/501,932 dated Nov. 26, 2014.
U.S. Office Action for U.S. Appl. No. 14/501,942 dated Dec. 15, 2014.
U.S. Office Action for U.S. Appl. No. 14/501,957 dated Mar. 19, 2015.
U.S. Office Action for U.S. Appl. No. 14/501,957 dated Nov. 14, 2014.
U.S. Office Action for U.S. Appl. No. 14/537,362 dated Feb. 11, 2015.
U.S. Office Action on U.S. Appl. No. 13/336,491 dated May 11, 2016.
EPO Examination Report on EP 17715304.6 dated Aug. 3, 2020.
Japanese Office Action for JP Appl. Ser. No. 2018-548686 dated Apr. 6, 2021 (13 pages).

* cited by examiner

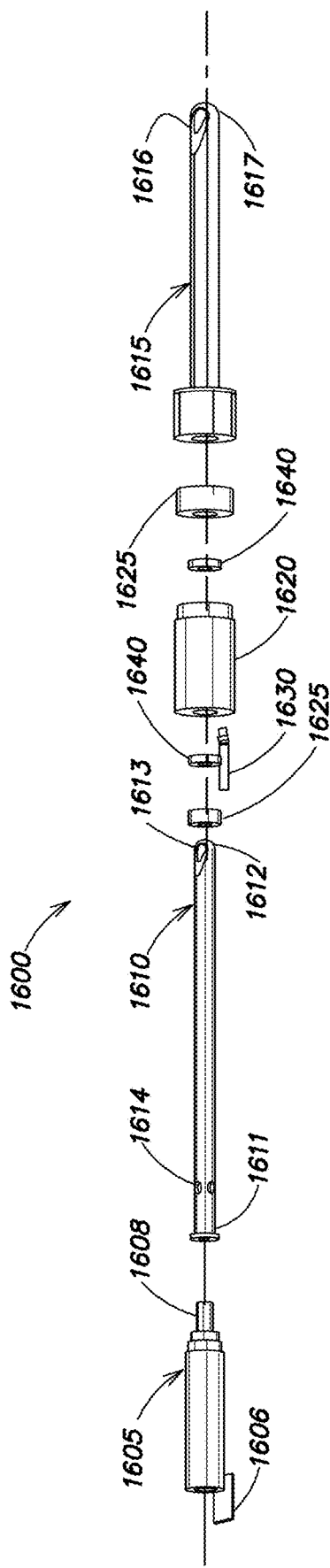
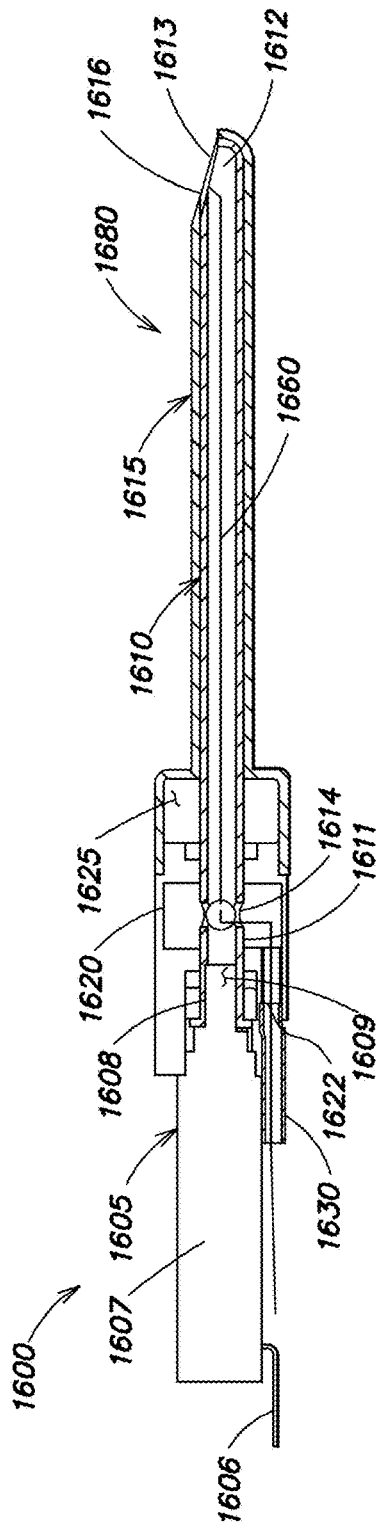
FIG. 16A
FIG. 16B

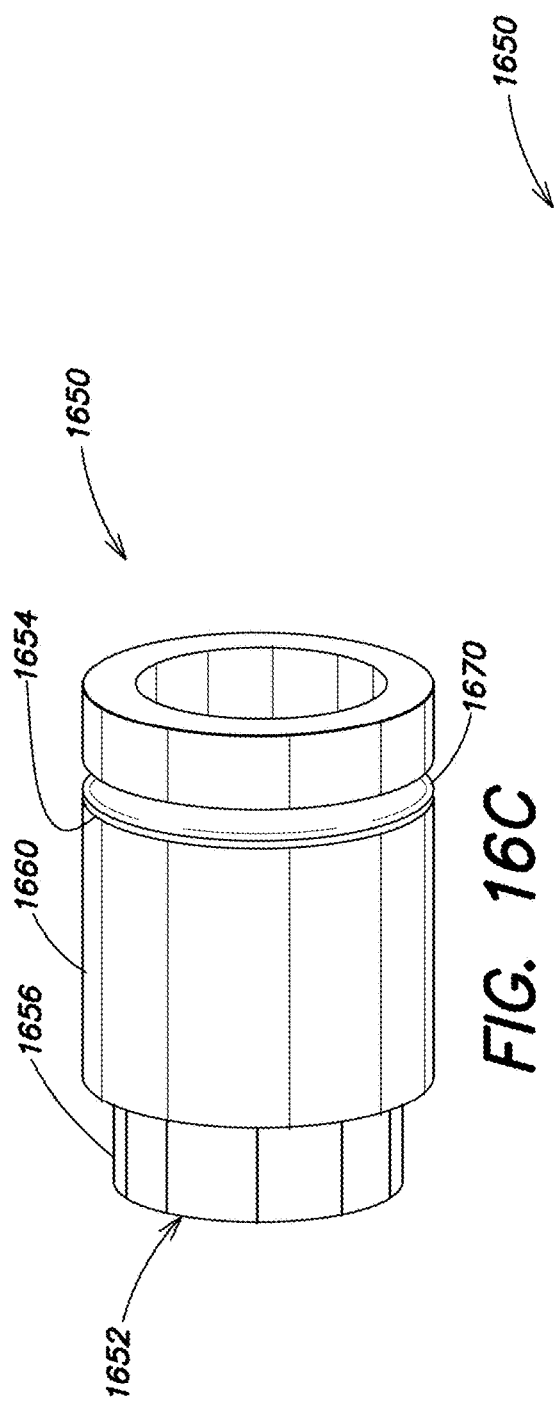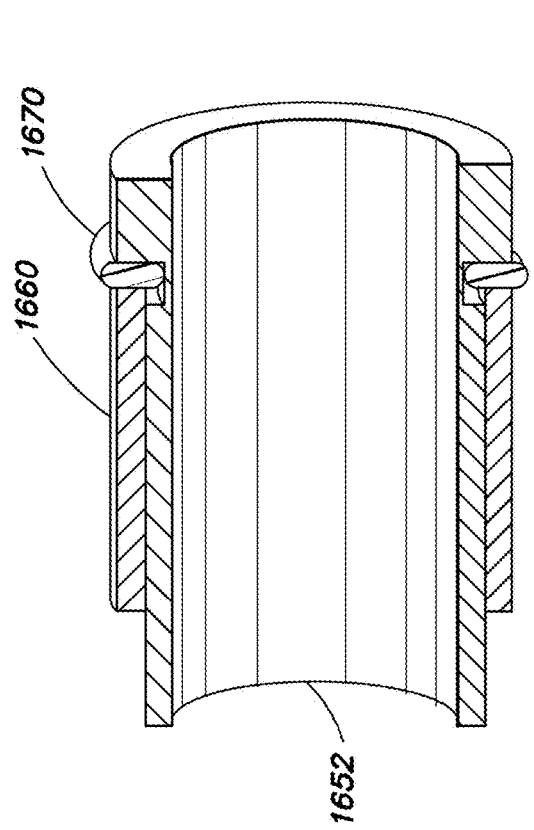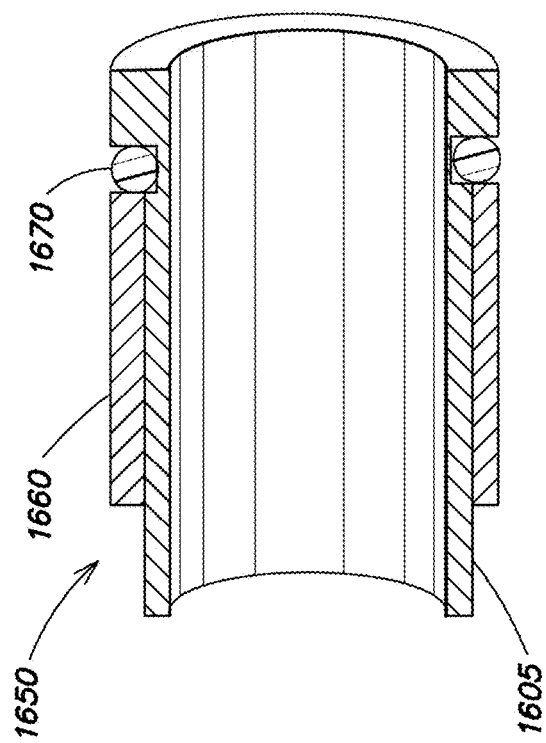

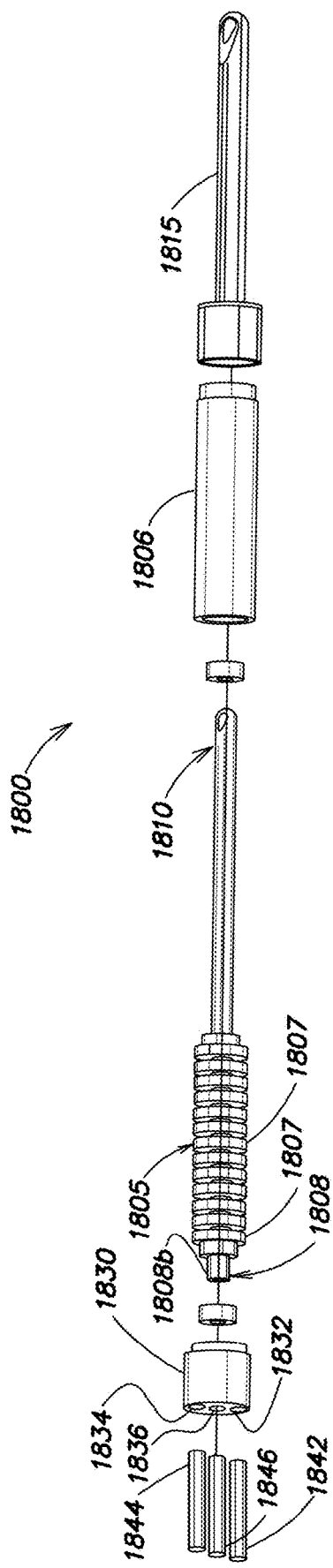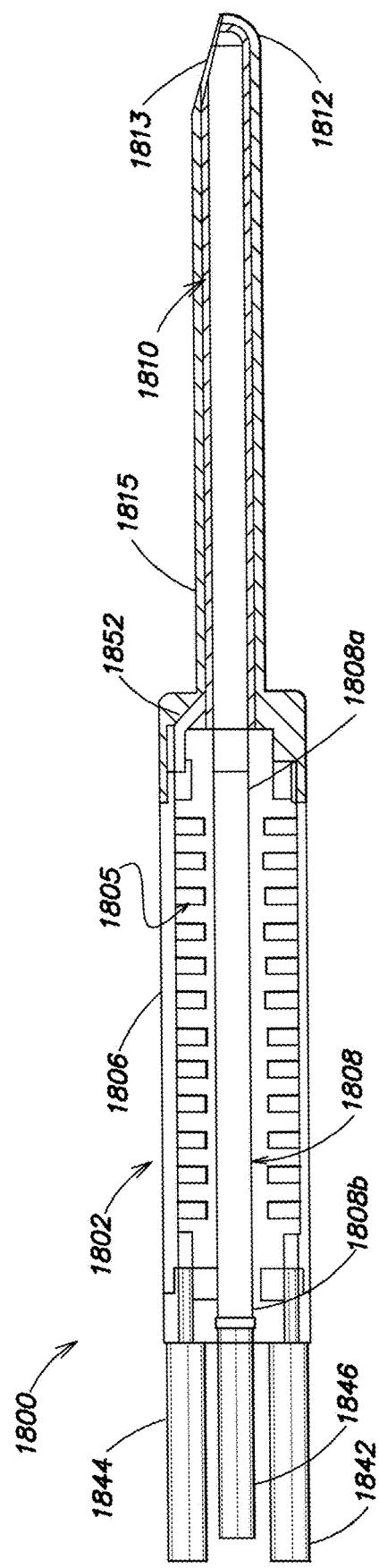
FIG. 18A
FIG. 18B

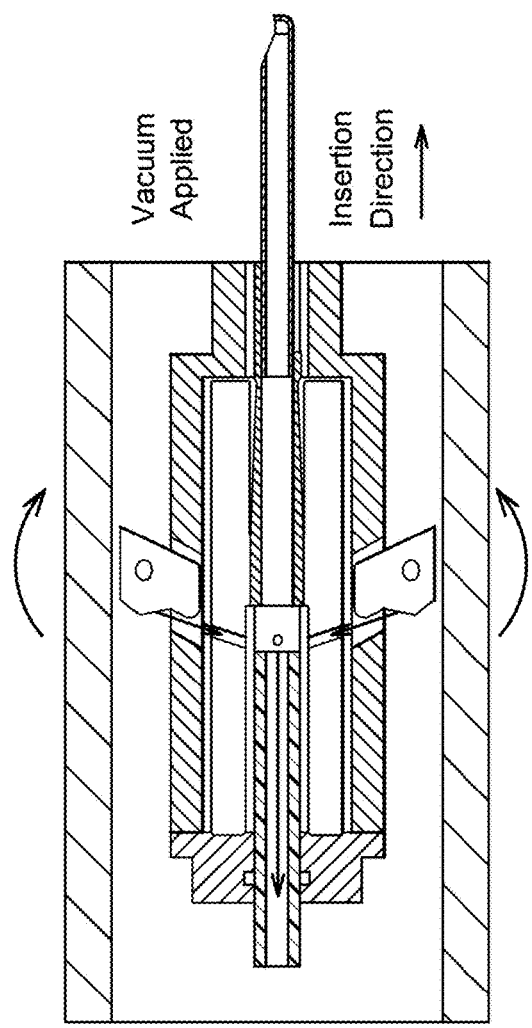
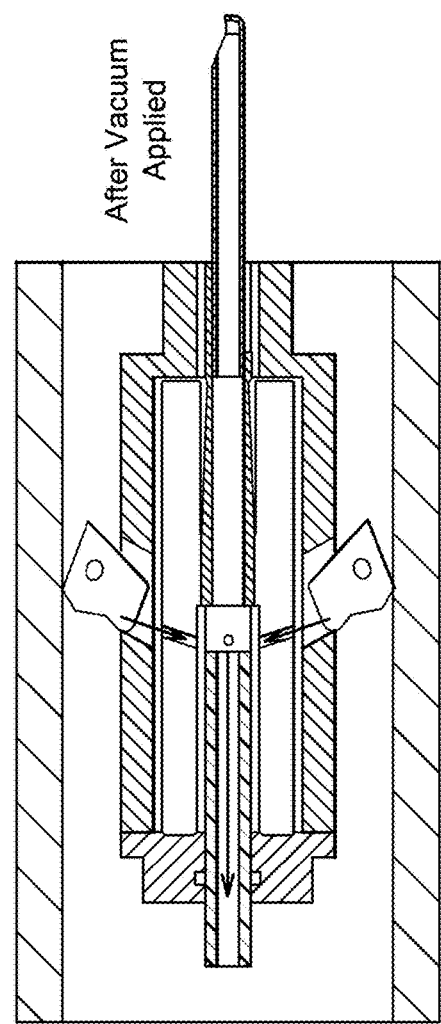

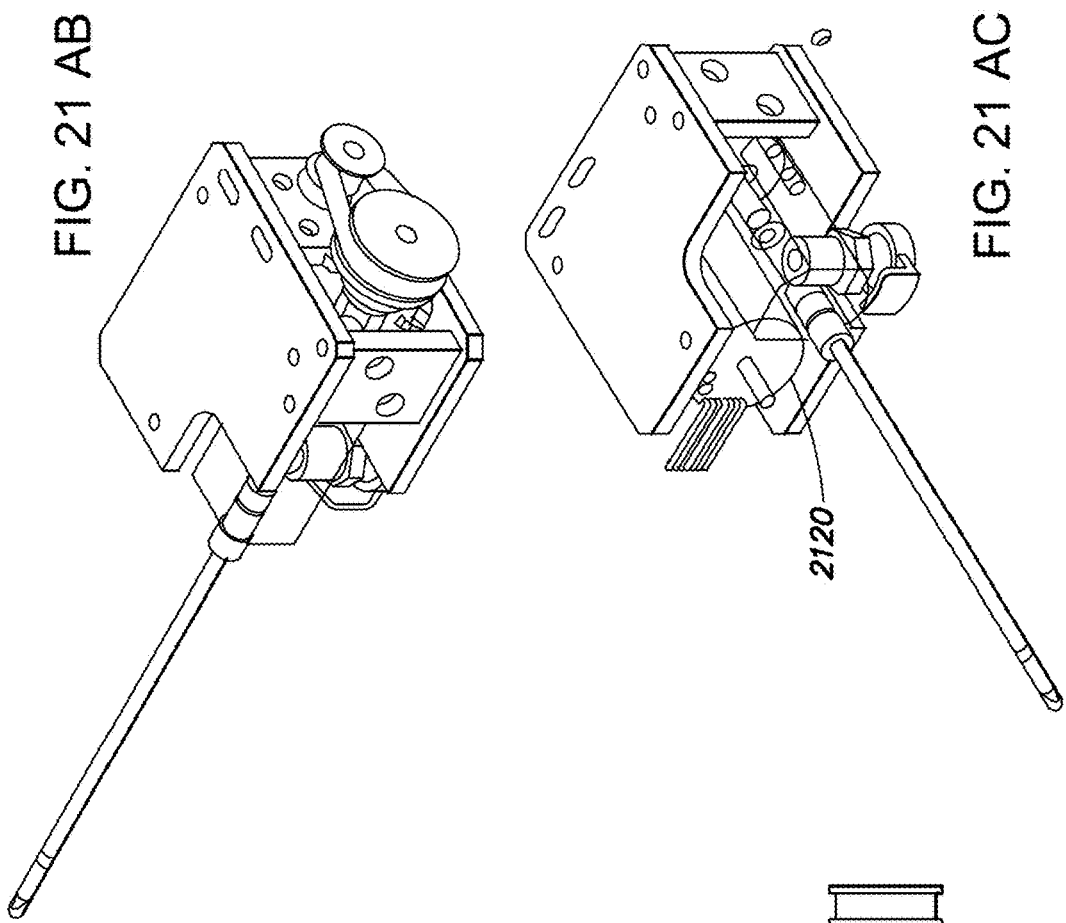
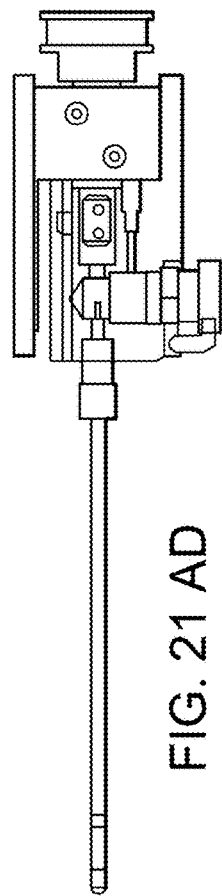
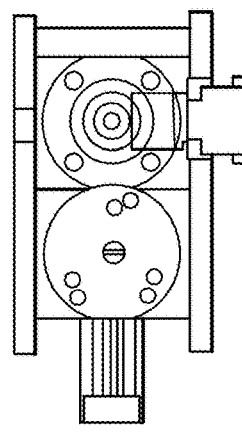
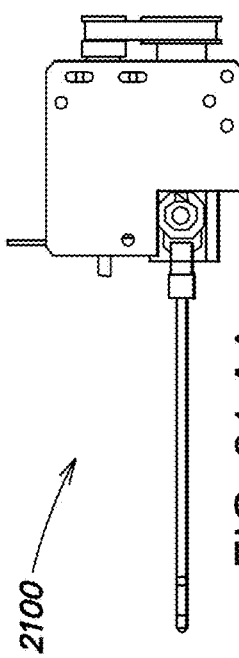

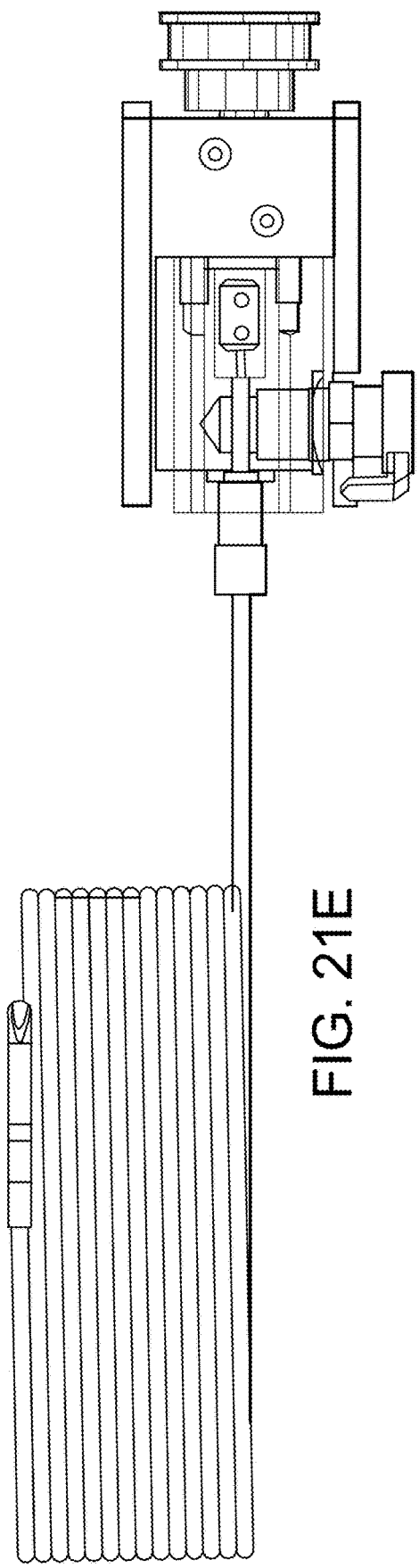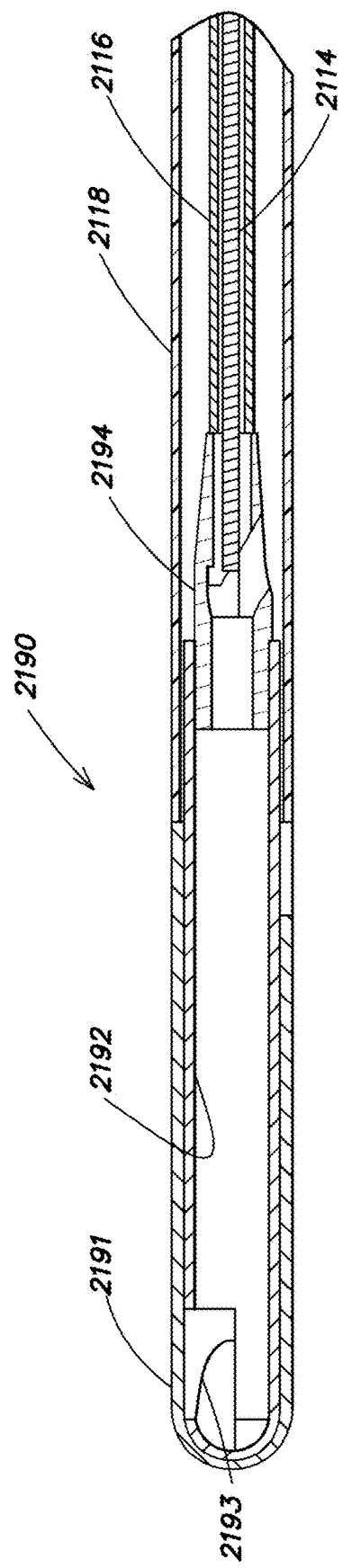
FIG. 21E
FIG. 21F

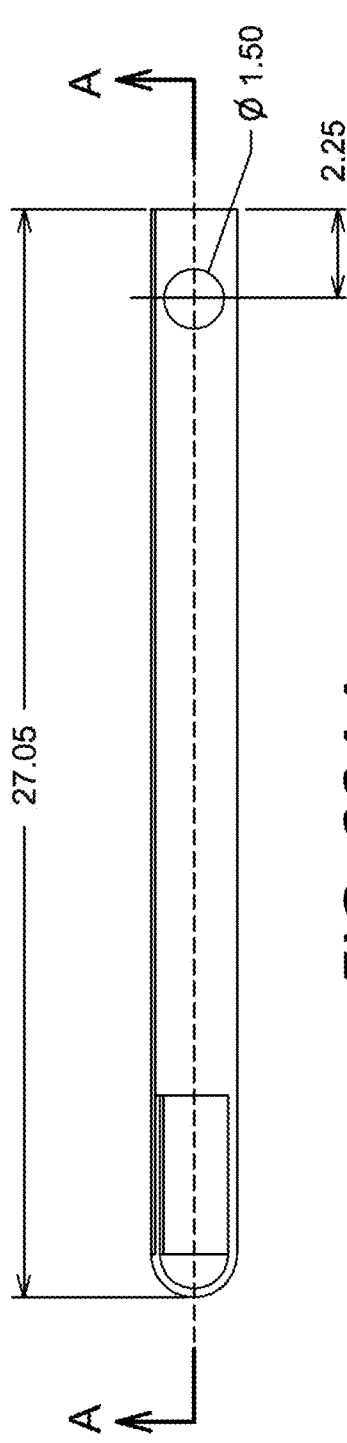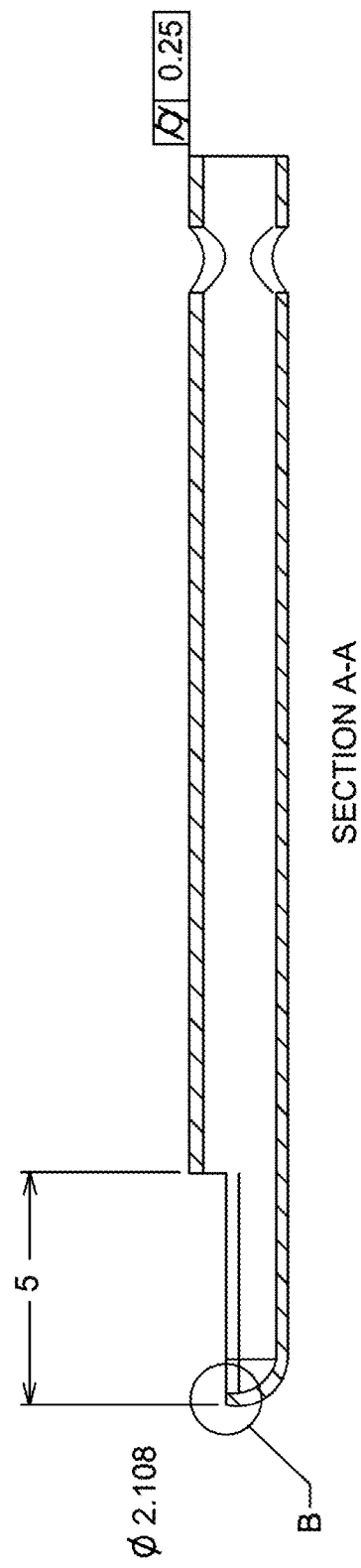
FIG. 23AA
FIG. 23AB

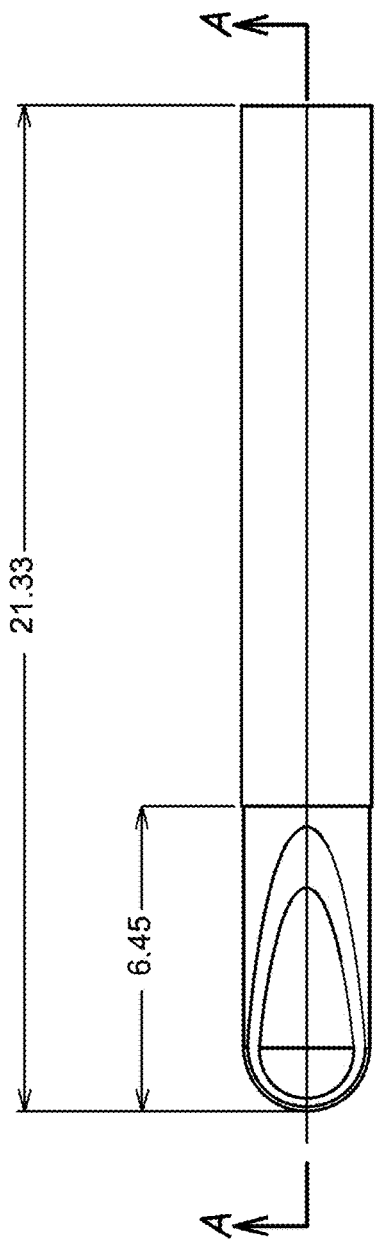
FIG. 23BA
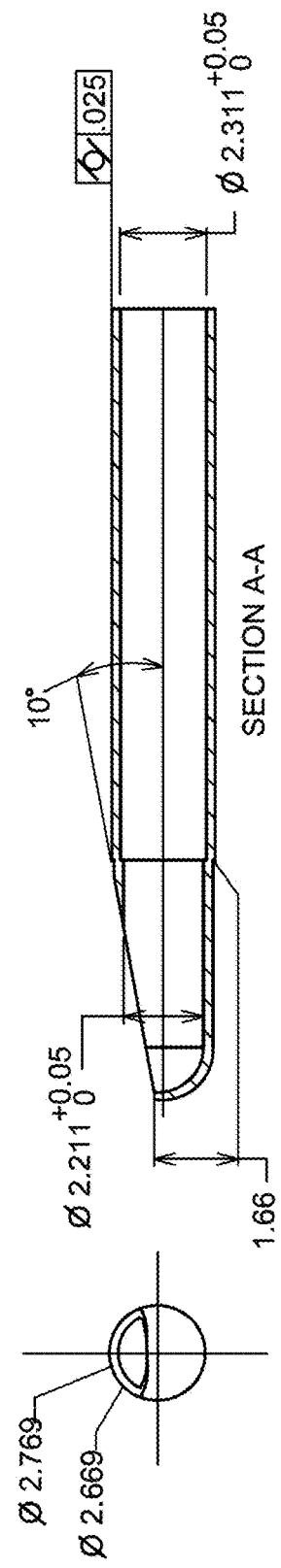
FIG. 23BB
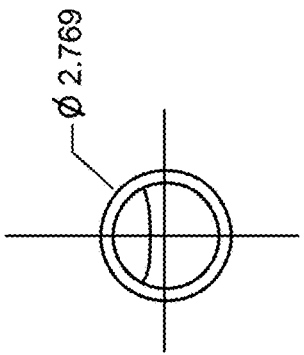

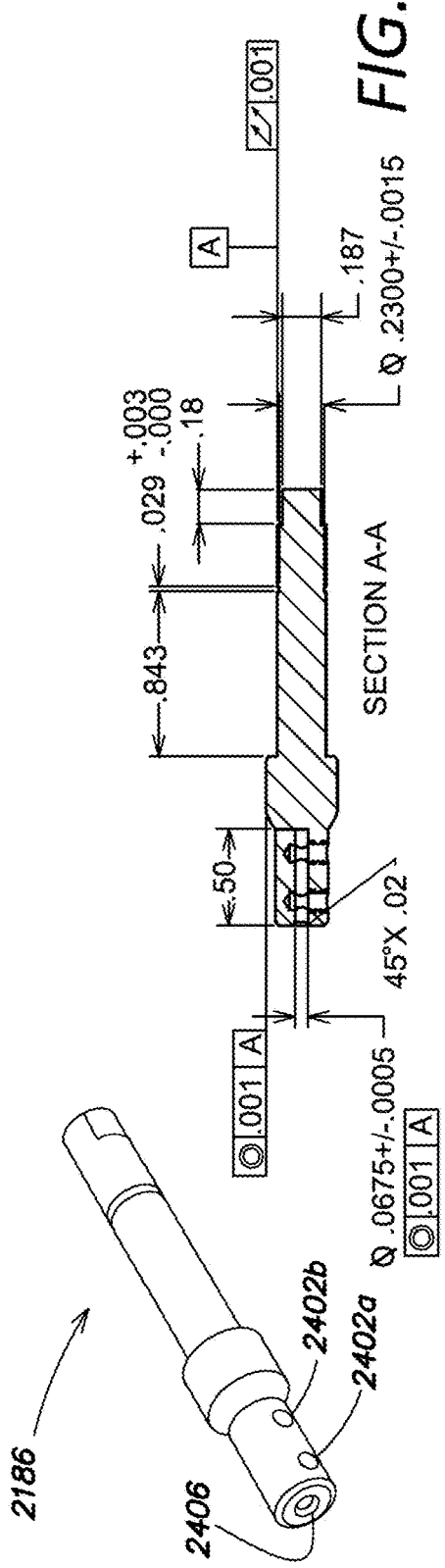
FIG. 24A
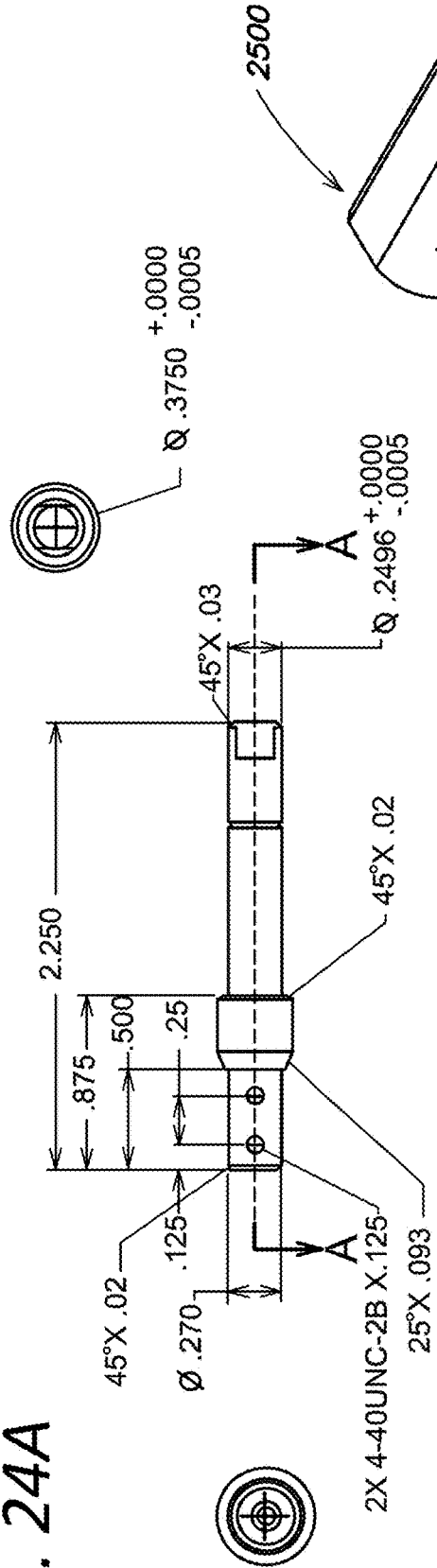
FIG. 24B
FIG. 24C
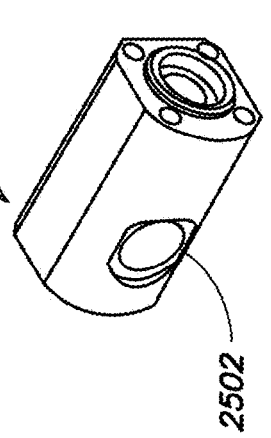
FIG. 25

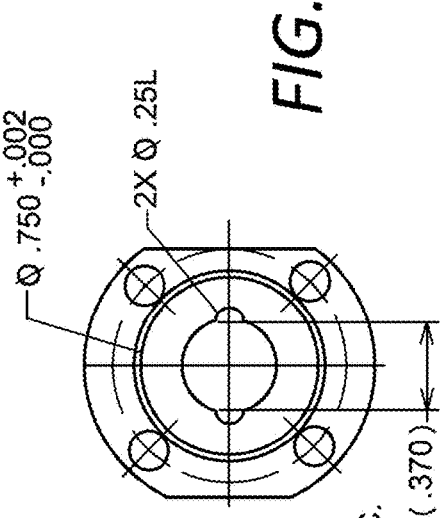
FIG. 26A
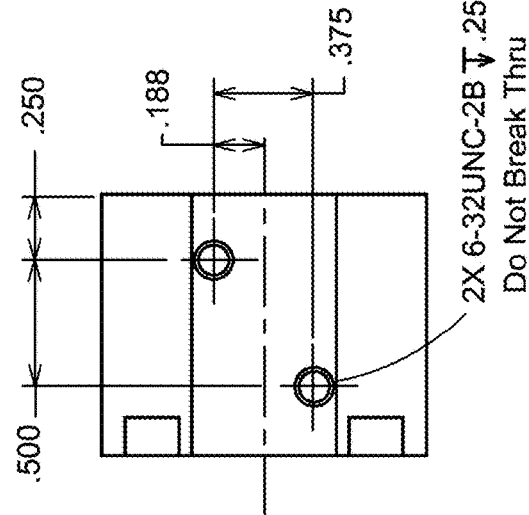
FIG. 26B
FIG. 26E
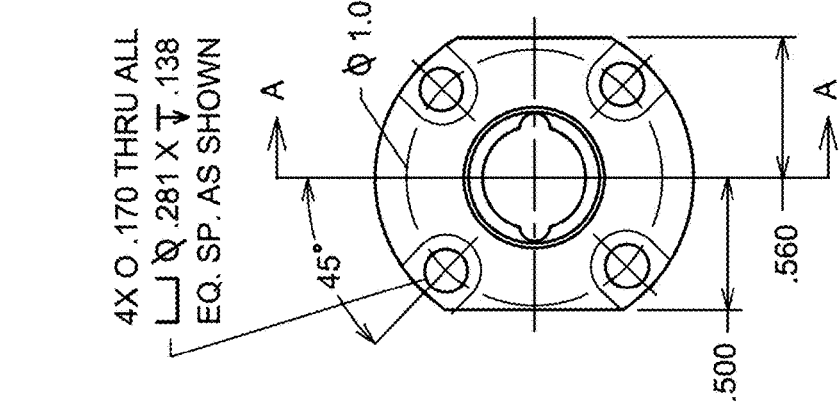
FIG. 26D
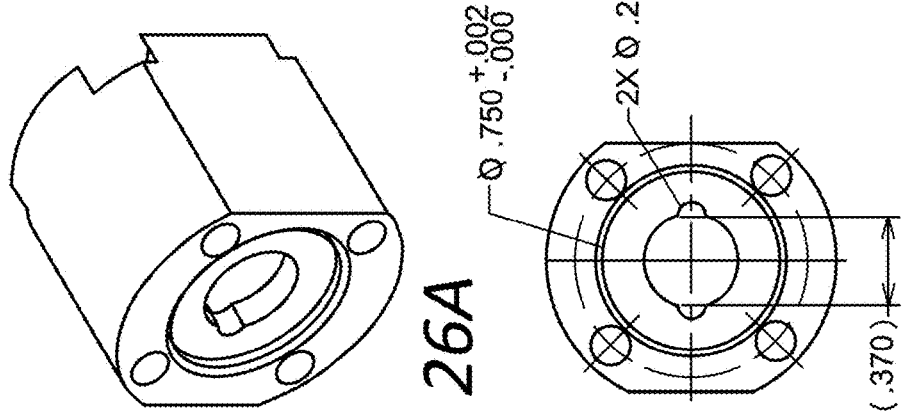
FIG. 26C

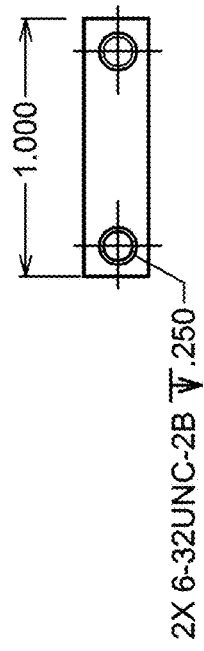
FIG. 28B
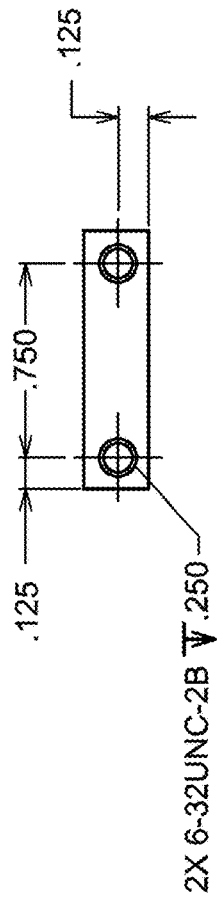
FIG. 28D
FIG. 28C
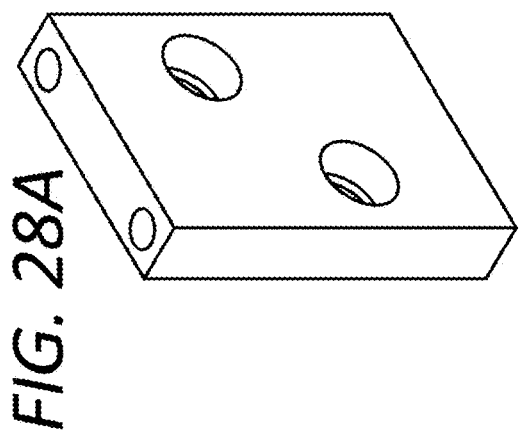
FIG. 28A

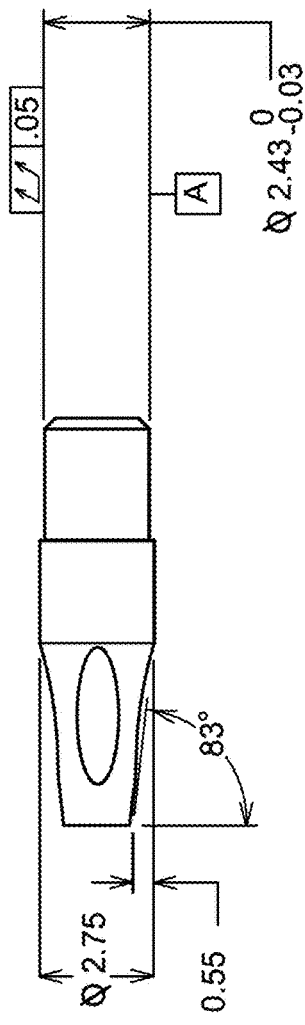
FIG. 29AB
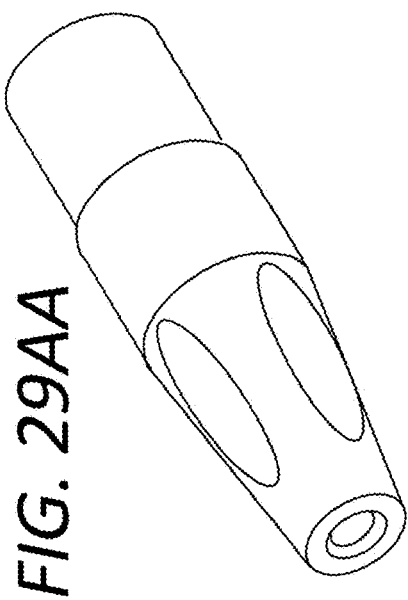
FIG. 29AA
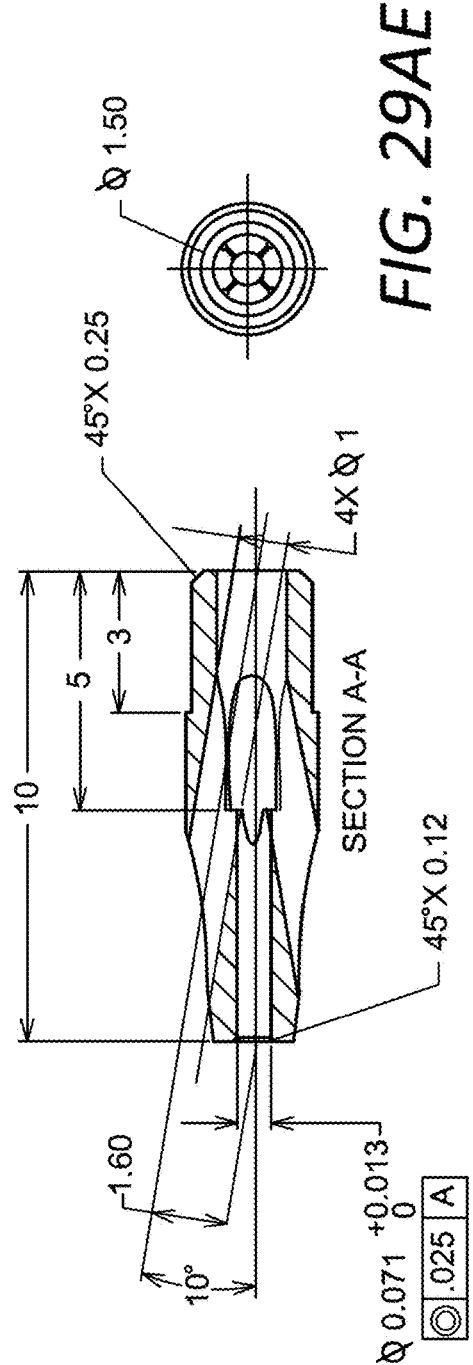
FIG. 29AE
FIG. 29AD
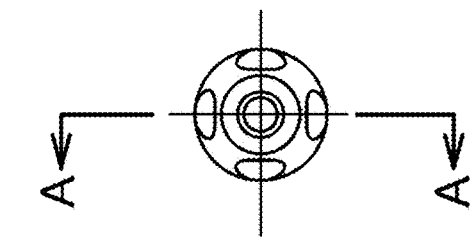
FIG. 29AC

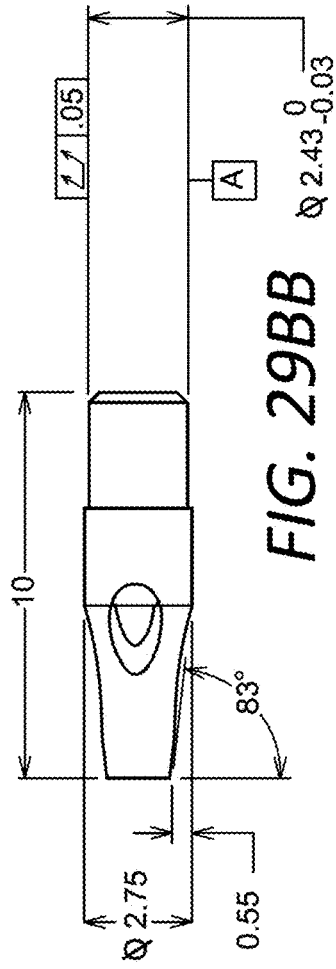
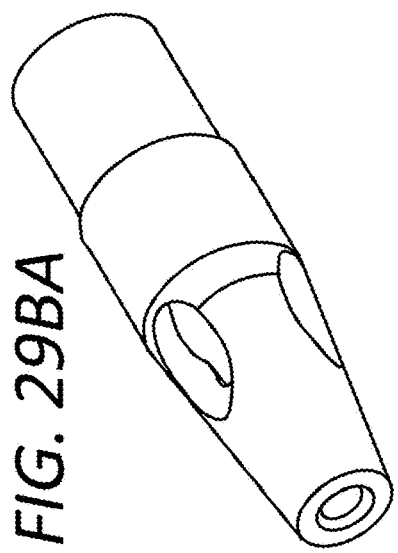
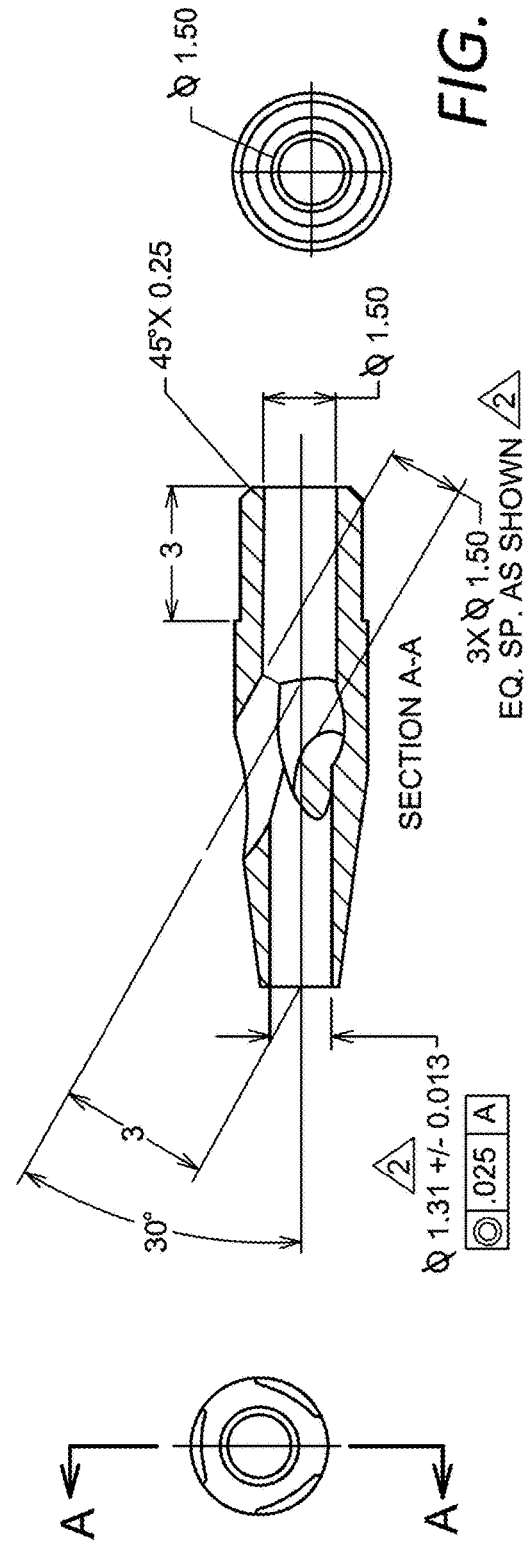
FIG. 29BA
FIG. 29BB
FIG. 29BC
FIG. 29BD
FIG. 29BE

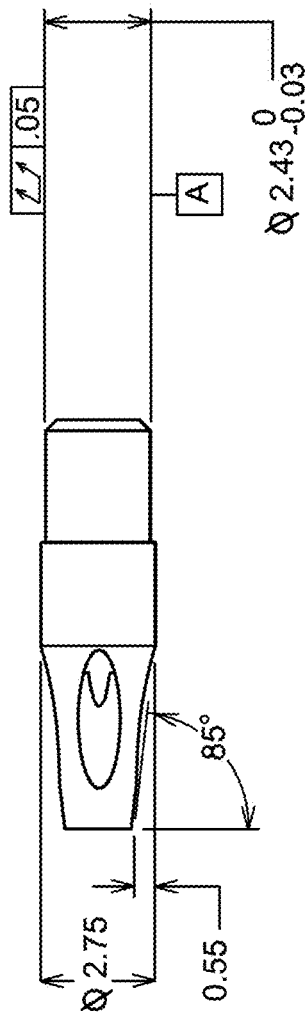
FIG. 29DB
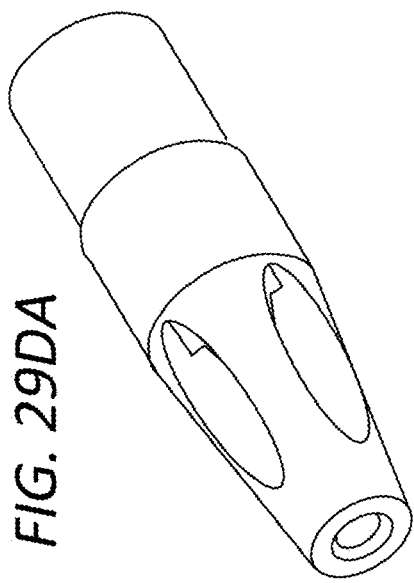
FIG. 29DA
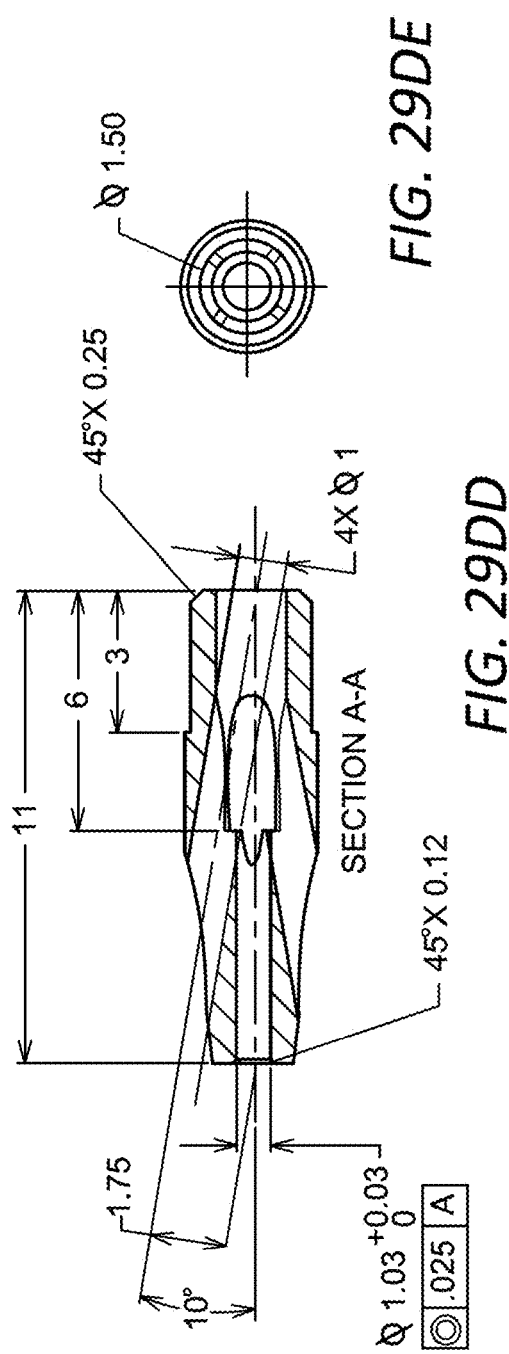
FIG. 29DE
FIG. 29DD
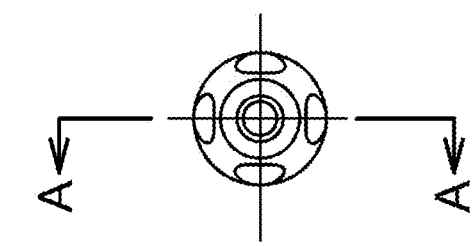
FIG. 29DC

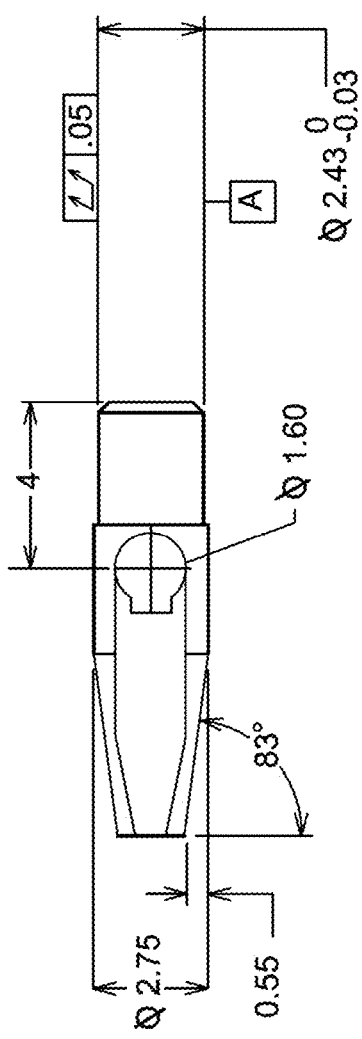
FIG. 29EB
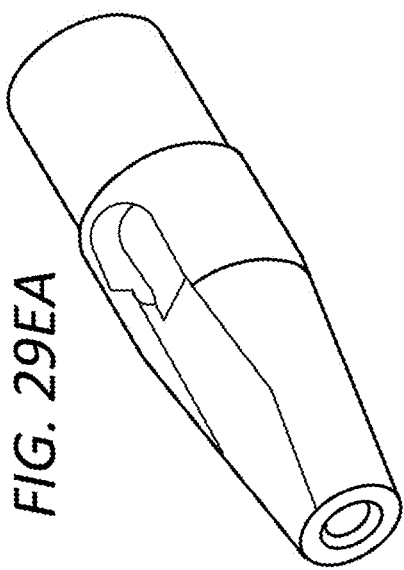
FIG. 29EA
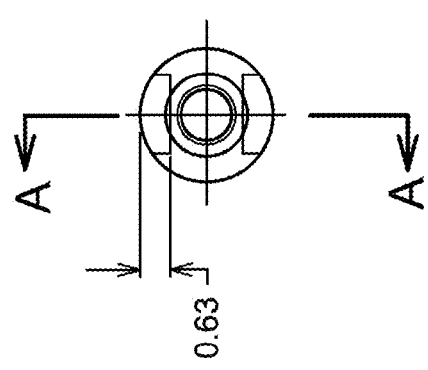
FIG. 29EC
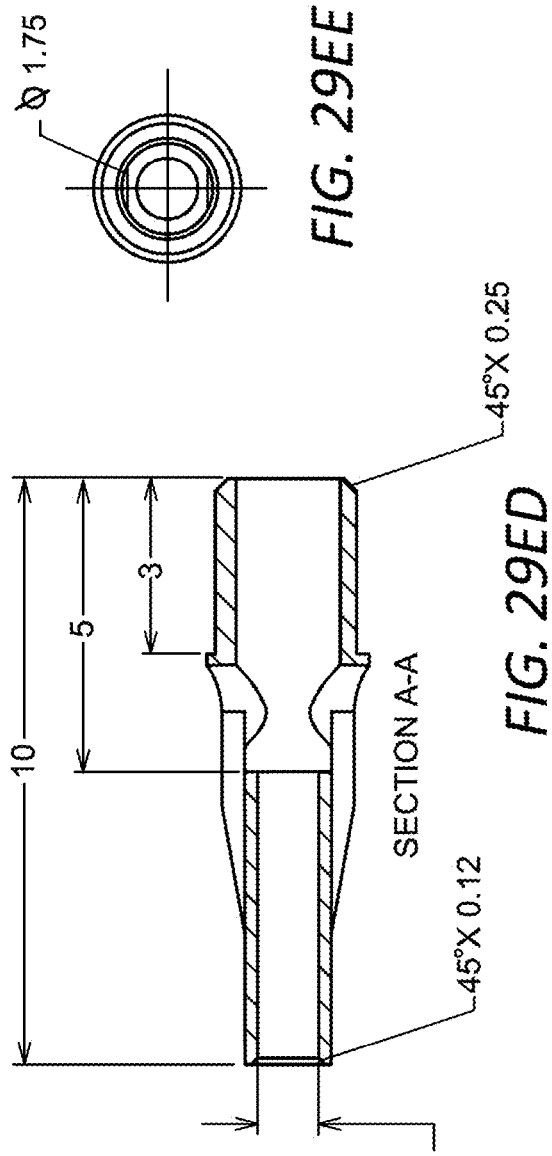
FIG. 29EE
FIG. 29ED

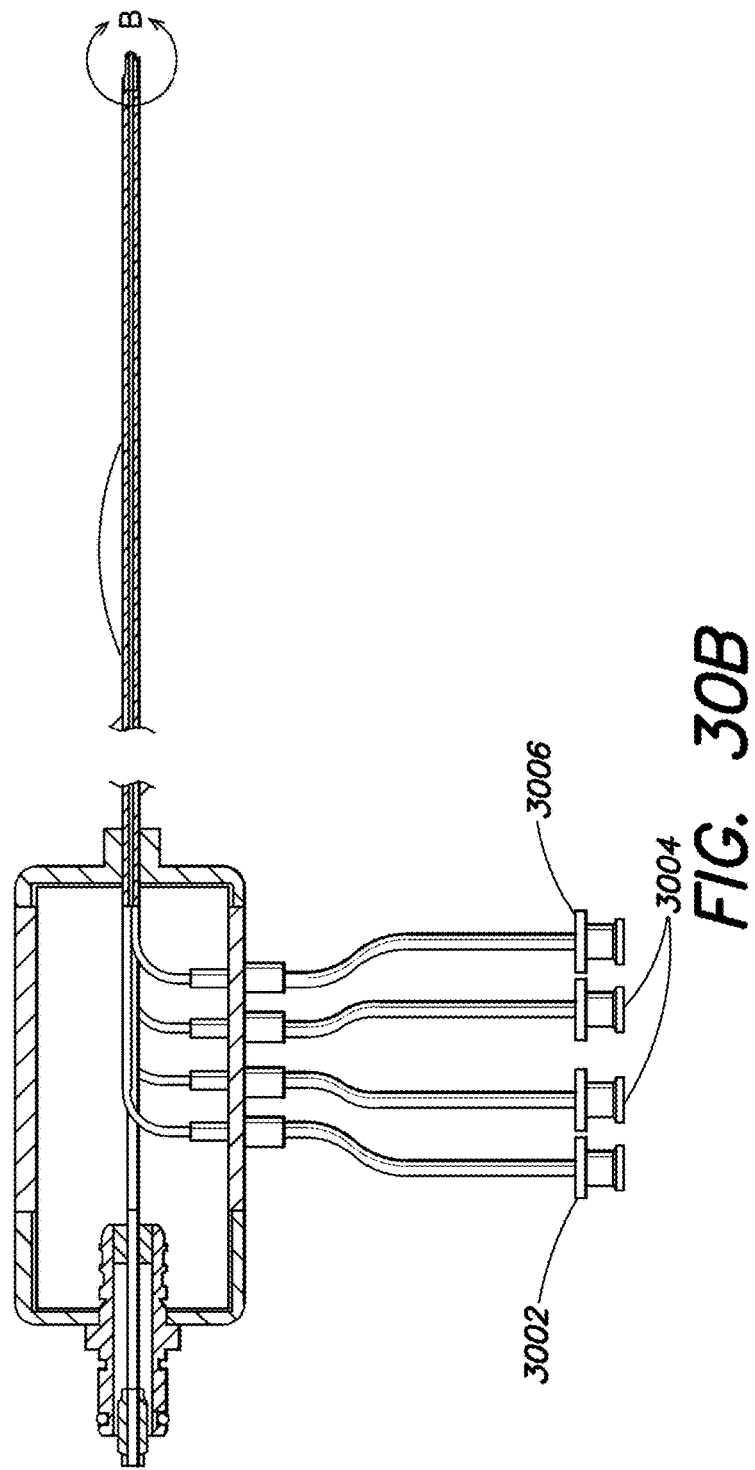
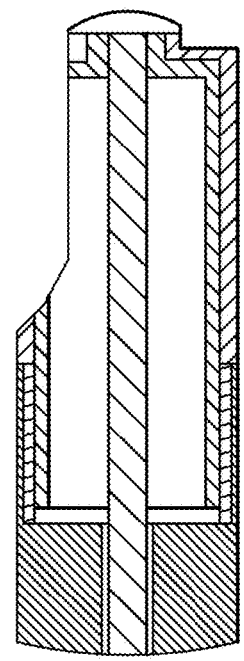
FIG. 30B
FIG. 30C

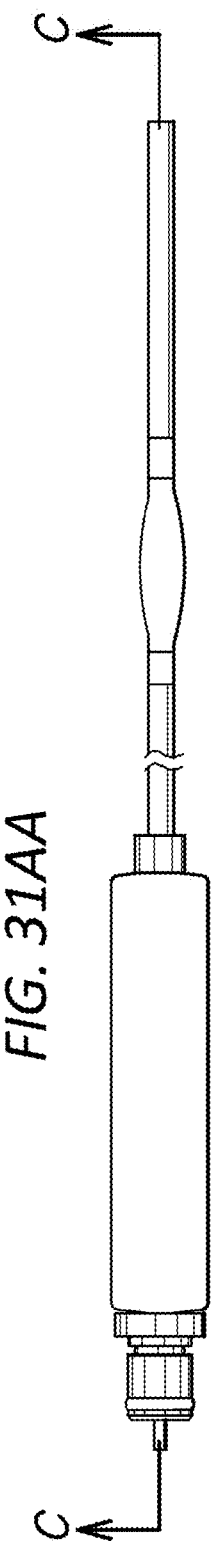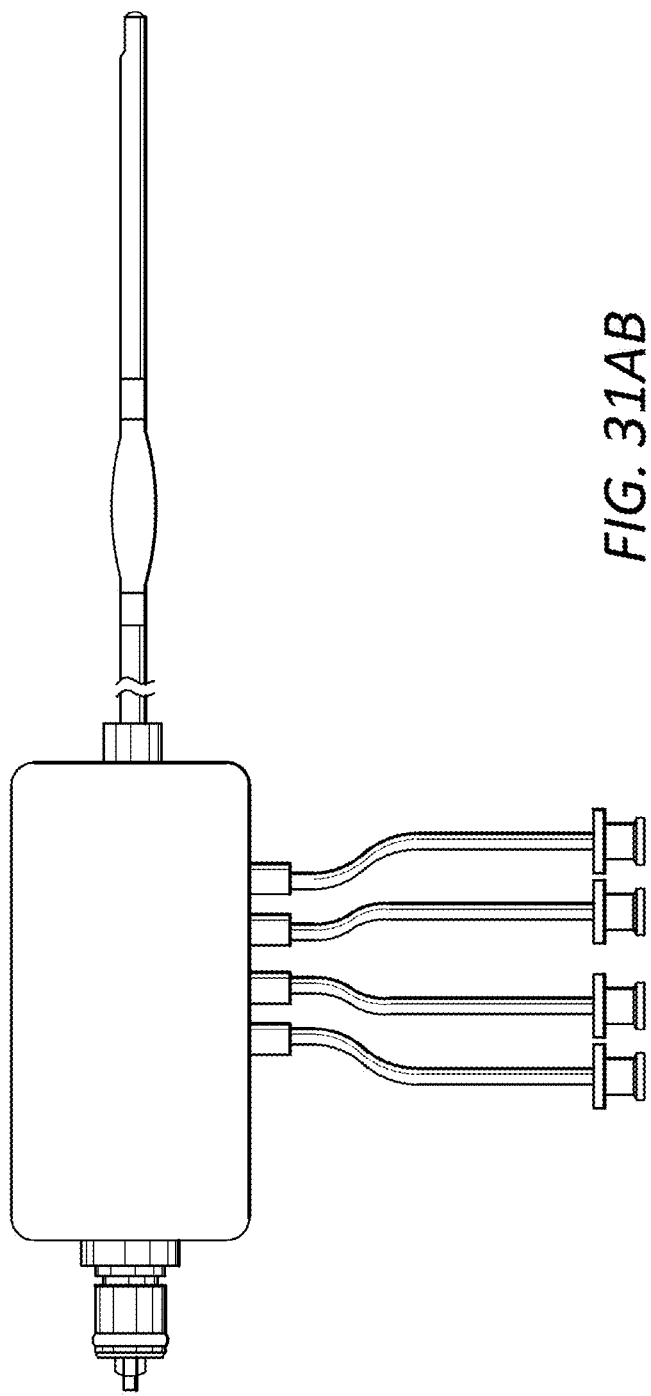
FIG. 31AA
FIG. 31AB

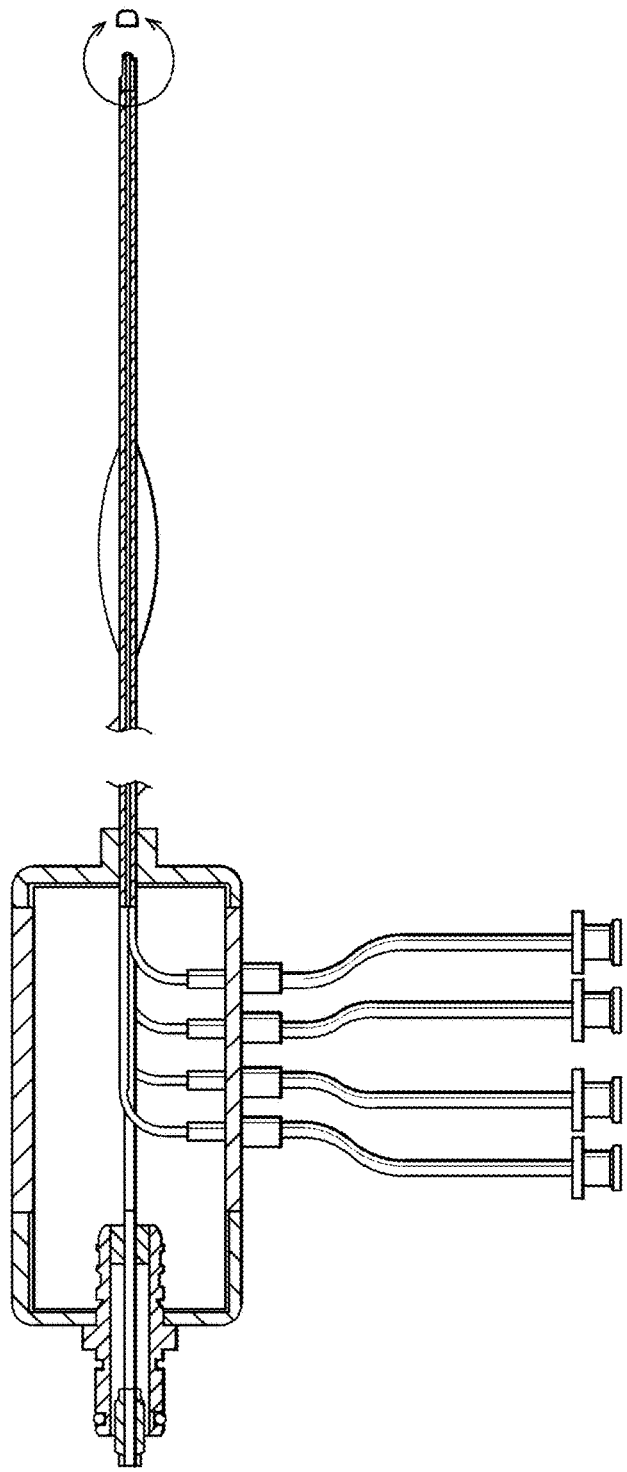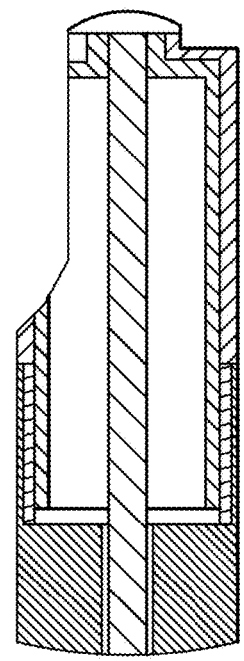
FIG. 31B
FIG. 31C

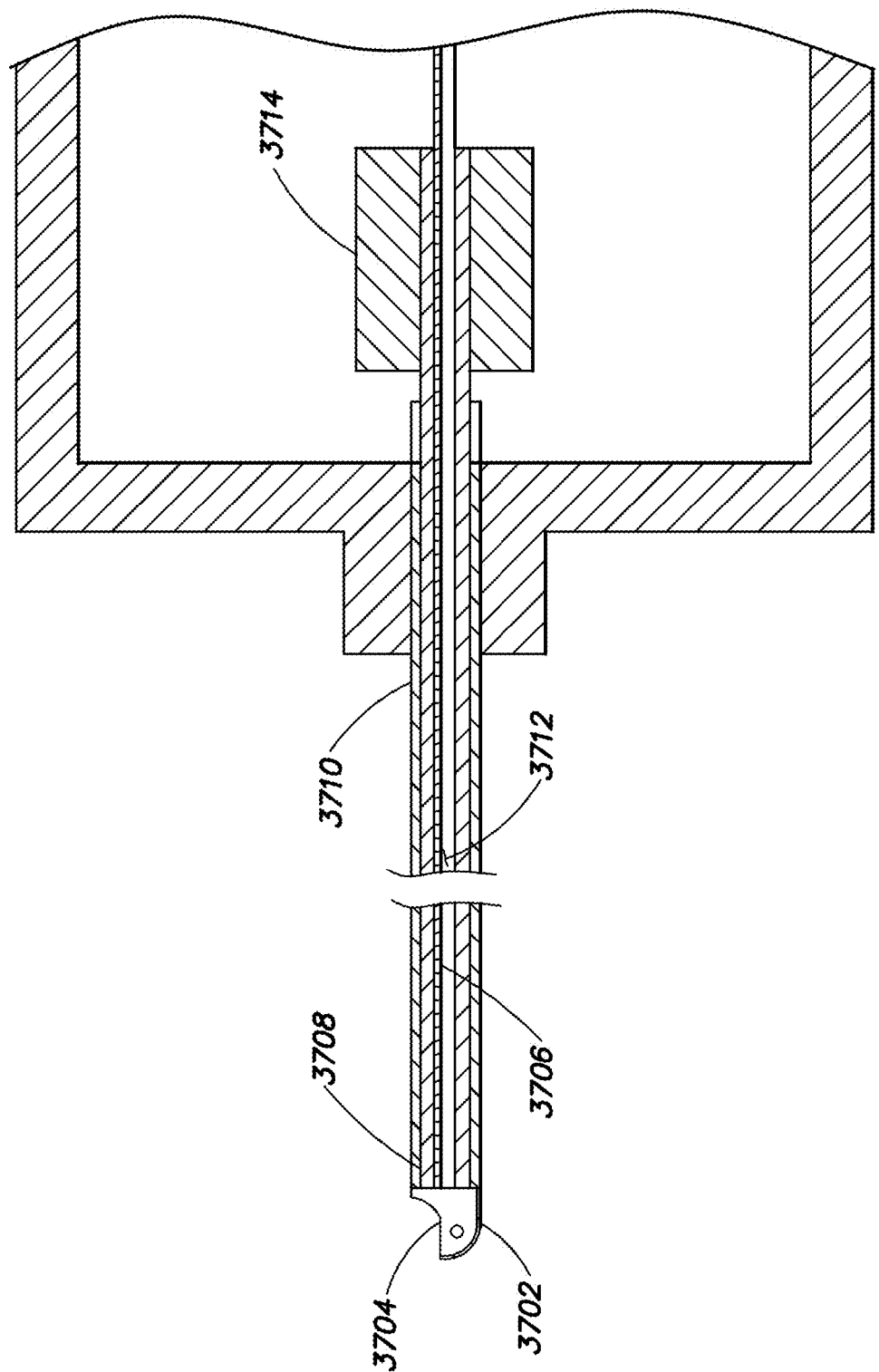

SECTION C-C

SECTION B-B

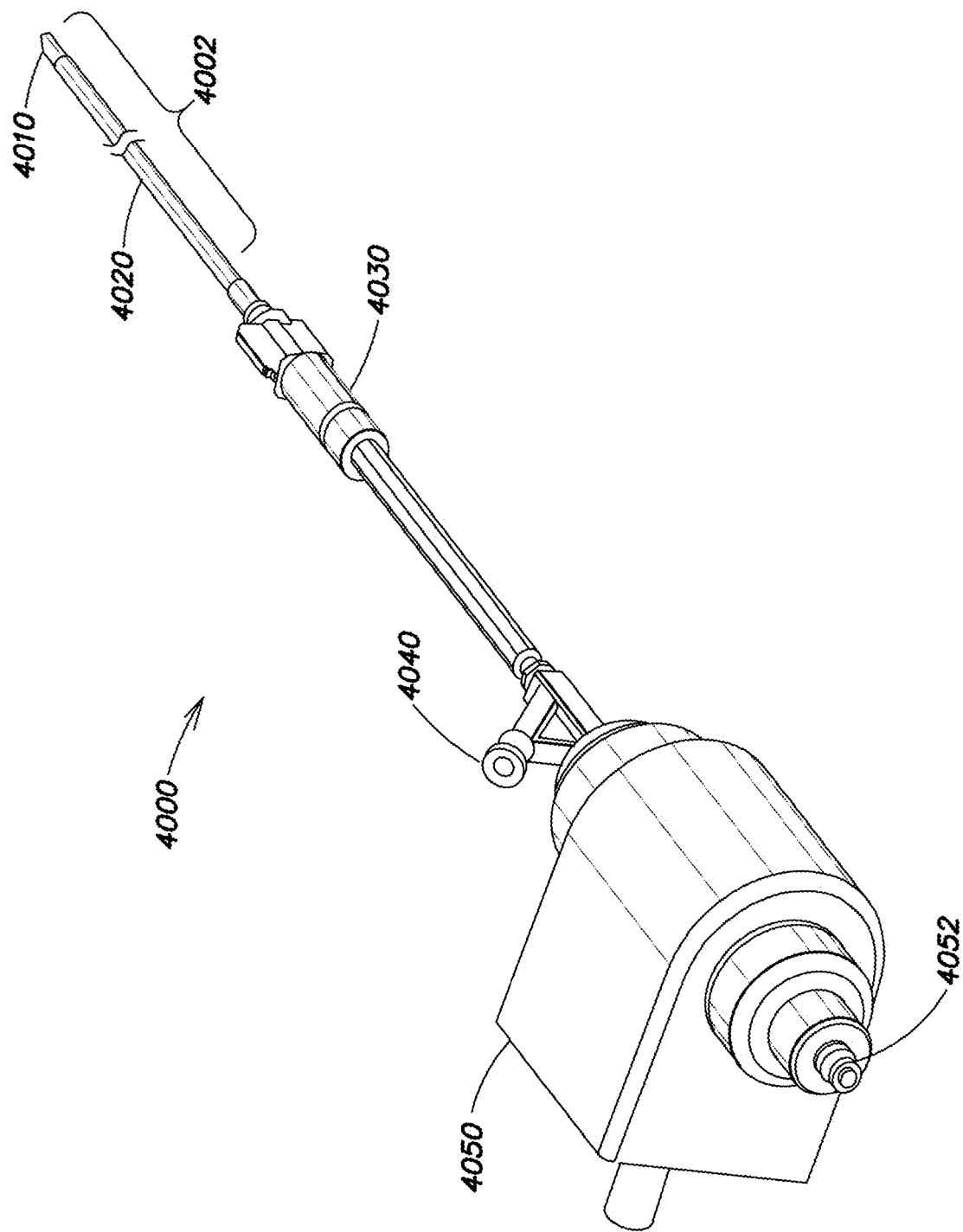

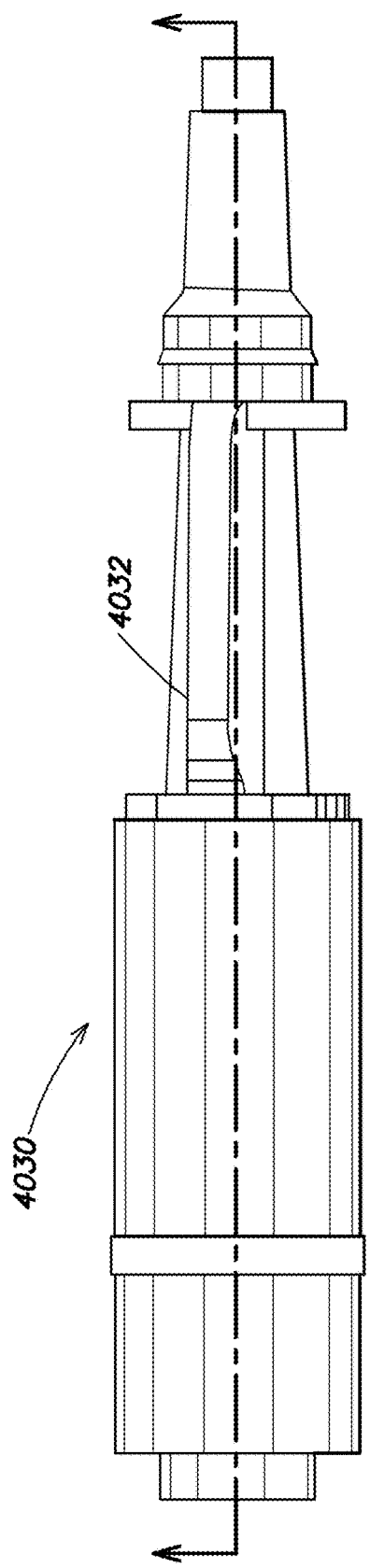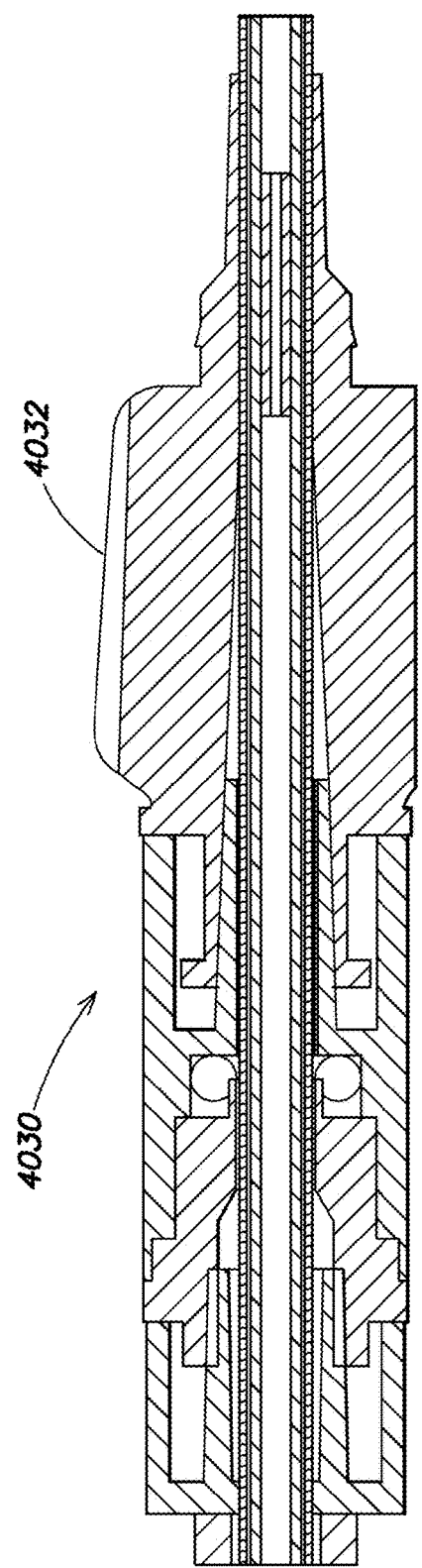

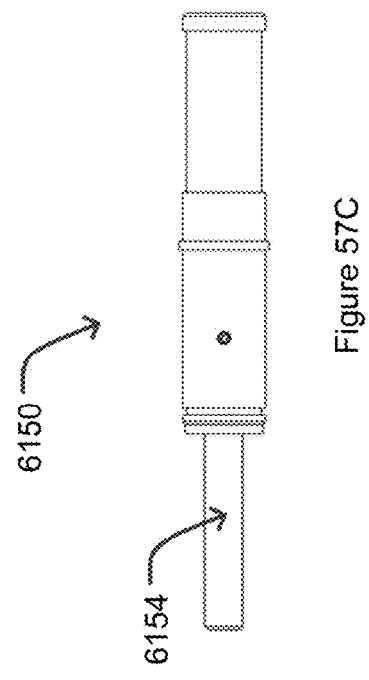
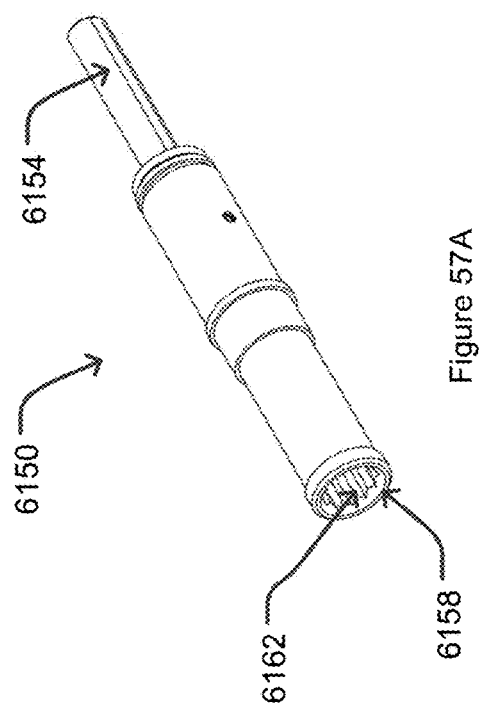
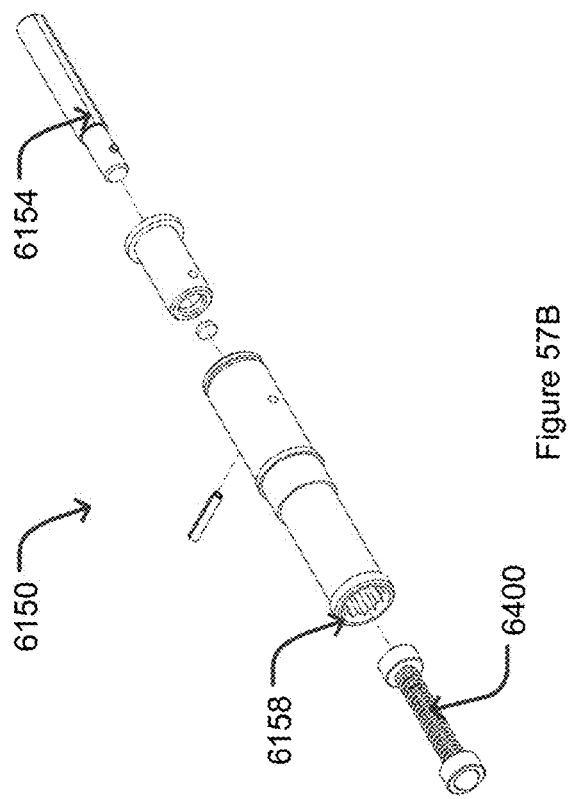

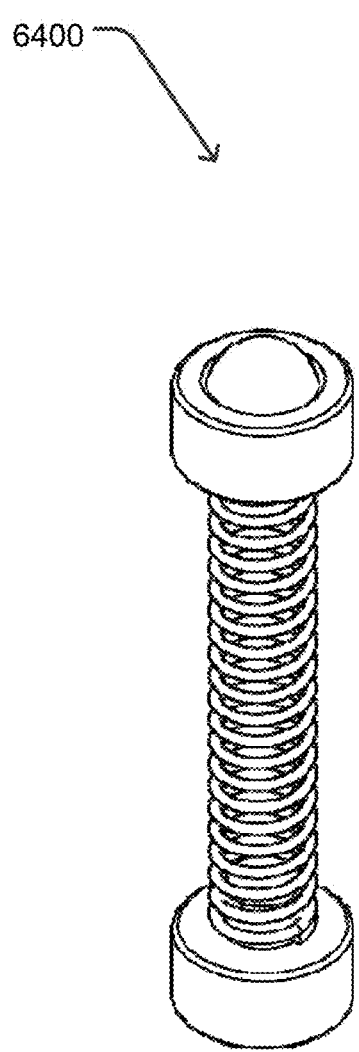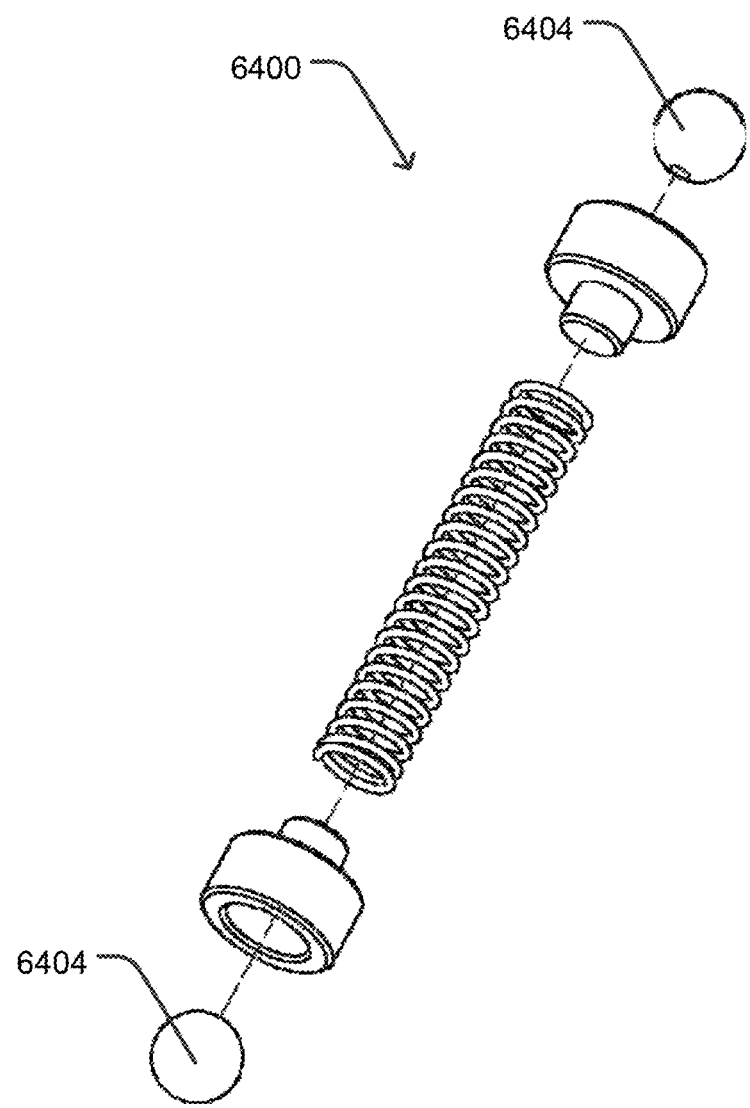
Figure 58A        Figure 58B
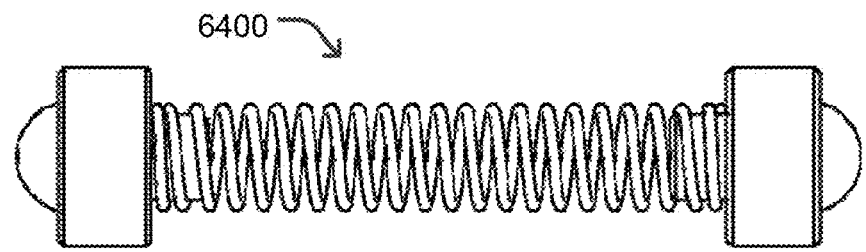
Figure 58C

SECTION B-B

SURGICAL CONSOLE, SPECIMEN RECEIVER, AND INSERTABLE ENDOSCOPIC INSTRUMENT FOR TISSUE REMOVAL

RELATED APPLICATIONS

The present application claims the benefit of and priority to U.S. Provisional Application 62/308,829, entitled "Surgical Console, Specimen Receiver, and Insertable Endoscopic Instrument for Tissue Removal," filed Mar. 15, 2016. This application is a continuation-in part of and claims priority to U.S. application Ser. No. 14/792,369, entitled "Insertable Endoscopic instrument for Tissue Removal," filed on Jul. 6, 2015, which is a continuation of and claims priority to U.S. patent application Ser. No. 14/537,362, entitled "Insertable Endoscopic Instrument for Tissue Removal", filed on Nov. 10, 2014, now U.S. Pat. No. 9,072,505, which is a continuation of and claims priority to U.S. patent application Ser. No. 14/280,202, entitled "Insertable Endoscopic Instrument for Tissue Removal", filed May 16, 2014, now U.S. Pat. No. 8,882,680, which claims the benefit of and priority to U.S. Provisional Patent Application No. 61/824,760, entitled "Insertable Endoscopic Instrument for Tissue Removal," filed on May 17, 2013. U.S. patent application Ser. No. 14/280,202 is also a continuation-in-part of U.S. patent application Ser. No. 13/336,491, entitled "Endoscopic Tool For Debriding and Removing Polyps," filed on Dec. 23, 2011, which claims the benefit of and priority to U.S. Provisional Patent Application No. 61/566,472, entitled "Endoscopic Tool For Debriding and Removing Polyps," filed on Dec. 2, 2011. Each of these applications are hereby incorporated by reference in their entirety for all purposes.

BACKGROUND

Colon cancer is the third leading cause of cancer in the United States but is the second leading cause of cancer-related deaths. Colon cancer arises from pre-existing colon polyps (adenomas) that occur in as many as 35% of the US population. Colon polyps can either be benign, precancerous or cancerous. Colonoscopy is widely regarded as an excellent screening tool for colon cancer that is increasing in incidence worldwide. According to the literature, a 1% increase in colonoscopy screening results in a 3% decrease in the incidence of colon cancer. The current demand for colonoscopy exceeds the ability of the medical system to provide adequate screening. Despite the increase in colon cancer screening the past few decades, only 55% of the eligible population is screened, falling far short of the recommended 80%, leaving millions of patients at risk.

Due to the lack of adequate resources, operators performing a colonoscopy typically only sample the largest polyps, exposing the patient to sample bias by typically leaving behind smaller less detectable polyps that could advance to colon cancer prior to future colonoscopy. Because of the sample bias, a negative result from the sampled polyps does not ensure the patient is truly cancer-free. Existing polyps removal techniques lack precision are cumbersome and time consuming.

At present, colon polyps are removed using a snare that is introduced into the patient's body via a working channel defined within an endoscope. The tip of the snare is passed around the stalk of the polyp to cut the polyp from the colon wall. Once the cut has been made, the cut polyp lies on the intestinal wall of the patient until it is retrieved by the operator as a sample. To retrieve the sample, the snare is first removed from the endoscope and a biopsy forceps or suction is fed through the same channel of the endoscope to retrieve the sample.

Accordingly, there is a need for an improved endoscopic instrument that increases the precision and speed of polyp removal for biopsy.

SUMMARY

An improved endoscopic instrument is provided that can precisely remove sessile polyps and efficiently obtain samples of multiple polyps from a patient. In particular, the improved endoscopic instrument is capable of debriding one or more polyps and retrieving the debrided polyps without having to alternate between using a separate cutting tool and a separate sample retrieving tool. The sampling can be integrated with colonoscopy inspection. In some implementations, the endoscopic instrument can cut and remove tissue from within a patient. In some such implementations, the endoscopic instrument can cut and remove tissue substantially simultaneously from within a patient accessed through a flexible endoscope.

In one aspect, an endoscopic instrument insertable within a single instrument channel of an endoscope includes a power-driven instrument head configured to resect material at a site within a subject having been reached by a flexible endoscope with working channel. The power-driven instrument head has a first distal end and a first proximal end. The first distal end of the power-driven instrument head defines a material entry port through which the resected material can enter the flexible endoscopic instrument. A body is coupled to the first proximal end of the power-driven instrument head and configured to drive the power-driven instrument head. The body includes a flexible portion that has a second distal end and a second proximal end. The second proximal end of the flexible portion defines a material exit port. An aspiration channel extends from the material entry port of the power-driven instrument head to the material exit port of the flexible portion. The second proximal end of the flexible portion is configured to couple to a vacuum source such that the resected material entering the aspiration channel via the material entry port is removed from the aspiration channel at the material exit port while the endoscopic instrument is disposed within an instrument channel of a flexible endoscope.

In some implementations, the body further includes a powered actuator. The powered actuator is coupled to the first proximal end of the power-driven instrument head and configured to drive the power-driven instrument head. In some implementations, the powered actuator is one of a hydraulically powered actuator, a pneumatically powered actuator or an electrically powered actuator. In some implementations, the powered actuator includes at least one of an electric motor, a tesla rotor, and a vane rotor. In some implementations, the endoscopic instrument includes an energy storage component configured to power the powered actuator. In some implementations, the aspiration channel is defined by the power-driven instrument head, the powered actuator and the flexible portion.

In some implementations, the powered actuator is one of a hydraulically powered actuator or a pneumatically powered actuator. In some such implementations, the flexible portion includes a fluid inlet tubular member configured to supply irrigation to actuate the power actuator and a fluid outlet tubular member configured to remove the fluid being supplied to actuate the actuator. In some implementations, the flexible portion includes an aspiration tubular member that defines a proximal portion of the aspiration channel.

In some implementations, the powered actuator includes a hollow portion, the hollow portion fluidly coupling the material entry port of the power-driven instrument head and the material exit port of the flexible portion.

In some implementations, the instrument includes an engagement assembly configured to contact the walls of the instrument channel of the endoscope when actuated. In some implementations, the engagement assembly includes a compliant ring structure configured to be deformed.

In some implementations, the power-driven instrument head includes an outer structure and a cutting shaft disposed within the outer structure, the cutting shaft coupled to the powered actuator and configured to rotate relative to the outer structure when the powered actuator is actuated. In some implementations, the cutting shaft includes a hollow portion and the material entry port.

In some implementations, the flexible portion includes a hollow flexible torque cable. The flexible torque cable has a distal region configured to couple to the first proximal end of the power-driven instrument head and has a proximal region configured to couple to a powered actuator. In some implementations, the flexible torque cable defines a portion of the aspiration channel. The distal region of the flexible torque cable is fluidly coupled to the material entry port of the power-driven instrument head and the proximal region of the flexible torque cable includes the material exit port.

In some implementations, the instrument has an outer diameter that is less than about 5 mm. In some implementations, the flexible portion is at least 40 times as long as the power-driven instrument head. In some implementations, the outer diameter of the powered actuator is less than about 4 mm.

According to another aspect, an endoscopic instrument includes a power-driven instrument head configured to resect material at a site within a subject. The power-driven instrument head includes a cutting tip and a material entry port configured to allow material to enter a distal end of the endoscopic instrument. A body is coupled to the power-driven instrument head. The body includes an elongated hollow flexible tubular member that includes a material exit port configured to allow material to exit a proximal end of the endoscopic instrument. An aspiration channel extends from the material entry port of the power-driven instrument head to a material exit port of the elongated hollow flexible tubular member. The second proximal end of the flexible portion is configured to fluidly couple to a vacuum source such that the resected material that enters the aspiration channel via the material entry port of the power-driven instrument head is removed from the endoscopic instrument via the material exit port. The endoscopic instrument is configured to travel through a tortuous instrument channel of an endoscope. In some implementations, the instrument has an outer diameter that is less than about 5 mm and wherein the flexible tubular member is at least 72 inches long.

In same implementations, the body further comprises a powered actuator, the powered actuator coupled to the first proximal end of the power-driven instrument head and configured to drive the power-driven instrument head. In some implementations, the powered actuator is an electrically powered actuator and further comprising an electrically conducting wire configured to couple to a power source. In some implementations, the aspiration channel is defined by the power-driven instrument head, the powered actuator and the flexible portion. In some implementations, the flexible tubular member defines a proximal portion of the aspiration channel.

In some implementations, the powered actuator is one of a hydraulically powered actuator or a pneumatically powered actuator, and further includes a fluid inlet tubular member configured to supply fluid to actuate the power actuator and a fluid outlet tubular member configured to remove the fluid being supplied to actuate the actuator.

In some implementations, the instrument includes an engagement assembly configured to contact the walls of the instrument channel of the endoscope when actuated. In some implementations, the engagement assembly includes a vacuum actuated structure configured to move into an engaged position in which the vacuum actuated structure is not in contact with the instrument channel when the vacuum is actuated and configured to move into a retracted position in which the vacuum actuated structure is not in contact with the instrument channel when the vacuum is not actuated.

In some implementations, the power-driven instrument head includes an outer structure and a cutting shaft disposed within the outer structure, the cutting shaft coupled to the powered actuator and configured to rotate relative to the outer structure when the powered actuator is actuated.

In some implementations, the flexible tubular member includes a hollow flexible torque cable. The flexible torque cable has a distal region configured to couple to the first proximal end of the power-driven instrument head and has a proximal region configured to couple to a powered actuator located external to the endoscopic instrument. In some implementations, the flexible torque cable further defines a portion of the aspiration channel, wherein the distal region of the flexible torque cable is fluidly coupled to the material entry port of the power-driven instrument head and the proximal region of the flexible torque cable includes the material exit port. In some implementations, the instrument includes a sheath surrounding the flexible torque cable.

According to another aspect, a flexible endoscopic biopsy retrieval tool adapted for use with an endoscope includes a housing, a debriding component coupled to the housing, and a sample retrieval conduit disposed within the housing for retrieving debrided material that is debrided by the debriding component. In various embodiments, an improved flexible endoscope may be configured with an integrated endoscopic biopsy retrieval tool that includes a debriding component and a sample retrieval conduit for retrieving debrided material that is debrided by the debriding component.

According to another aspect, a method of retrieving polyps from a patient's body includes disposing an endoscopic instrument within an instrument channel of an endoscope, inserting the endoscope in a patient's body, actuating a debriding component of the endoscopic instrument to cut a polyp within the patient's body, and actuating a sample retrieval component of the endoscopic instrument to remove the cut polyp from within the patient's body.

According to yet another aspect, an endoscope includes a first end and a second end separated by a flexible housing. An instrument channel extends from the first end to the second end and an endoscopic instrument is coupled to the instrument channel at the first end of the endoscope. The endoscopic instrument includes a debriding component and a sample retrieval conduit partially disposed within the instrument channel.

According to yet another aspect, an endoscopic instrument insertable within a single instrument channel of an endoscope includes a cutting assembly that is configured to resect material at a site within a subject. The cutting assembly includes an outer cannula and an inner cannula disposed within the outer cannula. The outer cannula defines an opening through which material to be resected enters the cutting assembly. The endoscopic instrument also includes a flexible outer tubing coupled to the outer cannula and configured to cause the outer cannula to rotate relative to the inner cannula. The flexible outer tubing can have an outer diameter that is smaller than the instrument channel in which the endoscopic instrument is insertable. The endoscopic instrument also includes a flexible torque coil having a portion disposed within the flexible outer tubing. The flexible torque coil having a distal end coupled to the inner cannula. The flexible torque coil is configured to cause the inner cannula to rotate relative to the outer cannula. The endoscopic instrument also includes a proximal connector coupled to a proximal end of the flexible torque coil and configured to engage with a drive assembly that is configured to cause the proximal connector, the flexible torque coil and the inner cannula to rotate upon actuation. The endoscopic instrument also includes an aspiration channel having an aspiration port configured to engage with a vacuum source. The aspiration channel is partially defined by an inner wall of the flexible torque coil and an inner wall of the inner cannula and extends from an opening defined in the inner cannula to the aspiration port. The endoscopic instrument also includes an irrigation channel having a first portion defined between an outer wall of the flexible torque coil and an inner wall of the flexible outer tubing and configured to carry irrigation fluid to the aspiration channel.

In some implementations, the proximal connector is hollow and an inner wall of the proximal connector defines a portion of the aspiration channel. In some implementations, the proximal connector is a rigid cylindrical structure and is configured to be positioned within a drive receptacle of the drive assembly. The proximal connector can include a coupler configured to engage with the drive assembly and a tensioning spring configured to bias the inner cannula towards a distal end of the outer cannula. In some implementations, the tensioning spring is sized and biased such that the tensioning spring causes a cutting portion of the inner cannula to be positioned adjacent to the opening of the outer cannula. In some implementations, the proximal connector is rotationally and fluidly coupled to the flexible torque coil.

In some implementations, the endoscopic instrument also includes a lavage connector including an irrigation entry port and a tubular member coupled to the lavage connector and the flexible outer tubing. An inner wall of the tubular member and the outer wall of the flexible torque coil can define a second portion of the irrigation channel that is fluidly coupled to the first portion of the irrigation channel. In some implementations, the endoscopic instrument also includes a rotational coupler coupling the flexible outer tubing to the tubular member and configured to cause the flexible outer tubing to rotate relative to the tubular member and cause the opening defined in the outer cannula to rotate relative to the inner cannula. In some implementations, the lavage connector defines an inner bore within which the flexible torque coil is disposed.

In some implementations, the endoscopic instrument also includes a lining within which the flexible torque coil is disposed, the outer wall of the lining configured to define a portion of the irrigation channel. In some implementations, the inner cannula is configured to rotate axially relative to the outer cannula and the aspiration channel is configured to provide a suction force at the opening of the inner cannula.

In some implementations, the flexible torque coil includes a plurality of threads. Each of the plurality of threads can be wound in a direction opposite to a direction in which one or more adjacent threads of the plurality of threads is wound. In some implementations, the flexible torque coil includes a plurality of layers. Each of the plurality of layers can be wound in a direction opposite to a direction in which one or more adjacent layers of the plurality of layers is wound. In some implementations, each layer can include one or more threads.

In some implementations, the flexible outer tubing has a length that exceeds the length of the endoscope in which the endoscopic instrument is insertable. In some implementations, the flexible outer tubing has a length that is at least 100 times larger than an outer diameter of the flexible outer tubing. In some implementations, the flexible portion is at least 40 times as long as the cutting assembly.

According to yet another aspect, a specimen receiver includes a first receiver member, a specimen capture member, and a second receiver member. The first receiver member includes a first receiver port configured to receive a fluid flow including a material, the first receiver member defining a first portion of an interior of the specimen receiver. The specimen capture member is in fluid communication with the first portion of the interior. The specimen capture member is configured to obtain a sample of a material from the fluid flow. The specimen capture member is disposed between the first portion of the interior and the second portion of the interior. The specimen capture member is configured to filter the fluid flow to obtain the sample of the material. The second receiver member is configured to be coupled to the first receiver member. The second receiver member defines a second portion of the interior of the specimen receiver. The second portion is downstream of the first portion. The second receiver member includes a second receiver port configured to be coupled to a vacuum source.

According to yet another aspect, a method of obtaining a sample of material from an endoscopic tool in a specimen receiver includes positioning a specimen capture member between a first receiver member and a second receiver member. The method includes receiving a fluid flow including a material at a first receiver port of the first receiver member, the first receiver member defining a first portion of an interior of the specimen receiver in which the specimen capture member is positioned. The method includes coupling the second receiver member to the first receiver member, the second receiver member defining a second portion of the interior of the specimen receiver. The method includes coupling a vacuum source to a second receiver port of the second receiver member to flow the fluid through the specimen receiver. The method includes obtaining a sample of the material by filtering the fluid flow using the specimen capture member.

According to yet another aspect, a surgical console includes a drive assembly, a vacuum interface, a fluid transfer device, a user interface, and a control circuit. The drive assembly is configured to be coupled to an endoscopic tool. The drive assembly is configured to be rotated by a motor. The motor is configured to rotate the drive assembly at a speed associated with rotation of the endoscopic tool. The vacuum interface is configured to be coupled to the endoscopic tool to apply a vacuum to the endoscopic tool. The fluid transfer device is configured to be coupled to the endoscopic tool to flow fluid through the endoscopic tool. The user interface is configured to receive a user input indicating at least one of instructions to rotate the endoscopic tool while applying the vacuum to the endoscopic tool, or instructions to flow fluid through the endoscopic tool. The control circuit is configured to extract the instructions from the user input and control operation of at least one of the drive assembly, the vacuum interface, or the fluid transfer device based on the instructions. The control circuit is configured to cause the drive assembly to rotate the endoscopic tool while the vacuum interface applies the vacuum to the endoscopic tool responsive to the user input indicating instructions to rotate the endoscopic tool.

According to yet another aspect, a method for operating a surgical console includes receiving, at a user interface, a user input. The user input indicates at least one of (1) instructions to rotate an endoscopic tool using a drive assembly while applying a vacuum to the endoscopic tool using a vacuum interface, the drive assembly configured to be coupled to an endoscopic tool, the drive assembly configured to rotated by a motor, the motor configured to rotate the drive element at a speed associated with rotation of the endoscopic tool; the vacuum interface configured to be coupled to the endoscopic tool to apply a vacuum to the endoscopic tool; or (2) instructions to flow fluid through the endoscopic tool using a fluid transfer device configured to be coupled to the endoscopic tool. The method includes extracting, from the user input, the instructions. The method includes controlling operation of at least one of the drive assembly, the vacuum interface, or the fluid transfer device based on the instructions. Controlling operation includes causing the drive assembly to rotate the endoscopic tool while causing the vacuum interface to apply the vacuum responsive to the user input indicating instructions to rotate the endoscopic tool.

According to yet another aspect, a method of operating an endoscopic tool includes engaging a drive element of the endoscopic tool to a drive assembly of a surgical console. The method includes fluidly coupling a vacuum port of the endoscopic tool to a first end of a specimen receiver. The method includes fluidly coupling a second end of the specimen receiver to a vacuum interface. The method includes fluidly coupling an irrigation port of the endoscopic tool to a fluid transfer device. The method includes inserting the endoscopic tool in an instrument channel of an endoscope. The method includes identifying material to be resected at a site within a subject. The method includes resecting the material by rotating the endoscopic tool while flowing fluid through the endoscopic tool using the fluid transfer device. The method includes obtaining a sample of the material in the specimen receiver by applying a vacuum to the endoscopic tool using the vacuum interface.

According to yet another aspect, a connector assembly for an endoscopic tool includes a first connector end, a second connector end, a driver transfer assembly, an irrigation channel, and an aspiration channel. The first connector end defines a first opening configured to receive a drive assembly. The second connector end is opposite the first connector end and defines a second opening and a third opening. The drive transfer assembly extends between the first connector end and the second connector end. The drive transfer assembly is configured to be coupled to the drive assembly via the first opening to be rotated by the drive assembly. The drive transfer assembly is configured to be coupled to a flexible torque delivery assembly at the second connector end to rotate the flexible torque delivery assembly responsive to rotation by the drive assembly. The irrigation channel includes an irrigation port and a first channel portion fluidly coupled to the irrigation port and to the second opening. The irrigation port is configured to receive fluid and flow the received fluid through the irrigation channel. The aspiration channel includes a vacuum port and a second channel portion fluidly coupled to the vacuum port and to the third opening. The vacuum port is configured to transmit a suction force applied to the vacuum port to the second channel portion.

According to yet another aspect, a method of operating an endoscopic tool includes receiving a drive assembly at a first opening defined by a first connector end of a connector assembly of the endoscopic tool. The method includes coupling the drive assembly to a drive transfer assembly of the connector assembly. The drive transfer assembly extends between the first connector end and a second connector end of the connector assembly. The second connector end defines a second opening and a third opening. The method includes coupling the drive transfer assembly to a flexible torque delivery assembly at the second connector end. The method includes rotating the flexible torque delivery assembly responsive to rotation by the drive transfer assembly. The method includes receiving fluid at an irrigation port of the connector assembly. The method includes flowing the fluid through an irrigation channel, the irrigation channel including the irrigation port and a first channel portion fluidly coupled to the irrigation port and to the second opening. The method includes applying a suction force to a vacuum port of the connector assembly. The method includes transmitting the suction force through an aspiration channel including the vacuum port and a second channel portion fluidly coupled to the vacuum port and to the third opening to obtain a sample of a material resected by the endoscopic tool.

This Summary is provided to introduce a selection of concepts in a simplified form that are further described below in the Detailed Description. This Summary is not intended to identify key features or essential features of the claimed subject matter, nor is it intended that this Summary be used to limit the scope of the claimed subject matter. Furthermore, the claimed subject matter is not limited to implementations that offer any or all advantages or solve any or all state of the art problems.

BRIEF DESCRIPTION OF THE DRAWINGS

The present disclosure is illustratively shown and described in reference to the accompanying drawing in which:

FIG. 16A illustrates an exploded view of an example endoscopic instrument according to embodiments of the present disclosure.

FIG. 16B illustrates a cross-sectional view of the endoscopic instrument shown in FIG. 16A according to embodiments of the present disclosure.

FIG. 16C illustrates a schematic view of an example engagement assembly of an example endoscopic instrument according to embodiments of the present disclosure.

FIG. 16D shows a cut-open view of the engagement assembly shown in FIG. 16C when the engagement assembly is disengaged according to embodiments of the present disclosure.

FIG. 16E shows a cut-open view of the engagement assembly shown in FIG. 16A when the engagement assembly is configured to engage with an instrument channel of an endoscope according to embodiments of the present disclosure.

FIG. 18A illustrates an exploded view of an example endoscopic instrument utilizing a tesla rotor according to embodiments of the present disclosure.

FIG. 18B illustrates a cross-sectional view of the endoscopic instrument shown in FIG. 18A according to embodiments of the present disclosure.

FIG. 19E shows a cut-open view of the engagement assembly shown in FIG. 19D in a disengaged position according to embodiments of the present disclosure.

FIG. 19F shows a cut-open view of the engagement assembly shown in FIG. 19D in an engaged position according to embodiments of the present disclosure.

FIGS. 23AA-23BB show an example implementation of a cutting tool according to embodiments of the present disclosure.

FIGS. 24A-24C illustrate various aspects of the drive shaft of the coupling component according to embodiments of the present disclosure.

FIG. 25 illustrates an example housing component according to embodiments of the present disclosure.

FIGS. 26A-26E show an example sleeve bearing according to embodiments of the present disclosure.

FIGS. 28A-28D show an example side plate that forms a portion of the casing according to embodiments of the present disclosure.

FIGS. 31AA-31AB and 31B-31C illustrate aspects of an endoscopic assembly in which the tip is press-fit according to embodiments of the present disclosure.

FIG. 37 shows a cross-section view of one implementation of the endoscopic tool according to embodiments of the present disclosure.

FIGS. 40A-40B show a perspective view of an endoscopic tool and a portion of a drive assembly configured to drive the endoscopic tool according to embodiments of the present disclosure.

FIG. 40B shows a perspective view of the endoscopic tool and the portion of the drive assembly configured to drive the endoscopic tool shown in FIG. 40A according to embodiments of the present disclosure.

FIG. 47A and FIG. 47B show a top view and a cross-sectional view of the rotational coupler of the endoscopic tool according to embodiments of the present disclosure.

FIG. 57A is a perspective view of a console drive assembly for a console configured for operation with an endoscopic tool according to embodiments of the present disclosure.

FIG. 57B is an exploded perspective view of the console drive assembly shown in FIG. 57A according to embodiments of the present disclosure.

FIG. 57C is a side view of the console drive assembly shown in FIG. 57A according to embodiments of the present disclosure.

FIG. 58A is a perspective view of the torque coil of the console drive assembly shown in FIG. 57A according to embodiments of the present disclosure.

FIG. 58B is an exploded perspective view of the torque coil of the console drive assembly shown in FIG. 57A according to embodiments of the present disclosure.

FIG. 58C is a section view along line B-B of FIG. 58A according to embodiments of the present disclosure.

DETAILED DESCRIPTION

Technologies provided herein are directed towards an improved flexible endoscopic instrument that can precisely and efficiently obtain samples of single and multiple polyps and neoplasms from a patient. In particular, the improved endoscopic instrument is capable of debriding samples from one or more polyps and retrieving the debrided samples without having to remove the endoscopic instrument from the treatment site within the patient's body.

Figure 1A:
FIG. 1A illustrates various types of polyps that can form within a body.

FIG. 1A illustrates various types of polyps that can form within a body. Most polyps may be removed by snare polypectomy, though especially large polyps and/or sessile or flat polyps must be removed piecemeal with biopsy forceps or en bloc using endoscopic mucosal resection (EMR). A recent study has concluded that depressed sessile polyps had the highest rate for harboring a malignancy at 33%. The same study has also found that non-polypoid neoplastic lesions (sessile polyps) accounted for 22% of the patients with polyps or 10% of all patients undergoing colonoscopy. There are multiple roadblocks to resecting colon polyps, namely the difficulties in removing sessile polyps, the time involved in removing multiple polyps and the lack of reimbursement differential for resecting more than one polyp. Since resecting less accessible sessile polyps presents challenges and multiple polyps take more time per patient, most polyps are removed piece meal with tissue left behind as polyps increase in size, contributing to a sampling bias where the pathology of remaining tissue is unknown, leading to an increase in the false negative rate.

Colonoscopy is not a perfect screening tool. With current colonoscopy practices the endoscopist exposes the patient to sample bias through removal of the largest polyps (stalked polyps), leaving behind less detectable and accessible sessile/flat polyps. Sessile polyps are extremely difficult or impossible to remove endoscopically with current techniques and often are left alone. An estimated 28% of stalked polyps and 60% of sessile (flat) polyps are not detected, biopsied or removed under current practice, which contributes to sample bias and a 6% false-negative rate for colonoscopy screening. Current colonoscopy instruments for polyp resection are limited by their inability to adequately remove sessile polyps and inefficiency to completely remove multiple polyps. According to the clinical literature, sessile polyps greater than 10 mm have a greater risk of malignancy. Sessile polyp fragments that are left behind after incomplete resection will grow into new polyps and carry risks for malignancy.

In the recent past, endoscopic mucosal resection (EMR) has been adopted to remove sessile polyps. EMR involves the use of an injection to elevate surrounding mucosa followed by opening of a snare to cut the polyp and lastly use of biopsy forceps or a retrieval device to remove the polyp. The introduction and removal of the injection needle and snare through the length of the colonoscope, which is approximately 5.2 feet, must be repeated for the forceps.

The present disclosure relates to an endoscopic tool that is capable of delivering an innovative alternative to existing polyp removal tools, including snares, hot biopsy and EMR, by introducing a flexible powered instrument that that works with the current generation colonoscopes and can cut and remove any polyp. The endoscopic tool described herein can be designed to enable physicians to better address sessile or large polyps as well as remove multiple polyps in significantly less time. Through the adoption of the endoscopic tool described herein, physicians can become more efficient at early diagnosis of colorectal cancer.

The present disclosure will be more completely understood through the following description, which should be read in conjunction with the drawings. In this description, like numbers refer to similar elements within various embodiments of the present disclosure. Within this description, the claims will be explained with respect to embodiments. The skilled artisan will readily appreciate that the methods, apparatus and systems described herein are merely exemplary and that variations can be made without departing from the spirit and scope of the disclosure.

Figure 1B:
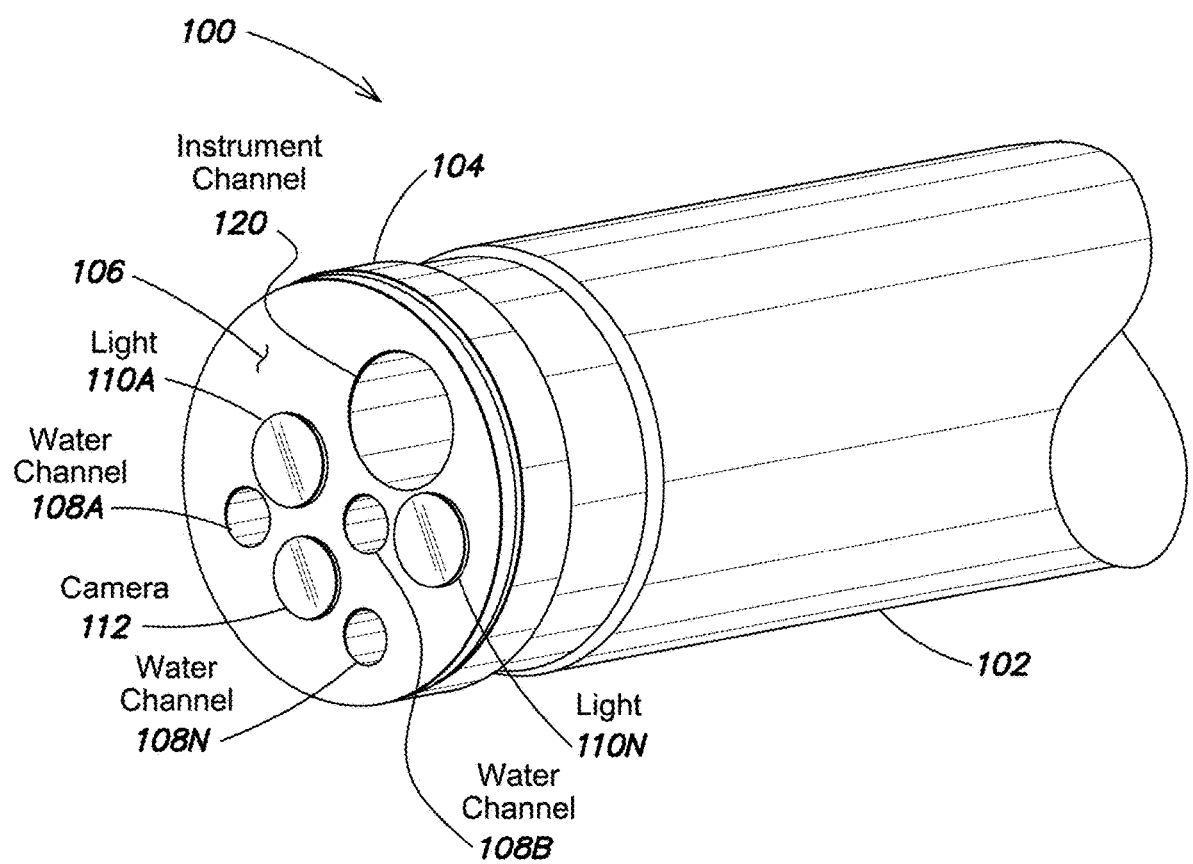
FIG. 1B illustrates a perspective partial view of an endoscope according to embodiments of the present disclosure.

Referring back to the drawings, FIG. 1B illustrates a perspective partial view of an endoscope according to embodiments of the present disclosure. Although the present disclosure is directed towards endoscopic instruments adapted for use with any type of endoscope, for sake of convenience, the teachings of the present disclosure are directed towards endoscopic instruments used with a lower GI scope, such as a colonoscope. It should, however, be appreciated that the scope of the present disclosure is not limited to endoscopic instruments for use with GI scopes, but extends to any type of flexible endoscope, including but not limited to bronchoscopes, gastroscopes and laryngoscopes, or other medical devices that may be used to treat patients.

According to various embodiments, a typical lower GI scope 100 includes a substantially flexible member that extends from a first end or head portion 102 to a second end or handle portion. The head portion 102 may be configured to swivel so as to orient a tip 104 of the head portion 102 in any direction within a hemispherical space. The handle portion has controls that allows the operator of the endoscope 100 to steer the colonoscope towards an area of interest within the colon and turn the corners between colon segments with two steering wheels.

A series of instruments reside on the face 106 of the scope's tip 104, including but not limited to, one or more water channels 108A-108N, generally referred to as water channels 108, for irrigating the area with water, one or more light sources 110A-110N, generally referred to as light sources 110, a camera lens 112, and an instrument channel 120 through which an endoscopic instrument can be passed through to conduct a number of operations. The instrument channel 120 can vary in size based on the type of endoscope 100 being used. In various embodiments, the diameter of the instrument channel 120 can range from about 2 mm to 6 mm, or more specifically, from about 3.2 mm to 4.3 mm. Some larger scopes may have two instrument channels 120 so that two tools can be passed into the patient simultaneously. However, larger scopes may cause discomfort to the patient and may be too large to enter the patient's body through some of the smaller cavities.

Figure 1C:
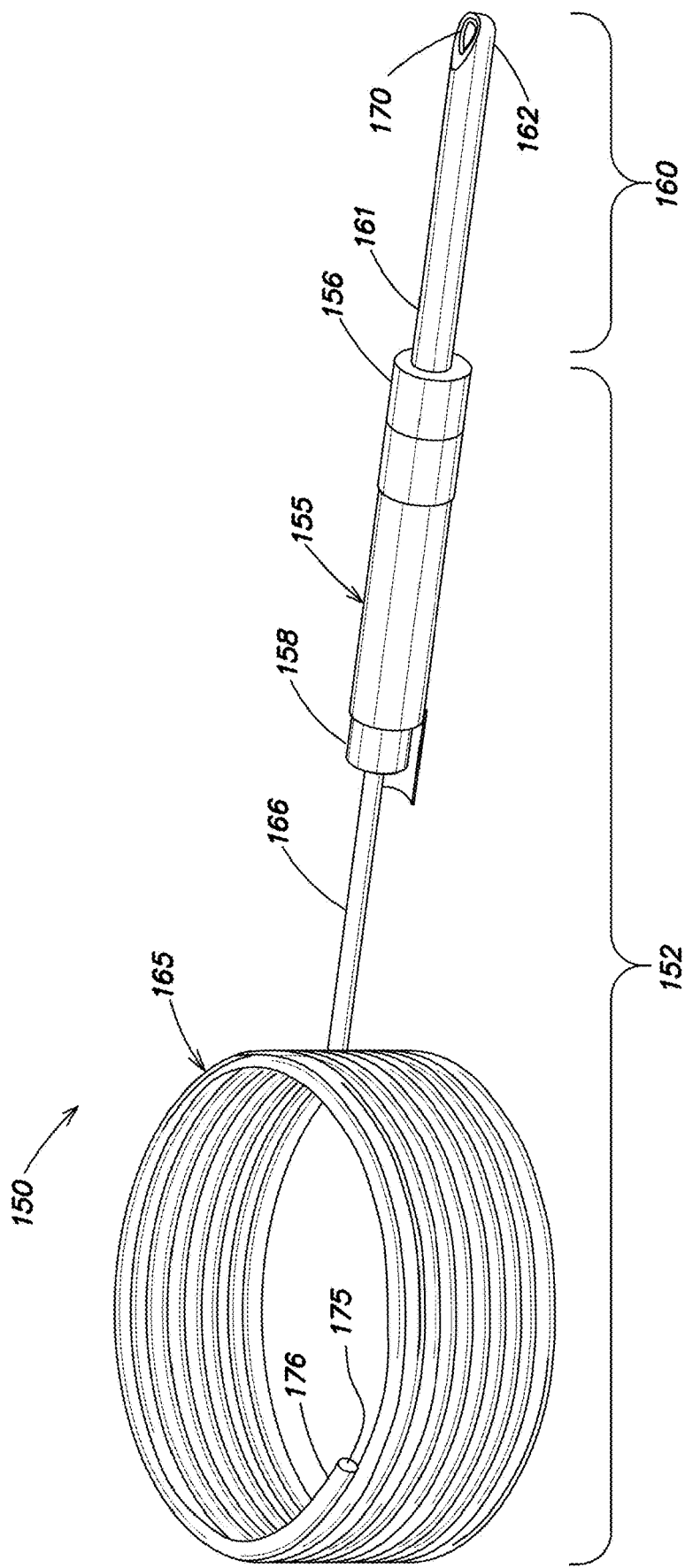
FIG. 1C illustrates a perspective view of an endoscopic instrument according to embodiments of the present disclosure.

FIG. 1C illustrates a perspective view of an endoscopic instrument 150 according to embodiments of the present disclosure. The endoscopic instrument 150 is configured to be fed through the instrument channel 120 of the endoscope 100 depicted in FIG. 1B. The endoscopic instrument 150 is configured to be inserted within an instrument channel of an endoscope, such as the instrument channel 120 of the endoscope 100 depicted in FIG. 1B. In some implementations, the portion of the endoscopic instrument 150 that is configured to be inserted within the instrument channel 120 may be sized to have an outer diameter that is smaller than the inner diameter of the instrument channel 120 of the endoscope. In some such implementations, the endoscopic instrument 150 can be sized to have an outer diameter that is sufficiently small to be slidably inserted within the instrument channel while the endoscope is coiled or bent. When the endoscope is coiled or bent, the instrument channel can form a tortuous path that includes one or more curves and bends. In one example implementations, an endoscope includes an instrument channel that has an inner diameter of about 4.3 mm when the endoscope is straightened. However, when the endoscope is coiled or bent, portions of the endoscope near the bends can have clearances that are smaller than the inner diameter of about 4.3 mm. In some implementations, the endoscope can have clearances that may be about 3.8 mm instead of the 4.3 mm achieved when the endoscope is straightened. In some implementations, the endoscope can have clearances that may be about 3.2 mm. As such, in some implementations, the endoscopic instrument 150 may be sized such that it can be slidably inserted within the instrument channel of the endoscope with which it is to be used even when the endoscope is coiled or bent.

In some implementations, the endoscopic instrument 150 includes a power-driven instrument head 160 configured to resect material at a site within a subject. The power-driven instrument head 160 has a distal end 162 and a proximal end 161. The distal end 162 of the power-driven instrument head 160 defines a material entry port 170 through which the resected material can enter the endoscopic instrument 150. The power-driven instrument head 160 can include a cutting section at the distal end 162 that is configured to cut tissue and other material. As used herein, a port can include any opening, aperture, or gap through which material can either enter or exit. In some implementations, the material entry port can be an opening through which resected material can enter the endoscopic instrument 150. In some implementations, material to be resected can be suctioned into the material entry port where the instrument head can then resect the material.

A body 152 includes a head portion 155 and a flexible portion 165. A distal end 156 of the head portion 155 of the body 152 is coupled to the proximal end 161 of the power-driven instrument head 160. In some implementations, the head portion 155 of the body 152 is configured to drive the power-driven instrument head 160. A proximal end 158 of the head portion 155 can be coupled to a distal end 166 of the flexible portion 165. A proximal end 176 of the flexible portion 165 defines a material exit port 175. The flexible portion 165 can include a hollow flexible tubular member.

The endoscopic instrument also includes an aspiration channel that extends from the material entry port 170 of the power-driven instrument head 160 to the material exit port 175 of the flexible portion 165. In some implementations, the aspiration channel is defined by the power-driven instrument head 160, the head portion 155 of the body 152 and the flexible portion 165 of the body. The proximal end 176 of the flexible portion 165 is configured to couple to a vacuum source such that the resected material entering the aspiration channel via the material entry port 170 is removed from the aspiration channel at the material exit port 175 while the endoscopic instrument 150 is disposed within an instrument channel of an endoscope.

The head portion 155 includes a housing that has an outer diameter that is configured such that the endoscopic instrument 150 can be slidably inserted into an instrument channel of an endoscope. In some implementations, the head portion 155 can include a powered actuator that is configured to drive the power-driven instrument head 160. In some implementations, the powered actuator is disposed within the head portion 155. In some implementations, the powered actuator is located external to the portion of the endoscopic instrument 150 that can be inserted into an instrument channel of an endoscope. In some implementations, the powered actuator is capable of driving the power-driven instrument head via a shaft that can translate motion generated by the power actuator to the power-driven instrument head. In some implementations, the powered actuator is not a part of the endoscopic instrument 150, but instead, is coupled to the power-driven instrument head 160. In some implementations, the shaft may be a flexible shaft. In some such implementations, the flexible shaft can be a flexible torque coil, additional details of which are provided below with respect to FIGS. 19A-19C.

The endoscopic instrument 150 can be sized to be insertable within an instrument channel of an endoscope. In some implementations, the endoscopic instrument 150 may be sized such that the endoscopic instrument can be inserted within the instrument channel of the endoscope while the endoscope is inserted within a subject. In some such implementations, the endoscope, for example, a colonoscope, may be curved or bent thereby requiring the endoscopic instrument 150 to be sized such that it can be inserted into a curved or bent endoscope.

In some implementations, the head portion 155 and the power-driven instrument head 160 of the endoscopic instrument 150 may be substantially stiff or rigid, while the flexible portion 165 may be relatively flexible or compliant. The head portion 155 and the power-driven instrument head 160 can be substantially rigid. As such, in some such implementations, the head portion 155 and the power-driven instrument head 160 may be sized, at least in thickness and in length, such that endoscopic instrument 150 can maneuver through sharp bends and curves during insertion of the endoscopic instrument 150 within the instrument channel of the endoscope. In some implementations, the length of the power-driven instrument head 160 may be between about 0.2"-2", about 0.2" and 1" or in some implementations, between 0.4" and 0.8". In some implementations, the outer diameter of the power-driven instrument head 160 may be between about 0.4"-1.5", 0.6" and 1.2" and 0.8" and 1". In some implementations, the length of the head portion 155 of the body may be between about 0.5"-3", about 0.8" and 2" and 1" and 1.5".

The length of the flexible portion 165 may be substantially and/or relatively longer than the length of the head portion and the power-driven instrument head 160. In some implementations, the flexible portion 165 can be sufficiently long such that the combined length of the endoscopic instrument exceeds the length of instrument channel of an endoscope in which the instrument can be inserted. As such, the length of the flexible portion 165 may have a length that exceeds about 36", about 45" or about 60". For endoscopic instruments configured for use with other types of endoscopes, the length of the flexible portion may be shorter than 36", but still sufficiently long to allow for the body of the endoscopic instrument to be approximately the same length or greater than the length of the endoscope with which the instrument is being used.

The outer diameter of the flexible portion 165 can also be configured such that the endoscopic instrument can be inserted into the instrument channel of the endoscope. In some implementations, the outer diameter of the flexible portion 165 can be sized smaller than a corresponding inner diameter of the instrument channel of the endoscope. In some such implementations, the endoscopic instrument can be sized to have an outer diameter that is sufficiently small to be slidably disposed within the endoscope while the endoscope is coiled or bent. For example, an endoscope can include an instrument channel that has an inner diameter of about 4.3 mm when the endoscope is straightened. However, when the endoscope is coiled or bent, portions of the endoscope near the bends can have clearances that are smaller than the inner diameter of about 4.3 mm. In some implementations, the endoscope can have clearances that may be as low as 3.2 mm. As such, in some implementations, the endoscopic instrument may be sized such that the endoscopic instrument can be slidably inserted within the instrument channel of the endoscope even when the endoscope is coiled or bent.

Figure 2B:
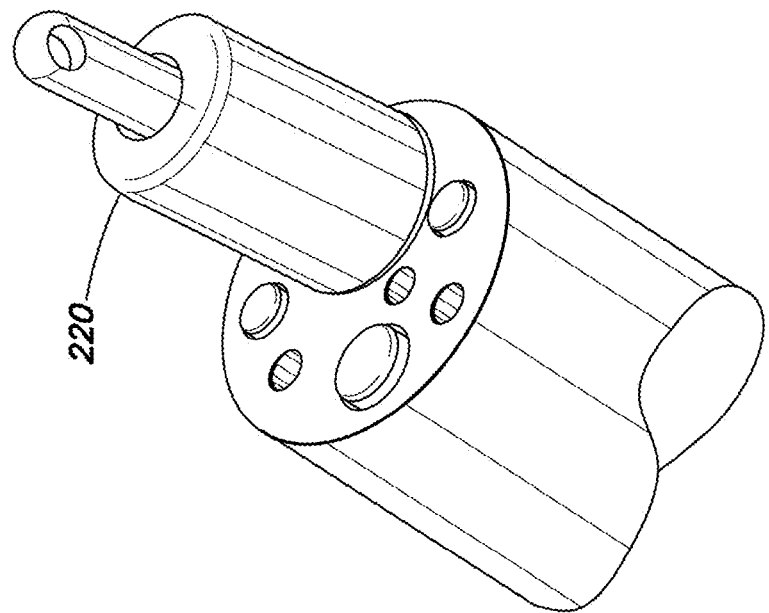
FIGS. 2A and 2B illustrate side perspective views of an endoscopic instrument coupled with the endoscope shown in FIG. 1 according to embodiments of the present disclosure.
Figure 2A:
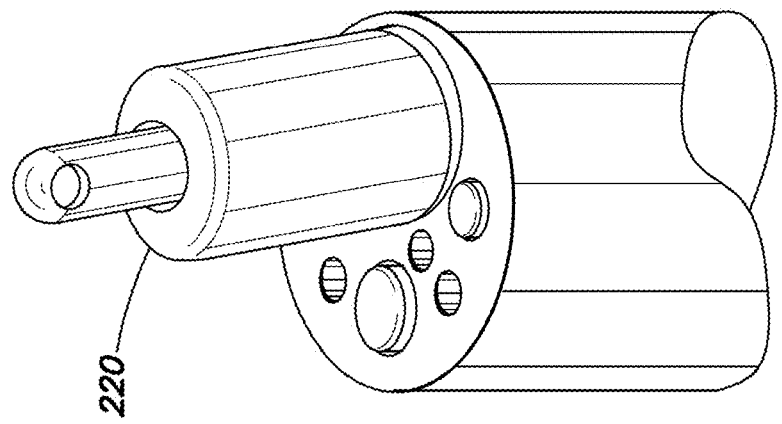
Figure 3B:
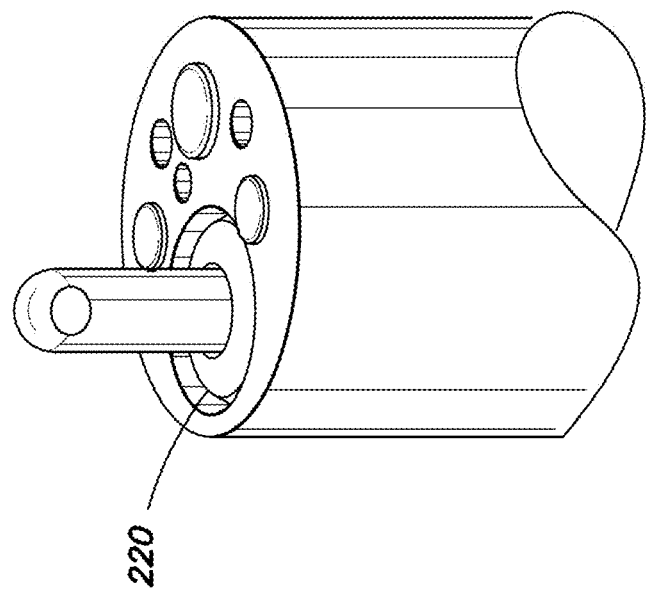
FIGS. 3A and 3B illustrate side perspective views of an example endoscopic instrument coupled with the endoscope shown in FIG. 1 according to embodiments of the present disclosure.
Figure 3A:
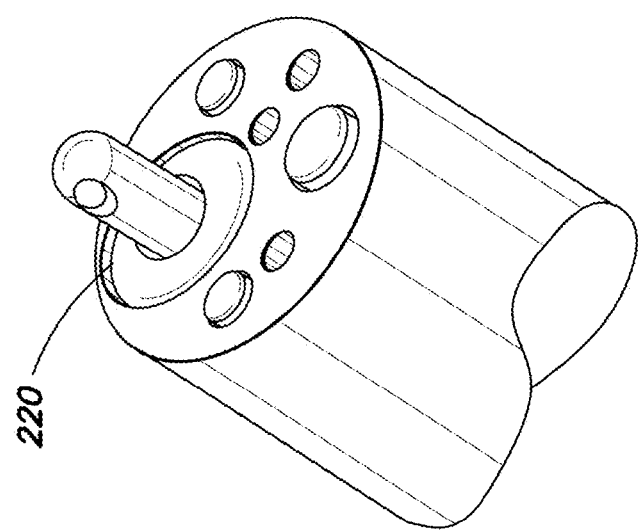

FIGS. 2A and 2B and 3A and 3B illustrate side perspective views of an endoscopic instrument coupled with the endoscope shown in FIG. 1B according to embodiments of the present disclosure. The endoscopic instrument 220 is configured to be fed through the instrument channel 120 of the endoscope 100. As shown in FIGS. 2A and 2B, the endoscopic instrument 220 is capable of extending outside the tip 104 of the endoscope 100, while FIGS. 3A and 3B show that the endoscope tool 220 can be retracted within the endoscope such that no part of the endoscopic instrument 220 is extending beyond the tip 104 of the endoscope 100. As will be described in further detail with respect to FIG. 4, the endoscopic instrument 220 is capable of cutting or debriding a polyp as well as obtaining the debrided polyp from the treatment site without having to remove the endoscopic instrument 220 from the endoscope 100.

Figure 4A:
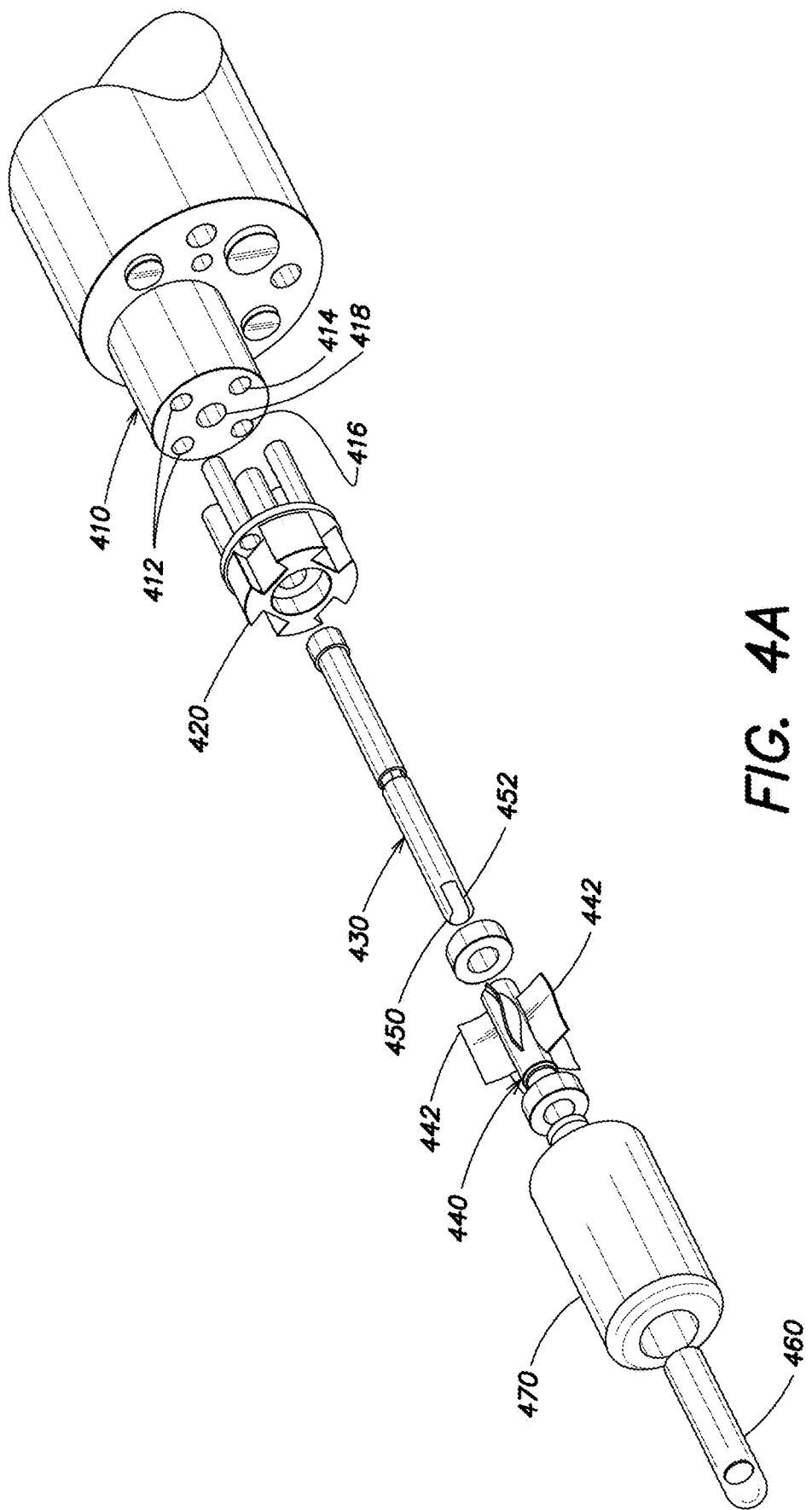
FIG. 4A illustrates an exploded view of the endoscopic instrument that can be coupled with the endoscope according to embodiments of the present disclosure.

FIG. 4A illustrates an exploded view of the endoscopic instrument 220 adapted for use with the endoscope 100 according to embodiments of the present disclosure. The endoscopic instrument 220 includes a debriding component for debriding polyps grown in the patient's body, and a sample retrieval component for retrieving the debrided polyps from the surgical site. The endoscopic instrument 220 includes a tubing 410 coupled to a cap 420. In various embodiments, the cap 420 may be sealingly engaged with the tubing 410. The cap can be aligned with a spindle 430 at a first portion of the spindle 430. In various embodiments, the spindle 430 may be substantially hollow. The spindle 430 can be coupled to a rotor 440, which is configured to rotate the spindle 430. A second portion of the spindle 430 includes an inner blade 450 that may be configured to interact with an outer blade 460. In some implementations, the outer blade 460 can be separated from the inner blade by a gap that forms an irrigation channel (not shown). A casing 470 is configured to encompass the cap 420 and the rotor 440, as shown above with respect to FIGS. 2A and 3A. It should be appreciated that other components, such as washers, bearings, seals, and the like, may be included in the endoscopic instrument 220.

Figure 4B:
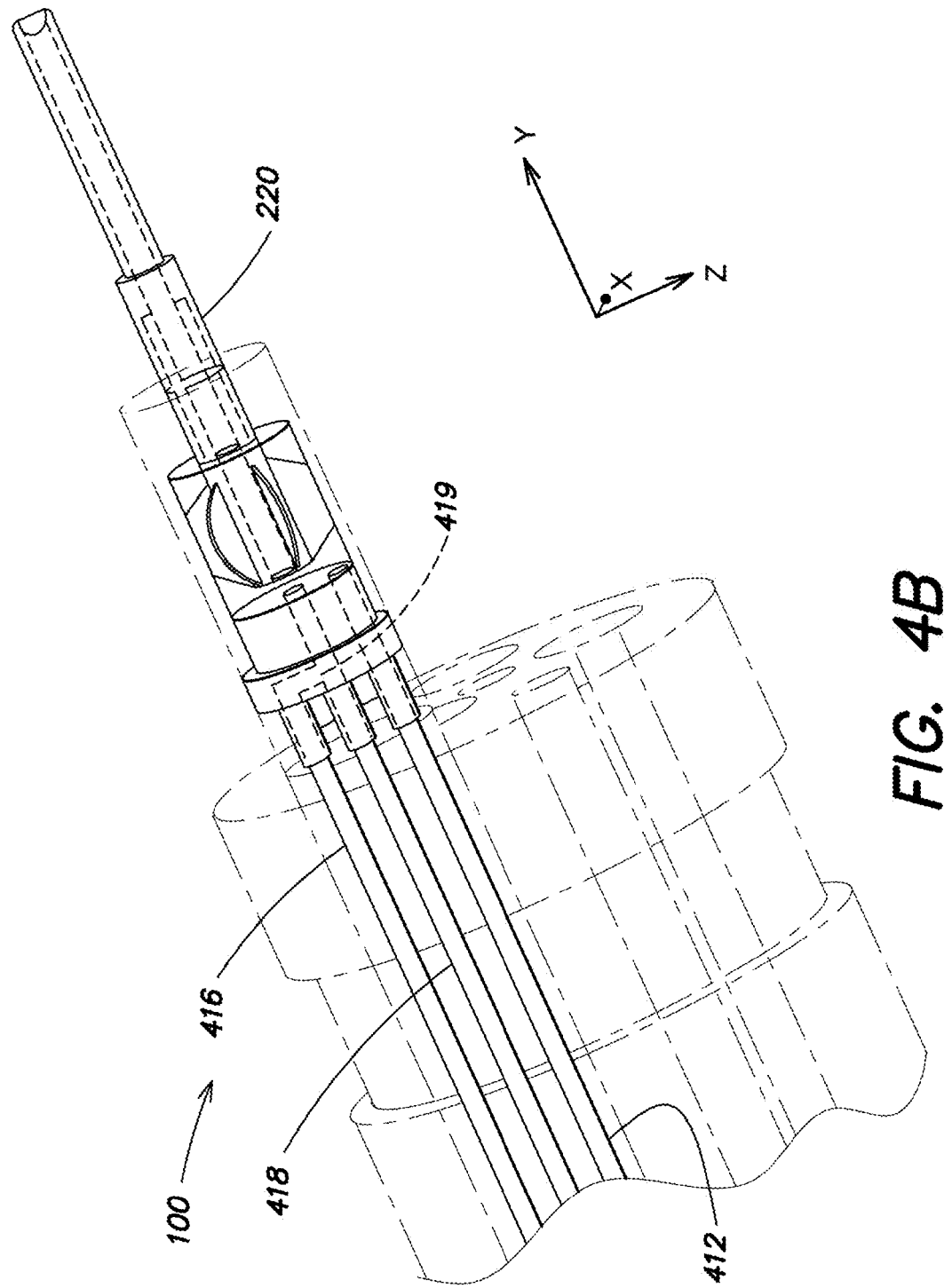
FIG. 4B illustrates a perspective view diagram of the endoscopic instrument coupled to the endoscope illustrating the various conduits associated with the endoscopic instrument.

FIG. 4B is a schematic diagram of an endoscopic instrument partially inserted within an instrument channel of an endoscope endoscopic instrument. In various embodiments, the cap, connector, rotor and casing may be made from injection molded plastic. The spindle and the cannula may be made from surgical grade steel, and the tubing may be made from silicone. However, it should be appreciated that these materials are merely examples of materials that can be used. Those skilled in the art will appreciate that other materials may be used instead of the ones described above.

The tubing 410 in FIG. 4A may be sized to pass through the instrument channel 120 of the endoscope 100 in FIGS. 4A and 4B. The tubing 410 may include one or more pneumatic fluid entry conduits 412, one or more pneumatic fluid exit conduits 414, one or more irrigation conduits 416, and one or more suction conduits 418. The pneumatic fluid entry conduits 412 are configured to supply pressurized air to pneumatically drive the rotor 440, while the pneumatic fluid exit conduits 414 remove the air supplied by the pneumatic fluid entry conduits 412 to prevent a large amount of air from entering the patient's body. The irrigation conduits 416 supply an irrigation fluid, such as water, between the inner blade 450 and the outer blade 460 to help lubricate the area between the inner blade 450 and the outer blade 460. In addition, the irrigation fluid then flows from the outside of the inner blade 450 to the inside portion of the inner blade 450. It should be appreciated that the inside portion of the inner blade 450 may be aligned with the suction conduit 418 of the tubing 410 via the cap 420 such that any fluid that enters the inner blade 450 can pass through the inner blade 450 into the suction conduit 418 of the tubing 410. The irrigation fluid that flows through the inside portion of the inner blade 450 and the suction conduit 418 helps lubricate the suction conduit 418, through which the debrided polyps and other waste from the patient's body are removed. As described above, the tubing 410 is coupled to the cap 420 at a first end, but is coupled to one or more components at a second end (not shown). For instance, at the second end, the pneumatic air entry conduits 412 may be coupled to a compressed air source, while the irrigation fluid conduit 416 may be coupled to a water supply source. In addition, the pneumatic fluid exit conduits 414 may be coupled to the compressed air source or simply left exposed outside the patient's body for venting.

In various embodiments, the suction conduit 418 may be coupled to a disposable cartridge that is configured to catch the cut polyps and store them for examination at a later time. In various embodiments, the disposable cartridge may include multiple collection bins. The operator may be capable of selecting the collection bin in which to collect a sample of a particular cut polyp. Upon selecting the collection bin, the suction conduit 418 supplies the collected material from within the patient's body to the particular collection bin. As such, the operator may be able to collect samples for each polyp in individual collection bins. In this way, the cancerous nature of individual polyps can be determined.

The cap 420 may be sized to fit within the first end of the tubing 410. In various embodiments, the first end of the tubing 410 may include a connector that is configured to couple with the cap 420. In various embodiments, the cap 420 may be press fitted into the connector of the tubing 410. As such, the cap 420 may include corresponding conduits that match the conduits of the tubing 410. Accordingly, compressed air from the compressed air source may be supplied through the pneumatic air entry conduits 412 of the tubing 410 and corresponding pneumatic air entry conduits of the cap 420 towards the rotor 440. The rotor 440 may include one or more rotor blades 442 on which the compressed air is impinged thereby causing the rotor 440 to rotate. The air impinging on the rotor blades 442 may then exit through the corresponding pneumatic air exit conduits of the cap and the pneumatic air entry conduits 414 of the tubing 410. The speed at which the rotor 440 can rotate depends on the amount of air and the pressure at which the air is supplied to the rotor 440. In various embodiments, the speed at which the rotor 440 rotates may be controlled by the operator of the endoscope 100. Although the present disclosure discloses pneumatic means for operating the rotor, some embodiments may include hydraulic means for operating the rotor. In such embodiments, a fluid, such as water, may be supplied in lieu of compressed air, in the pneumatic air entry conduit 412.

As described above, the spindle 430 is coupled to the rotor 440, such that when the rotor 440 rotates, the spindle 430 also rotates. In various embodiments, the first end of the spindle 430 includes the inner blade 450, which correspondingly, also rotates along with the rotor 440. The inner blade 450 may be sized to fit within the diameter of the outer blade 460. In various embodiments, irrigation fluid supplied from an irrigation fluid source may be supplied through the irrigation fluid conduit 416 of the tubing 410 and the corresponding conduit of the cap 420, along the space between the inner blade 450 and the outer blade 460, and into the suction conduit 418 defined by the inner diameter of the inner blade 450. It should be appreciated that since the suction conduit 418 is coupled to a vacuum source, fluids and other material may be suctioned through the suction conduit. In this way, the irrigation fluid is able to lubricate at least a substantial length of the suction conduit 418, from the tip 452 of the inner blade 450, through the spindle 430, cap 420, and tubing 410 into the disposable cartridge described above.

The inner blade 450 may rotate relative to the outer blade 460 such that the interaction between the inner blade 450 and the outer blade 460 causes polyps to be cut upon contact with the inner blade 450. In various embodiments, other mechanisms for cutting polyps may be utilized, which may or may not include the use of a rotor 440, inner blade 450 or outer blade 460.

The debriding component may generally be configured to debride a polyp. Debriding can, for example, include any action involving detaching the polyp or a portion of the polyp from a surface of the patient's body. Accordingly, actions, including but not limited to, cutting, snaring, shredding, slicing, shattering, either entirely or partially, are also examples of debriding. Accordingly, the debriding component may be a component that is capable of cutting, snaring, shredding, slicing, shattering, a polyp from a surface of the patient's body. As such, the debriding component may be implemented as a forceps, scissor, knife, snare, shredder, or any other component that can debride a polyp. In some embodiments, the debriding component may be manually actuated such that the debriding component may be operated through the translation of mechanical forces exerted by an operator or automatically actuated, using a turbine, electrical motor, or any other force generating component to actuate the debriding component. For instance, the debriding component may be actuated hydraulically, pneumatically, or electrically. In various embodiments, a separate conduit passing through the tubing or a channel of the endoscope may be configured to carry an electrical wire to provide power to the electrically powered actuator, such as an electrical motor.

According to various embodiments, the debriding component may include a turbine assembly, which is made up of the rotor 440, the rotor blades 442, and the spindle 430. The operator may actuate the debriding component of the endoscopic instrument by supplying compressed air to the turbine assembly. When the operator is ready to begin debriding the polyp, the operator actuates the turbine assembly causing the debriding component to be actuated. In embodiments, such as the embodiment disclosed in FIG. 4, actuating the debriding component may constitute causing the inner blade 450 to rotate relative to the outer blade 460. Upon actuation, the operator may bring the endoscopic instrument 220 towards the polyp to be debrided causing the inner blade 450 to debride the polyp, causing portions of the debrided polyp to lie in the vicinity around the area where the polyp had grown. The operator may then de-actuate the turbine assembly and actuate suction through the suction conduit 418. The operator may then bring the inner blade close to the cut polyp causing the cut polyp to be retrieved through the suction conduit 418. In various embodiments, the suction component of the endoscopic instrument may be actuated while the debriding component is actuated, thereby allowing any debrided material to be retrieved by the suction component.

Although the above embodiment houses a debriding component that utilizes a turbine assembly, the scope of the present disclosure is not limited to such embodiments. Rather, it should be appreciated by those skilled in the art that the debriding component may be manually operated or may utilize any other means of debriding a polyp such that the debrided polyps are capable of being retrieved from the surgical site via the suction conduit described above. Accordingly, examples of debriding components may include, but are not limited to, snips, blades, saws, or any other sharp tools that may or may not be driven by a turbine assembly. It should be appreciated that using a debriding component that is able to cut a polyp into small enough pieces may be desirable such that the cut pieces may be retrieved via the suction conduit without having to remove the endoscopic instrument from the endoscope.

The geometry and assembly of the turbine assembly for rotating at least one of the cutting tool blades may be based on fluid dynamics. Bernoulli's equation can be used to explain the conversion between fluid pressure and the fluid velocity. According to this equation, the fluid velocity is related to the initial fluid pressure by the equation:

$$V = \sqrt{2 * \frac{P}{D}}$$

where V is Velocity, P is Pressure, and D is Mass density.

In order for the fluid to reach the calculated velocity, the fluid can be developed at the point of exit such that the channel through which the fluid is flowing meets an empirically determined L/D ratio of 2, where 'D' is the wetted diameter of the flow and the is the length of the channel.

To further understand the interaction of the rotor blades and the fluid, it is assumed that the rotor blade is made so that the air jet impinges the rotor blade on a plane. The equation of linear momentum can be applied to find the forces generated:

$$\sum F = \frac{d}{dt}\left(\iiint Vp * dVol.\right) + \sum (\dot{m}V)_{out} - \sum (\dot{m}V)_{in}$$

where: $\dot{m}$ is the mass flow of the impinging air jet, and V is Volume.

Assuming that the control volume remains constant (volume between blades), the force created on the blade can be solved for:

$$\Sigma F = \dot{m}(V_{out} - V_{in})$$

The quantity $V_{out}$ and $V_{in}$ are the same in an impulse turbine, the momentum change being created by the changing direction of the fluid only. The mass flow $\dot{m}$ is defined by the pump that is to be specified. The actual numerical value also needs to account for the velocity of the rotor. So finally, the force generated by a single blade-air jet interaction is:

$$\Sigma F = \dot{m}(V_{jet} - V_{rotor}) - (V_{jet} - V_{rotor}) \cos \theta$$

$$\Sigma F = \dot{m}(V_{jet} - V_{rotor})(1 - \cos \theta)$$

where 'θ' is the difference of the angle between the incoming air jet to that of the exiting air jet. Thought theoretically, the maximum amount of torque can be generated by a 'θ' value of 180°, but doing so will actually send the incoming jet onto the back of the following blade. Accordingly, the angle is best given a design value 15° to 20° below 180 to allow a fluid a clean exit. Finally, the force can be defined into a rotational torque:

$$\Sigma T = (\dot{m}/r)(V_{jet} - V_{rotor})(1 - \cos \theta)$$

A second force that can be considered comes from redirecting the air jet from the nozzle into the turbine wheel. To power the turbine, the air jet can be turned 90° into the direction of the blades from the direction of the air jet. The turning of the air jet will create a force on the stationary housing that is a function of the jet velocity, which in turn is proportional to the applied pressure:

$$\Sigma F = \dot{m} V_{jet}$$

This force can be reacted by the connection between the housing and the endoscope, a failure to do so can result in the ejection of the turbine assembly during operation.

Computational analyses based on Finite Element Methods (FEM) reveal that the areas where the greatest stresses are found are located near the root of the blade where a sharp corner is located. The design of air input channel can be simplified by the existing air nozzle channel in endoscope. The air nozzle in existing endoscopes directs pressurized air across objective lens to remove moisture and also provides distension of a cavity being examined or directs pressurized water across objective lens to clear debris.

Referring now to FIG. 4B, a perspective view diagram of the endoscopic instrument coupled to the endoscope illustrating the various conduits associated with the endoscopic instrument is shown. In particular, the pneumatic air entry conduit 412 is shown supplying pressurized air to the rotor assembly, while the pneumatic air exit conduit 412 (not shown in this view) removes the air from the rotor assembly to outside the endoscope 100. The irrigation channel 416 is shown to carry irrigation fluid into the endoscopic instrument 220, where the irrigation fluid enters into the suction conduit 418, which carries material from within the patient's body to a collection component outside the endoscope. As shown in FIG. 4B, the irrigation fluid may enter the suction conduit 418 at an irrigation fluid entry opening 419. It should be appreciated that the placement of the irrigation fluid entry opening 419 may be placed anywhere along the suction conduit. Due to the suction force being applied to the suction conduit, irrigation fluid may be forced into the suction conduit without the risk of the materials flowing in the suction conduit from flowing outside the suction conduit through the irrigation fluid entry opening 419. Moreover, in some embodiments, the irrigation channel may only supply irrigation fluid to the endoscopic instrument while suction is being applied to the suction conduit.

Figure 5:
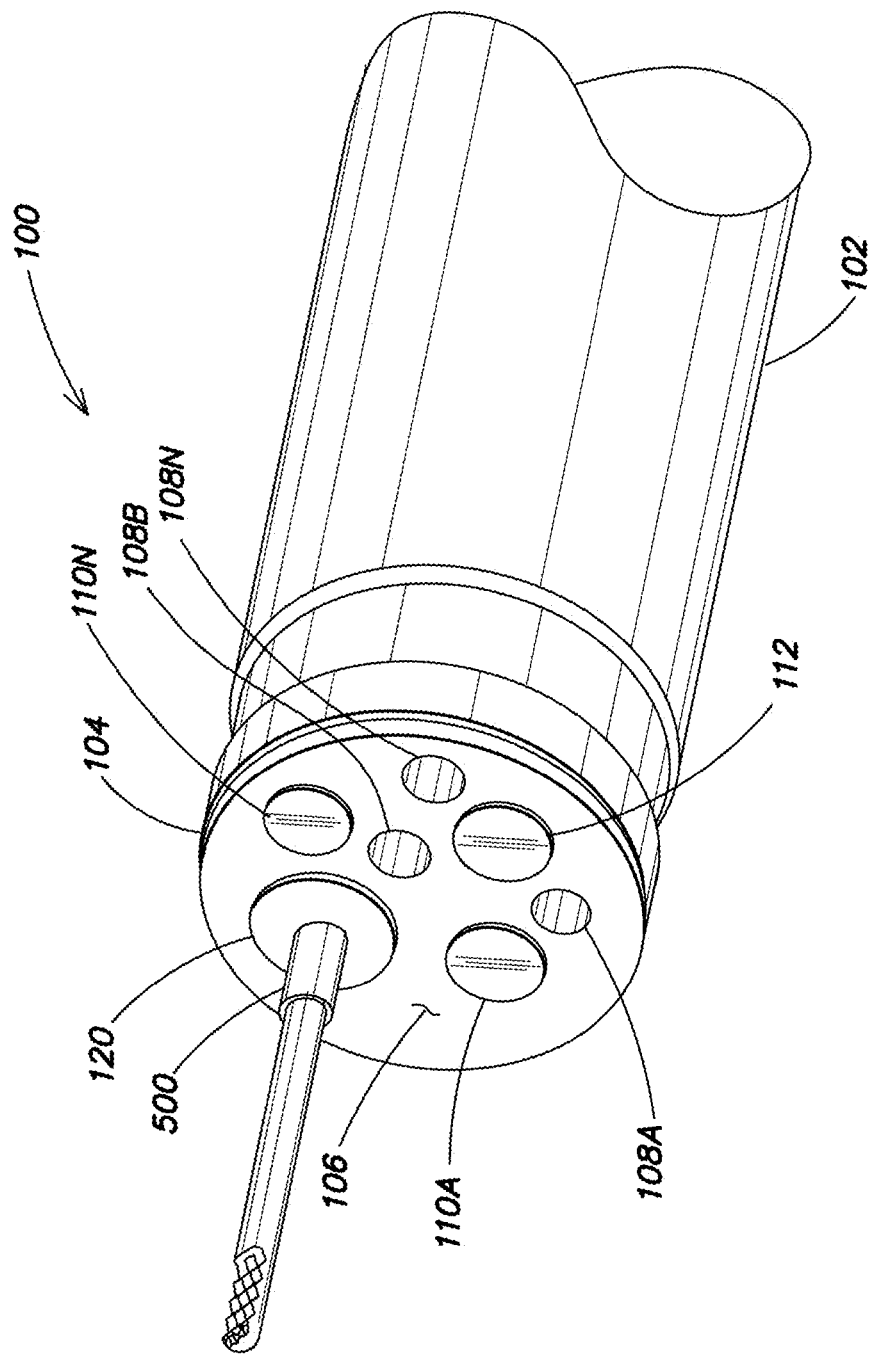
FIG. 5 illustrates a side perspective view of another example endoscopic instrument coupled with the endoscope shown in FIG. 1 according to embodiments of the present disclosure.

FIG. 5 illustrates a side perspective view of another endoscopic instrument coupled with the endoscope shown in FIG. 1 according to embodiments of the present disclosure. The add-on endoscopic instrument 500 is sized to couple with the walls defining the instrument channel 120 of the tip 104 of the endoscope 100. In various embodiments, the add-on endoscopic instrument 500 may be removably attached to the instrument channel 120 of the endoscope 100 at the tip 104 of the endoscope 104 by way of an interference fit or a press fit. In other embodiments, the add-on endoscopic instrument 500 may be coupled to the endoscope 100 using other attachment means known to those skilled in the art.

Figure 6:
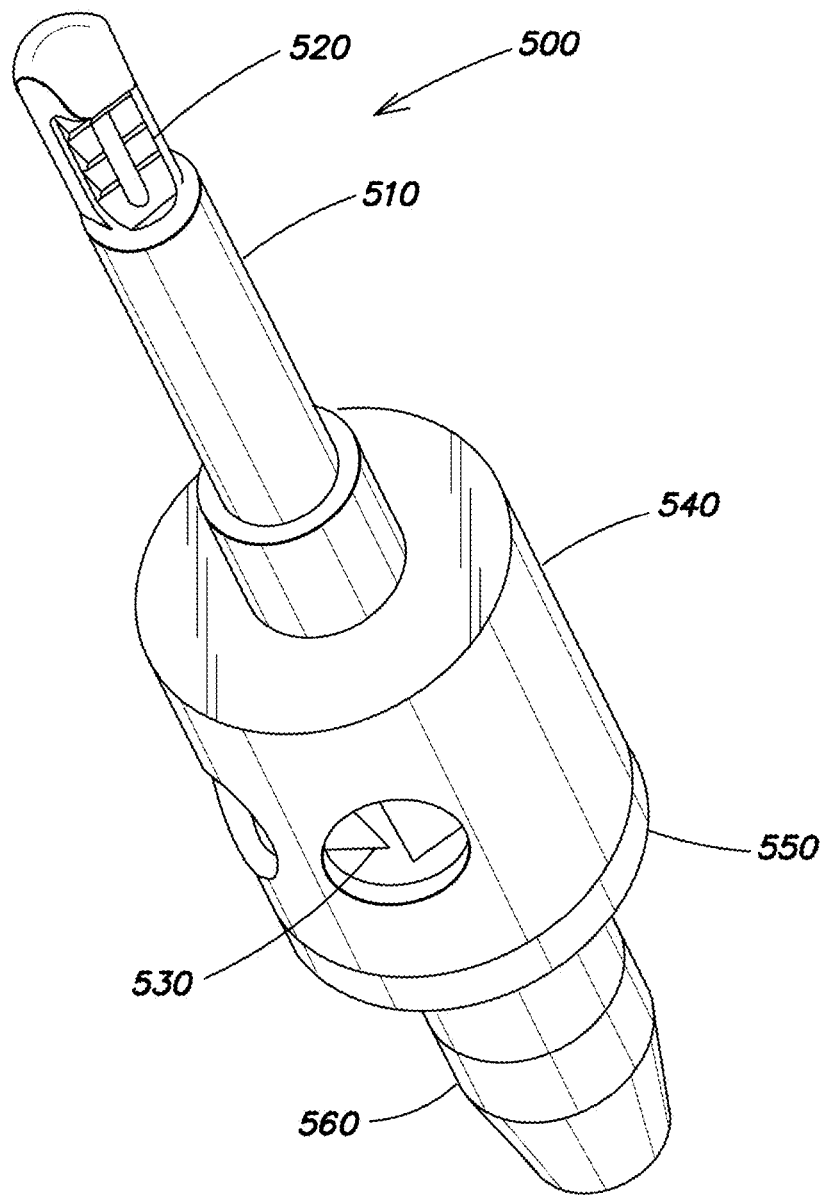
FIG. 6 illustrates an enlarged view of an example endoscopic instrument according to embodiments of the present disclosure.
Figure 7:
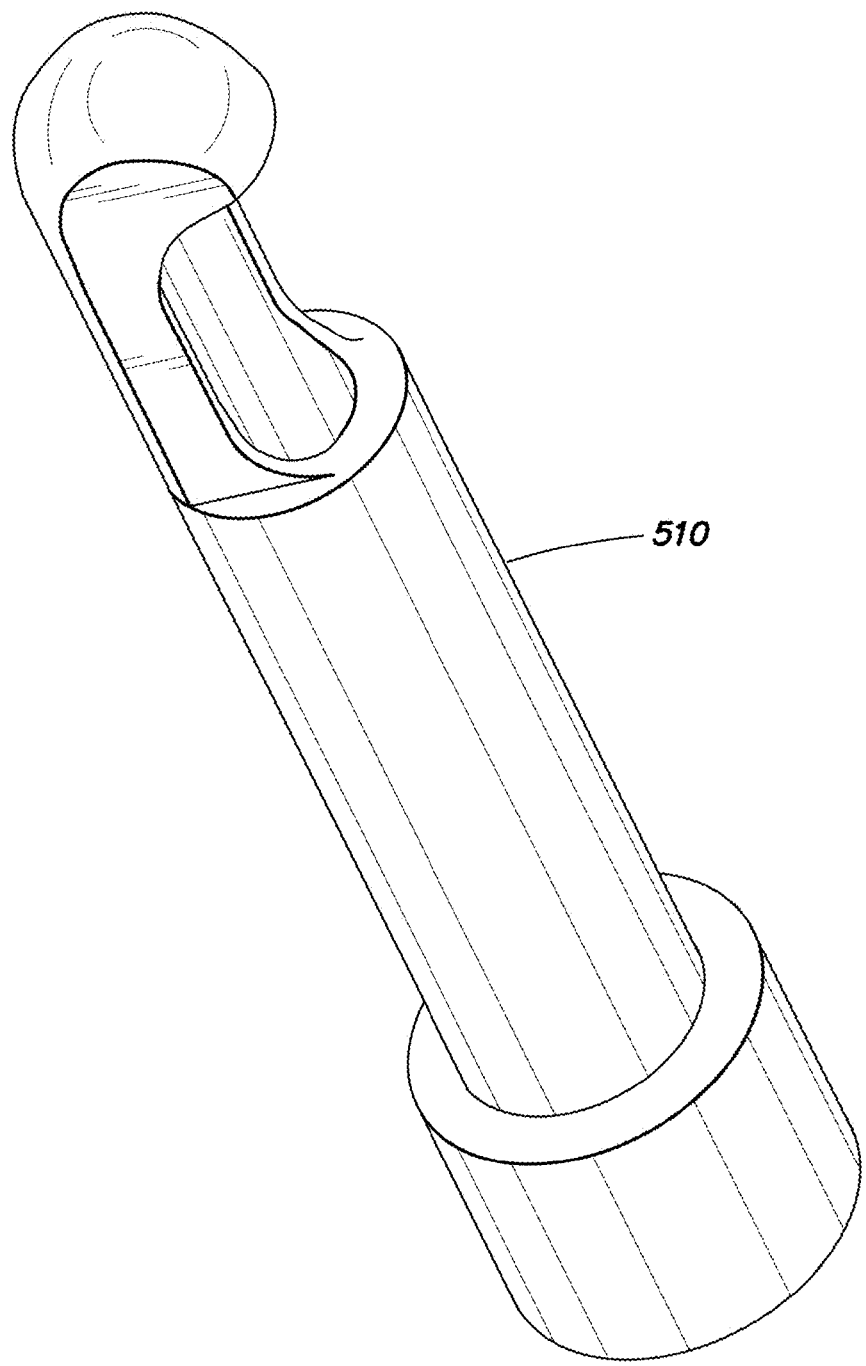
FIG. 7 illustrates a perspective view of an outer blade of a cutting tool of the endoscopic instrument shown in FIG. 6 according to embodiments of the present disclosure.
Figure 8:
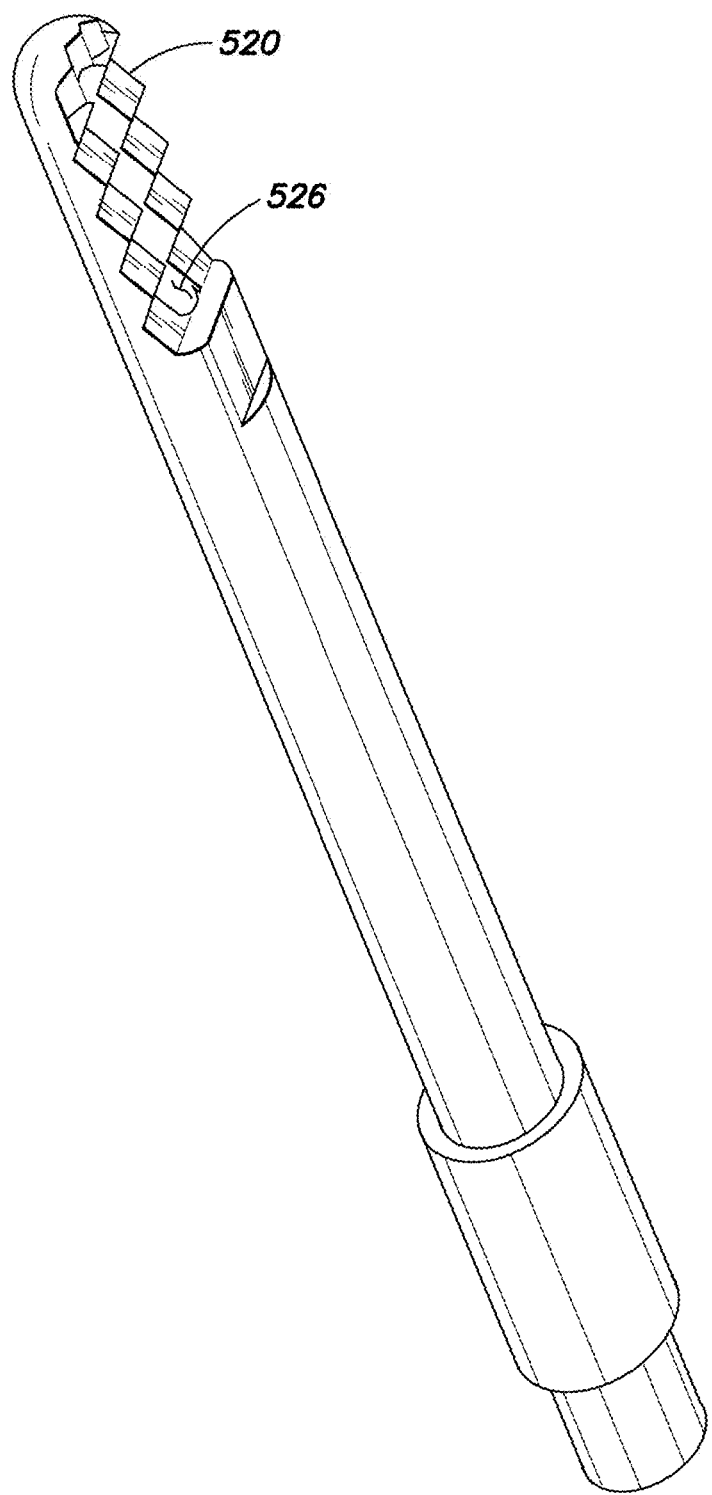
FIG. 8 illustrates a perspective view of an inner blade of the cutting tool of the endoscopic instrument shown in FIG. 6 according to embodiments of the present disclosure.
Figure 9:
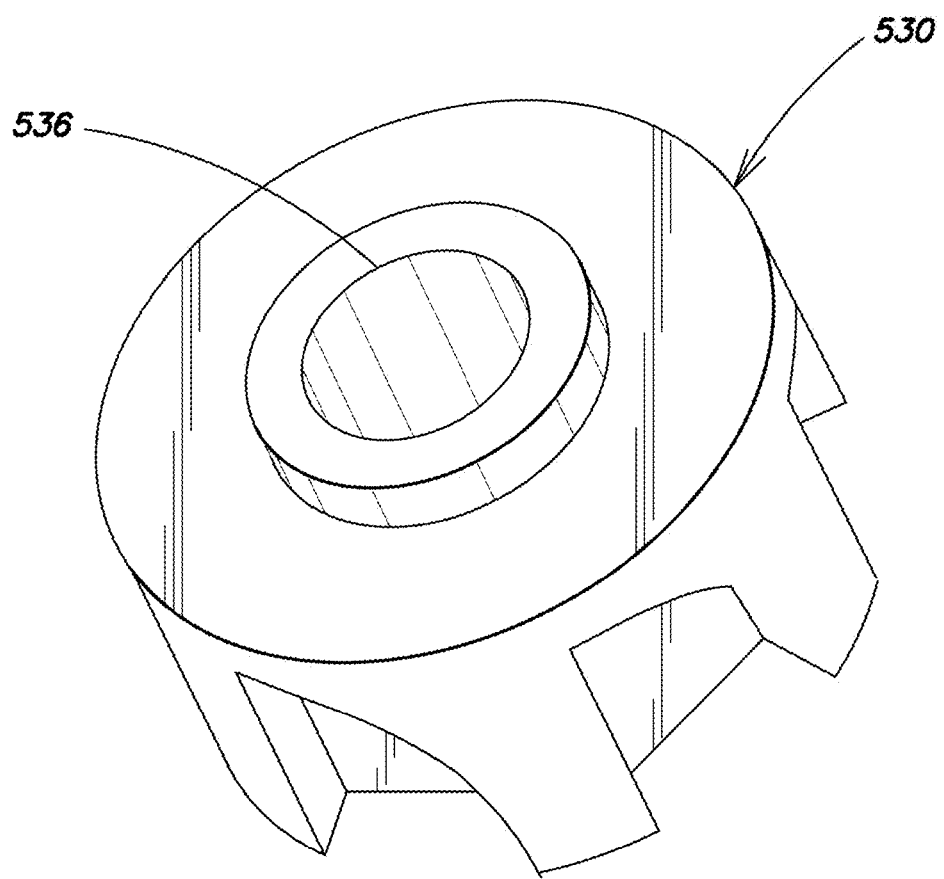
FIG. 9 illustrates a perspective view of a rotor of the endoscopic instrument shown in FIG. 6 according to embodiments of the present disclosure.

Referring now to FIG. 6, an enlarged view of the add-on endoscopic instrument 500 is shown. The add-on endoscopic instrument includes an outer blade or support member 510, an inner blade 520 disposed within the outer blade 510, a rotor 530 coupled to the inner blade 520 and encompassed by a casing 540. The casing is coupled to a cap 550, which is further coupled to a connector 560. In some embodiments, the connector 560 may be sized to engage with the inner diameter of the instrument channel 120 of the endoscope 100. In some embodiments, any other component of the endoscopic instrument may be configured to engage with the endoscope 100 in such a manner as to secure the endoscopic instrument to the instrument channel 120.

FIGS. 7-12 illustrate perspective views of the individual components of the add-on endoscopic instrument shown in FIG. 6 according to embodiments of the present disclosure. In contrast to the endoscopic instrument 220 disclosed with respect to FIGS. 1-4, the add-on endoscopic instrument 500 may be adapted to fit within a first end of instrument channel 120 of the endoscope 100.

In various embodiments, a second end of the instrument channel 120 may be coupled to a vacuum source, which causes material to be suctioned through the instrument channel 120. A suction conduit extends from the vacuum source through the instrument channel of the endoscope, and further through the connector 560, the cap 550, and the rotor 530, to a first end of the inner blade 520, which has an opening defined by the inner diameter of the inner blade 520. It should be appreciated that the connector 560, the cap 550, the casing 540, and the rotor 530 have respective center bores 566, 556, 546 and 536 that are aligned such that materials are allowed to flow from the opening of the inner blade 520 to the vacuum source via the second end of the instrument channel 120.

Figure 10:
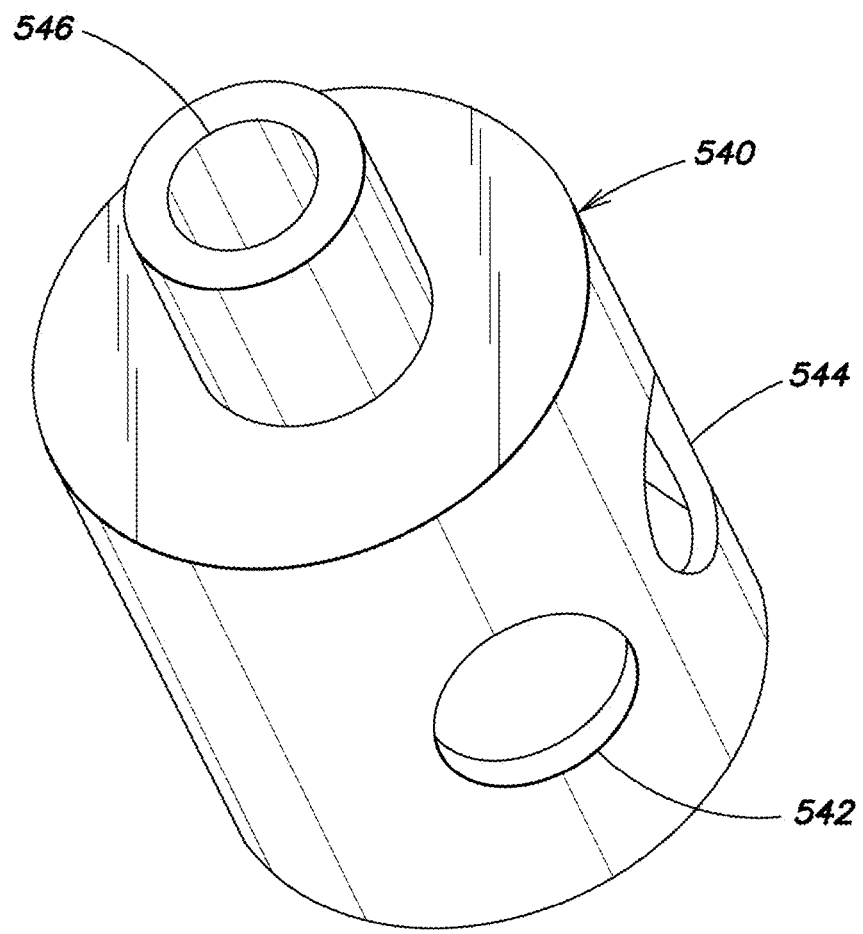
FIG. 10 illustrates a perspective view of a casing of the endoscopic instrument shown in FIG. 6 according to embodiments of the present disclosure.
Figure 11:
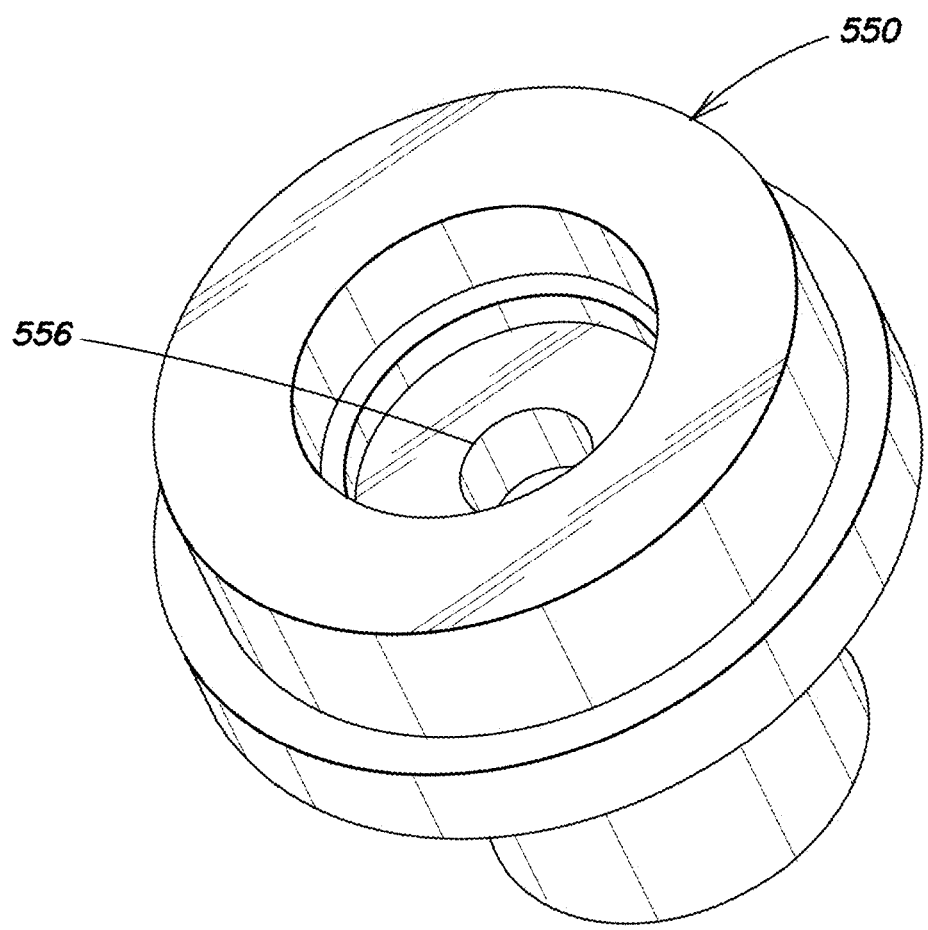
FIG. 11 illustrates a perspective view of a cap of the endoscopic instrument shown in FIG. 6 according to embodiments of the present disclosure.
Figure 12:
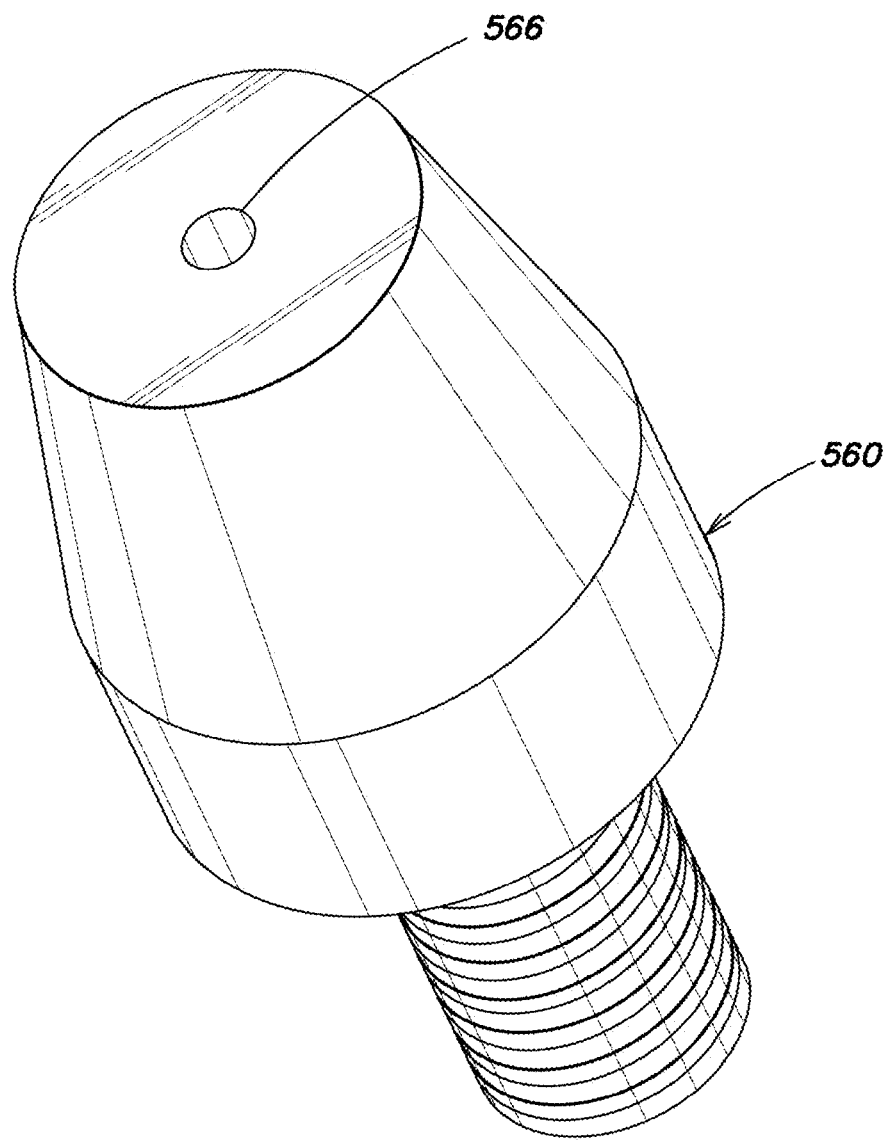
FIG. 12 illustrates a perspective view of a coupling member of the endoscopic instrument shown in FIG. 6 according to embodiments of the present disclosure.

In addition, the casing 540 of the add-on endoscopic instrument 500 includes a pneumatic air entry port 542 and a pneumatic air exit port 544 as shown in FIG. 10. The pneumatic air entry port 542 may be adapted to receive compressed air from a compressed air source through a pneumatic air entry conduit that passes along the length of the endoscope 100 to outside the patient's body, while the pneumatic air exit port 544 may be adapted to vent air that is impinged on the rotor 530 through a pneumatic air exit conduit that passes along the length of the endoscope 100 to outside the patient's body. In this way, the rotor may be actuated by supplying compressed air from the compressed air source, as described above with respect to FIGS. 1-4. It should be appreciated that although the rotor and associated components disclosed herein describe the use of pneumatic air, the rotor may be driven hydraulically. In such embodiments, the pneumatic air conduits may be configured to carry a liquid, such as water, to and from the area around the rotor.

Figure 13:
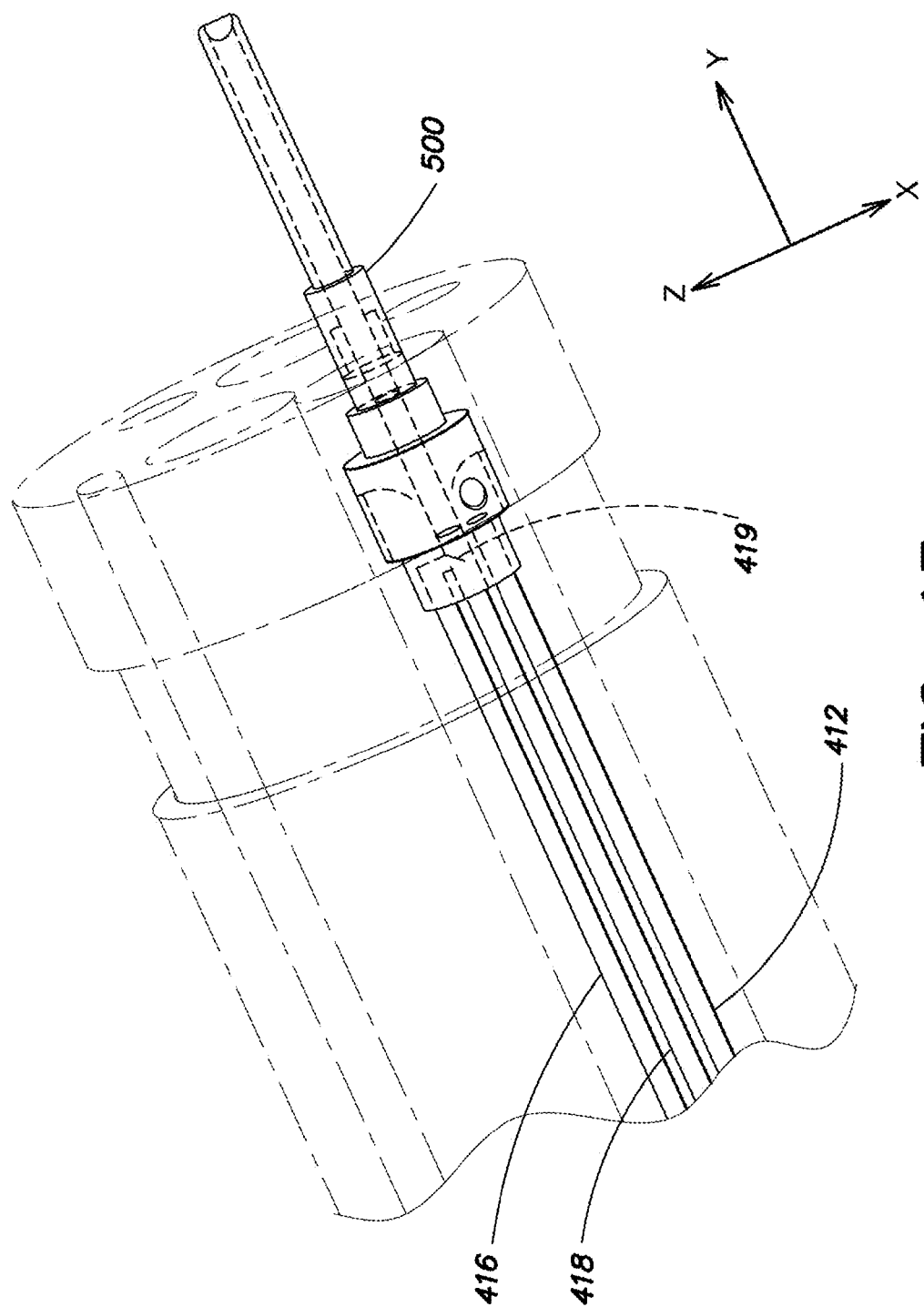
FIG. 13 illustrates a perspective view diagram of the endoscopic instrument coupled to the endoscope illustrating the various conduits associated with the endoscopic instrument.

Referring now also to FIG. 13, it should be appreciated that the pneumatic air entry and exit conduits may extend from the add-on endoscopic instrument to a pneumatic air source through the instrument channel 120 of the endoscope 100. In such embodiments, a tubing that includes separate conduits for the pneumatic air entry and exit conduits and the suction conduit may extend from outside the endoscope to the add-on endoscopic instrument within the endoscope. The tubing may be capable of being fed through the instrument channel of the endoscope and coupled to the add-on endoscopic instrument 500. In such embodiments, the add-on endoscopic instrument 500 may be configured with an additional component that has predefined channels that couple the respective channels of the tubing with the associated with the pneumatic air entry and exit openings of the add-on endoscopic instrument and the suction conduit formed within the add-on endoscopic instrument. In addition, an irrigation fluid channel may also be defined within the tubing such that irrigation fluid may be supplied to the add-on endoscopic instrument 500, from where the irrigation fluid is diverted into the suction conduit.

In various embodiments, the tip of the outer blade 510 may be sharp and may cause discomfort to the patient while entering a cavity of the patient's body. As such, a guard structure (not shown), such as a gel cap or other similar structure, may be attached to the outer blade prior to inserting the add-on endoscopic instrument into the patient's body to prevent injuries from the outer blade contacting a surface of the patient's body. Once the endoscopic instrument is inserted in the patient's body, the guard structure may be released from the outer blade 510. In various embodiments, the guard structure may dissolve upon entering the patient's body.

Figure 14:
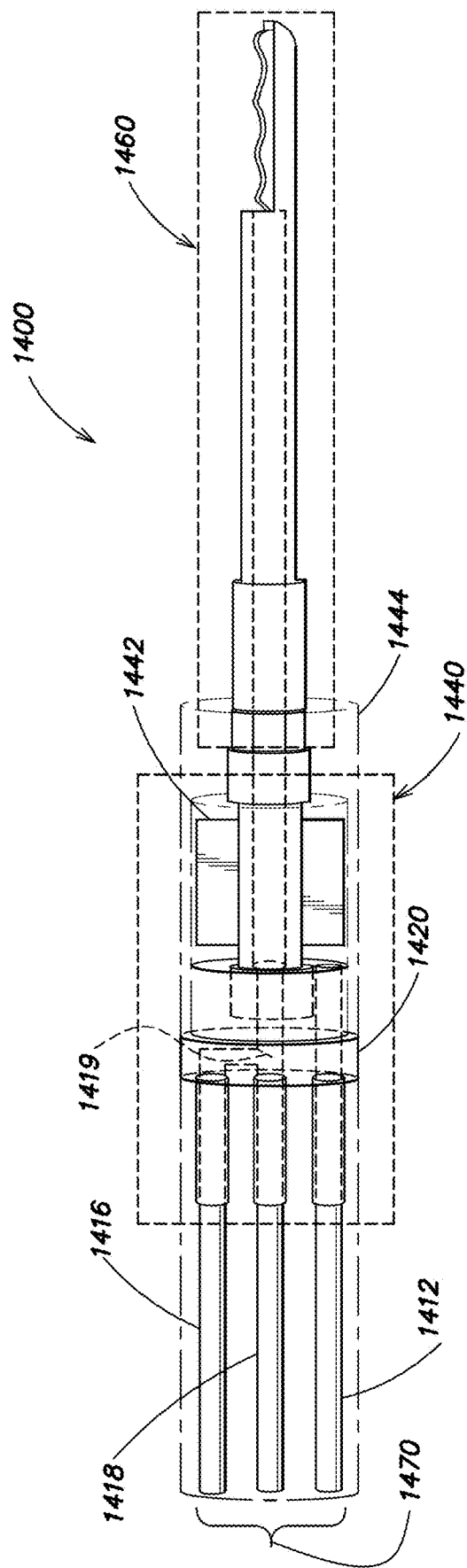
FIG. 14 illustrates another perspective view diagram of the endoscopic instrument coupled to the endoscope illustrating the various conduits associated with the endoscopic instrument.

Referring now to FIG. 14, an improved endoscope having a built in polyp removal assembly is shown according to embodiments of the present disclosure. The improved endoscope 1400 may be similar to conventional endoscopes in many aspects, but may differ in that the improved endoscope may include a built in polyp removal assembly 1440 within an instrument channel of the endoscope 1400. The polyp removal assembly 1440 may include a turbine assembly having a rotor 1442 with rotor blades sealed in a casing 1444 that has one or more inlet and outlet ports for allowing either pneumatic or hydraulic fluid to actuate the rotor 1442. The inlet ports may be designed such that the fluid may interact with the rotor blades at a suitable angle to ensure that the rotor can be driven at desired speeds.

In addition, the polyp removal assembly 1440 may be coupled to a connector 1420, which is configured to couple the polyp removal assembly 1440 to a tubing 1470. The tubing 1470 may include a pneumatic air entry conduit 1412, a pneumatic air exit conduit (not shown), an irrigation fluid conduit 1416 and a suction conduit 1418 that passes through the center of the turbine assembly. The tubing 1440 may be sized such that the tubing 1440 can be securely coupled to the connector 1420 such that one or more of the conduits of the tubing 1440 are coupled to corresponding conduits within the connector 1440. The connector 1420 may be designed to include an irrigation fluid entry opening 419, which allows irrigation fluid to pass into the suction conduit 1418 of the tubing 1440 when the tubing is coupled to the connector.

The turbine assembly of the endoscope 1400 may be configured to couple with a removable debriding assembly 1460, which includes a spindle and a cannula, in a manner that causes the debriding assembly to be operational when the turbine assembly is operating.

In other embodiments of the present disclosure, an endoscope may be designed to facilitate debriding one or more polyps and removing the debrided material associated with the polyps in a single operation. In various embodiments, the endoscope may include one or more separate channels for removing debrided material, supplying irrigation fluid, and supplying and removing at least one of pneumatic or hydraulic fluids. In addition, the endoscope may include a debriding component that may be fixedly or removably coupled to one end of the endoscope. In various embodiments, based on the operation of the debriding component, a separate debriding component channel may also be designed for the debriding component. In addition, the endoscope may include a light and a camera. In one embodiment, the endoscope may utilize existing channels to supply pneumatic or hydraulic fluids to the actuator of the endoscopic instrument for actuating the debriding component. For instance, in the endoscope shown in FIG. 1, the water channels 108A-N may be modified to supply fluids to the actuator pneumatically or hydraulically. In such embodiments, the endoscopic instrument may include a connector having a first end capable of being coupled to an opening associated with existing channels 108 of the endoscope, while another end of the connector is exposed to an opening at the actuator.

In various embodiments of the present disclosure, the endoscopic instrument may further be configured to detect the presence of certain layers of tissue. This may be useful for physicians to take extra precautions to prevent bowel perforations while debriding polyps. In some embodiments, the endoscopic instrument may be equipped with a sensor that can communicate with a sensor processing component outside the endoscope to determine the type of tissue. The sensor may gather temperature information as well as density information and provide signals corresponding to such information to the sensor processing unit, which can identify the type of tissue being sensed. In some implementations, the sensor may be an electrical sensor.

In addition, the endoscopic instrument may be equipped with an injectable dye component through which a physician may mark a particular region within the patient's body. In other embodiments, the physician may mark a particular region utilizing the debriding component, without the use of an injectable dye.

Although the present disclosure discloses various embodiments of an endoscopic instrument, including but not limited to a tool that may be attached to the tip of the endoscope, and a tool that may be fed through the length of the endoscope, the scope of the present disclosure is not intended to be limited to such embodiments or to endoscopic instruments in general. Rather, the scope of the present disclosure extends to any device that may debride and remove polyps from within a patient's body using a single tool. As such, the scope of the present disclosure extends to improved endoscopes that may be built with some or all of the components of the endoscopic instruments described herein. For instance, an improved endoscope with an integrated turbine assembly and configured to be coupled to a debriding component is also disclosed herein. Furthermore, the endoscope may also include predefined conduits that extend through the length of the endoscope such that only the suction conduit may be defined by a disposable tubing, while the air entry and exit conduits and the irrigation conduit are permanently defined within the improved endoscope. In other embodiments, the suction conduit is also predefined but made such that the suction conduit may be cleaned and purified for use with multiple patients. Similarly, the debriding component may also be a part of the endoscope, but also capable of being cleaned and purified for use with multiple patients. Furthermore, it should be understood by those skilled in the art that any or all of the components that constitute the endoscopic instrument may be built into an existing endoscope or into a newly designed endoscope for use in debriding and removing polyps from within the patient's body.

Figure 15:
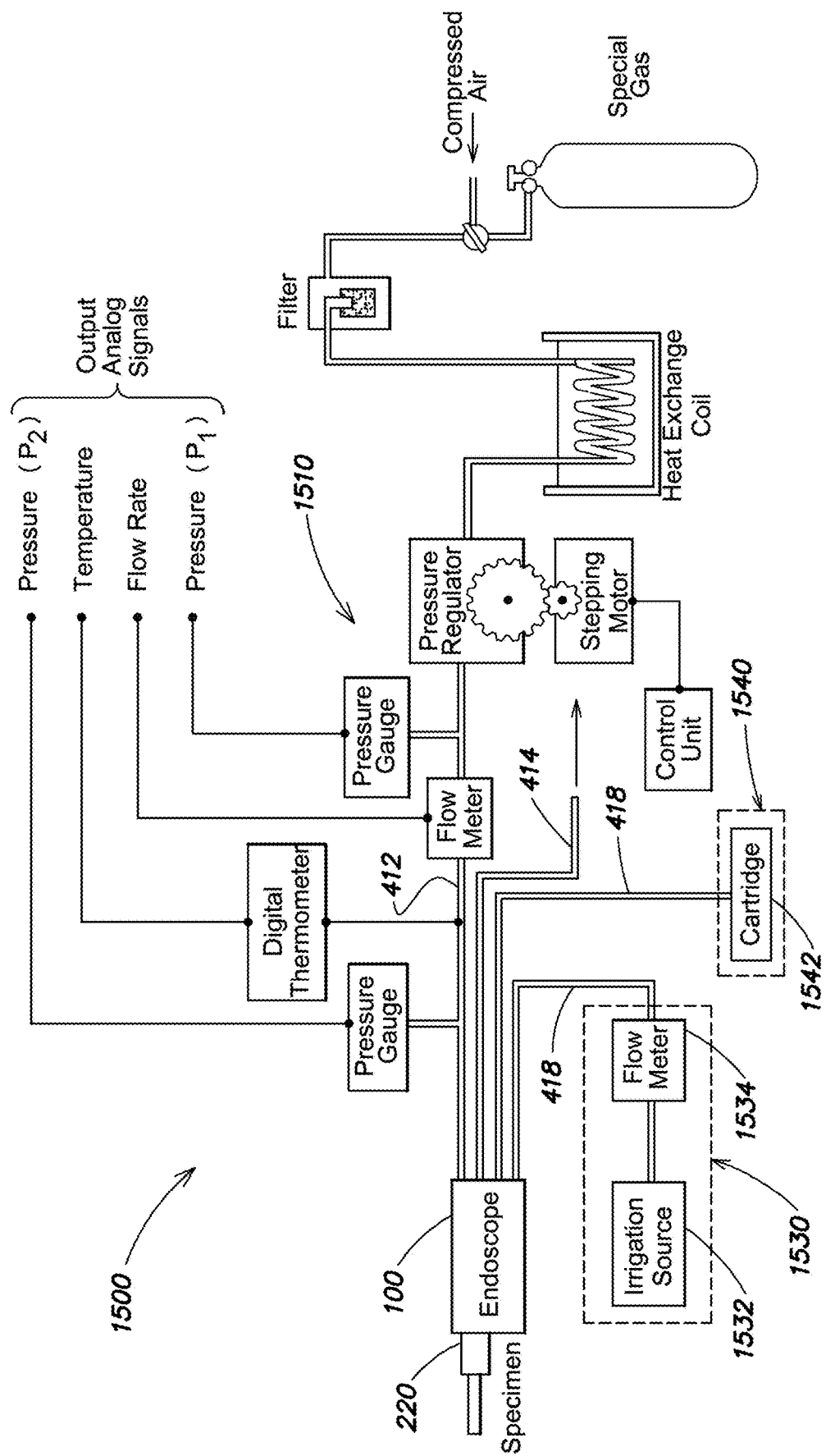
FIG. 15 is a conceptual system architecture diagram illustrating various components for operating the endoscopic instrument according to embodiments of the present disclosure.

Referring now to FIG. 15, a conceptual system architecture diagram illustrating various components for operating the endoscopic instrument according to embodiments of the present disclosure is shown. The endoscopic system 1500 includes an endoscope 100 fitted with an endoscopic instrument 220, and which may be coupled to an air supply measurement system 1510, an irrigation system 1530 and a polyp removal system 1540. As described above, the tubing that extends within the endoscope 100 may include one or more pneumatic air entry conduits 412 and one or more pneumatic air exit conduits 414. The pneumatic air entry conduits 412 are coupled to the air supply measurement system 1510, which includes one or more sensors, gauges, valves, and other components to control the amount of gas, such as air, being supplied to the endoscope 100 to drive the rotor 440. In some embodiments, the amount of air being supplied to the rotor 440 may be controlled using the air supply measurement system 1510. Furthermore, delivery of the air to actuate the rotor 440 may be manually controlled by the physician using the endoscope 100. In one embodiment, the physician may use a foot pedal or a hand-actuated lever to supply air to the rotor 440.

The pneumatic air exit conduit 414, however, may not be coupled to any component. As a result, air exiting from the rotor 440 may simply exit the endoscope via the pneumatic air exit conduit 414 into the atmosphere. In some embodiments, the pneumatic air exit conduit 414 may be coupled to the air supply measurement system 1510 such that the air exiting the pneumatic air exit conduit 414 is supplied back to the rotor via the pneumatic air entry conduit 412. It should be appreciated that a similar setup may be used for a hydraulically driven turbine system.

The endoscope 100 may also be coupled to the irrigation system 1530 via the irrigation fluid conduit 416. The irrigation system 1530 may include a flow meter 1534 coupled to an irrigation source 1532 for controlling the amount of fluid flowing from the irrigation source 1532 to the endoscope 100.

As described above, the endoscope 100 may also include a suction conduit 418 for removing polyps from within the patient's body. The suction conduit 418 may be coupled to the polyp removal system 1540, which may be configured to store the polyps. In various embodiments, the physician may be able to collect samples in one or more cartridges 1542 within the polyp removal system 1540 such that the removed polyps can be tested individually.

In various embodiments of the present disclosure, an endoscope, comprises a first end and a second end separated by a flexible housing, an instrument channel extending from the first end to the second end, and an endoscopic instrument comprising a debriding component and a sample retrieval conduit disposed within the instrument channel. The endoscopic instrument may further include a flexible tubing in which the sample retrieval conduit is partially disposed, the flexible tubing extending from the first end to the second end of the endoscope. The flexible tubing may also include a pneumatic air entry conduit and a fluid irrigation conduit. In various embodiments, the debriding component may include a turbine assembly and a cutting tool. In various embodiments in which the endoscope is configured to have a built in endoscopic instrument, the instrument channel may have a diameter that is larger than the instrument channels of existing endoscopes. In this way, larger portions of debrided material may be suctioned from within the patient's body without clogging the suction conduit.

In other embodiments, an endoscope may include a first end and a second end separated by a flexible housing; an instrument channel extending from the first end to the second end; and an endoscopic instrument coupled to the instrument channel at the first end of the endoscope, the endoscopic instrument comprising a debriding component and a sample retrieval conduit partially disposed within the instrument channel. In some embodiments, the endoscopic instrument may be removably attached to the endoscopic instrument.

In other embodiments of the present disclosure, an endoscopic system, includes an endoscope comprising a first end and a second end separated by a flexible housing and an instrument channel extending from the first end to the second end and an endoscopic instrument coupled to the instrument channel at the first end of the endoscope. The endoscopic instrument may include a debriding component and a flexible tubing having a length that is greater than the length of the endoscope. Moreover, the flexible tubing may include a sample retrieval conduit, an pneumatic air entry conduit, and a fluid irrigation conduit, a disposable cartridge configured to couple with the sample retrieval conduit proximal the second end of the endoscope, a pressurized air source configured to couple with the pneumatic air entry conduit proximal the second end of the endoscope, and a fluid irrigation source configured to couple with the fluid irrigation conduit proximal the second end of the endoscope. In various embodiments, the endoscope may also include at least one camera source and at least one light source. In some embodiments of the present disclosure, the pneumatic air entry conduit supplies pressurized air to a turbine assembly of the debriding component proximal the first end of the endoscope and the fluid irrigation conduit supplies irrigation fluid to the sample retrieval conduit proximal the first end of the endoscope.

FIG. 16A illustrates an exploded partial view of an endoscopic instrument 1600, which is similar to the endoscopic instrument 150 depicted in FIG. 1C in that the endoscopic instrument 1600 is configured to be inserted within an instrument channel of an endoscope, such as the endoscope 100 depicted in FIG. 1B. FIG. 16B illustrates a cross-sectional partial view of the endoscopic instrument shown in FIG. 16A. As shown in FIGS. 16A and 16B, a head portion of the endoscopic instrument 1600 can include a powered actuator 1605, a power-driven instrument head 1680 including a cutting shaft 1610 and an outer structure 1615 and a feedthrough connector 1620 coupled to a distal end of a flexible tubular member 1630. The flexible tubular member 1630 forms the tail portion of the endoscopic instrument 1600. As such, FIGS. 16A and 16B illustrate the head portion of the endoscopic instrument 1600.

The endoscopic instrument 1600 is configured to define an aspiration channel 1660 that extends from a proximal end of the flexible tubular member 1630 to a distal tip 1614 of the power-driven instrument head 1680. In some implementations, the proximal end of the flexible tubular member 1630 may be configured to fluidly couple to a vacuum source. In this way, upon the application of a suction force at the proximal end of the flexible tubular member 1630, material at or around the distal tip 1614 of the power-driven instrument head 1680 can enter the endoscopic instrument 1600 at the distal tip and flow through the aspiration channel 1660 all the way to the proximal end of the flexible tubular member 1630.

The powered actuator 1605 can be configured to drive a power-driven instrument head 1680, which includes the cutting shaft 1610 disposed within the outer structure 1615. In some implementations, the powered actuator 1605 can include a drive shaft 1608 that is mechanically coupled to the cutting shaft 1610. In some implementations, one or more coupling elements may be used to couple the drive shaft 1608 to a proximal end 1611 of the cutting shaft 1610 such that the cutting shaft 1610 is driven by the drive shaft 1608. The powered actuator 1605 can be an electrically powered actuator. In some implementations, the electrically powered actuator can include an electrical terminal 1606 configured to receive an electrical conducting wire for providing electrical current to the electrically powered actuator 1605. In some implementations, the electrically powered actuator can include an electric motor. In some implementations, the electric motor can be a micro-sized motor, such that the motor has an outer diameter of less than a few millimeters. In some implementations, the powered actuator 1605 has an outer diameter that is smaller than about 3.8 mm. In addition to having a small footprint, the powered actuator 1605 may be configured to meet certain torque and rotation speed parameters. In some implementations, the powered actuator 1605 can be configured to generate enough torque and/or rotate at sufficient speeds to be able to cut tissue from within a subject. Examples of motors that meet these requirements include micromotors made by Maxon Precision Motors, Inc., located in Fall River, Mass., USA. Other examples of electrical motors include any type of electric motors, including AC motors, DC motors, piezoelectric motors, amongst others.

The power-driven instrument head 1680 is configured to couple to the powered actuator 1605 such that the powered actuator 1605 can drive the power-driven instrument head. As described above, the proximal end 1611 of the cutting shaft 1610 can be configured to couple to the drive shaft 1608 of the powered actuator 1605. The distal end 1614 of the cutting shaft 1610 opposite the proximal end 1611 can include a cutting tip 1612. The cutting tip 1612 can include one or more sharp surfaces capable of cutting tissue. In some implementations, the cutting shaft 1610 can be hollow and can define a material entry port 1613 at or around the culling tip 1612 through which material that is cut can enter the endoscopic instrument 1610 via the material entry port 1613. In some implementations, the proximal end 1611 of the cutting shaft 1610 can include one or more outlet holes 1614 that are sized to allow material flowing from the material entry port 1613 to exit from the cutting shaft 1610. As shown in FIGS. 16A and 16B, the outlet holes 1614 are defined within the walls of the cutting shaft 1610. In some implementations, these outlet holes 1614 can be sized such that material entering the cutting shaft 1610 via the material entry port 1613 can flow out of the cutting shaft 1610 via the outlet holes 1614. In some implementations, the portion of the cutting shaft 1610 proximal the drive shaft 1608 may be solid such that all the material that enters the cutting shaft 1610 flows out of the cutting shaft 1610 via the outlet holes 1614.

The outer structure 1615 can be hollow and configured such that the cutting shaft can be disposed within the outer structure 1615. As such, the outer structure 1615 has an inner diameter that is larger than the outer diameter of the cutting shaft 1610. In some implementations, the outer structure 1615 is sized such that the cutting shaft 1610 can rotate freely within the outer structure 1615 without touching the inner walls of the outer structure 1615. The outer structure 1615 can include an opening 1616 at a distal end 1617 of the outer structure 1615 such that when the cutting shaft 1610 is disposed within the outer structure 1615, the cutting tip 1612 and the material entry port 1613 defined in the cutting shaft 1610 is exposed. In some implementations, the outer surface of the cutting shaft 1610 and the inner surface of the outer structure 1615 can be coated with a heat-resistant coating to help reduce the generation of heat when the cutting shaft 1610 is rotating within the outer structure 1615. A proximal end of the outer structure 1615 is configured to attach to the housing that houses the powered actuator 1605.

The feedthrough connector 1620 can be positioned concentrically around the portion of the cutting shaft 1610 that defines the outlet holes 1614. In some implementations, the feedthrough connector 1620 can be hollow and configured to enclose the area around the outlet holes 1614 of the cutting shaft 1610 such that material leaving the outlet holes 1614 of the cutting shaft 1610 is contained within the feedthrough connector 1620. The feedthrough connector 1620 can include an exit port 1622, which can be configured to receive the distal end of the tubular member 1630. In this way, any material within the feedthrough connector 1620 can flow into the distal end of the flexible tubular member 1630. The feedthrough connector 1620 can serve as a fluid coupler that allows fluid communication between the cutting shaft 1610 and the tubular member 1630.

The tubular member 1630 can be configured to couple to the exit port 1622 of the feedthrough connector 1620. By way of the cutting shaft 160, the feedthrough connector 1620 and the flexible tubular member 1630, the aspiration channel 1660 extends from the material entry port 1613 of the cutting shaft 1610 to the proximal end of the tubular member 1630. In some implementations, the tubular member 1630 can be configured to couple to a vacuum source at the proximal end of the tubular member 1630. As such, when a vacuum source applies suction at the proximal end of the tubular member 1630, material can enter the aspiration channel via the material entry port 1613 of the cutting shaft 1610 and flow through the aspiration channel 1660 towards the vacuum source and out of the endoscopic instrument 1600. In this way, the aspiration channel 1660 extends from one end of the endoscopic instrument to the other end of the endoscopic instrument 1600. In some implementations, a vacuum source can be applied to the tubular member 1630 such that the material at the treatment site can be suctioned from the treatment site, through the aspiration channel 1660 and withdrawn from the endoscopic instrument 1600, while the endoscopic instrument 1600 remains disposed within the instrument channel of the endoscope and inside the subject being treated. In some implementations, one or more of the surfaces of the cutting shaft 1610, the feedthrough connector 1620 or the tubular member 1630 can be treated to improve the flow of fluid. For example, the inner surfaces of the cutting shaft 1610, the feedthrough connector 1620 or the tubular member 1630 may be coated with a superhydrophobic material to reduce the risk of material removed from within the patient from clogging the suction conduit.

Examples of various types of instrument heads that can be coupled to the powered actuator 1605 are disclosed in U.S. Pat. Nos. 4,368,734, 3,618,611, 5,217,479, 5,931,848 and U.S. Pat. Publication 2011/0087260, amongst others. In some other implementations, the instrument head can include any type of cutting tip that is capable of being driven by a powered actuator, such as the powered actuator 1650, and capable of cutting tissue into small enough pieces such that the tissue can be removed from the treatment site via, the aspiration channel defined within the endoscopic instrument 1600. In some implementations, the power-driven instrument head 1680 may be configured to include a portion through which material from the treatment site can be removed. In some implementations, the circumference of the aspiration channel can be in the order of a few micrometers to a few millimeters.

In some implementations, where the powered actuator 1620 utilizes an electric current for operation, the current can be supplied via one or more conductive wires that electrically couple the powered actuator to an electrical current source. In some implementations, the electrical current source can be external to the endoscopic instrument 1600. In some implementations, the endoscopic instrument 1600 can include an energy storage component, such as a battery that is configured to supply electrical energy to the electrical actuator. In some implementations, the energy storage component can be positioned within the endoscopic instrument. In some implementations, the energy storage component or other power source may be configured to supply sufficient current to the powered actuator that cause the powered actuator to generate the desired amount of torque and/or speed to enable the cutting shaft 1610 to cut tissue material. In some implementations, the amount of torque that may be sufficient to cut tissue can be greater than or equal to about 2.5 N mm. In some implementations, the speed of rotation of the cutting shaft can be between 1000 and 5000 rpm. However, these torque ranges and speed ranges are examples and are not intended to be limiting in any manner.

The endoscopic instrument 1600 can include other components or elements, such as seals 1640 and bearings 1625, which are shown. In some implementations, the endoscopic instrument 1600 can include other components that are not shown herein but may be included in the endoscopic instrument 1600. Examples of such components can include sensors, cables, wires, as well as other components, for example, components for engaging with the inner wall of the instrument channel of an endoscope within which the endoscopic instrument can be inserted. In addition, the endoscopic instrument can include a housing that encases one or more of the powered actuator, the feedthrough connector 1620, any other components of the endoscopic instrument 1600. In some implementations, the tail portion of the endoscopic instrument 1600 can also include a flexible housing, similar to the flexible portion 165 shown in FIG. 1C, that can carry one or more flexible tubular members, such as the flexible tubular member 1630, as well as any other wires, cables or other components.

In some implementations, the endoscopic instrument can be configured to engage with the instrument channel of an endoscope in which the instrument is inserted. In some implementations, an outer surface of the head portion of the endoscopic instrument can engage with an inner wall of the instrument channel of the endoscope such that the endoscopic instrument does not experience any unnecessary or undesirable movements that may occur if endoscopic instrument is not supported by the instrument channel. In some implementations, the head portion of the body of the endoscopic instrument can include a securing mechanism that secures the head portion of the body to the inner wall of the instrument channel. In some implementations, the securing mechanism can include deploying a frictional element that engages with the inner wall. The frictional element can be a seal, an o-ring, a clip, amongst others.

FIG. 16C illustrates a schematic view of an engagement assembly of an example endoscopic instrument. FIG. 16D shows a cut-open view of the engagement assembly when the engagement assembly is disengaged. FIG. 16E shows a cut-open view of the engagement assembly when the engagement assembly is configured to engage with an instrument channel of an endoscope. As shown in FIGS. 16C and 16D, the engagement assembly 1650 includes a housing portion 1652 that defines a cylindrical groove 1654 around an outer surface 1656 of the housing portion. The groove 1654 is sized such that a compliant seal component 1670 can be partially seated within the groove 1654. A cylindrical actuation member 1660 is configured to encompass the housing portion 1652. The cylindrical actuation member 1660 can slidably move along the length of the housing portion 1652. The cylindrical actuation member 1660 is configured to engage the securing member 1670 by pressing on the surface of the securing member 1670. The actuation member 1660 can apply a force on the securing member 1670 causing the securing member 1670 to deform such that the securing member 1670 becomes flatter and wider. The securing member 1670 is configured such that when the securing member 1670 widens, the outer surface of the securing member 1670 can engage with an inner surface of the instrument channel of an endoscope in which the endoscopic instrument is inserted. In this way, when the cylindrical actuation member 1660 is actuated, the endoscopic instrument 1600 can engage with the instrument channel thereby preventing the endoscopic instrument 1600 from moving relative to the instrument channel. This can help provide stability to the operator while treating the subject. In some implementations, more than one engagement assembly 1650 can be positioned along various portions of the endoscopic instrument 1600.

Figure 17A:
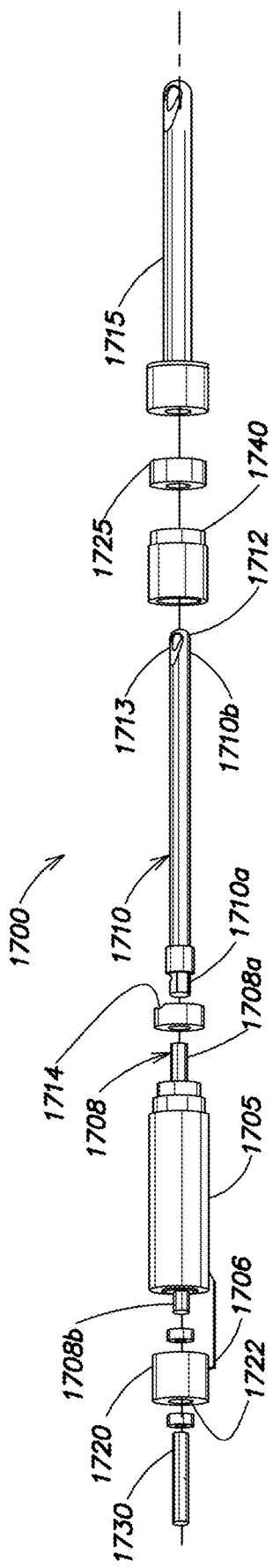
FIG. 17A illustrates an exploded view of an example endoscopic instrument according to embodiments of the present disclosure.
Figure 17B:
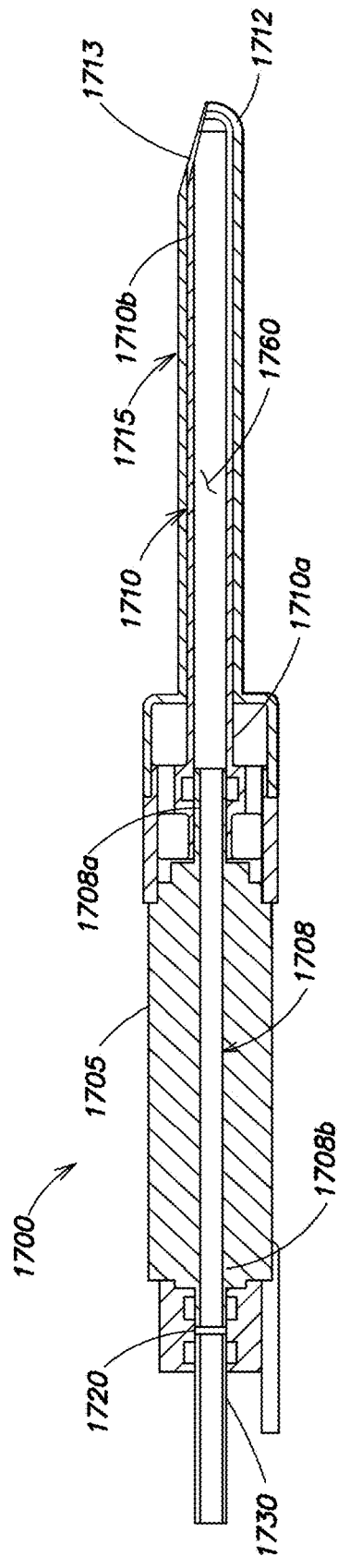
FIG. 17B illustrates a cross-sectional view of the endoscopic instrument shown in FIG. 17A according to embodiments of the present disclosure.

FIG. 17A illustrates an exploded view of an example endoscopic instrument 1700 according to embodiments of the present disclosure. FIG. 17B illustrates a cross-sectional view of the endoscopic instrument 1700. The endoscopic instrument 1700, similar to the endoscopic instrument 1600 shown in FIGS. 16A and 16B, can also be configured to be inserted within an instrument channel of an endoscope, such as the endoscope 100 depicted in FIG. 1B. The endoscopic instrument 1700, however, differs from the endoscopic instrument 1600 in that the endoscopic instrument 1700 defines an aspiration channel 1760 that extends through a powered actuator 1705. In this way, material entering a material entry port 1713 of the endoscopic instrument 1700 can flow through the endoscopic instrument 1700 and out of the endoscopic instrument in a straight line.

As shown in FIGS. 17A and 17B, the endoscopic instrument 1700 is similar to the endoscopic instrument 1600 except that the endoscopic instrument includes a different powered actuator 1705, a different cutting shaft 1710 and a different feedthrough connector 1720. The powered actuator 1705 is similar to the powered actuator 1605 shown in FIG. 16A but differs in that the powered actuator 1705 includes a drive shaft 1708 that is hollow and extends through the length of the powered actuator 1705. Since some of the components are different, the manner in which the endoscopic instrument is assembled is also different.

In some implementations, the powered actuator 1605 can be any actuator capable of having a hollow shaft that extends through the length of the motor. The distal end 1708a of the drive shaft 1708 includes a first opening and is coupled to the proximal end 1711 of the cutting shaft 1705. Unlike cutting shaft 1610, the cutting shaft 1710 includes a fluid outlet hole 1714 at the bottom of the cutting shaft 1710. As a result, the entire length of the cutting shaft 1710 is hollow. The proximal end 1708b of the drive shaft 1708 is configured to couple to the feedthrough connector 1720, which differs from the feedthrough connector 1620 in that the feedthrough connector 1720 includes a hollow bore 1722 defining a channel in line with the proximal end of the drive shaft such that the drive shaft 1708 and the hollow bore 1722 are fluidly coupled. The hollow bore 1722 can be configured to couple to the flexible tubular member 1730, which like the flexible tubular member 1630, extends from the feedthrough connector at a distal end to a proximal end that is configured to couple to a vacuum source.

As shown in FIGS. 17A and 17B, the drive shaft 1708 can be hollow, such that the drive shaft 1708 defines a first opening at a distal end 1708a and a second opening at a proximal end 1708b of the drive shaft 1708. The cutting shaft 1710 is also hollow and defines an opening 1714 at the bottom end 1710a of the cutting shaft 1710. The distal end 1708a of the drive shaft 1708 is configured to couple to the bottom end 1710a of the cutting shaft 1710 such that the first opening of the drive shaft 1708 is aligned with the opening at the bottom end 1710a of the cutting shaft 1710. In this way, the drive shaft 1708 can be fluidly coupled to the cutting shaft 1710. A distal end 1710b of the cutting shaft 1710 includes a cutting tip 1712 and the material entry port 1713.

The proximal end 1708a of the drive shaft 1708 is fluidly coupled to a distal end of the flexible tubular member 1730 via the feedthrough connector 1720. In some implementations, the feedthrough connector 1720 couples the drive shaft and the flexible tubular member such that the flexible tubular member does not rotate with the drive shaft. The proximal end of the flexible tubular member can be configured to couple to a vacuum source.

As shown in FIG. 17B, the endoscopic instrument 1700 defines an aspiration channel 1760 that extends from the material entry port 1713 through the cutting shaft, the drive shaft, the feedthrough connector 1720 to the second end of the flexible tubular member 1730. In this way, material that enters the material entry port 1713 can flow through the length of the endoscopic instrument and exit from the endoscopic instrument at the second end of the endoscopic instrument.

Other components of the endoscopic instrument 1700 are similar to those shown in the endoscopic instrument 1600 depicted in FIGS. 16A and 16B. For example, the outer structure 1715, the encoding component 1606, the seals and the bearings may be substantially similar to the outer structure 1615, the encoding component 1606, the seals 1640 and the bearings 1625 depicted in FIG. 16. Other components, some of which are shown, may be included to construct the endoscopic instrument and for proper functioning of the instrument.

FIG. 18A illustrates an exploded view of an example endoscopic instrument 1800 according to embodiments of the present disclosure. FIG. 18B illustrates a cross-sectional view of the endoscopic instrument 1800. The endoscopic instrument 1800, similar to the endoscopic instrument 1700 shown in FIGS. 17A and 17B, can also be configured to be inserted within an instrument channel of an endoscope, such as the endoscope 100 depicted in FIG. 1B. The endoscopic instrument 1800, however, differs from the endoscopic instrument 1700 in that the endoscopic instrument 1800 includes a pneumatic or hydraulically powered actuator 1805.

In some implementations, the powered actuator 1802 includes a tesla turbine that includes a tesla rotor 1805, a housing 1806 and a connector 1830 that along with the housing 1806 encases the tesla rotor 1805. The tesla rotor 1805 can include a plurality of disks 1807 spaced apart and sized such that the tesla rotor 1805 fits within the housing. In some implementations, the tesla rotor can include between 7 and 13 disks having a diameter between about 2.5 mm and 3.5 mm and thicknesses between 0.5 mm to 1.5 mm. In some implementations, the disks are separated by gaps that range from 0.2 mm to 1 mm. The tesla turbine 1802 also can include a hollow drive shaft 1808 that extends along a center of the tesla rotor 1805. In some implementations, a distal end 1808a of the drive shaft 1808 is configured to be coupled to a cutting shaft 1810 such that the cutting shaft 1810 is driven by the tesla rotor. That is, in some implementations, the cutting shaft 1810 rotates as the drive shaft 1808 of the tesla rotor 1805 is rotating. In some implementations, the cutting shaft 1810 can include outlet holes similar to the cutting shaft 1610 shown in FIG. 16A. In some such implementations, the feedthrough connector fluidly couples the cutting shaft and the flexible portion similar to the feedthrough connector 1630 shown in FIG. 16A.

The connector 1830 of the tesla turbine 1802 can include at least one fluid inlet port 1832 and at least one fluid outlet port 1834. In some implementations, the fluid inlet port 1832 and the fluid outlet port 1834 are configured such that fluid can enter the tesla turbine 1802 via the fluid inlet port 1832, cause the tesla rotor 1805 to rotate, and exit the tesla turbine 1802 via the fluid outlet port 1834. In some implementations, the fluid inlet port 1832 is fluidly coupled to a fluid inlet tubular member 1842 configured to supply fluid to the tesla rotor via the fluid inlet port 1832. The fluid outlet port 1834 is fluidly coupled to a fluid outlet tubular member 1844 and configured to remove the fluid supplied to the tesla turbine 1802. The amount of fluid being supplied and removed from the tesla turbine 1802 can be configured such that the tesla rotor 1805 can generate sufficient torque, while rotating at a sufficient speed to cause the cutting shaft 1810 to cut tissue at a treatment site. In some implementations, the fluid can be air or any other suitable gas. In some other implementations, the fluid can be any suitable liquid, such as water. Additional details related to how fluid can be supplied or removed from pneumatic or hydraulic actuators, such as the tesla turbine 1802 has been described above with respect to FIGS. 4A-15.

The connector 1830 also includes a suction port 1836 that is configured to couple to an opening defined at a proximal end 1808b of the hollow drive shaft 1808. The suction port 1836 is further configured to couple to a distal end of a flexible tubular member 1846, similar to the flexible tubular member 1730 shown in FIG. 17A, which is configured to couple to a vacuum source at a proximal end. In some implementations, a flexible tubular housing can include one or more of the fluid inlet tubular member 184, fluid outlet tubular member 1844 and the flexible tubular member 1846. In some implementations, the flexible tubular housing can include other tubular members and components that extend from the head portion of the endoscopic instrument to the proximal end of the tail portion of the endoscopic instrument 1800.

The cutting shaft 1810 and an outer structure 1815 are similar to the cutting shaft 1710 and the outer structure 1715 of the endoscopic instrument 1700 depicted in FIG. 17A. The cutting shaft 1810 is hollow and defines an opening at a proximal end 1810b of the cutting shaft 1810. The proximal end 1810b of the cutting shaft 1810 is configured to couple to a distal end 1808a of the drive shaft 1808 such that an opening at the distal end 1808a of the drive shaft 1808 is aligned with the opening defined at the proximal end 1808*b* of the cutting shaft 1810. In this way, the drive shaft 1808 can be fluidly coupled to the cutting shaft 1810. A distal end 1810*b* of the cutting shaft 1810 includes a cutting tip 1812 and a material entry port 1813 similar to the cutting shafts 1610 and 1710 shown in FIGS. 16A and 17A.

In some implementations, an irrigation opening 1852 can be formed in the housing 1806. The irrigation opening 1852 is configured to be fluidly coupled to the aspiration channel 1860. In some such implementations, the irrigation opening 1852 is configured to be fluidly coupled to a gap (not clearly visible) that separates the walls of outer structure 1815 and the cutting shaft 1810. In this way, fluid supplied to the tesla turbine 1802 can escape via the irrigation opening 1852 in to the gap. The fluid can flow towards the material entry port 1813 of the cutting shaft 1810, through which the fluid can enter the aspiration channel 1860. In some implementations, since the aspiration channel 1860 is fluidly coupled to a vacuum source, the fluid from the tesla turbine 1802 can be directed to flow through the aspiration channel 1860 as irrigation fluid along with any other material near the material entry port 1813. In this way, the irrigation fluid can irrigate the aspiration channel 1860 to reduce the risk of blockages.

In addition, as the irrigation fluid flows in the gap separating the outer structure 1815 and the cutting shaft 1810, the irrigation fluid can serve to reduce the generation of heat. In some implementations, one or both of the cutting shaft 1810 and the outer structure 1815 can be coated with a heat-resistant layer to prevent the cutting shaft and the outer structure from getting hot. In some implementations, one or both of the cutting shaft 1810 and the outer structure 1815 can be surrounded by a heat-resistant sleeve to prevent the cutting shaft 1810 and the outer structure 1815 from getting hot.

In some implementations, other types of hydraulically or pneumatically powered actuators can be utilized in place of the tesla turbine. In some implementations, a multi-vane rotor can be used. In some such implementations, the powered actuator can be configured to be fluidly coupled to a fluid inlet tubular member and a fluid outlet tubular member similar to the tubular members 1842 and 1844 shown in FIG. 18B.

As described above with respect to the endoscopic instruments 1600, 1700 and 1800 depicted in FIGS. 16A, 17A and 18A, an endoscopic instrument is configured to meet certain size requirements. In particular, the endoscopic instrument can be long enough such that when the endoscopic instrument is completely inserted into the endoscope, the power-driven instrument head can extend beyond the face of the endoscope at one end such that the cutting tip is exposed, while the tail portion of the endoscopic instrument can extend out of the other end of the endoscope such that the tail portion can be coupled to a vacuum source. As such, in some implementations, the endoscopic instrument may be configured to be longer than the endoscopes in to which the endoscopic instrument will be inserted. Further, since endoscopes have instrument channels that have different diameters, the endoscopic instrument may also be configured to have an outer diameter that is sufficiently small such that the endoscopic instrument can be inserted into the instrument channel of the endoscope in to which the endoscopic instrument will be inserted.

Some endoscopes, such as colonoscopes, can have instrument channels that have an inner diameter that can be as small as a few millimeters. In some implementations, the outer diameter of the endoscopic instrument can be less than about 3.2 mm. As such, powered actuators that are part of the endoscopic instrument may be configured to have an outer diameter than is less than the outer diameter of the endoscopic instrument. At the same time, the powered actuators may be configured to be able to generate sufficient amounts of torque, while rotating at speeds sufficient to cut tissue at a treatment site within a subject.

In some other implementations, the endoscopic instrument can be configured such that a powered actuator is not housed within the endoscopic instrument at all or at least within a portion of the endoscopic instrument that can be inserted within the instrument channel of an endoscope. Rather, the endoscopic instrument includes a flexible cable that is configured to couple a power-driven instrument head of the endoscopic instrument to a powered actuator that is located outside of the endoscope.

Figure 19A:
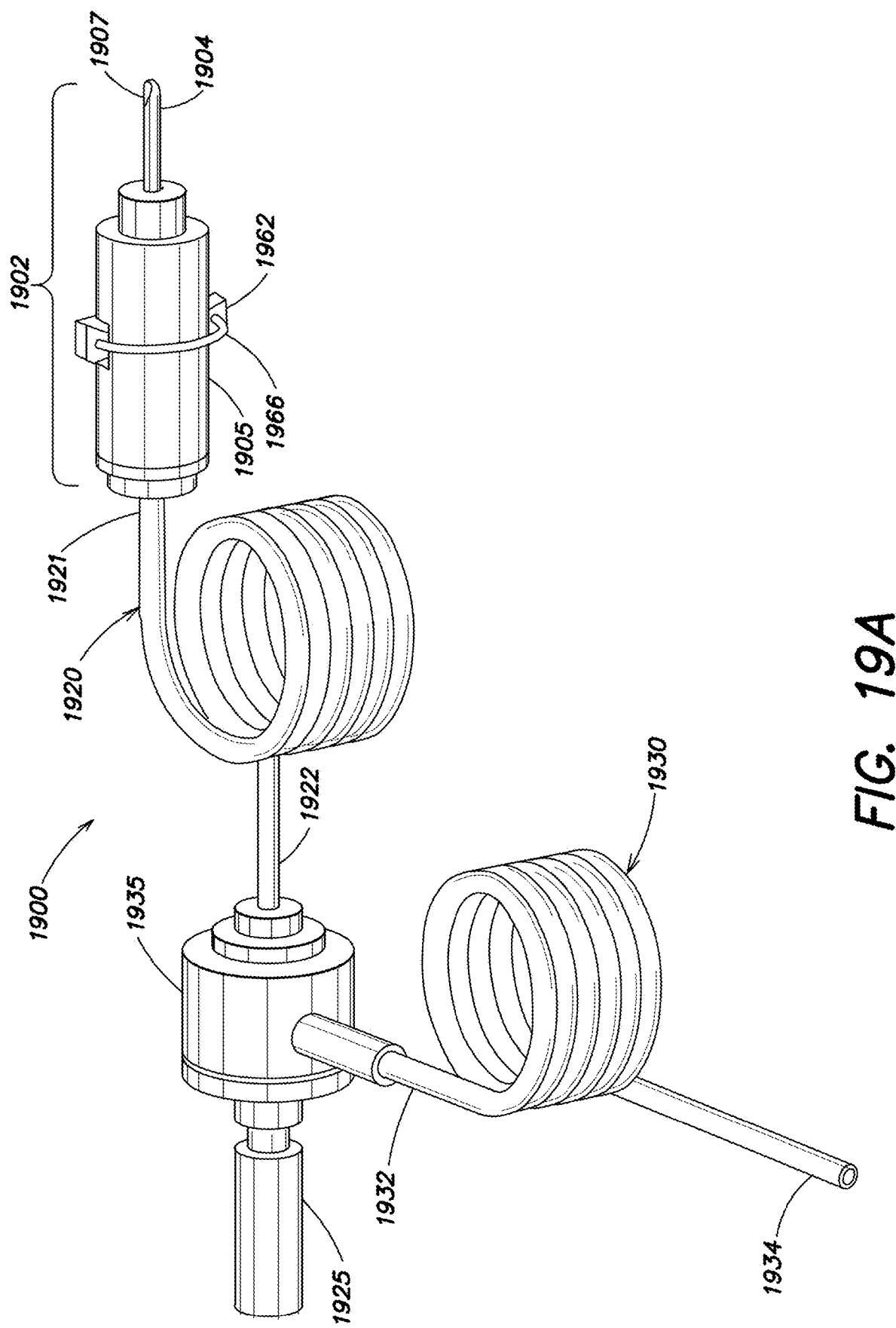
FIG. 19A illustrates an example endoscopic instrument that is coupled to a powered actuation and vacuum system according to embodiments of the present disclosure.

FIG. 19A illustrates an example endoscopic instrument 1900 that is coupled to a powered actuation and vacuum system 1980. The endoscopic instrument includes a head portion 1902 and a tail portion. The tail portion includes the flexible cable 1920, which can provide torque to the head portion 1902. The powered actuation and vacuum system 1980 includes a powered actuator 1925, a coupler 1935 and a vacuum tubing 1930 configured to couple to the couple 1935 at a first end 1932 and couple to a vacuum source at a second end 1934. In some implementations, the flexible cable 1920 can be hollow and configured to carry fluid from the head portion 1902 to the coupler 1935.

Figure 19B:
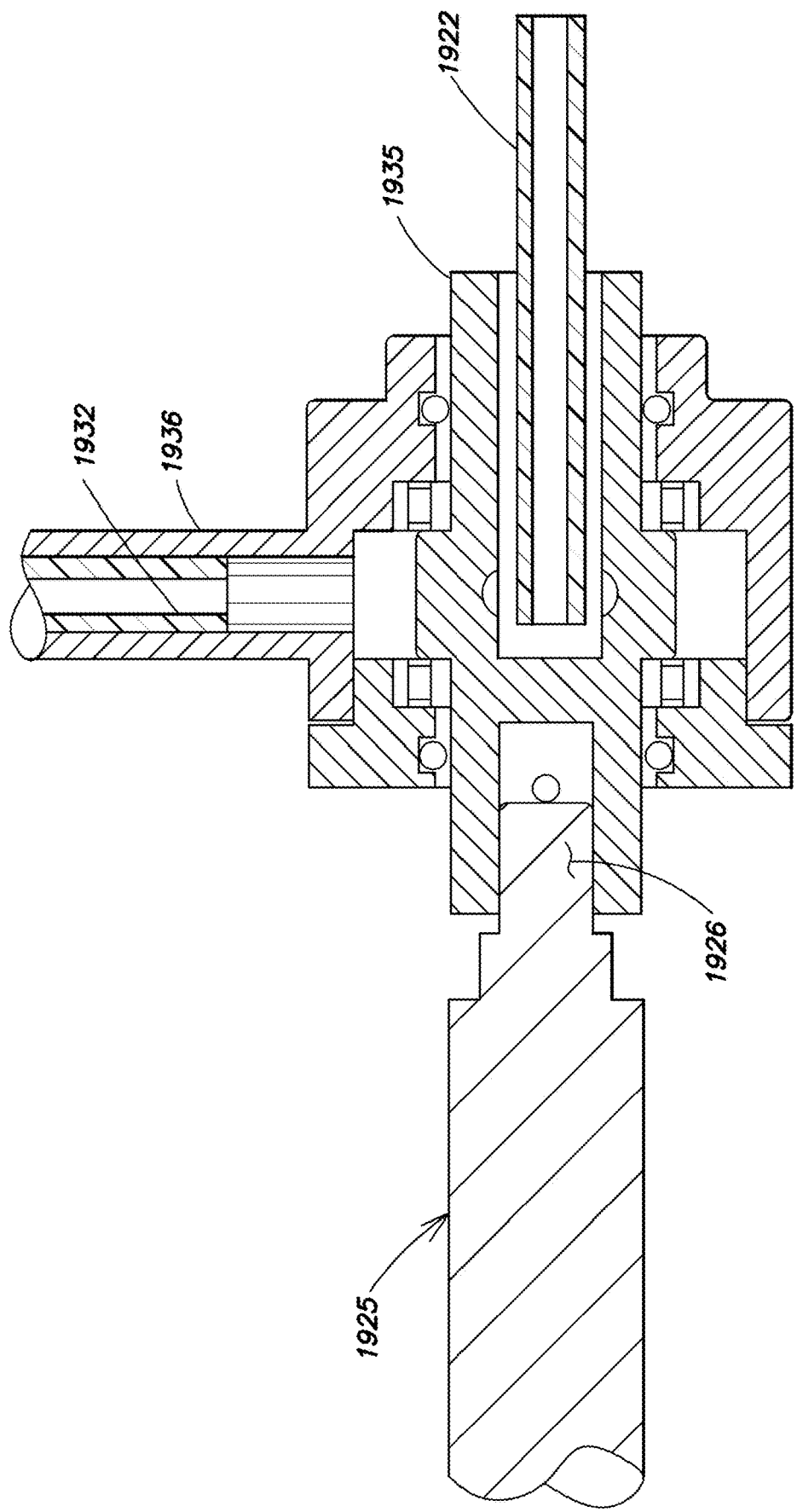
FIG. 19B illustrates a cross-section view of the powered actuation and vacuum system shown in FIG. 19A according to embodiments of the present disclosure.

FIG. 19B illustrates a cross-section view of the powered actuation and vacuum system 1980 of FIG. 19A. The powered actuator 1925 includes a drive shaft 1926 that is mechanically coupled to a proximal end 1922 of the flexible cable 1920. In some implementations, the drive shaft 1926 and the flexible cable 1920 are mechanically coupled via the coupler 1935. The coupler 1935 includes a vacuum port 1936 to which a first end 1932 of the vacuum tubing 1930 can be fluidly coupled. The coupler 1935 can be enclosed such that the vacuum tubing 1930 and the flexible cable are fluidly coupled. In this way, suction applied in the vacuum tubing 1930 can be applied all the way through the flexible cable 1920 to the head portion 1902 of the endoscopic instrument 1900. Further, any material that is in the flexible cable 1920 can flow through the flexible cable to the vacuum tubing 1930 via the coupler 1935. In some implementations, the coupling between the flexible cable and the vacuum tubing can occur within the head portion 1902. In such implementations, the coupler 1935 may be configured to be small enough to be positioned within the head portion 1902.

Figure 19C:
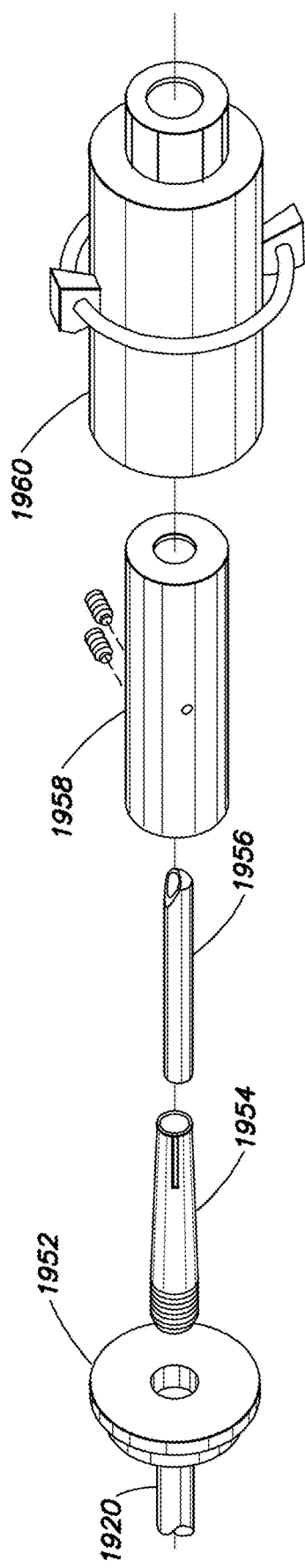
FIG. 19C illustrates an exploded view of an example head portion of the endoscopic instrument shown in FIG. 19A according to embodiments of the present disclosure.

FIG. 19C illustrates an exploded view of an example head portion of the endoscopic instrument 1900 shown in FIG. 19A. The head portion includes a housing cap 1952, a collet 1954, a cutting shaft 1956, a shaft coupler 1958 and a head portion housing 1960. In some implementations, the collet 1954 is slightly tapered towards a distal end such that the collet 1954 can couple with the cutting shaft 1956 that is disposed within the collet 1954. The shaft coupler 1958 is configured to couple the cutting shaft to the distal end of the flexible cable 1920. The head portion 1960 and the housing cap 1952 are configured to house the shaft coupler 1958.

Figure 19D:
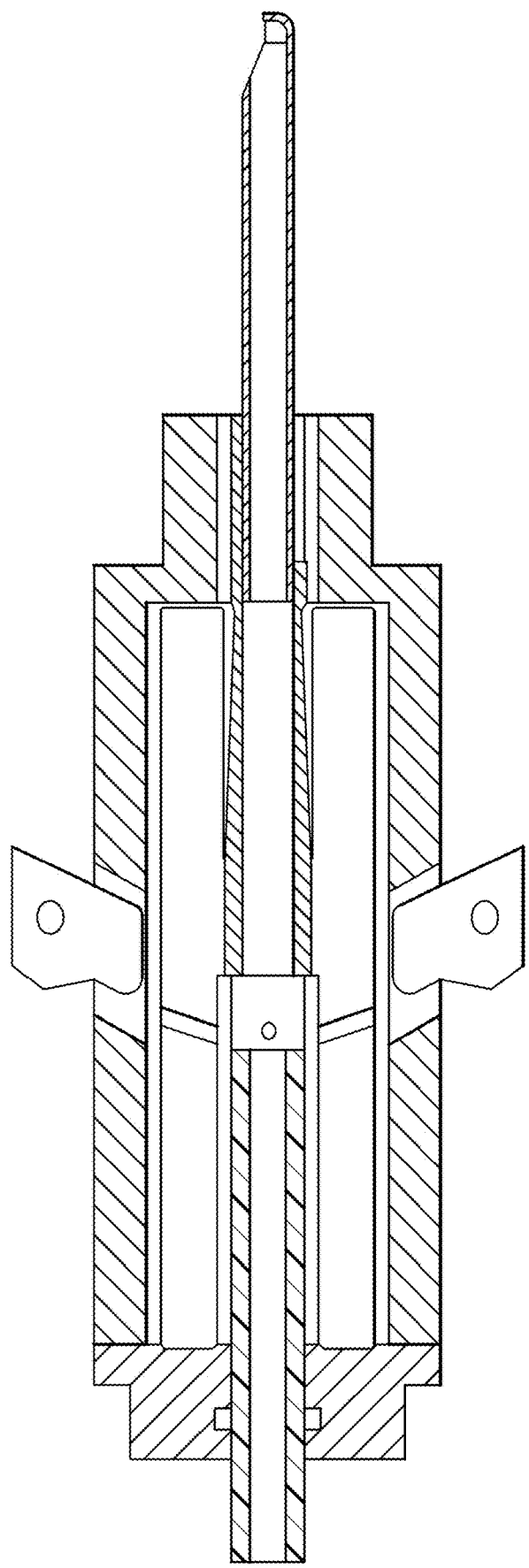
FIG. 19D illustrates a cut-open view of a portion of the endoscopic instrument having an engagement assembly according to embodiments of the present disclosure

FIG. 19D illustrates a cut-open view of a portion of the endoscopic instrument 1900 having an engagement assembly. In some implementations, the head portion housing 1960 can include an engagement assembly for engaging with the inner walls of an instrument channel. The engagement assembly can be similar to the engagement assembly 1650 shown in FIG. 16C. In some implementations, the engagement assembly can be actuated via a vacuum source.

FIG. 19E shows a cut-open view of the engagement assembly shown in FIG. 19D in a disengaged position. FIG. 19F shows a cut-open view of the engagement assembly shown in FIG. 19D in an engaged position.

The engagement assembly can include a pair of vacuum actuated members 1962 that are configured to rotate between an extended position in which the members 1962 are extended outwardly to engage with a wall of the instrument channel 1990 and a retracted position in which the members 1962 are positioned such that they lie substantially parallel to the walls of the instrument channel 1990. The grooves 1964 are fluidly coupled to an aspiration channel 1970 defined within the flexible cable 1920. In some implementations, fluid channels 1966 fluidly couple the grooves 1964 to the aspiration channel 1970. When a vacuum source is applied to the aspiration channel 1970, a suction force is applied to the members 1962 causing them to move from a retracted position (as shown in FIG. 19E) to an extended position (as shown in FIG. 19F). In some implementations, the engagement assembly can also include an outer ring supported by the vacuum actuated members 1964. The outer ring 1966 can be configured to assist in guiding the endoscopic instrument through the instrument channel of the endoscope. In particular, the outer ring can prevent the endoscopic instrument from tilting to one side causing the power-driven instrument head from jarring against the instrument channel.

The endoscopic instrument 1900 is similar to the endoscopic instruments 1600, 1700 and 1800 depicted in FIGS. 16A-18A respectively but differs from them in that the endoscopic instrument 1900 does not include a powered actuator within the head portion 1902 of the endoscopic instrument 1900. Instead, the endoscopic instrument 1900 includes a flexible cable 1920 for providing torque to a power-driven instrument head 1904 of the endoscopic instrument 1900. In some implementations, the power-driven instrument head 1904 can be similar to the power-driven instrument heads depicted in FIGS. 16A-18A. In some implementations, the flexible cable 1920 can be hollow such that fluid can flow through the flexible cable 1920. In some such implementations, a proximal end 1922 of the flexible cable 1920 can be configured to couple to a vacuum source, while a distal end 1921 of the flexible cable 1920 can be coupled to the power-driven instrument head 1904. In this way, fluid that enters a material entry port 1907 can flow through the power-driven instrument head 1904 and into the flexible cable 1920, from which the fluid can flow through the flexible cable 1920 and be removed from the endoscopic instrument 1900 at the proximal end 1922 of the flexible cable 1920.

In some implementations, a flexible cable, such as the flexible cable 1920 can replace a powered actuator and drive shaft that are housed within an endoscopic instrument. For example, the endoscopic instruments 1600, 1700 and 1800 depicted in FIGS. 16A, 17A and 18A can be configured to utilize a flexible cable that is coupled to a cutting shaft of a power-driven instrument head at a distal end and coupled to a powered actuator located outside the endoscopic instrument at a proximal end. The powered actuator located outside the endoscopic instrument may be significantly larger than the powered actuators 1605, 1705 or 1805. As the powered actuator is actuated, torque generated by the powered actuator can be translated from the powered actuator to the power-driven instrument head via the flexible cable. The flexible cable 1920 is configured to translate torque from the powered actuator to the cutting shaft. In some implementations, the flexible cable 1920 is or includes a fine coil with multiple threads and multiple layers, which can transmit the rotation of one end of the flexible cable to an opposite end of the flexible cable. The flexibility of the cable allows the coil to maintain performance even in sections of the coil that are bent. Examples of the flexible cable 1920 include torque coils made by ASAHI INTECC USA, INC located in Santa Ana, Calif., USA. In some implementations, the flexible cable 1920 can be surrounded by a sheath to avoid frictional contact between the outer surface of the flexible cable and other surfaces. In some implementations, the flexible cable 1920 can be coated with Polytetrafluoroethylene (PFTE) to reduce frictional contact between the outer surface of the flexible cable and other surfaces.

Figure 20:
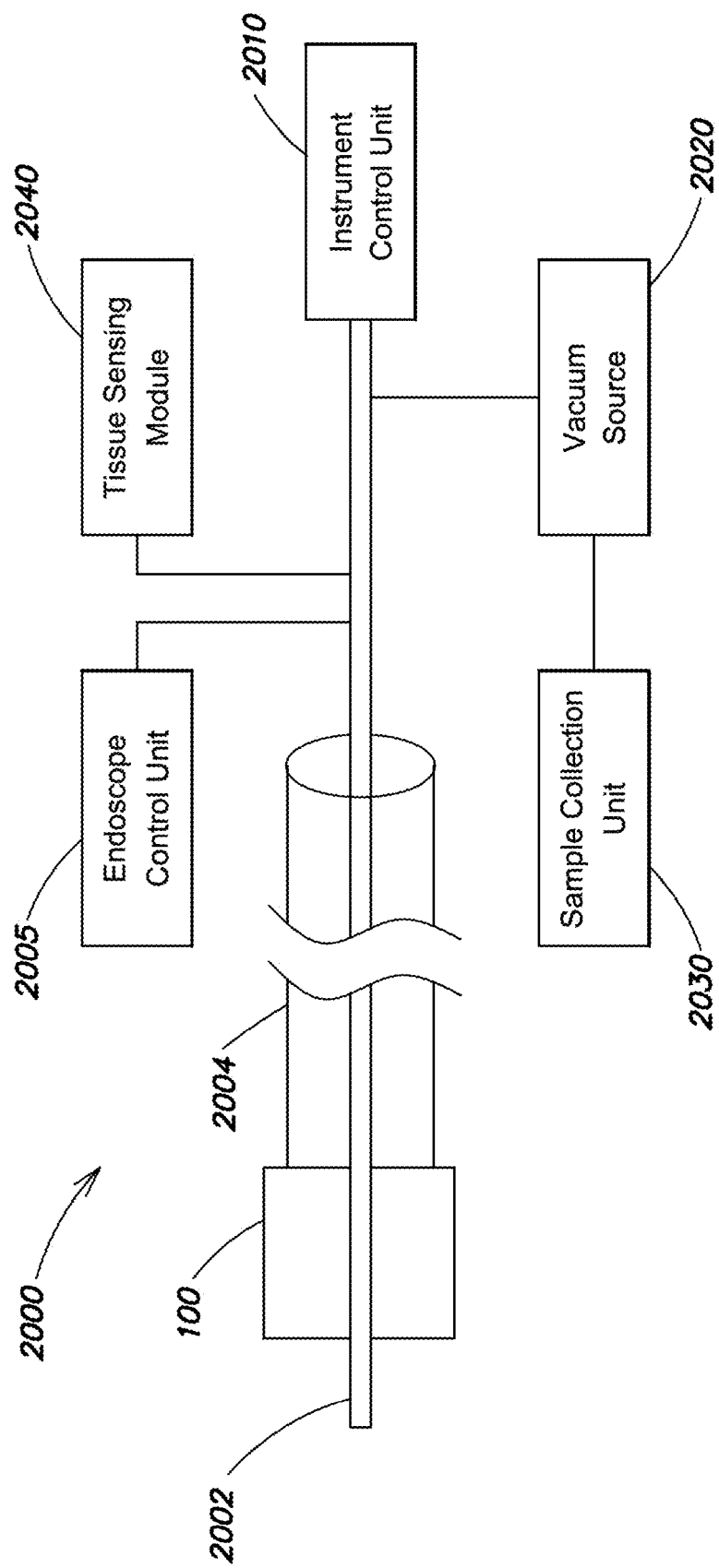
FIG. 20 is a conceptual system architecture diagram illustrating various components for operating the endoscopic instrument according to embodiments of the present disclosure.

FIG. 20 is a conceptual system architecture diagram illustrating various components for operating the endoscopic instrument according to embodiments of the present disclosure. The endoscopic system 2000 includes an endoscope 100 fitted with an endoscopic instrument 2002 that includes a flexible tail portion 2004. The endoscopic instrument can, for example, be the endoscopic instrument 220, 1600, 1700, 1800 or 1900 shown in FIGS. 4A-14, 16A, 17A, 18A and 19A. The system also includes an endoscope control unit 2005 that controls the operation of the endoscope 100 and an instrument control unit 2010 that controls the operation of the endoscopic instrument 2002.

In addition, the endoscopic instrument also includes a vacuum source 1990, a sample collection unit 2030 and a tissue sensing module 2040. The vacuum source 1990 is configured to fluidly couple to a flexible tubular member that forms a portion of the aspiration channel. In this way, material that flows from the endoscopic instrument through the aspiration channel towards the vacuum source 1990 can get collected at 2030 sample collection unit. The tissue sensing module can be communicatively coupled to a tissue sensor disposed at a distal tip of the endoscopic instrument 2000. In some such implementations, the tissue sensing module can also be configured to be communicatively coupled to the instrument control unit 2010 such that the tissue sensing module can send one or more signals instructing the control unit 2010 to stop the actuation of the powered actuator.

In some implementations in which the powered actuator is electrically actuated and disposed within the endoscopic instrument, the powered actuator can be electrically coupled to the instrument control unit 2010. In some such implementations, the powered actuator is coupled to the control unit via one or more electric cables. In some implementations, the powered actuator may be battery operated in which case, the tubing may include cables extending from the control unit to the powered actuator or the battery for actuating the powered actuator.

In some implementations in which the power-driven instrument head is coupled to a flexible torque coil that couples the power-driven instrument head to a powered actuator that resides outside of the endoscope, the powered actuator can be a part of the instrument control unit.

In various embodiments of the present disclosure, an endoscope, comprises a first end and a second end separated by a flexible housing, an instrument channel extending from the first end to the second end, and an endoscopic instrument comprising a debriding component and a sample retrieval conduit disposed within the instrument channel. The endoscopic instrument may further include a flexible tubing in which the sample retrieval conduit is partially disposed, the flexible tubing extending from the first end to the second end of the endoscope. The flexible tubing may also include a pneumatic air entry conduit and a fluid irrigation conduit. In various embodiments, the debriding component may include a turbine assembly and a cutting tool. In various embodiments in which the endoscope is configured to have a built in endoscopic instrument, the instrument channel may have a diameter that is larger than the instrument channels of existing endoscopes. In this way, larger portions of debrided material may be suctioned from within the patient's body without clogging the suction conduit.

In other embodiments, an endoscope may include a first end and a second end separated by a flexible housing; an instrument channel extending from the first end to the second end; and an endoscopic instrument coupled to the instrument channel at the first end of the endoscope, the endoscopic instrument comprising a debriding component and a sample retrieval conduit partially disposed within the instrument channel. In some embodiments, the endoscopic instrument may be removably attached to the endoscopic instrument.

In other embodiments of the present disclosure, an endoscopic system, includes an endoscope comprising a first end and a second end separated by a flexible housing and an instrument channel extending from the first end to the second end and an endoscopic instrument coupled to the instrument channel at the first end of the endoscope. The endoscopic instrument may include a debriding component and a flexible tubing having a length that is greater than the length of the endoscope. Moreover, the flexible tubing may include a sample retrieval conduit, an pneumatic air entry conduit, and a fluid irrigation conduit, a disposable cartridge configured to couple with the sample retrieval conduit proximal the second end of the endoscope, a pressurized air source configured to couple with the pneumatic air entry conduit proximal the second end of the endoscope, and a fluid irrigation source configured to couple with the fluid irrigation conduit proximal the second end of the endoscope. In various embodiments, the endoscope may also include at least one camera source and at least one light source. In some embodiments of the present disclosure, the pneumatic air entry conduit supplies pressurized air to a turbine assembly of the debriding component proximal the first end of the endoscope and the fluid irrigation conduit supplies irrigation fluid to the sample retrieval conduit proximal the first end of the endoscope.

As described above with respect to FIGS. 19A-19C, the endoscopic tool can include a flexible cable that can be configured to be driven by a powered actuator that resides outside the endoscopic tool itself. The flexible cable can be a torque coil or rope.

Figure 21B:
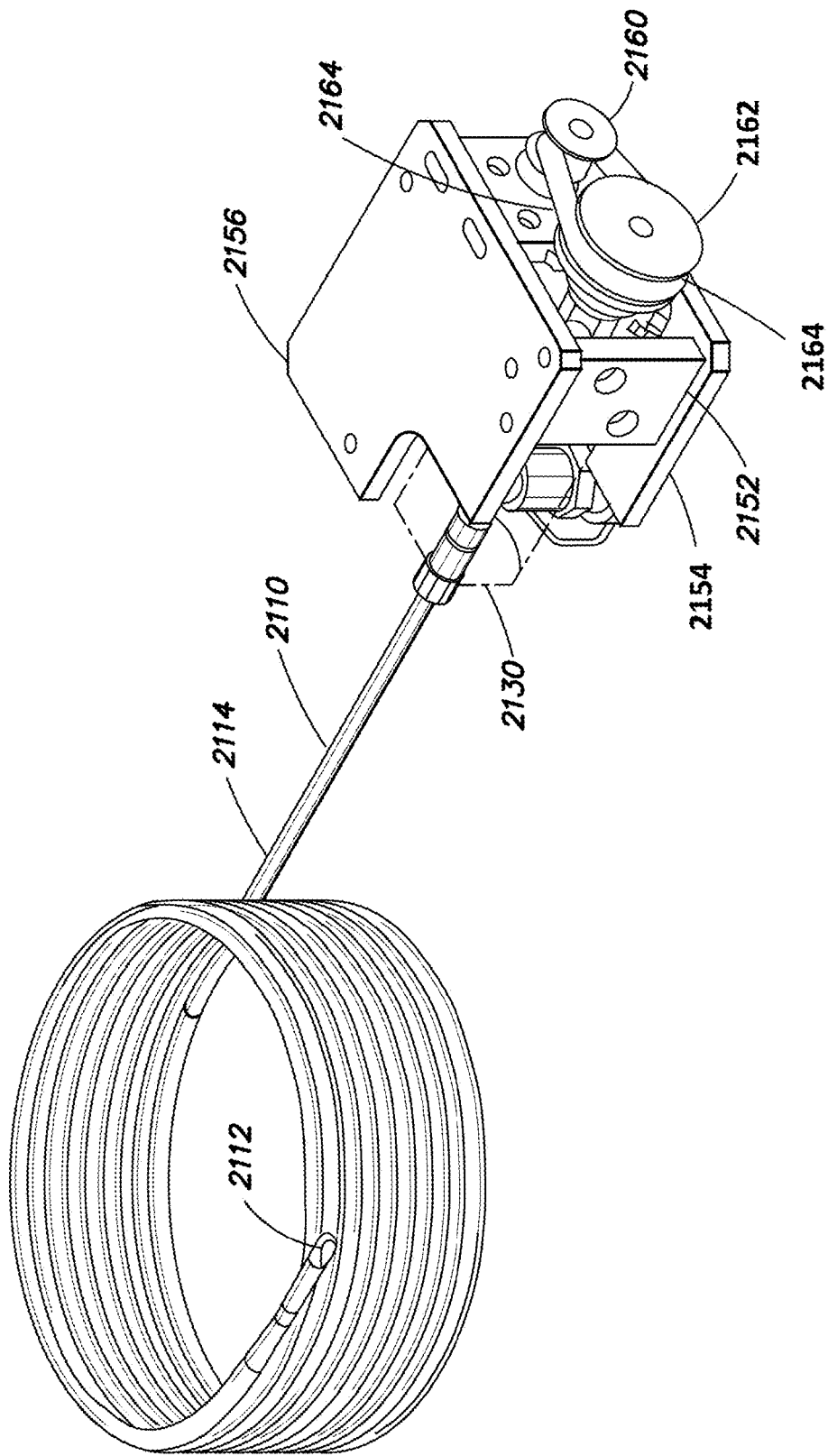
FIGS. 21AA-21F illustrate aspects of an endoscopic assembly according to embodiments of the present disclosure.
Figure 21C:
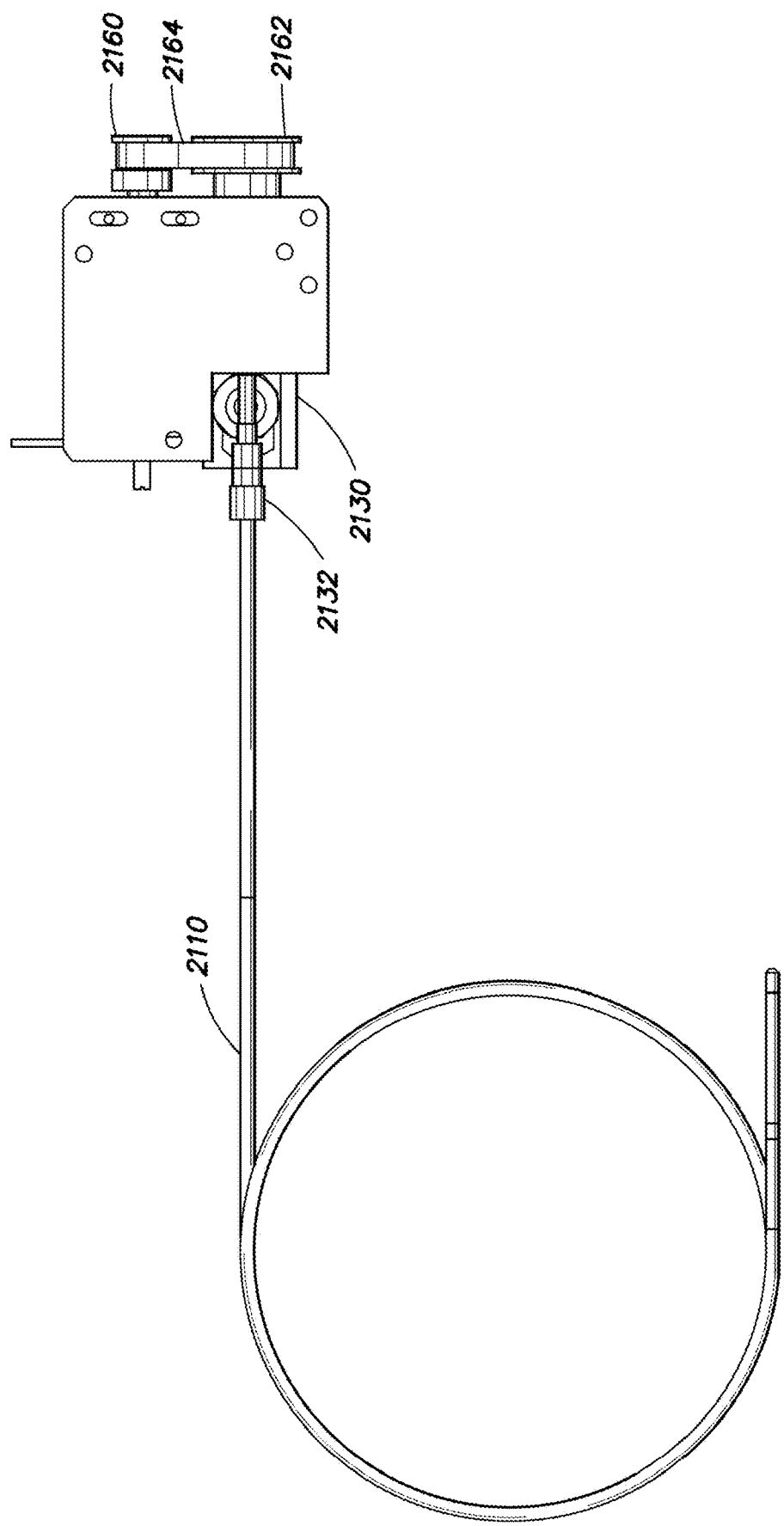
Figure 21D:
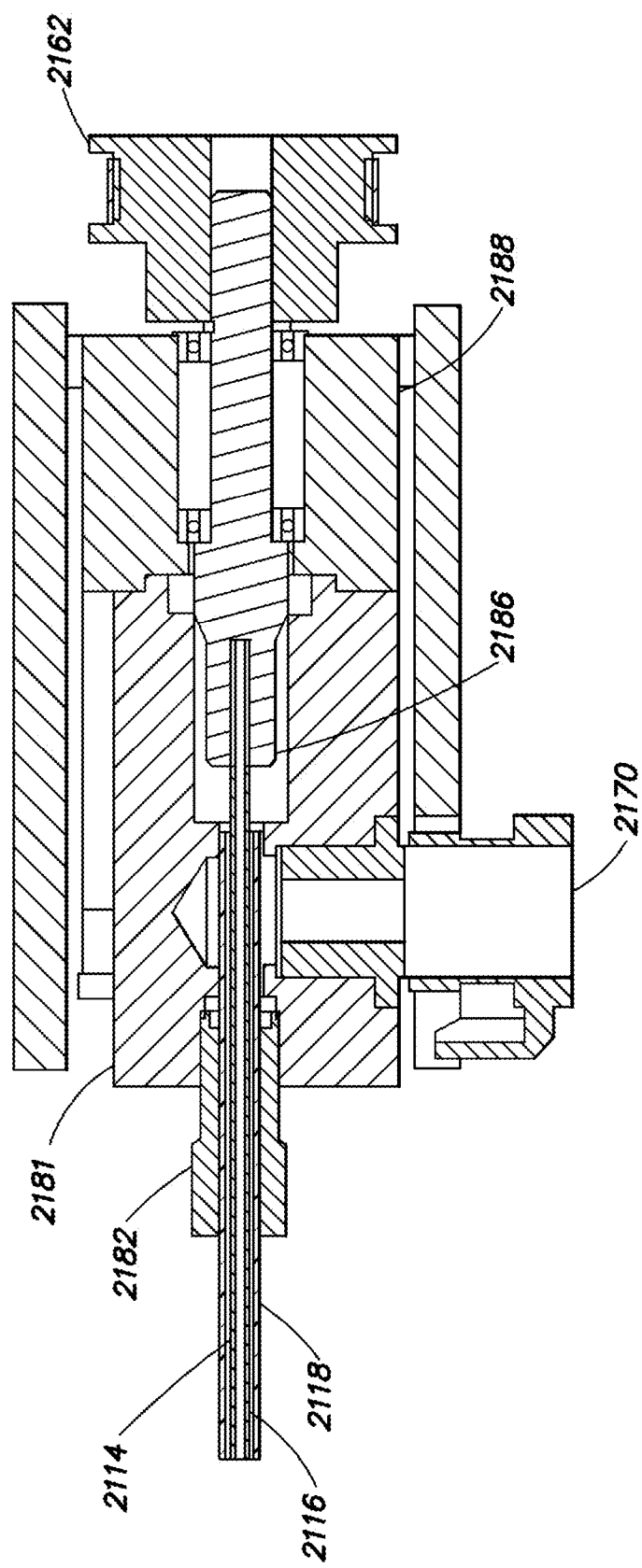
Figure 22A:
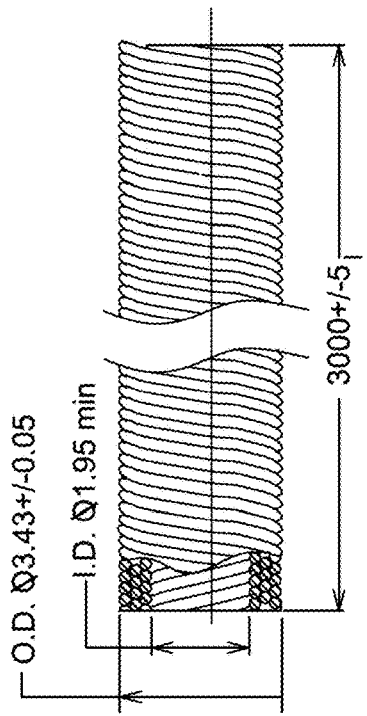
FIGS. 22A-22H show various implementations of example flexible cables according to embodiments of the present disclosure.
Figure 22B:
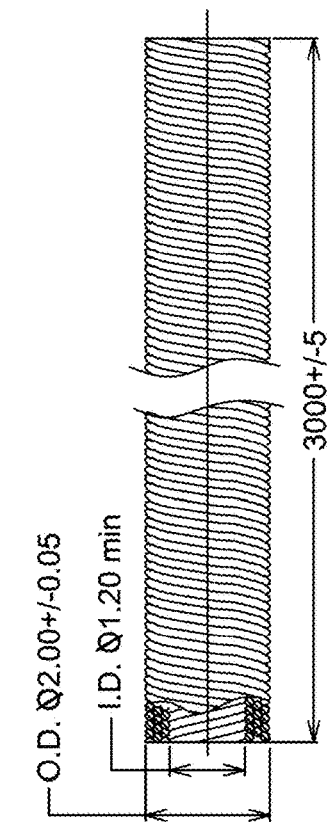
Figure 22C:
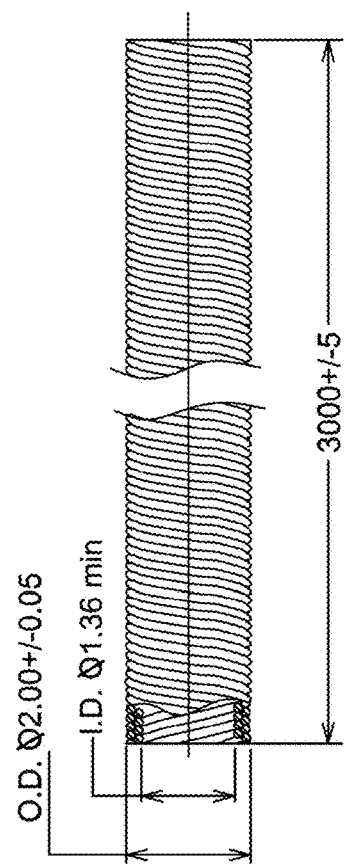
Figure 22D:
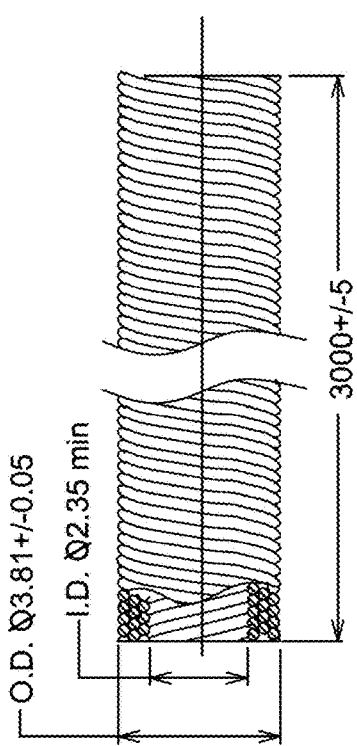
Figure 22E:
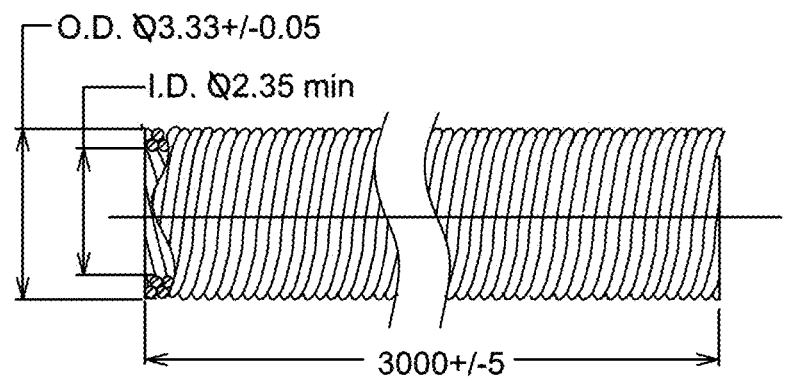
Figure 22F:
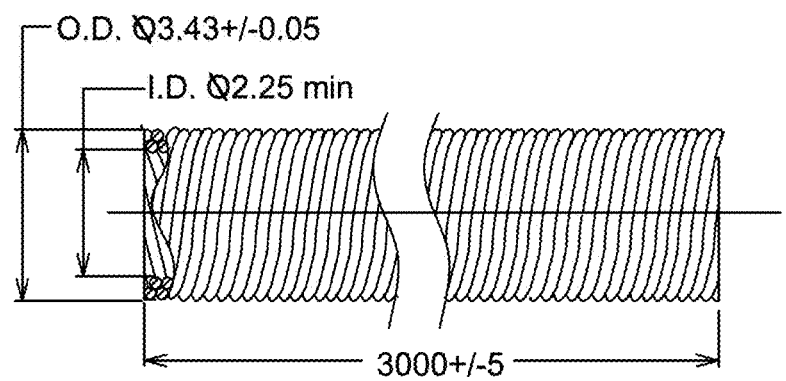
Figure 22G:
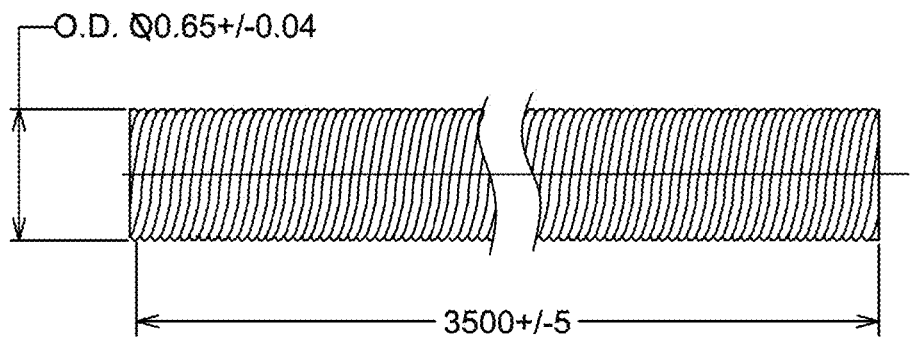
Figure 22H:
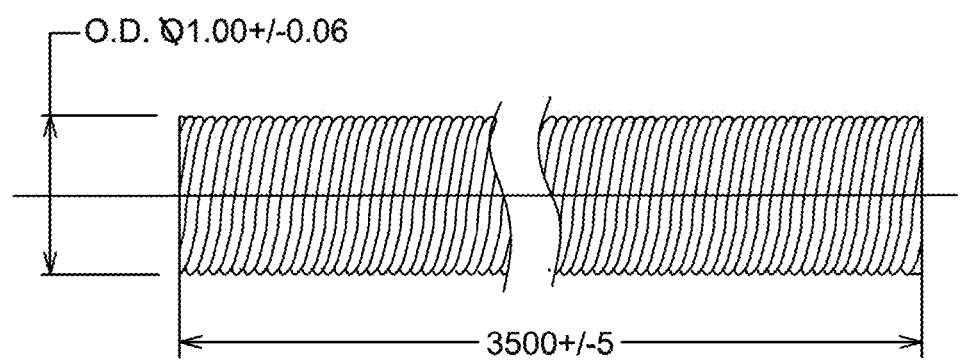

FIGS. 21AA-21F illustrate aspects of an endoscopic assembly. In particular, FIGS. 21AA-21F illustrate various views of an endoscopic tool 2110 coupled to a powered actuator 2120 encased in a housing 2150. As shown in FIG. 21, the powered actuator 2120 can be a motor that is operatively coupled to a flexible cable via a pulley system. A casing 2150 including one or more structures, such as a base plate 2152, one or more side plates 2154 and a top plate 2156 can encase the motor 2120. A coupling component 2130 can be configured to couple the flexible cable 2114 to the motor 2120, while providing a suction mechanism to remove any fluids passing through the endoscopic tool 2110. The coupling component 2130 can include a suction port 2170 through which fluid within the endoscopic tool 2110 can be removed and collected. In FIG. 21B, a pair of pulleys 2160 and 2162 coupled to a timing belt 2164 are configured such that rotational energy from the motor is transferred to one end of the flexible cable 2114. The other end of the flexible cable 2114 can be coupled to a cutting member 2112. Additional details regarding the flexible cable 2114 are described herein with respect to FIGS. 22A-22H.

FIGS. 22A-22H show various implementations of example flexible cables. In some implementations, the flexible cable can be made of three separate threads or wires. An inner wire can have a left-hand wound, a middle wire can have a right-hand wound and the outer wire can have a left-hand wound. In some implementations, the inner wire can have a right-hand wound, a middle wire can have a left-hand wound and the outer wire can have a right-hand wound. In some implementations, the flexible cable can be made of two separate threads or wires. In some such implementations, the inner wire can have a left-hand wound and the outer wire can have a right-hand wound. In some other implementations, the inner wire can have a right-hand wound and the outer wire can have a left-hand wound. In some implementations, the wirerope strands can be twisted in either Z-lay or S-lay. Examples of flexible cables include wireropes and torque coils manufactured by ASAHI INTECC. In some implementations, the outer diameter of the torque rope or coil is limited by the size of the working channel of the endoscope with which the endoscopic tool will be used. Other size considerations that need to be taken into account include providing enough space for the aspiration channel, irrigation channel, amongst others. In some implementations, the outer diameter of the torque coil or torque rope can range between 0.1 mm and 4 mm. In some implementations, the torque coil or rope can have an outer diameter of 0.5 mm to 2.0 mm.

Referring back to FIG. 21D, a cross-sectional view of the coupling component 2130 is shown. The coupling component 2130 couples one end of the endoscopic tool to the powered actuator 2120 via the pulleys 2160 and 2162 and to the suction port 2170. The coupling component includes a collection chamber 2181, which is where fluid within the aspirating tube 2118 of the endoscopic tool 2110 can be collected before being suctioned out from the coupling component 2130. The coupling component includes a collection chamber 2181 can also include a drive shaft 2186 that is configured to engage with the pulley 2162. The flexible cable or torque rope 2114 can be coupled to one end of the drive shaft 2186. An opposite end of the drive shaft 2186 is coupled to the pulley 2162, such that the drive shaft is operatively coupled with the motor 2120. In this way, as the motor rotates, the pulleys and the timing belt 2164 are configured to rotate the drive shaft 2186, and in turn, the torque rope 2114. FIGS. 24A-24C illustrate various aspects of the drive shaft of the coupling component 2130. As shown in FIGS. 24A-24C, the drive shaft 2186 can be configured to receive one end of the flexible cable via an opening 2406. A pair of holes 2402a and 2402b can be configured to receive set screws or other securing members for securing the flexible cable to the drive shaft 2186.

The coupling component 2130 also includes a housing component 2500 that couples a flexible portion of the endoscopic tool to the suction port 2170 via an opening 2502. FIG. 25 illustrates an example housing component 2500.

FIGS. 26A-26E show an example sleeve bearing.

Figure 27C:
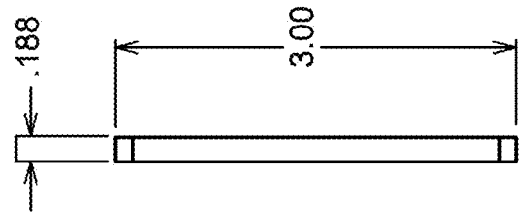
FIGS. 27A-27C show an example base plate that forms a portion of the casing according to embodiments of the present disclosure.
Figure 27B:
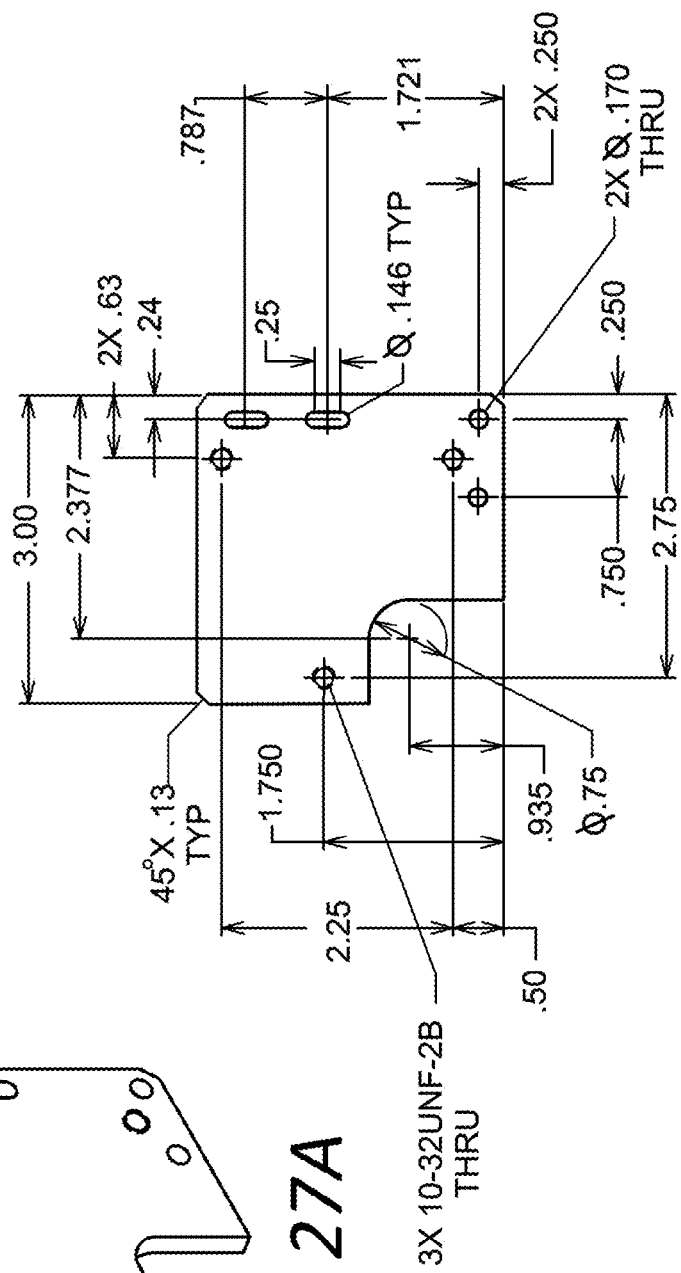
Figure 27A:
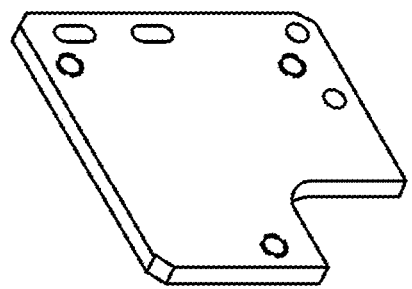

FIGS. 27A-27C show an example base plate 2152 that forms a portion of the casing. FIGS. 28A-28D show an example side plate that forms a portion of the casing. The side plate can also serve as a feedthrough mount.

In some implementations, the coupling component is a part of the endoscopic tool. In some implementations, the coupling component is coupled to a flexible portion of the endoscopic tool via a compression fitting component 2182.

The flexible portion of the endoscopic tool includes an outer tubing, which includes an aspiration tube 2118, the torque rope 2114 and a sheath 2116 that surrounds the outer circumference of the torque rope 2114. The sheath can help reduce friction or the formation of kinks. The aspiration tube 2118 is configured to couple to a cutting tool 2190 such that material that enters into the cutting tool 2190 via an opening 2193 can pass through the length of the endoscopic tool 2110 via the aspiration tube 2118.

As shown in FIGS. 21E-21F, the torque rope is configured to be coupled to an inner cannula 2192 that forms a portion of the cutting tool. The inner cannula 2192 can be surrounded by or disposed within the outer cannula 2191. The opening 2193 is formed within the outer cannula 2191 at one end of the cutting tool 2190. Details of the cutting tool 2190 have been provided herein. FIGS. 23AA-23BB show an example implementation of a cutting tool. The cutting tool can be any type of cutting tool used in existing medical devices. The cutting tool shown in FIGS. 23AA-23BB are shown only for the sake of example and the present disclosure is not intended to be limited to such sizes, shapes, or dimension. Commercially available cutting tools can be used. In some implementations, the cutting tools can be modified in length. In some implementations, the inner cannula can be bonded to the ferrule, while the outer cannula can be coupled to the outer aspirating tube. In some implementations, the connection between the outer cannula and the aspiration channel may be sealed to prevent material from leaking through the connection.

Figure 29C:
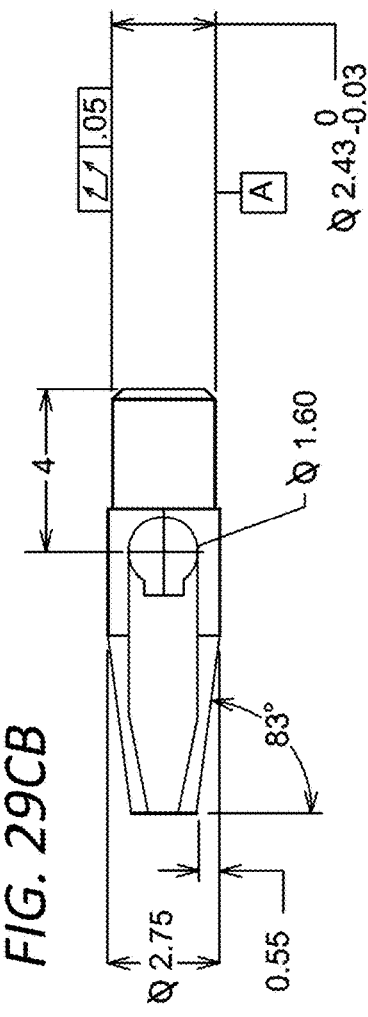
FIGS. 29AA-29EE show various aspects of ferrules according to embodiments of the present disclosure FIGS. 30AA-30C illustrate aspects of an endoscopic assembly in which the tip is press-fit according to embodiments of the present disclosure.
Figure 29C:
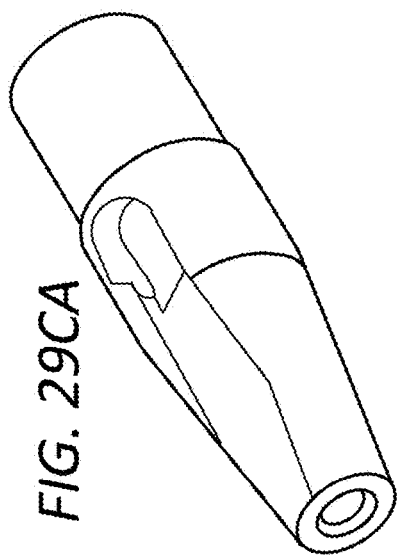
Figure 29C:
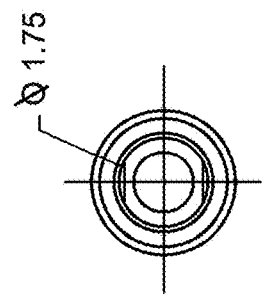
Figure 29C:
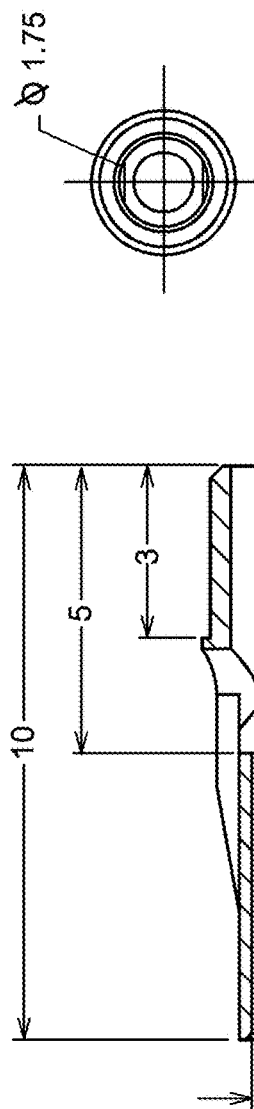
Figure 29C:
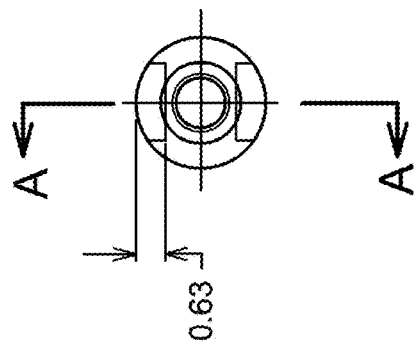

In some implementations, the torque rope 2114 is coupled to the inner cannula 2192 via a ferrule 2194. The ferrule can be a component that couples the torque rope to the inner cannula such that rotational energy within the torque rope is transferred to the inner cannula. Additional details regarding the shape, size and dimensions of the ferrule are shown in FIGS. 29AA-29EE. Depending on the size of the torque rope or flexible cable used in the endoscopic tool 2110, the shape and size of the ferrule may vary. Further, the ferrules shown in FIGS. 29A-29E are merely shown for the sake of example and are not intended to be limited to the particular size, shape, or dimensions shown in the Figures. In some implementations, the ends of the torque rope can be inserted into and bonded to short lengths of hypodermic tubing. Doing so can make it easier to attach the ferrule to the distal end, and to clamp onto on the proximal end (towards the drive shaft). In some implementations, a graphite filled cyanoacrylate, such as loctite black max, can be used. Other similar types of materials can also be used instead.

Figure 30A:
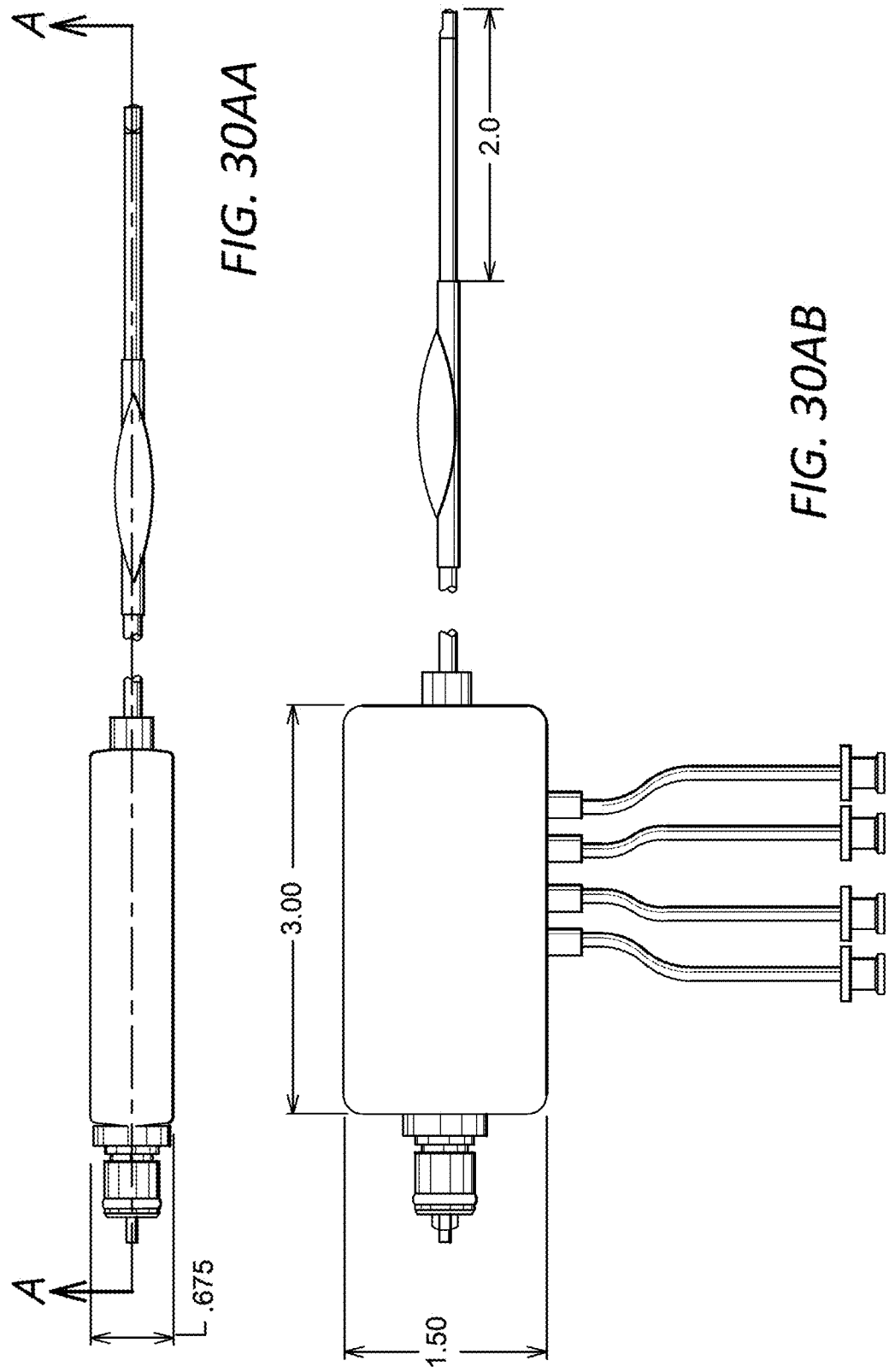

FIGS. 30AA-30C illustrate aspects of an endoscopic assembly in which the tip is press-fit. In some implementations, the flexible portion of the endoscopic tool can include a balloon structure that can be deployed such that the balloon structure can engage with the inner walls of the endoscope. The balloon structure can be coupled to an air supply line 3006 that is coupled to an air supply source, such that when air is supplied, the balloon can expand and engage with the inner wall of the endoscope. In some implementations, the balloon structure can expand asymmetrically, as shown in FIG. 30AA-30AB. In some implementations, the air supply source can be actuated via a foot pedal. An irrigation line 3002 can be configured to supply an irrigation fluid. The irrigation fluid can flow towards the cutting tool, where the irrigation fluid can then flow through the suction channels 3004. The irrigation fluid can prevent the suction channels from blockages. As shown in FIG. 30C, the flexible cable or torque rope can be press fit into a button at one end of the cutting tool.

FIGS. 31AA-31AB and 31B-31C illustrate aspects of an endoscopic assembly in which the tip is press-fit. In some implementations, the flexible portion of the endoscopic tool can include a balloon structure that can be deployed such that the balloon structure can engage with the inner walls of the endoscope. The balloon structure can be coupled to an air supply source such that when air is supplied, the balloon can expand and engage with the inner wall of the endoscope. In some implementations, the balloon stricture can expand symmetrically, as shown in FIGS. 31AA and 31AB. An irrigation line can be configured to supply an irrigation fluid. The irrigation fluid can flow towards the cutting tool, where the irrigation fluid can then flow through the suction channels. The irrigation fluid can prevent the suction channels from blockages. As shown in FIG. 31C, the flexible cable or torque rope can be welded to one end of the cutting tool.

Figure 32:
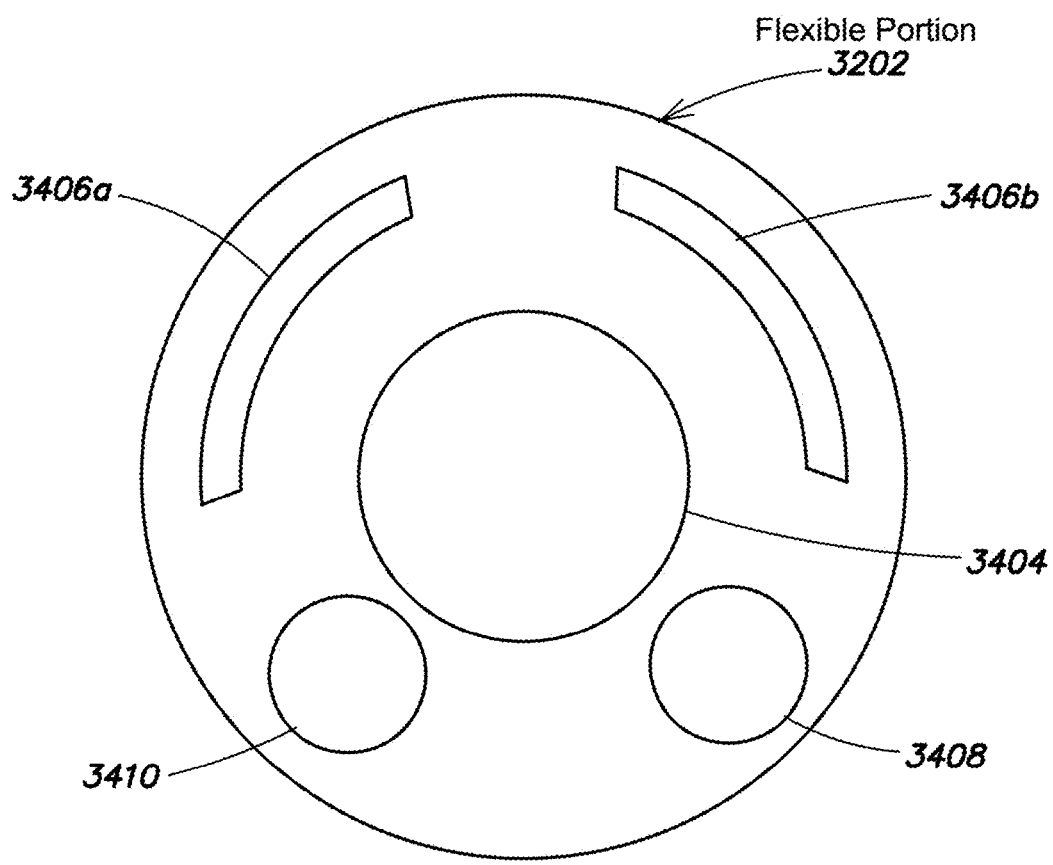
FIG. 32 shows a top view of an example flexible portion of an endoscopic tool according to embodiments of the present disclosure.

FIG. 32 shows a top view of an example flexible portion of an endoscopic tool. In some implementations, the flexible portion shown in FIG. 32 can be used with the implementations shown in FIGS. 30AA-30C and 31AA-31AB and 31B-31C. The flexible portion 3202 includes a center channel 3204 through which the flexible cable passes through. The flexible portion 3202 also includes two aspiration channels 3406a and 3406b, an irrigation channel 3408 and an air supply channel 3410.

In some implementations, the operating speed of the torque rope can vary. In some example implementations, the torque rope can have an operating speed within the range of 0.5 k RPM to 20 k RPM. In some implementations, the torque rope can have an operating speed within the range of 1 k RPM and 4 k RPM. In some implementations, the operating speed of the torque rope can vary. In some example implementations, the torque rope can operate with a torque of 5 to 100 mN*m (milliNewton Meters). In some implementations, the torque rope can operate with a torque of 20 to 50 mN*m (milliNewton Meters). However, it should be appreciated by those skilled in the art that the torque and running speed of the flexible cable can be altered based on the performance of the endoscopic tool. In some implementations, various factors contribute to the performance of the endoscopic tool, including the amount of suction, the type of cutter, the size of the opening in the cutter, amongst others. As such, the torque and running speed at which to operate the flexible cable can be dependent on a plurality of factors.

Figure 33:
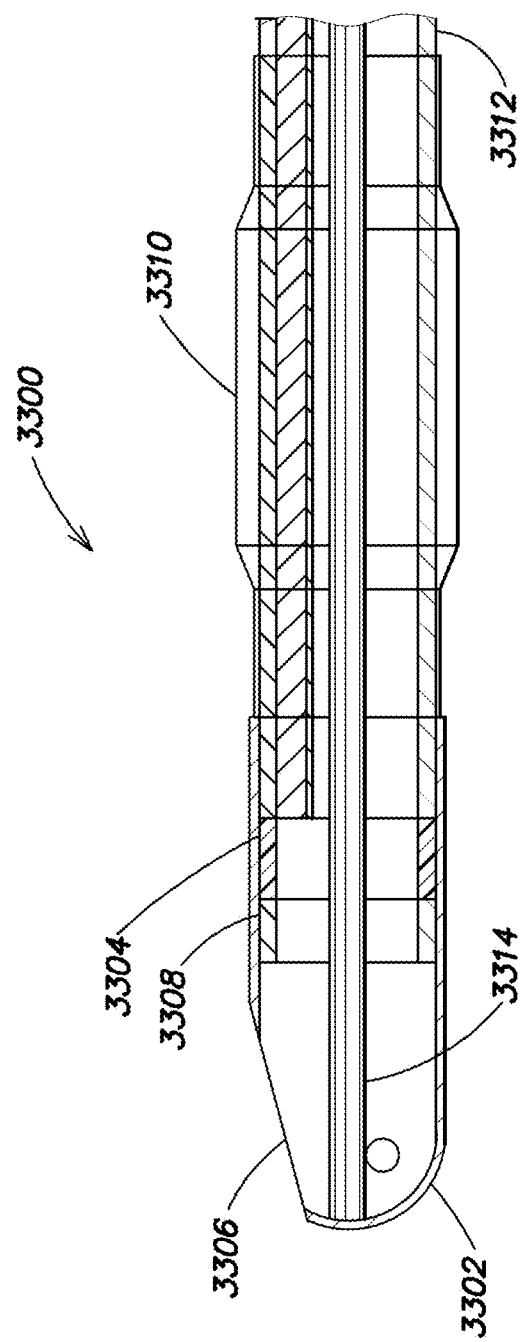
FIG. 33 is a cross-sectional view of an example cutting assembly of an endoscopic tool using a torque rope according to embodiments of the present disclosure.
Figure 34B:
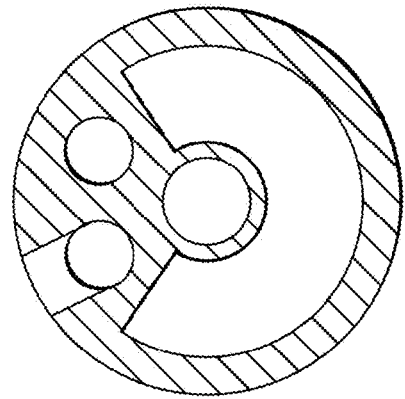
FIGS. 34A-34C are cross-sectional views of different configurations of the flexible portion region of one implementation of an endoscopic tool described herein.
Figure 34C:
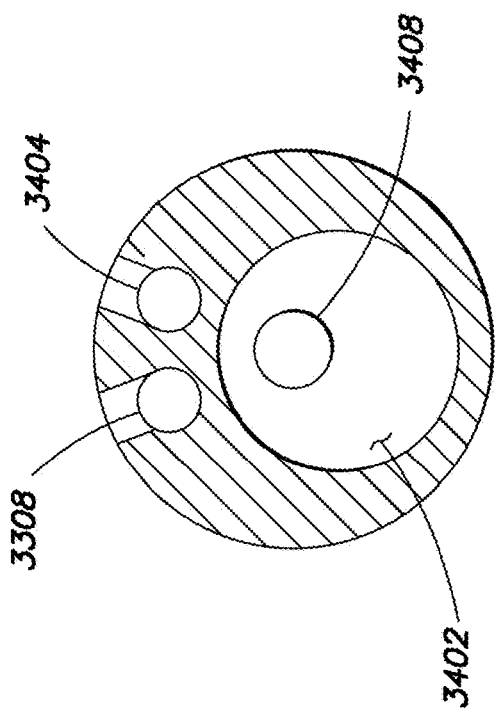
Figure 34A:
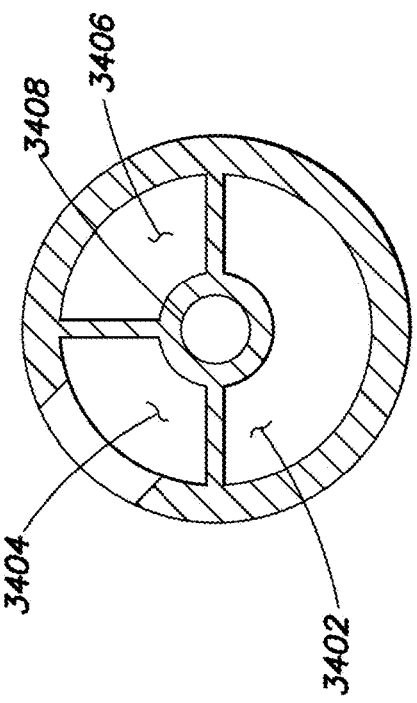

FIG. 33 is a cross-sectional view of an example cutting assembly of an endoscopic tool using a torque rope. The cutting assembly 3300 includes an outer cannula 3302, an inner cannula 3304 including an inner cutter 3306 disposed within the outer cannula 3302, a PTFE bearing 3308, a semi-compliant balloon 3310, and a multilumen extrusion 3312. A torque rope 3314 can be coupled to the inner cutter 3306. The diameter of the outer cannula can be between 0.05 inches to a size suitable to pass through an instrument channel of an endoscope.

Figures 35A, 35B, 35C:
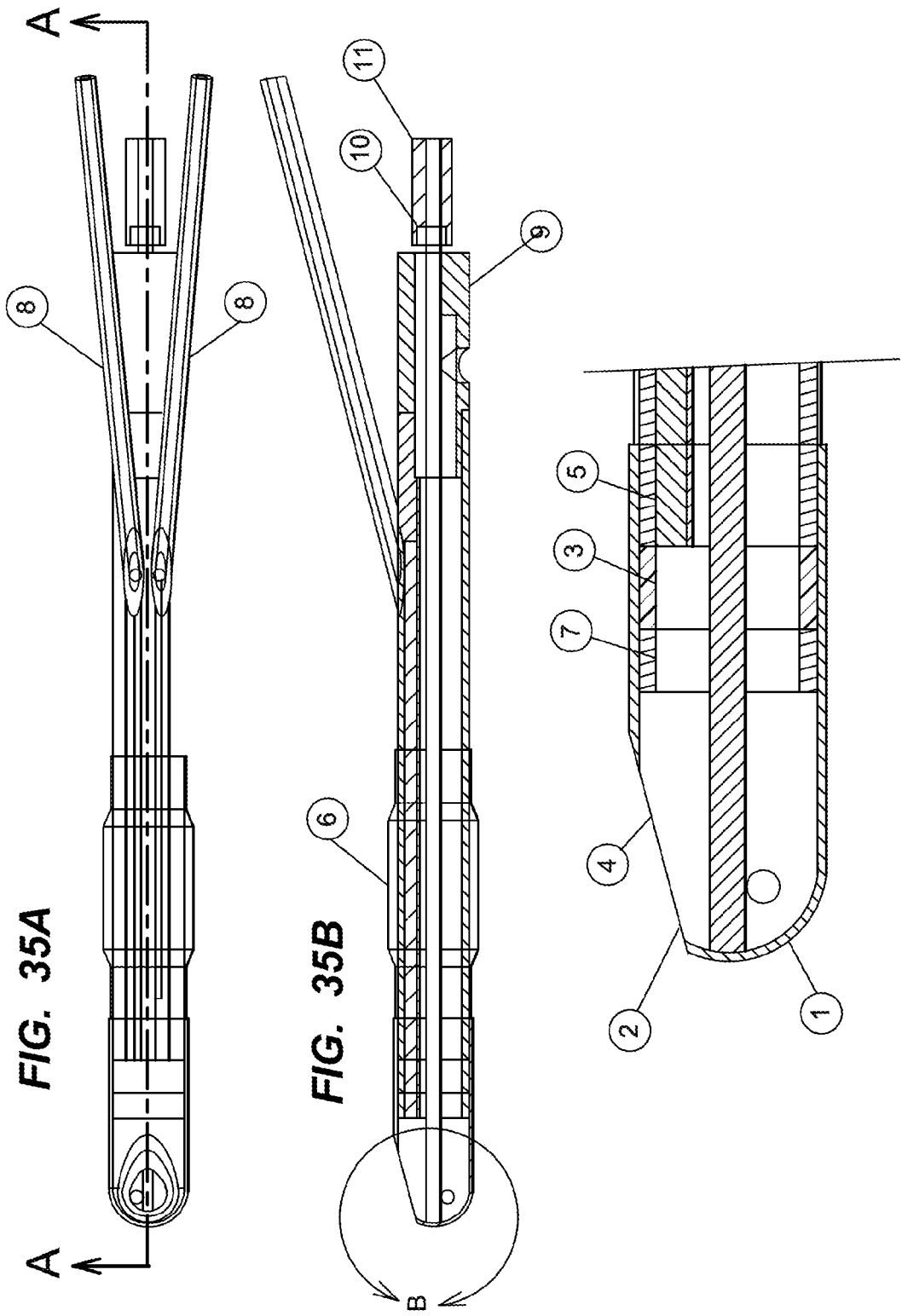
FIGS. 35A-35C show various views of portions of an endoscopic tool according to embodiments of the present disclosure.

FIGS. 35AA-35AC show are cross-sectional views of different configurations of the flexible portion region of one implementation of an endoscopic tool described herein. The flexible portion region can include an aspiration lumen 3402, an inflation lumen 3404, a lavage or irrigation lumen 3406 and a torque rope.

FIG. 35 shows various views of portions of an endoscopic tool. The endoscopic tool can include an outer cannula 1, an inner cutter 2, an inner cannula 3, a torque rope 4, a trilumen extrusion 5, a balloon 6, a PTFE washer 7, two sidearms 8, a proximal plug 9, an PTFE gasket 10 and a gasket cap 11.

Figure 36:
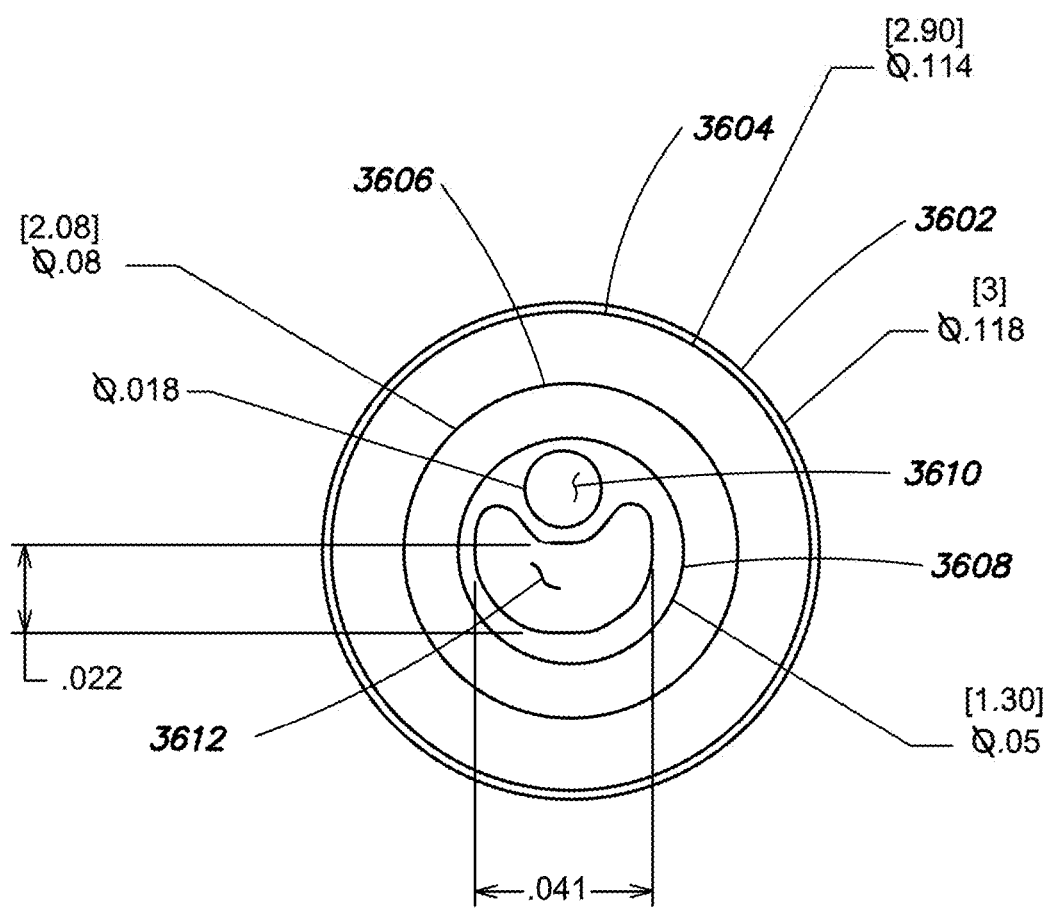
FIG. 36 shows a cross-sectional view of the flexible portion region of one implementation of an endoscopic tool according to embodiments of the present disclosure.

FIG. 36 shows a cross-sectional view of the flexible portion region of one implementation of an endoscopic tool described herein. The flexible portion region can include an outer inflation jacket 3602, an outer coil 3604, a torque coil 3606, a multi-lumen extrusion 3608 disposed within the torque coil. The multi-lumen extrusion 3608 can include a lavage lumen 3610 and an aspiration lumen 3612.

FIG. 37 shows a cross-section view of one implementation of the endoscopic tool described herein. The endoscopic tool includes an outer cannula 3702, an inner cutter 3704, an inner torque coil 3706, an outer coil 3708, an outer inflation jacket and balloon 3710, and a multi-lumen extrusion 3712. A gear 3714, such as a worm gear can engage with the torque coil to drive the inner cutter.

Figure 38A:
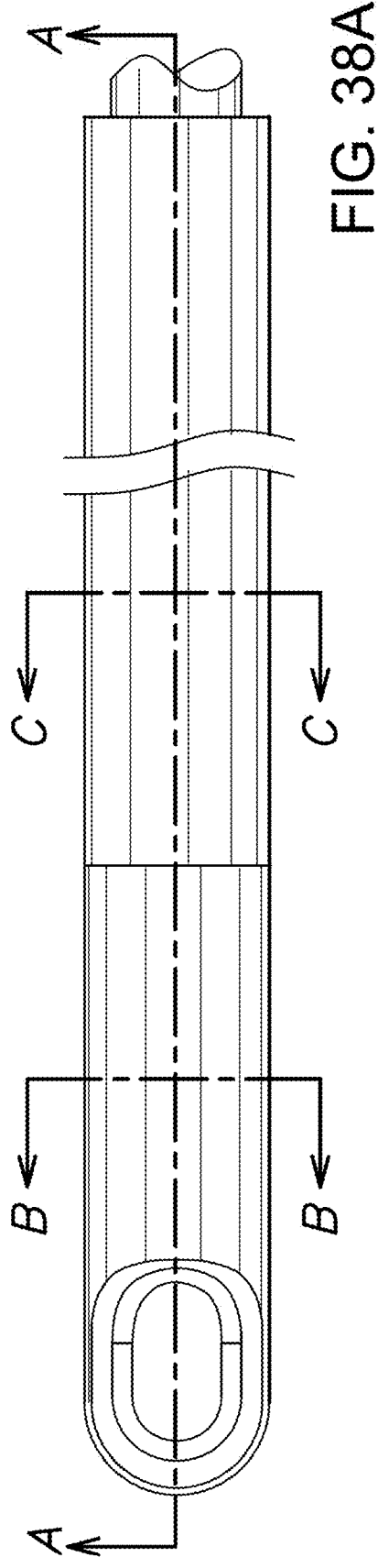
FIGS. 38A and 38B show various views of a distal portion of one implementation of an endoscopic tool according to embodiments of the present disclosure.
Figure 38B:
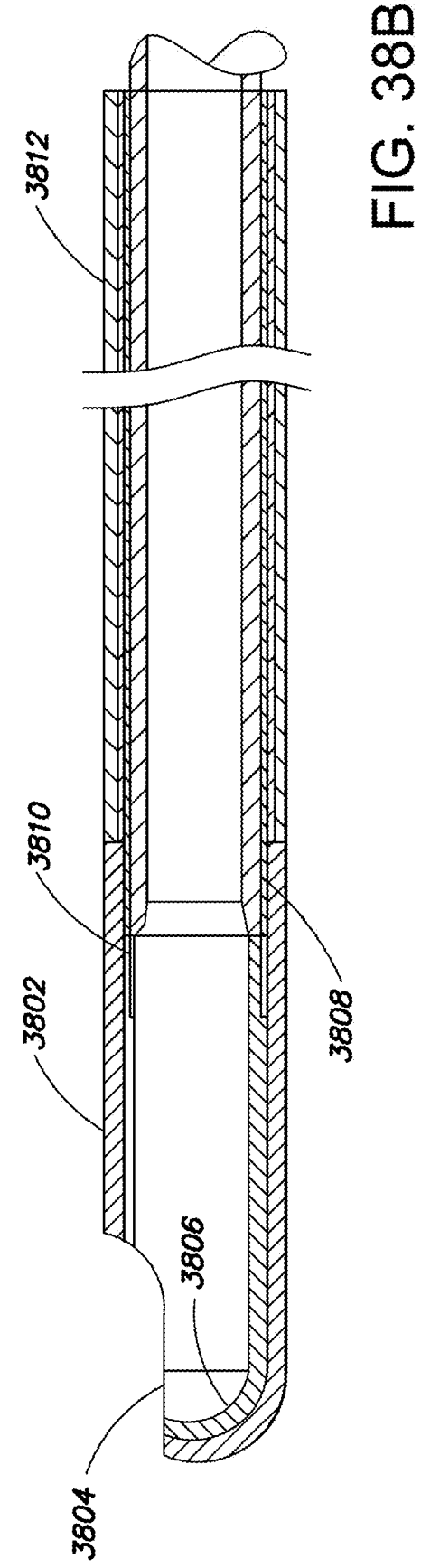

FIGS. 38A and 38B show various views of a distal portion of one implementation of an endoscopic tool described herein. The endoscopic tool includes an outer cutter 3802 that defines an opening 3804. The endoscopic tool also includes an inner cutter 3806 disposed within the outer cutter. The inner cutter is coupled to a torque coil 3808. The torque coil is disposed within a PET heat shrink 3810 or other type of tubing. The outer cutter is coupled to a braided shaft 3812 to allow the outer cutter 3802 to rotate relative to the inner cutter 3806.

Figure 39B:
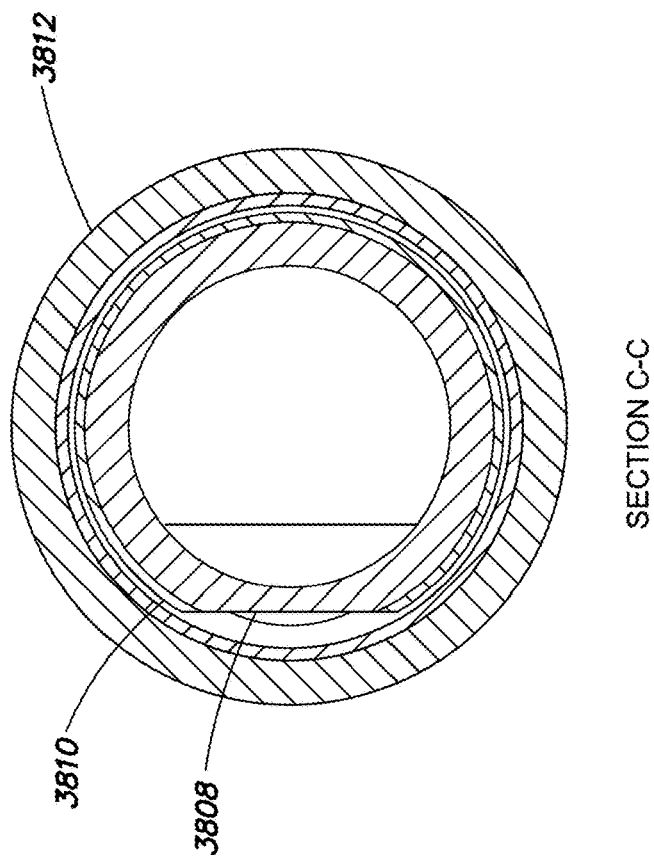
FIGS. 39A and 39B show cross-sectional views of the distal portion of the endoscopic tool shown in FIGS. 38A and 38B along the sections B-B and sections C-C according to embodiments of the present disclosure.
Figure 39A:
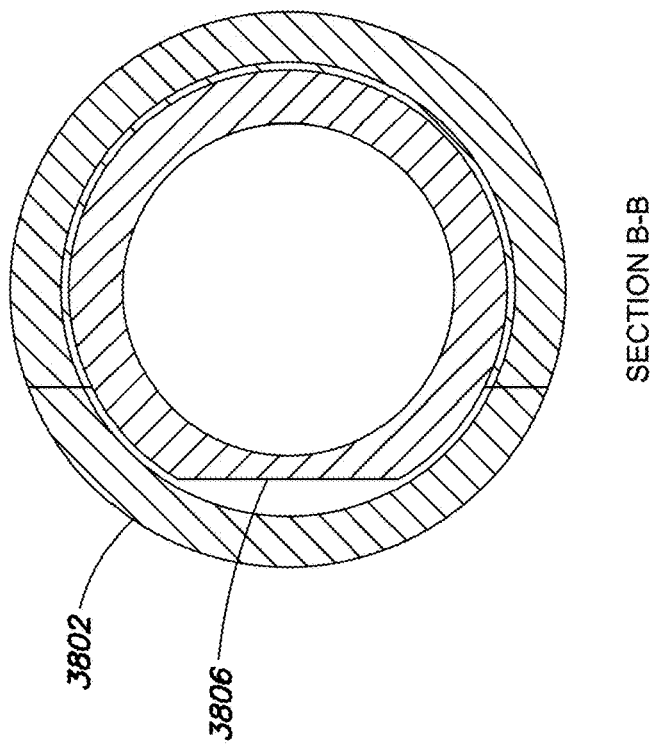

FIGS. 39A and 39B show cross-sectional views of the distal portion of the endoscopic tool shown in FIGS. 38A and 38B along the sections B-B and sections C-C.

In some implementations, an endoscopic instrument insertable within a single instrument channel of an endoscope can include a power driven instrument head or cutting assembly that is configured to resect material at a site within a subject. The cutting assembly includes an outer cannula and an inner cannula disposed within the outer cannula. The outer cannula defines an opening through which material to be resected enters the cutting assembly. The endoscopic instrument also includes a flexible outer tubing coupled to the outer cannula and configured to cause the outer cannula to rotate relative to the inner cannula. The flexible outer tubing can have an outer diameter that is smaller than the instrument channel in which the endoscopic instrument is insertable. The endoscopic instrument also includes a flexible torque coil having a portion disposed within the flexible outer tubing. The flexible torque coil having a distal end coupled to the inner cannula. The flexible torque coil is configured to cause the inner cannula to rotate relative to the outer cannula. The endoscopic instrument also includes a proximal connector coupled to a proximal end of the flexible torque coil and configured to engage with a drive assembly that is configured to cause the proximal connector, the flexible torque coil and the inner cannula to rotate upon actuation. The endoscopic instrument also includes an aspiration channel having an aspiration port configured to engage with a vacuum source. The aspiration channel is partially defined by an inner wall of the flexible torque coil and an inner wall of the inner cannula and extends from an opening defined in the inner cannula to the aspiration port. The endoscopic instrument also includes an irrigation channel having a first portion defined between an outer wall of the flexible torque coil and an inner wall of the flexible outer tubing and configured to carry irrigation fluid to the aspiration channel.

In some implementations, the proximal connector is hollow and an inner wall of the proximal connector defines a portion of the aspiration channel. In some implementations, the proximal connector is a rigid cylindrical structure and is configured to be positioned within a drive receptacle of the drive assembly. The proximal connector can include a coupler configured to engage with the drive assembly and a tensioning spring configured to bias the inner cannula towards a distal end of the outer cannula. In some implementations, the tensioning spring is sized and biased such that the tensioning spring causes a cutting portion of the inner cannula to be positioned adjacent to the opening of the outer cannula. In some implementations, the proximal connector is rotationally and fluidly coupled to the flexible torque coil. In some implementations, the tensioning spring can be sized and biased such that the distal tip of the inner cannula can contact the inner distal wall of the outer cannula. This may limit any lateral or undesired movement generated due to whip at the distal end of the inner cannula caused by the rotation of the flexible torque coil.

In some implementations, the endoscopic instrument also includes a lavage connector including an irrigation entry port and a tubular member coupled to the lavage connector and the flexible outer tubing. An inner wall of the tubular member and the outer wall of the flexible torque coil can define a second portion of the irrigation channel that is fluidly coupled to the first portion of the irrigation channel. In some implementations, the endoscopic instrument also includes a rotational coupler coupling the flexible outer tubing to the tubular member and configured to cause the flexible outer tubing to rotate relative to the tubular member and cause the opening defined in the outer cannula to rotate relative to the inner cannula. In some implementations, the lavage connector defines an inner bore within which the flexible torque coil is disposed.

In some implementations, the endoscopic instrument also includes a lining within which the flexible torque coil is disposed, the outer wall of the lining configured to define a portion of the irrigation channel. In some implementations, the inner cannula is configured to rotate about a longitudinal axis of the inner cannula and relative to the outer cannula and the aspiration channel is configured to provide a suction force at the opening of the inner cannula.

In some implementations, the flexible torque coil includes a plurality of threads. Each of the plurality of threads can be wound in a direction opposite to a direction in which one or more adjacent threads of the plurality of threads is wound. In some implementations, the flexible torque coil includes a plurality of layers. Each of the plurality of layers can be wound in a direction opposite to a direction in which one or more adjacent layers of the plurality of layers is wound. In some implementations, each layer can include one or more threads. Additional details regarding the flexible torque coil are described above in regard to the discussion of the flexible cable with respect to at least FIGS. 22A-22H.

In some implementations, the flexible outer tubing has a length that exceeds the length of the endoscope in which the endoscopic instrument is insertable. In some implementations, the flexible outer tubing has a length that is at least 100 times larger than an outer diameter of the flexible outer tubing. In some implementations, the flexible portion is at least 40 times as long as the cutting assembly.

Figure 40B:
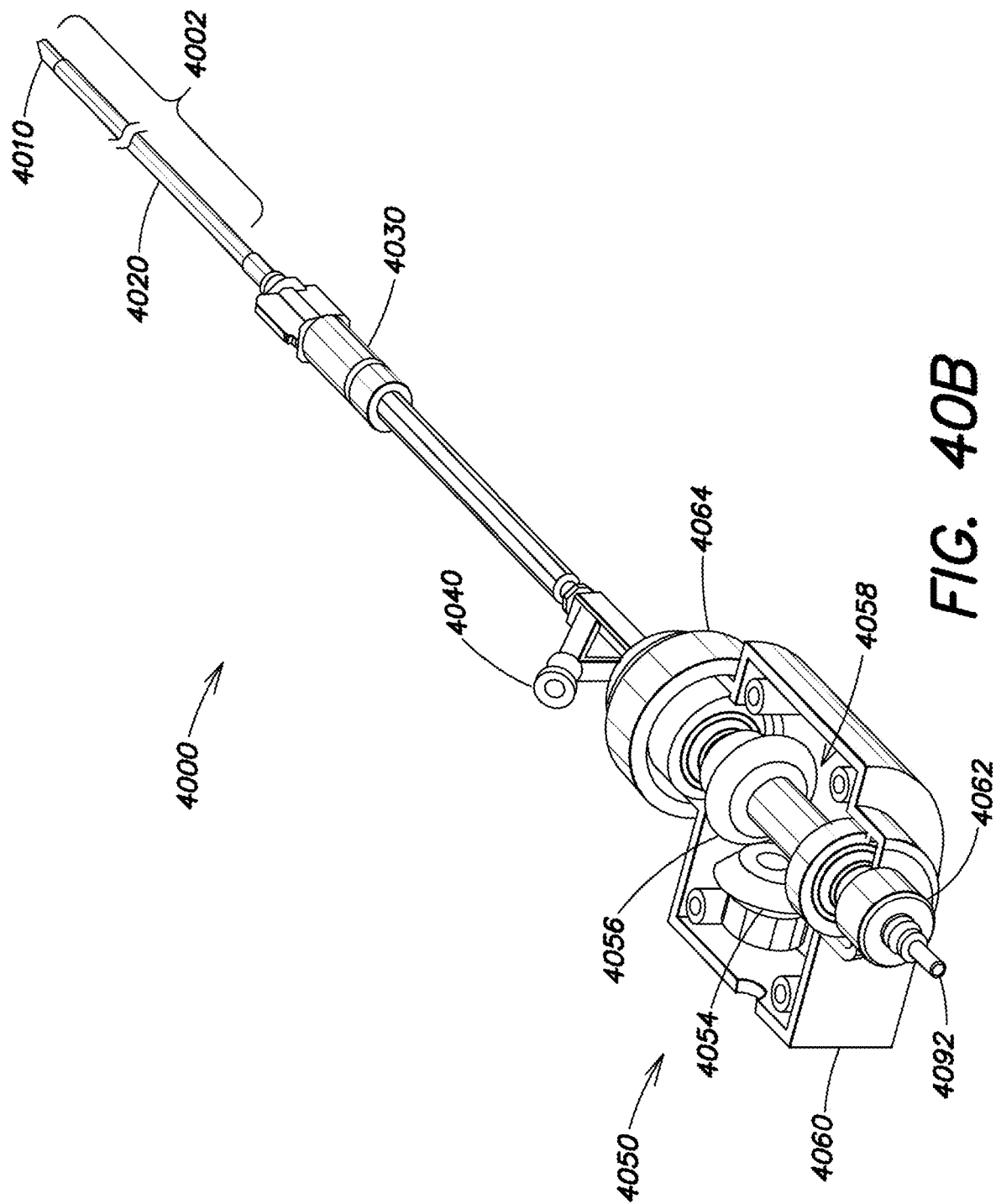
Figure 41:
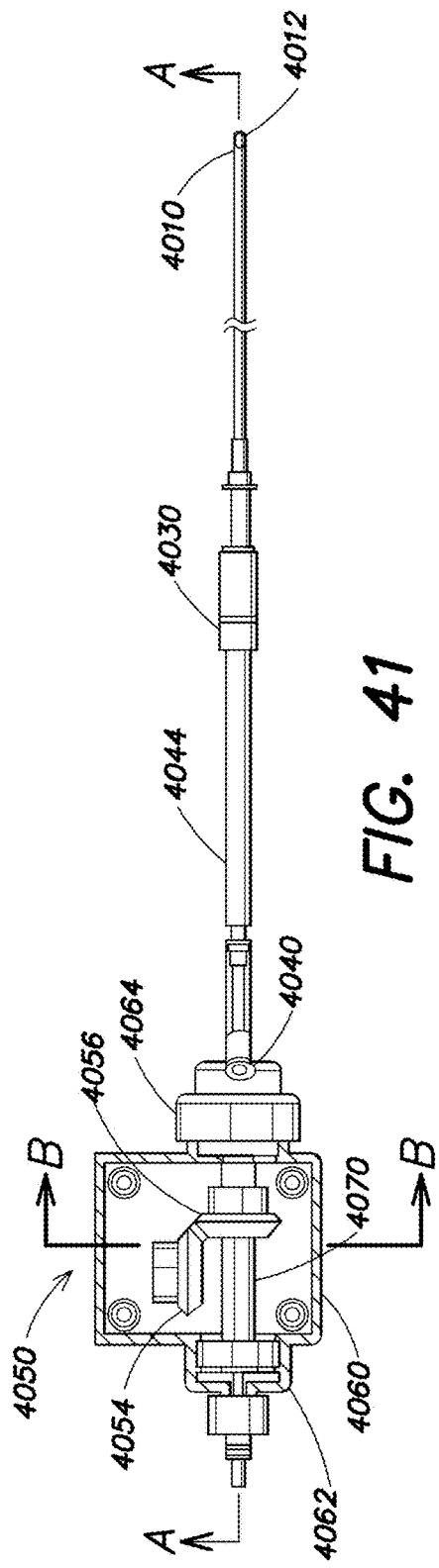
FIG. 41 shows a top view of the endoscopic tool and a top exposed view of the portion of the drive assembly shown in FIGS. 40A-40B according to embodiments of the present disclosure.
Figure 42:
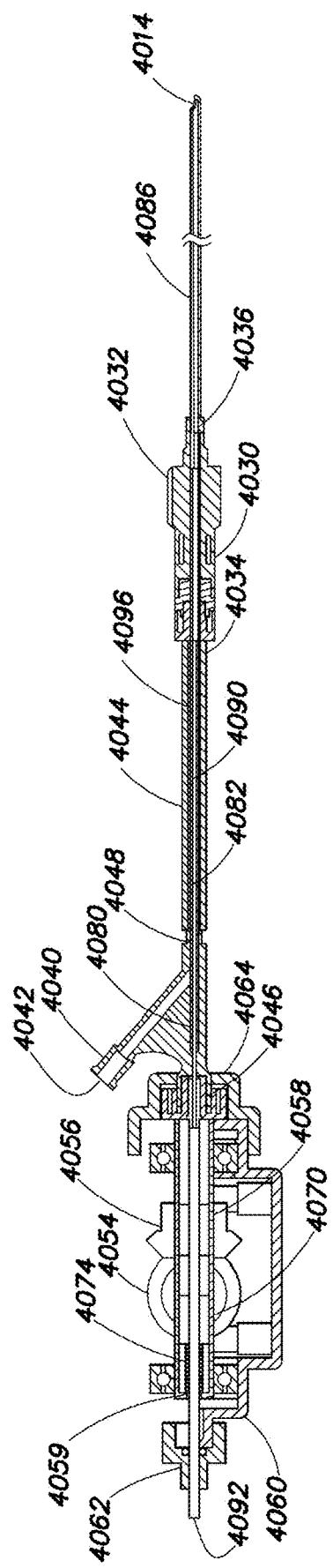
FIG. 42 shows a cross-sectional view of the endoscopic tool and the portion of the drive assembly across the section A-A shown in FIGS. 40A-40B according to embodiments of the present disclosure.
Figure 43:
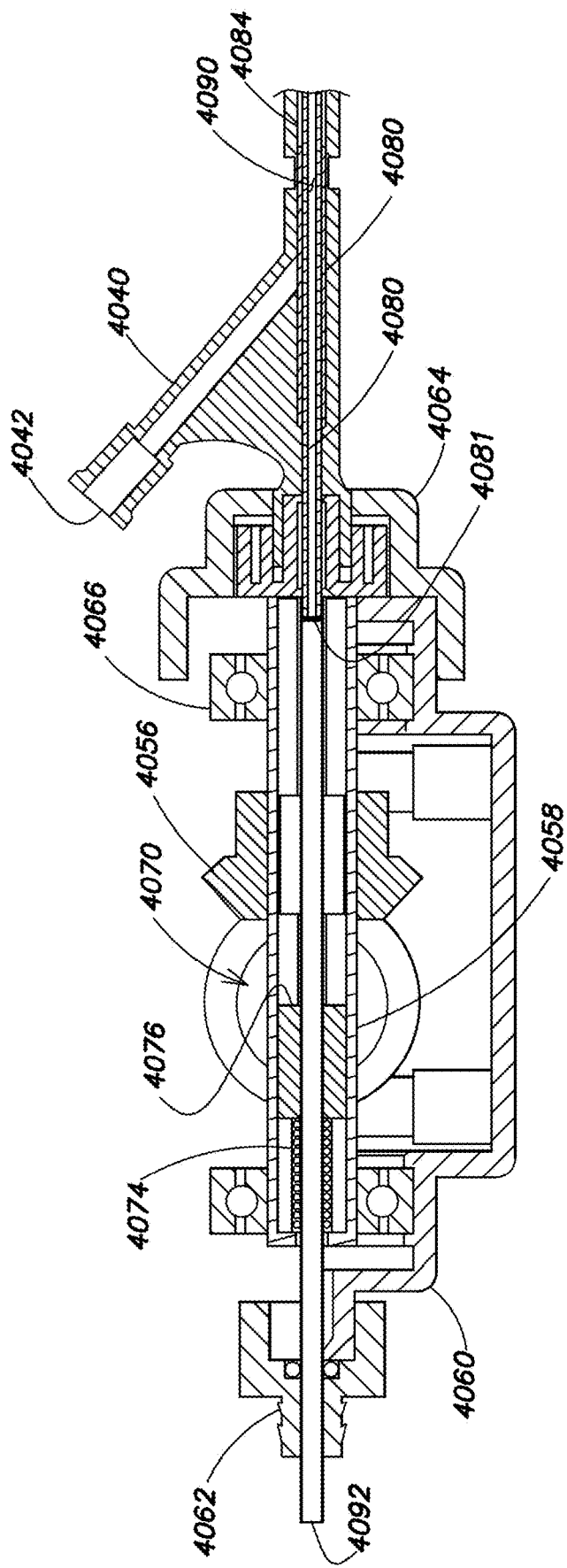
FIG. 43 shows an enlarged view of the drive connector of the endoscope and the portion of the drive assembly shown in FIGS. 40A-40B according to embodiments of the present disclosure.

FIGS. 40A-40B show a perspective view of an endoscopic tool 4000 and a portion of a drive assembly 4050 configured to drive the endoscopic tool. FIG. 40B shows a perspective view of the endoscopic tool and the portion of the drive assembly configured to drive the endoscopic tool shown in FIGS. 40A-40B. Referring now also to FIGS. 41, 42 and 43, FIG. 41 shows a top view of the endoscopic tool 4000 and a top exposed view of the portion of the drive assembly 4050 shown in FIGS. 40A-40B. FIG. 42 shows a cross-sectional view of the endoscopic tool 4000 and the portion of the drive assembly 4050 across the section A-A.

Figure 44:
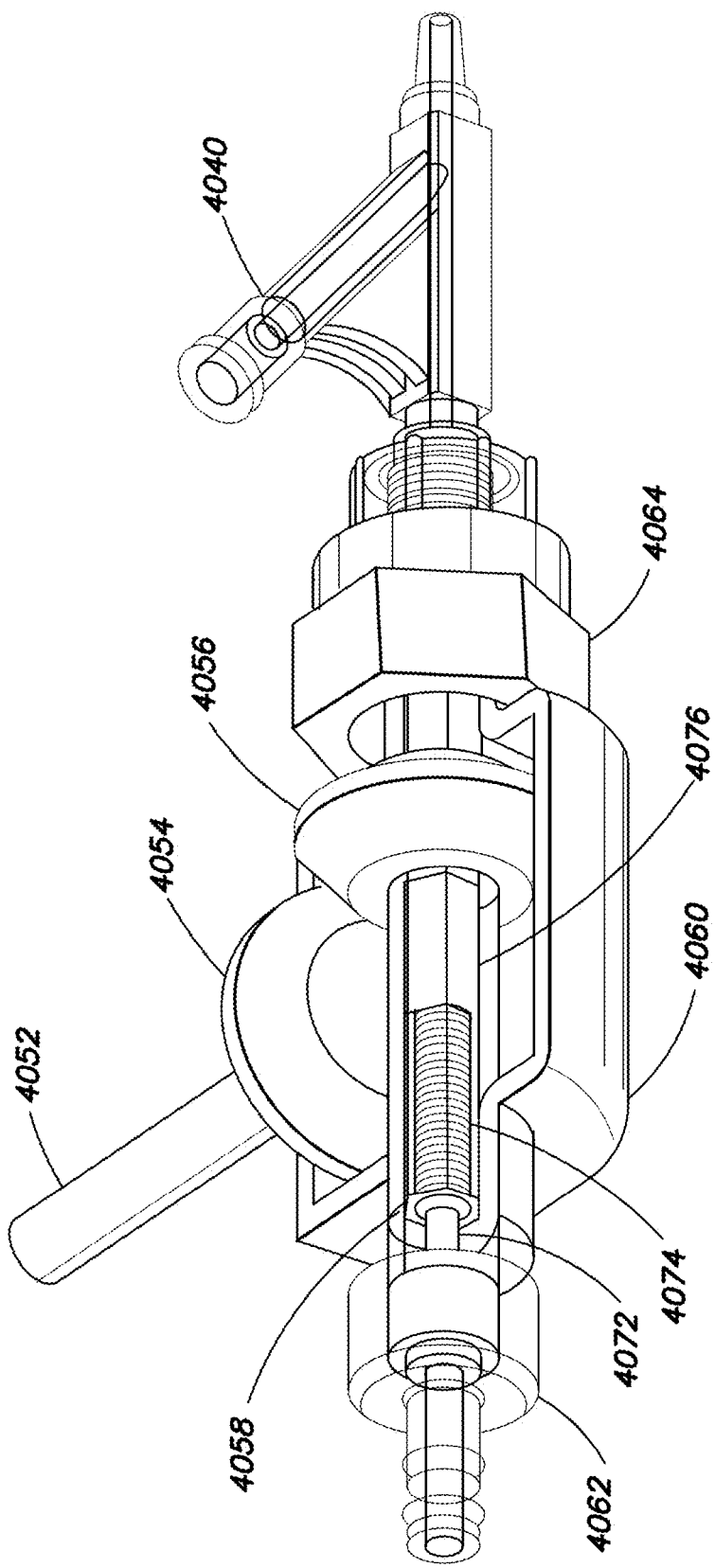
FIG. 44 shows a perspective view of the endoscopic tool and a portion of the drive assembly shown in FIGS. 40A-40B according to embodiments of the present disclosure.
Figure 45:
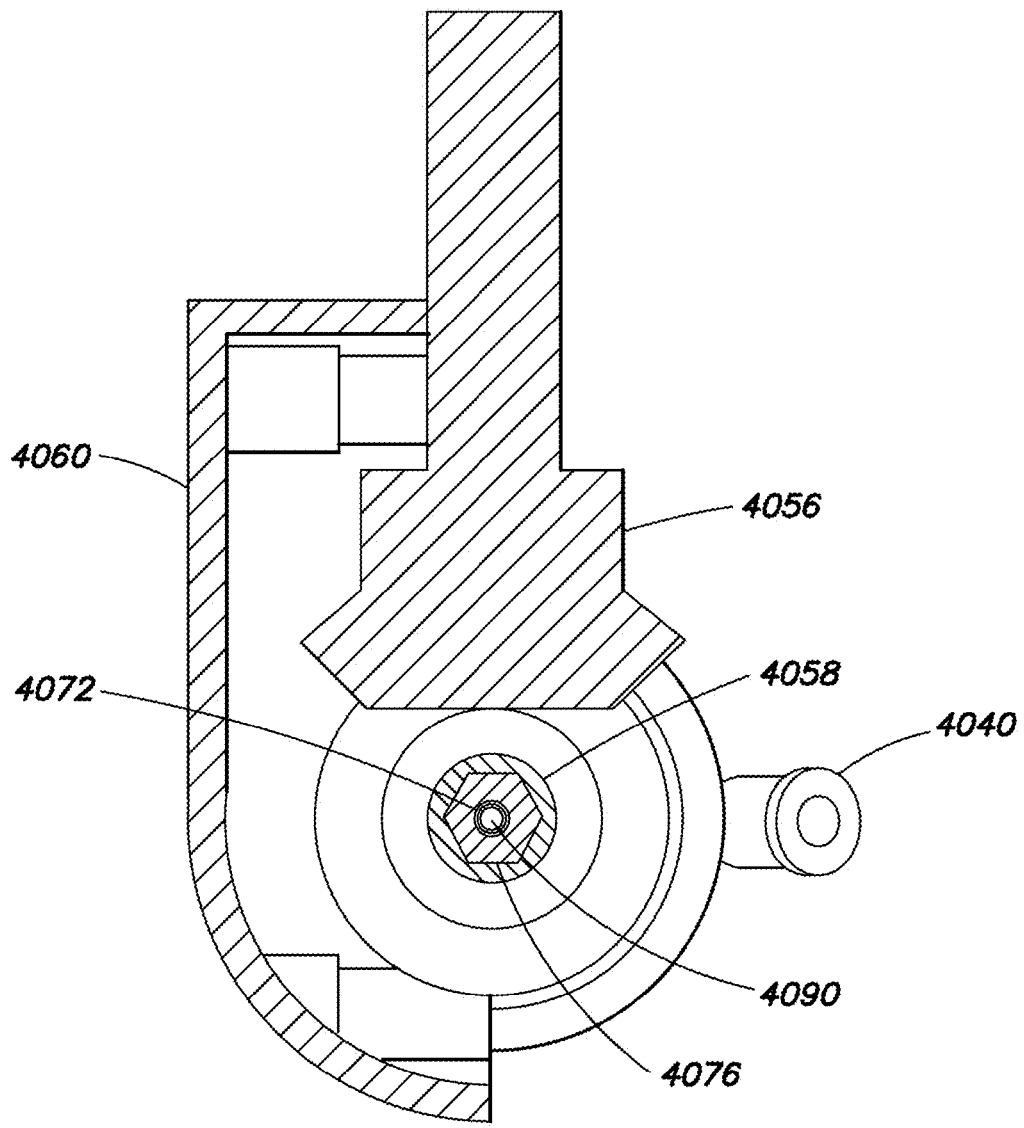
FIG. 45 shows a cross-sectional view of the endoscopic tool and the portion of the drive assembly across the section B-B according to embodiments of the present disclosure.
Figure 46:
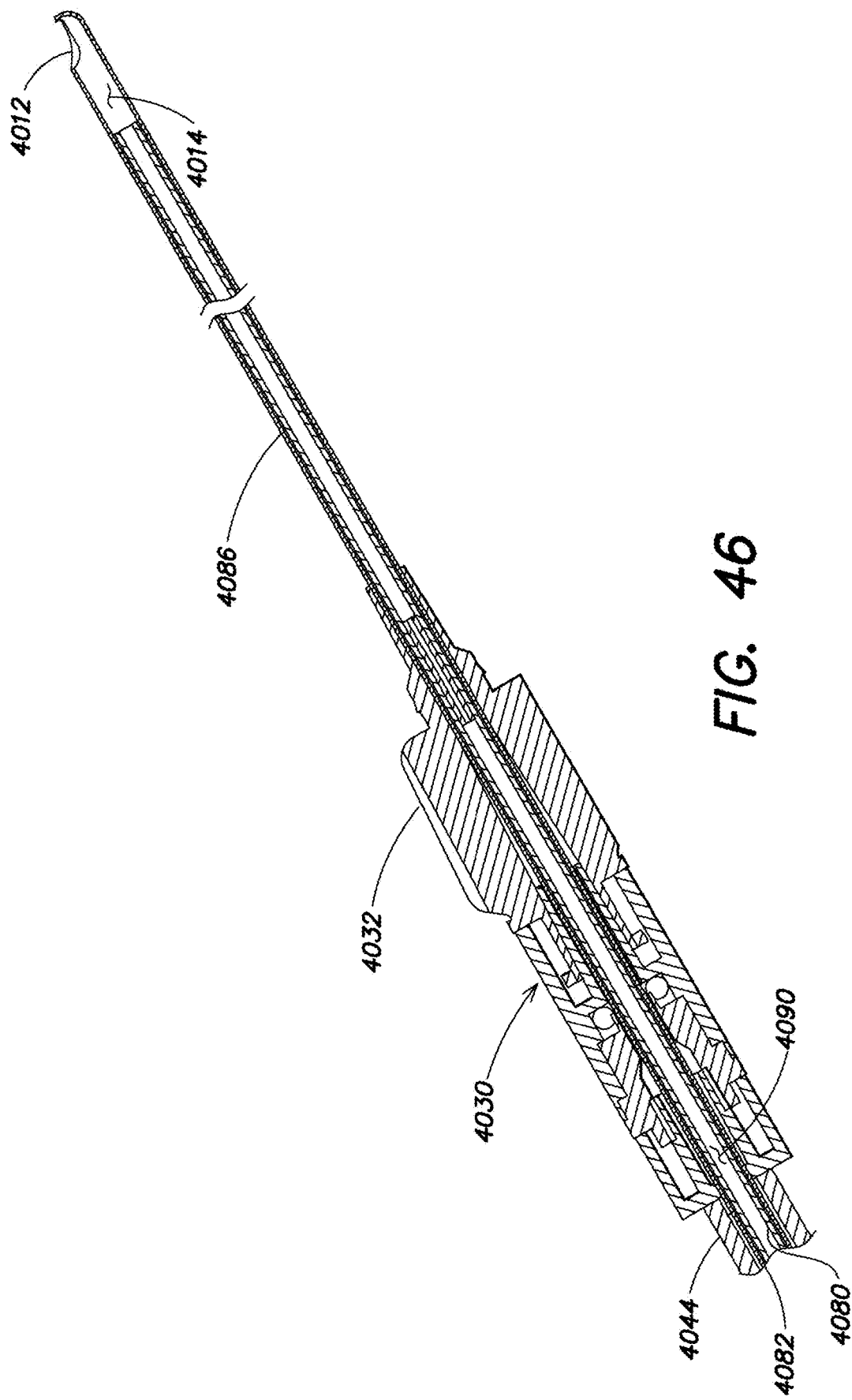
FIG. 46 shows an enlarged cross-sectional view of the rotational coupler section of the endoscopic tool according to embodiments of the present disclosure.

FIG. 43 shows an enlarged view of the drive connector of the endoscope and the portion of the drive assembly 4050. FIG. 44 shows a perspective view of the endoscopic tool 4000 and a portion of the drive assembly shown in FIGS. 40A-40B. FIG. 45 shows a cross-sectional view of the endoscopic tool and the portion of the drive assembly across the section B-B. FIG. 46 shows an enlarged cross-sectional view of the rotational coupler section of the endoscopic tool. FIG. 47A and FIG. 47B show a top view and a cross-sectional view of the rotational coupler of the endoscopic tool.

The endoscopic tool 4000, as shown in FIGS. 40A-47B, may be configured to be inserted within an instrument channel of an endoscope. Examples of the endoscope can include a gastroscope, such as a colonoscope, a laryngoscope, or any other flexible endoscope. The endoscopic tool can include a flexible portion 4002 that is shaped, sized and configured to be inserted within the instrument channel, while a remaining portion of the endoscopic tool 4000 can be configured to remain outside the instrument channel of the endoscope. The flexile portion 4002 can be shaped and sized to fit within the instrument channel and be configured to navigate through a tortuous path defined by the instrument channel while the endoscope is inserted within the patient. In the case of colonoscopes, the endoscope can form a series of bends of over at least 60 degrees and in some situations, over 90 degrees.

The endoscopic tool 4000 can include a cutting assembly 4010 configured to resect material at a site within a subject. The cutting assembly 4010 can be similar to the cutting assembly 160 described in FIG. 1C and elsewhere in the description and figures. In some implementations, the cutting assembly 4010 can include an outer cannula and an inner cannula disposed within the outer cannula. The outer cannula can define an opening 4012 through which material to be resected can enter the cutting assembly 4010. In some implementations, the opening 4012 is defines through a portion of the radial wall of the outer cannula. In some implementations, the opening may extend around only a portion of the radius of the outer cannula, for example, up to one third of the circumference of the radial wall. As the aspiration channel 4090 extends between the aspiration port 4092 and the opening 4012, any suction applied at the aspiration port 4092 causes a suction force to be exerted at the opening 4012. The suction force causes material to be introduced into the opening of the outer cannula, which can then be cut by the inner cannula of the cutting assembly.

The inner cannula can include a cutting section that is configured to be positioned adjacent to the opening 4012 such that material to be resected that enters the cutting assembly via the opening 4012 can be resected by the cutting section of the inner cannula. The inner cannula may be hollow and an inner wall of the inner cannula may define a portion of an aspiration channel that may extend through the length of the endoscopic tool. A distal end of the inner cannula can include the cutting section while a proximal end of the inner cannula can be open such that material entering the distal end of the inner cannula via the cutting section can pass through the proximal end of the inner cannula. In some implementations, the distal end of the inner cannula can come into contact with an inner surface of a distal end of the outer cannula. In some implementations, this can allow the inner cannula to rotate relative to the outer cannula along a generally longitudinal axis, providing more stability to the inner cannula while the inner cannula is rotating. In some implementations, the size of the opening can dictate the size of the materials being cut or resected by the inner cannula. As such, the size of the opening may be determined based in part on the size of the aspiration channel defined by the inner circumference of the flexible torque coil.

The endoscopic instrument 4000 can include a flexible torque coil 4080 that is configured to couple to the proximal end of the inner cannula at a distal end of the flexible torque coil 4080. The flexible torque coil can include a fine coil with multiple threads and multiple layers, which can transmit the rotation of one end of the flexible torque coil to an opposite end of the flexible torque coil. Each of the layer of thread of the flexible torque coil can be wound in a direction opposite to a direction in which each of the layer of thread adjacent to the layer of thread is wound. In some implementations, the flexible torque coil can include a first layer of thread wound in a clockwise direction, a second layer of thread wound in a counter-clockwise direction and a third layer of thread wound in a clockwise direction. In some implementations, the first layer of thread is separated from the third layer of thread by the second layer of thread. In some implementations, each of the layers of thread can include one or more threads. In some implementations, the layers of thread can be made from different materials or have different characteristics, such as thickness, length, among others.

The flexibility of the torque coil 4080 allows the coil to maintain performance even in sections of the torque coil 4080 that are bent. Examples of the flexible torque coil 4080 include torque coils made by ASAHI INTECC USA, INC located in Santa Ana, Calif., USA. In some implementations, the flexible torque coil 4080 can be surrounded by a sheath or lining to avoid frictional contact between the outer surface of the flexible torque coil 4080 and other surfaces. In some implementations, the flexible torque coil 4080 can be coated with Polytetrafluoroethylene (PFTE) to reduce frictional contact between the outer surface of the flexible torque coil 4080 and other surfaces. The flexible torque coil 4080 can be sized, shaped or configured to have an outer diameter that is smaller than the diameter of the instrument channel of the endoscope in which the endoscopic tool is to be inserted. For example, in some implementations, the outer diameter of the flexible torque coil can be within the range of 1-4 millimeters. The length of the flexible torque coil can be sized to exceed the length of the endoscope. In some implementations, the inner wall of the flexible torque coil 4080 can be configured to define another portion of the aspiration channel that is fluidly coupled to the portion of the aspiration channel defined by the inner wall of the inner cannula of the cutting assembly 4010. A proximal end of the flexible torque coil 4080 can be coupled to a proximal connector assembly 4070, details of which are provided below.

The endoscopic instrument 4000 can include a flexible outer tubing 4086 that can be coupled to the proximal end of the outer cannula. In some implementations, a distal end of the flexible outer tubing 4086 can be coupled to the proximal end of the outer cannula using a coupling component. In some implementations, the outer cannula can be configured to rotate responsive to rotating the flexible outer tubing. In some implementations, the flexible outer tubing 4086 can be a hollow, braided tubing that has an outer diameter that is smaller than the instrument channel of the endoscope in which the endoscopic instrument 4000 is to be inserted. In some implementations, the length of the flexible outer tubing 4086 can be sized to exceed the length of the endoscope. The flexible outer tubing 4086 can define a bore through which a portion of the flexible outer tubing 4086 extends. The flexible outer tubing 4086 can include braids, threads, or other features that facilitate the rotation of the flexible outer tubing 4086 relative to the flexible torque coil, which is partially disposed within the flexible outer tubing 4086.

The endoscopic instrument 4000 can include a rotational coupler 4030 configured to be coupled to a proximal end of the flexible outer tubing 4086. The rotational coupler 4030 may be configured to allow an operator of the endoscopic tool to rotate the flexible outer tubing 4086 via a rotational tab 4032 coupled to or being an integral part of the rotational coupler 4030. By rotating the rotational tab 4032, the operator can rotate the flexible outer tubing and the outer cannula along a longitudinal axis of the endoscope and relative to the endoscope and the inner cannula of the cutting assembly 4010. In some implementations, the operator may want to rotate the outer cannula while the endoscopic instrument is inserted within the endoscope while the endoscope is within the patient. The operator may desire to rotate the outer cannula to position the opening of the outer cannula to a position where the portion of the radial wall of the outer cannula within which the opening is defined may aligned with the camera of the endoscope such that the operator can view the material entering the endoscopic instrument for resection via the opening. This is possible in part because the opening is defined along a radial wall extending on a side of the outer cannula as opposed to an opening formed on the axial wall of the outer cannula.

In some implementations, a proximal end 4034 of the rotational coupler 4030 can be coupled to a lavage connector 4040. In some implementations, the rotational coupler 4030 can be a rotating luer component that allows a distal end 4036 of the rotational coupler 4030 rotate relative to the proximal end 4034 of the rotational coupler 4030. In this way, when the flexible outer tubing 4086 is rotated, the component to which the proximal end of the rotational coupler 4030 is coupled, is not caused to rotate. In some implementations, the proximal end 4034 of the rotational coupler 4030 can be coupled to an outer tubular member 4044 configured to couple the proximal end 4034 of the rotational coupler 4030 to the lavage connector 4040. The rotational coupler 4030 can define a bore along a central portion of the rotational coupler 4030 through which a portion of the flexible torque coil 4080 extends. In soiree implementations, the rotational coupler 4030 can be a male to male rotating luer connector. In some implementations, the rotational coupler can be configured to handle pressures up to 1200 psi.

The lavage connector 4040 can be configured to introduce irrigation fluid into the endoscopic tool 4000. The lavage connector 4040 includes a lavage port 4042 configured to engage with an irrigation source, such as a water container. In some implementations, the lavage connector 4040 can be a Y port used in fluid delivery systems that complies with medical device industry standards and is sized to couple to the flexible outer tubing 4086 or the outer tubular member 4044 that serves to couple a distal end 4048 of the lavage connector 4040 to the proximal end 4034 of the rotational coupler 4030. In some implementations, the lavage connector can define a hollow channel between the proximal end 4046 and the distal end 4048 of the lavage connector 4040 that is sized to allow the flexible torque coil 4080 to pass through the hollow channel defined through the lavage connector 4040.

As described above, the proximal connector assembly 4070 is configured to be coupled to a proximal end of the flexible torque coil 4080. The proximal connector assembly 4070 can be configured to engage with the drive assembly 4050 that is configured to provide torque to the inner cannula via the proximal connector assembly 4070 and the flexible torque coil 4080. The proximal connector assembly 4070 can further define a portion of the aspiration channel and be configured to fluidly couple the aspiration channel to a vacuum source to facilitate the removal of material entering the aspiration channel. In some implementations, a proximal end of the proximal connector assembly 4070 can include an aspiration port 4092 through which the material that enters the endoscopic tool 4000 can be withdrawn from the endoscopic tool 4000.

In some implementations, the endoscopic tool 4000 can be configured to be driven by the drive assembly 4050. The drive assembly 4050 is configured to provide rotational energy from an energy source to the endoscopic tool 4000. The drive assembly 4050 can include a housing 4060 that may house a first beveled gear 4054 and a second beveled gear 4056 that are positioned such that the rotation of the first beveled gear 4054 causes a rotation of the second beveled gear 4056. The second beveled gear 4056 can be coupled to a drive receptacle that is sized and shaped to receive and engage with the proximal connector assembly 4070 of the endoscopic tool 4000. In some implementations, the first beveled gear 4054 can be coupled to a motor (not shown) or other rotational source via a rotational input shaft 4052.

The proximal connector assembly 4070 can include a hollow drive shaft 4072, a coupler 4076 through which the hollow drive shaft 4072 passes and a tensioning spring 4074 coupled to the hollow drive shaft 4072. A distal end of the drive shaft 4072 can be coupled to the proximal end of the flexible torque coil 4080. In some implementations, the drive shaft 4072 and the flexible torque coil 4080 can be permanently coupled to one another. In some implementations, the drive shaft 4072 and flexible torque coil 4080 can be coupled using a coupler, a press fit, a weld, such as a butt weld, or any other attachment means that allows the flexible torque coil 4080 to rotate when the drive shaft 4072 rotates and to allow material passing through the flexible torque coil 4080 to flow through the drive shaft 4072. A proximal end of the drive shaft 4072 can define the aspiration port 4092. In some implementations, the aspiration port 4092 can be configured to engage with a vacuum source causing material entering the opening 4012 to flow through the aspiration channel 4090 and out of the endoscopic tool through the aspiration port 4092.

A coupler 4076, such as a hex-shaped coupler, can be configured to couple with the hollow drive shaft. In some implementations, the hex-shaped coupler is a part of the hollow drive shaft. The coupler 4076 can include an outer wall that is configured to engage with an inner wall of a drive receptacle 4058. The drive receptacle 4058 is coupled to the second beveled gear 4056 and is configured to rotate when the second beveled gear 4056 rotates. In some implementations, the drive receptacle 4058 can be a hollow cylindrical tube. In some implementations, a proximal end 4059 of the drive receptacle 4058 can include an opening defined by an inner wall of the proximal end of the drive receptacle 4058 that has a diameter that smaller than the inner diameter of the remaining portion of the drive receptacle 4058. In some implementations, the diameter of the opening through the proximal end 4059 of the drive receptacle 4058 can be large enough to receive the drift shaft 4072 but small enough to prevent the tensioning spring 4074 coupled to the drive shaft 4072 from passing through the opening. In some implementations, the inner diameter of the remaining portion of the drive receptacle is sized to engage with the coupler 4076.

The tensioning spring 4074 can be biased in such a way that, during operation of the endoscopic tool 4000, the tensioning spring 4074 may prevent the drive shaft 4072, the flexible torque coil 4080 and the inner cannula from sliding towards the proximal end of the endoscopic tool 4000. In some implementations, without the tensioning spring 4074, the inner cannula may slide away from the distal end of the endoscopic tool 4000. This may be due to a force applied by the material to be resected at the opening 4012. In some implementations, the tensioning spring 4074 provides a countering force that prevents the inner cannula from sliding away from the distal end when the inner cannula comes into contact with the material to be resected at the opening 4012. In some implementations, the tensioning spring 4074 can be configured to bias the distal end of the inner cannula to contact an inner wall of the distal end of the outer cannula. In some implementations, the tensioning spring 4074 can be sized and biased such that the distal tip of the inner cannula can contact the inner distal wall of the outer cannula. This may limit any lateral or undesired movement generated due to whip at the distal end of the inner cannula caused by the rotation of the flexible torque coil.

The housing 4060 can be configured to engage with an aspiration end cap 4062 and a locking collar 4064. In some implementations, the aspiration end cap 4062 can be configured to allow a vacuum source to maintain a secure connection with the aspiration port 4092 of the drive shaft 4072. In some implementations, the aspiration end cap 4062 can be configured to allow the drive shaft 4072 to rotate while maintaining a secure connection between the vacuum source and the aspiration port 4092 of the drive shaft 4072. In some implementations, the aspiration end cap 4062 can be configured to be secured to a portion of the housing 4060 in such a way that the aspiration port of the drive shaft 4072 is accessible via an opening of the aspiration end cap 4062. In some implementations, the vacuum source can be coupled to the end cap 4062 such that the vacuum source does not rotate along with the proximal end of the drive shaft 4072. In some implementations, one or more bearings or bushings can be used to allow facilitate a fluid connection between the aspiration port 4092 of the drive shaft 4072 and the vacuum source without causing the vacuum source to rotate with the drive shaft 4072.

The locking collar 4064 can be configured to secure the lavage connector 4040 to the proximal connector assembly 4070. In some implementations, the locking collar 4064 can be configured to secure a proximal end 4046 of the lavage connector 4040 to the housing 4060 of the drive assembly 4050. The locking collar 4064 can further be configured to prevent the proximal connector assembly 4070 from disengaging with the drive receptacle 4058 and moving towards the distal end of the endoscopic tool 4000. In some implementations, the locking collar 4064 can be configured to secure a lining 4082 within which the flexible torque coil 4080 is disposed to the flexible torque coil 4080, the drive shaft 4072 or the housing 4060. In some implementations, the lining 4082 can serve as a heat shrink to reduce the dissipation of heat generated in the flexible torque coil to other components of the endoscopic tool. In some implementations, the outer wall of the lining 4082 can define a portion of the irrigation channel, while the inner wall of the lining 4082 can serve to prevent any material passing through the aspiration channel from escaping through the walls of the flexible torque coil. In some implementations, the lining 4082 can also prevent the irrigation fluid passing through the irrigation channel to flow into the aspiration channel 4090 through the walls of the flexible torque coil 4080.

The distal end 4048 of the lavage connector 4040 can be configured to engage with an inner wall of the outer tubing 4044. In some implementations, the distal end 4048 of the lavage connector 4040 can be press fit into a proximal end of the outer tubing 4044. In some implementations, a connector connecting the distal end 4048 of the lavage connector 4040 and the outer tubing can be used. The inner wall of the outer tubing 4044 and the outer wall of the lining 4082 can define a portion of the irrigation channel 4096. The outer tubing 4044 can extend from the distal end 4048 of the lavage connector 4040 to a proximal end 4034 of the rotational coupler 4030. The distal end of the outer tubing 4044 can be configured to engage with the proximal end 4034 of the rotational coupler 4030.

In some implementations, the irrigation channel can extend from the irrigation entry port to the opening of the outer cannula. The irrigation channel can be defined by the inner wall of the outer tubular member, the rotational coupler, the inner wall of the outer tubing and the inner wall of outer cannula. In some implementations, the irrigation channel can also be defined by the outer wall of the inner cannula and the outer wall of the flexible torque coil 4080. In some implementations, the endoscopic instrument 4000 can also include the hollow lining 4082 that is sized to fit around the flexible torque coil 4080. In some implementations, the hollow lining 4082 can serve as a barrier between the irrigation channel 4096 and the aspiration channel 4090. In some implementations, the hollow lining 4082 can prevent air or other fluids to seep through the threads of the flexible torque coil 4080. In addition, the hollow lining can allow the aspiration channel to maintain a suction force throughout the length of the aspiration channel by preventing air to escape or enter through the threads of the flexible torque coil 4080.

As described above, the cutting assembly 4010 includes the outer cannula. The braided tubing 4086 is coupled to the outer cannula such that rotating the rotational tab 4032 of the rotational coupler 4030 results in rotating the outer cannula. The outer cannula includes the opening 4012 at a distal end of the outer cannula. The opening is defined within a portion of the radial wall of the outer cannula and may only extend around a portion of the radius of the outer cannula. As the aspiration channel 4090 extends between the aspiration port 4092 and the opening 4012, any suction applied at the aspiration port 4092 causes a suction force to be exerted at the opening 4012. The suction force causes material to be introduced into the opening of the outer cannula, which can then be cut by the inner cannula of the cutting assembly. In some implementations, the aspirated material can be collected in a collection cartridge. In some implementations, the collection cartridge can be fluidly coupled to the proximal end of the aspiration channel.

The inner cannula is disposed within the outer cannula and configured to resect any material that is sucked into or otherwise enters the opening 4012 due to the suction force in the aspiration channel 4090. The inner cannula can cut, resect, excise, debride or shave the material at the opening 4012 based in part on the interaction between the cutting surface and the wall of the outer cannula that defines the opening. In some implementations, the rotational movement of the cutting surface relative to the opening 4012 can cause the material to be cut, resected, excised, or shaved. The flexible torque coil is coupled to the inner cannula and causes the inner cannula to rotate along the longitudinal axis of the inner cannula. As the outer cannula is coupled to the outer tubing and is not rotationally coupled to the inner cannula or flexible torque coil, the inner cannula rotates relative to the outer cannula. A gap between an outer wall of the inner cannula and the inner wall of the outer cannula defines a portion of the irrigation channel through which irrigation fluid can flow from the lavage connector 4040 through the irrigation channel portion defined in part by the outer tubing 4044, the rotational coupler 4030, and the flexible outer tubing 4086 towards the cutting surface of the inner cannula. The inner cannula may define a portion of the aspiration channel through which excised or resected material and the irrigation fluid can flow from the cutting surface of the inner cannula towards the aspiration port 4092.

The length of the cutting assembly 4010 may be sized to allow the endoscopic instrument 4000 to traverse through the length of the endoscope while the endoscope is inserted inside a patient. In some implementations, the endoscope may be disposed within the patient and the endoscope may include bends that exceed 60 degrees. As such, the length of the cutting assembly 4010 may not exceed a few centimeters. In some implementations, the length of the cutting assembly 4010 may be less than 1% of the length of the endoscopic tool 4000, or the length of the flexible portion of the endoscope within which the endoscopic tool can be inserted. As described above, tissue sensing capabilities can be implemented with the cutting assembly serving as a portion of the tissue sensor.

It should be appreciated that one or more seals, bearings, and other components may be used. Seals may be used to maintain pressure, prevent fluid leaks, or to securely engage components to one another. In some implementations, bearings may be used to allow components to rotate relative to one another without adversely affecting the components or the performance of the endoscopic tool.

FIG. 45 shows a cross-sectional view of the endoscopic tool and the portion of the drive assembly across the section B-B. As shown in FIG. 45, the second beveled gear 4056 may be configured to engage with the drive receptacle 4058 of the drive assembly 4050. The proximal connector 4070 of the endoscopic tool 4000, which includes the coupler 4076 and the drive shaft 4072, can be inserted disposed within the drive receptacle 4058. The outer wall of the coupler 4076 is sized to engage with the inner wall of the drive receptacle 4058 such that when the drive receptacle 4058 rotates, the coupler 4076 also rotates. Because the coupler 4076 is coupled to the drive shaft 4072, the drive shaft 4072 may also rotate when the drive receptacle 4058 rotates. The inner wall of the drive shaft defines a portion of the aspiration channel 4090.

FIG. 46 shows an enlarged cross-sectional view of the rotational coupler section of the endoscopic tool. FIG. 47A and FIG. 47B show a top view and a cross-sectional view of the rotational coupler of the endoscopic tool.

As shown in FIGS. 46-47B, the outer tubing 4044 is configured to engage with the rotational coupler 4030. The outer tubing 4044 surrounds the lining 4082, which in turn surrounds the flexible torque coil 4080. The inner wall of the flexible torque coil 4080 may define a portion of the aspiration channel 4090. The space between the inner wall of the outer tubing 4044 and the outer wall or surface of the lining 4082 defines a portion of the irrigation channel. The tab 4032 can be configured to be rotated by an operator of the endoscopic tool. In some implementations, the operator can rotate the tab 4032 while the endoscopic tool is inserted within the instrument channel of the endoscope and cause the outer cannula to rotate relative to the inner cannula and the endoscope. In this way, the operator can position the opening defined through the outer cannula by rotating the outer cannula to a desired position. In some implementations, by providing a mechanism through which the outer cannula can be rotated relative to the endoscope, an operator does not have to be concerned about the position of the opening when the endoscopic tool is inserted within the instrument channel of the endoscope as the operator may be able to adjust the position of the opening by causing the outer cannula to rotate while the endoscopic tool is inserted within the endoscope.

Figure 48:
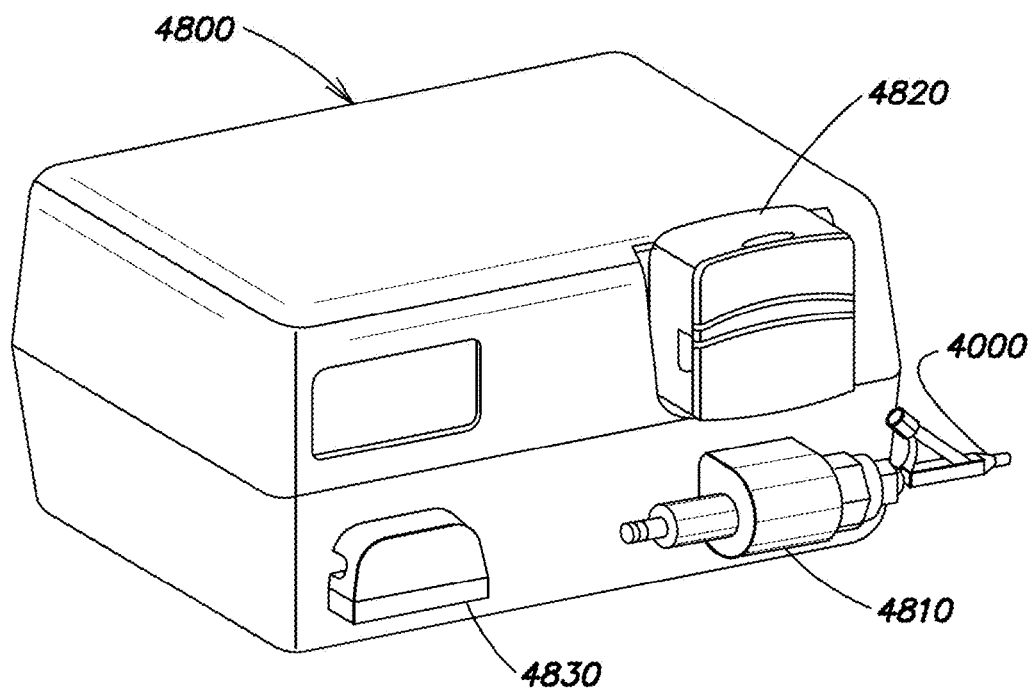
FIG. 48 is a perspective view of a portion of the endoscopic tool inserted for operation within a drive assembly according to embodiments of the present disclosure.

FIG. 48 is a perspective view of a portion of the endoscopic tool inserted for operation within a drive assembly. The drive assembly 4800 includes a drive interface 4810 configured to receive the proximal connector 4070 of the endoscopic tool 4000. The proximal connector 4070 can engage with the drive receptacle of the drive interface 4810 to translate rotational energy generated by the drive assembly 4800 to the cutting assembly of the endoscopic tool 4000. The drive assembly 4800 may include a pump 4820 or other fluid displacement device to control the flow of irrigation fluid into the lavage port 4042 of the endoscopic tool 4000. In some implementations, the pump 4820 can be a peristaltic pump. In some implementations, the pump can be any positive displacement fluid pump. In some implementations, a valve between the pump 4820 and the lavage port 4042 can be placed to control an amount of irrigation fluid entering the endoscopic tool. In some implementations, the speed at which the pump 4820 operates can dictate the rate at which irrigation fluid enters the endoscopic tool. The drive assembly can also include a pinch valve 4830. In some implementations, the pinch valve can be configured to control the application of a suction force applied to the aspiration channel.

In some implementations, an actuator, such as a control switch can be used to actuate the drive assembly 4800. In some implementations, the actuator can be a foot pedal, a hand switch, or any other actuation means for controlling the drive assembly 4800. In some implementations, the actuator can be coupled to the drive means, such as the pump 4820 such that when the actuator is actuated, the pump 4820 begins to rotate, generating torque, which is translated to the proximal connector of the endoscopic tool via the drive interface 4810. The torque applied to the proximal connector can be translated via the flexible torque coil to the inner cannula, thereby causing the inner cannula to rotate relative to the outer cannula. In some implementations, the actuator can be coupled to a pinch valve, such as the pinch valve 4830 to control the amount of suction applied to the aspiration channel. In some implementations, the actuator can be configured to actuate both the drive means and the pinch valve simultaneously, such that the inner cannula is rotating while suction is applied through the aspiration channel. In some implementations, the actuator can also be coupled to an irrigation control switch or valve that controls the flow of irrigation fluid into the endoscopic tool via the irrigation entry port 4042. In some implementations, the actuator can be configured to actuate the drive means, the pinch valve for aspiration and the irrigation control switch for irrigation simultaneously, such that the inner cannula is rotating while suction is applied through the aspiration channel and irrigation fluid is supplied to the endoscopic tool.

In some implementations, a separate irrigation control switch can be configured to control the flow of irrigation fluid through the irrigation channel of the endoscopic tool.

An operator can control the volume of irrigation fluid provided to the irrigation channel via the irrigation control switch.

The drive assembly configuration shown in FIGS. 40A-48 is one example configuration of a drive assembly. It should be appreciated that the endoscopic tool 4000 can be configured to be driven by other drive assembly configurations. In some implementations, the proximal connector portion of the endoscopic tool 4000 can be modified to engage with other drive assembly configurations. In some implementations, the endoscopic tool 400 can be configured to be packaged as one or more different components that can be assembled prior to inserting the endoscopic tool within the instrument channel of the endoscope. In some implementations, the proximal connector of the endoscopic tool 4000 can be assembled together by an operator of the endoscopic tool after one or more components of the endoscopic tool are caused to engage with components of the drive assembly.

Figure 49:
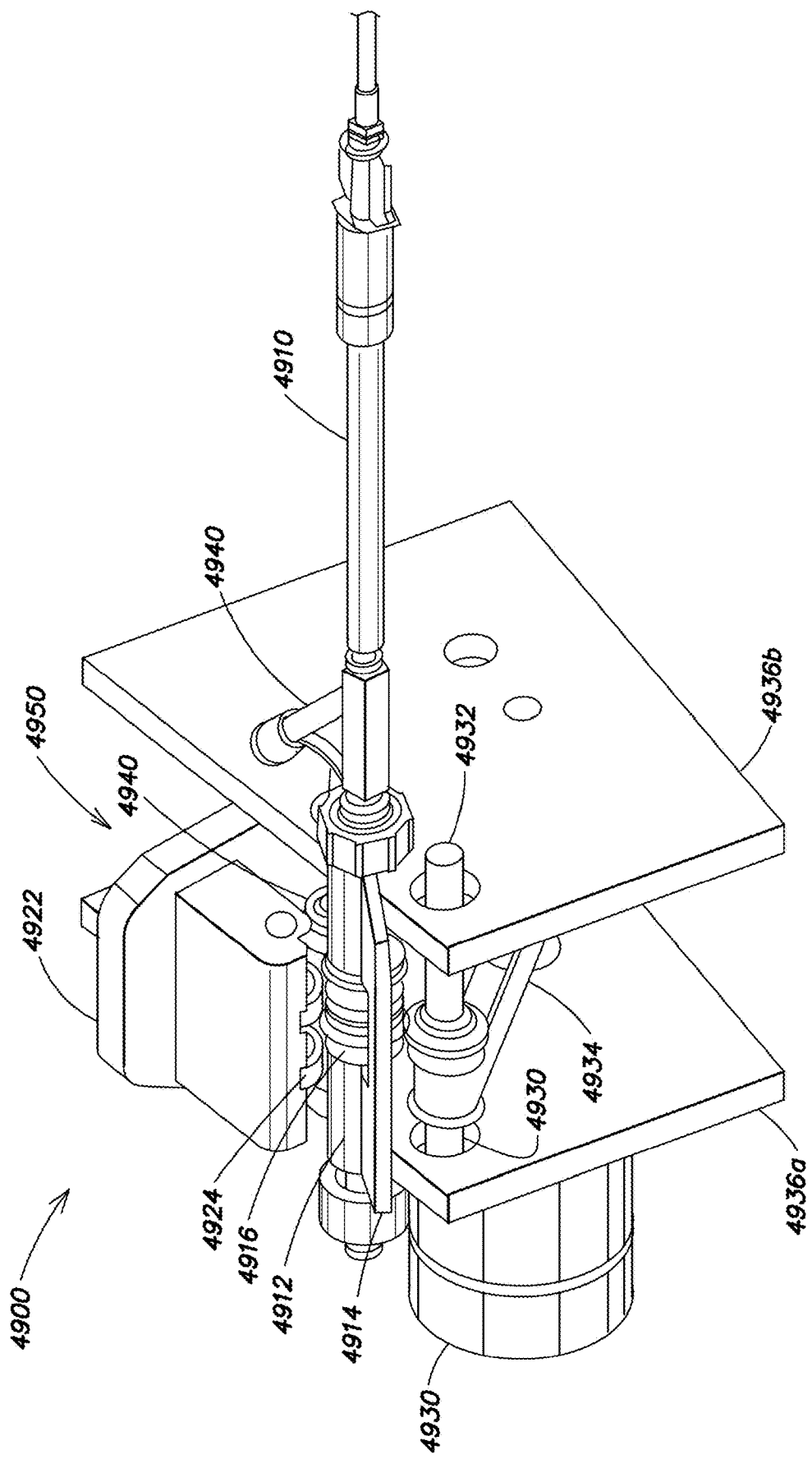
FIG. 49 illustrates another implementation of the endoscopic tool and a drive assembly configured to drive the endoscopic tool according to embodiments of the present disclosure.
Figure 50B:
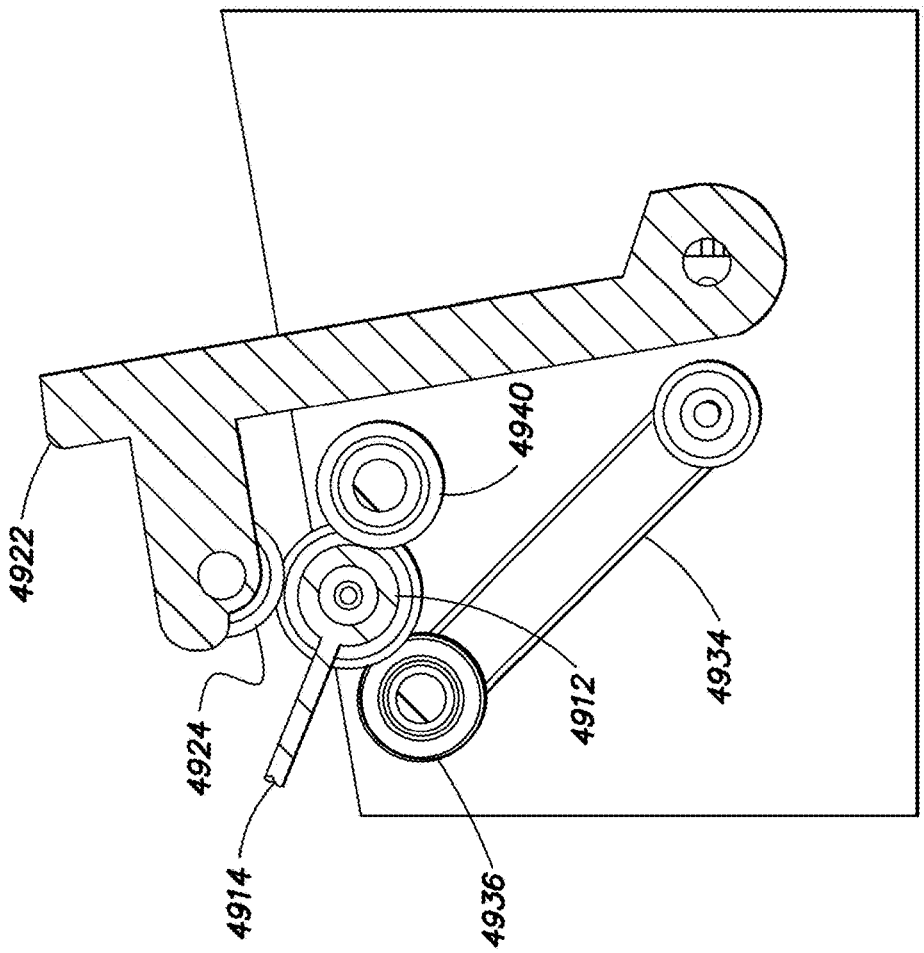
FIG. 50B is a cross-sectional view of the endoscopic tool and drive assembly shown in FIG. 49 taken along the section A-A according to embodiments of the present disclosure.
Figure 50A:
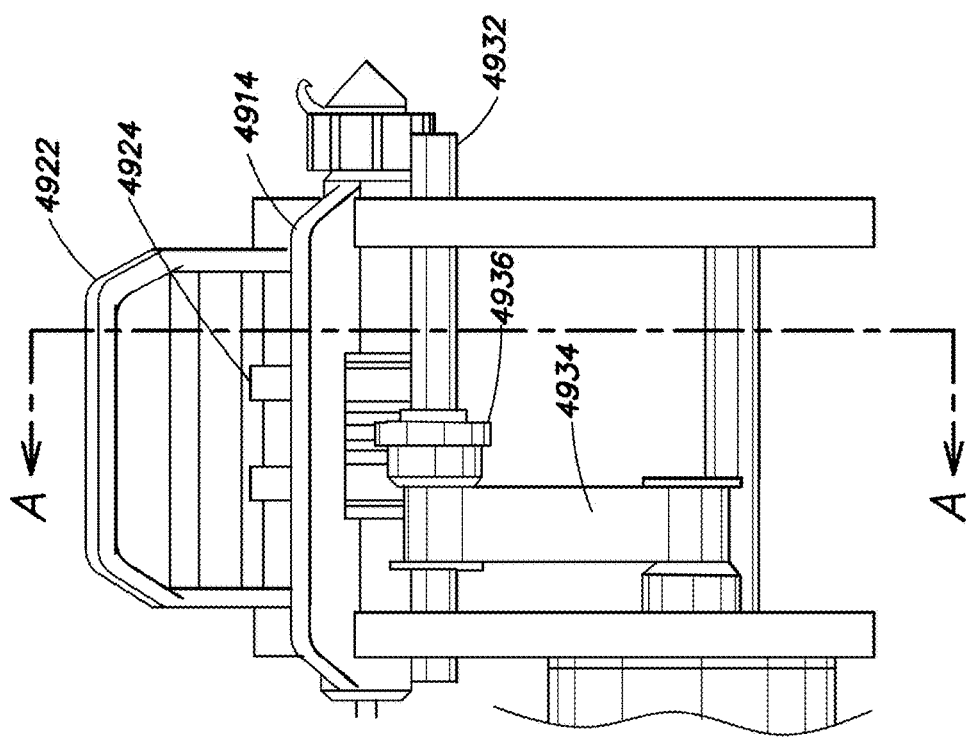
FIG. 50A is a side view of the endoscopic tool and drive assembly shown in FIG. 49 according to embodiments of the present disclosure.

FIG. 49 illustrates another implementation of the endoscopic tool and a drive assembly configured to drive the endoscopic tool. FIG. 50A is a side view of the endoscopic tool and drive assembly shown in FIG. 49. FIG. 50B is a cross-sectional view of the endoscopic tool and drive assembly shown in FIG. 49 taken along the section A-A. The endoscopic tool 4910 is similar to the endoscopic tool 4000 but differs from the endoscopic tool 4000 in that the endoscopic tool 4910 has a different proximal connector 4912. In this implementation, the proximal connector 4912 can be coupled to a flexible torque coil, similar to the flexible torque coil 4000 shown in FIGS. 40A-43, and include a proximal connector engagement structure 4914 that is configured to engage with a drive assembly 4950. The proximal connector engagement structure can be sized to engage with the drive assembly 4950 and include one or more engagement surfaces configured to engage with the drive assembly 4950. The engagement surfaces can be coupled to the drive shaft included within the proximal connector 4912 such that when the drive assembly 4950 applies a rotating force to the engagement surfaces, the drive shaft rotates, which in turn causes the flexible torque coil and cutting assembly of the endoscopic tool 4900 to rotate. In some implementations, the engagement surfaces 4914 can be cylindrical objects having an outer wall configured to engage with the drive assembly 4950 and an inner wall configured to engage with an outer wall of the drive shaft. In some implementations, the proximal connector 4910 can also include a fin 4916 or other structure that prevents the proximal connector 4910 and endoscopic tool 4910 from rotating relative to the drive assembly 4950. In some implementations, a side of the fin 4916 can rest on or engage with a mounting structure 4936a and 4936b. In this way, when a rotating force is applied by the drive assembly on the engagement surfaces, the fin 4916 prevents the proximal connector 4910 from rotating relative to the drive assembly 4950. The mounting structures 4936 can be configured such that various components of the drive assembly 4950 can be mounted on or receive support from the mounting structures 4936.

The drive assembly 4950 can include a retractable arm 4922, one or more spring loaded bearings 4924, a drive belt 4932 and a drive wheel 4936 and one or more stationary bearings 4940. The retractable arm 4922 can be configured to rotate between a first position and a second position. The spring loaded bearings 4924 can be mounted to the retractable arm 4922 and positioned such that when the retractable arm 4922 is in the first position as shown in FIGS. 49 and 50A-B, the spring loaded bearings 4924 can apply a force on the proximal connector 4912 causing the proximal connector to remain in place while the drive assembly 4950 is actuated. The spring loaded bearings 4924 can be positioned such that when the proximal connector 4912 of the endoscopic tool 4910 is engaged with the drive assembly 4950, the spring loaded bearings 4924 engage with an engagement component 4916 of a drive shaft (not shown) disposed within the proximal connector 4912. The engagement component 4916 can be strategically located on the proximal connector 4912 such that when the retractable arm 4922 is in the first position, the spring loaded bearings 4924 come into contact with the engagement component 4916. The engagement component 4916 can be cylindrical in shape and surround the drive shaft disposed within the proximal connector 4912. The engagement component 4916 can form a portion of the outer wall of the proximal connector 4912. In some implementations, the engagement component 4916 can rotate along a longitudinal axis of the proximal connector 4912 and rotate relative to the proximal connector 4912. In some implementations, the drive wheel 4936 can be an elastomeric friction drive wheel.

A drive means, such as a motor or other driving source, can drive the drive wheel 4936 mounted on a mounting shaft 4930 via the drive belt 4934 that moves when the drive means is actuated. The drive belt 4934 can cause the drive wheel 4936 to rotate. The engagement component 4916 of the proximal connector 4912 can be configured to contact the drive wheel 4936 when the endoscopic tool is positioned within the drive assembly 4950. A stationary bearing 4940 of the drive assembly 4950 can be positioned to hold the proximal connector 4912 in place while the rotation of the drive wheel 4936 causes the engagement component 4916 to rotate. The stationary bearing 4940 can also provide a force causing the drive wheel 4936 and the engagement component 4916 to maintain contact.

As shown in FIG. 50B, when the retractable arm is in the first position, or engaged position, the spring loaded bearings 4924 are in contact with the one or more engagement components 4916 at a first side and the drive wheel 4936 is in contact with the engagement components 4916 at a second side. The spring loaded bearings may allow the engagement components 4916 to rotate when the drive wheel is rotating. The fin 4914 rests against the mounting structures of the drive assembly preventing the endoscopic tool from rotating. When the retractable arm is in a second position, or disengaged position, the spring loaded bearings 4924 are not in contact with the one or more engagement components 4916. As such, the endoscopic tool is not securely positioned within the drive assembly, and as such, actuating the drive means may not cause the flexible torque coil within the endoscopic tool to rotate.

It should be appreciated that the outer diameter of the endoscopic instrument may be sized to be inserted within the instrument channel of an endoscope while the endoscope is inserted within a patient. In addition, the endoscopic instrument may be sized to be large enough that the endoscopic tool comes into contact with the inner walls of the instrument channel at various portions of the instrument channel to maintain stability of the endoscopic instrument. If the outer diameter of the endoscopic instrument is much smaller than the inner diameter of the instrument channel, there may be a large amount of space between the endoscopic instrument and the inner wall of the instrument channel, which may allow the endoscopic instrument to move, vibrate or otherwise experience some instability during operation.

Improved Endoscopic Tool for Removing Material from within a Patient

Figure 51A:
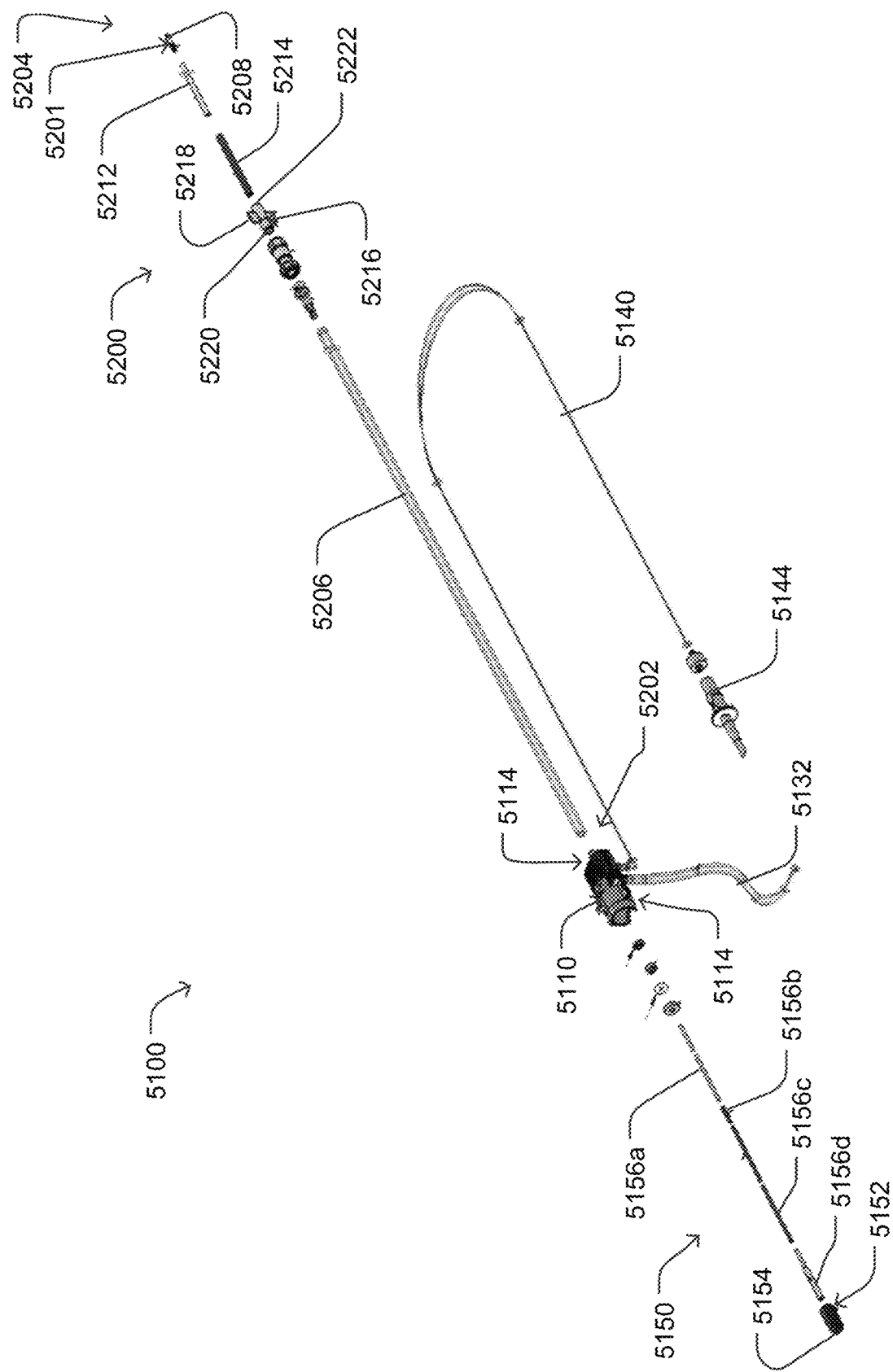
FIG. 51A is an exploded perspective view of an improved endoscopic tool according to embodiments of the present disclosure.
Figures 51B, 51C:
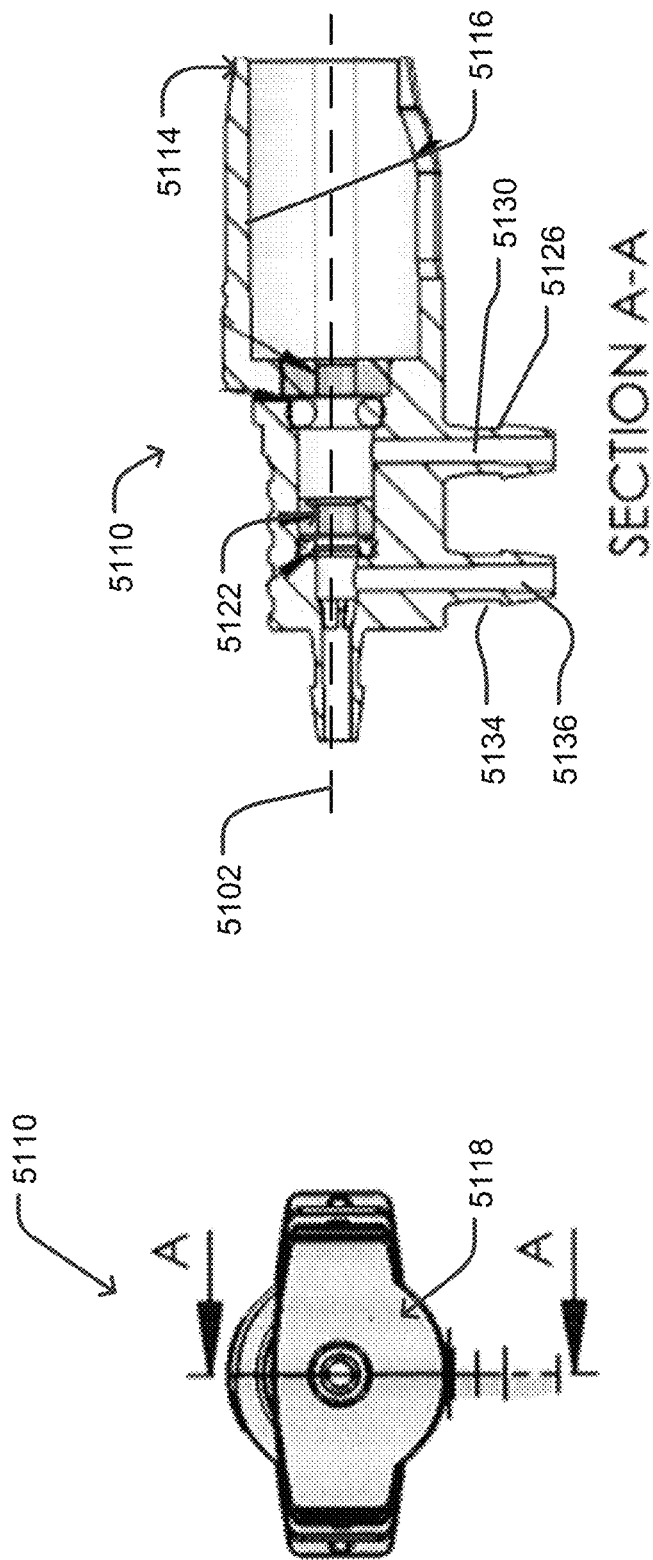
FIG. 51B is an end view of the improved endoscopic tool shown in FIG. 51A according to embodiments of the present disclosure.
FIG. 51C is a cross-sectional view of the improved endoscopic tool shown in FIG. 51B taken along the section A-A according to embodiments of the present disclosure.

FIGS. 51A-51C show an endoscopic tool 5100. The endoscopic tool 5100 may be similar to various endoscopic tools described herein, including the endoscopic tool 4000 (e.g., as shown in FIGS. 40A-40B, 41, and 42). The endoscopic tool 5100 can be configured to obtain samples of polyps and neoplasms from a patient. The endoscopic tool 5100 can be configured to be rotated by a torque source (e.g., a motor coupled to a drive assembly or drive shaft of the endoscopic tool 5100). The endoscopic tool 5100 can be configured to flow irrigation fluid out into a site within a subject (e.g., a site within a colon, esophagus, lung of the subject). The endoscopic tool 5100 can be configured to resect material at a site within a subject. The endoscopic tool 5100 can be configured to provide a suction force via an aspiration channel to obtain a sample of the material resected at a site within a subject. In some implementations, the endoscopic tool 5100 can be configured to be inserted within an instrument channel, such as an instrument channel of an endoscope (e.g., a gastroscope, such as a colonoscope, a laryngoscope, or any other flexible endoscope).

The endoscopic tool 5100 includes a proximal connector 5110 and a flexible torque delivery assembly 5200. The proximal connector 5110 is configured to couple a drive assembly 5150 (e.g., a drive assembly including a drive shaft configured to be rotated by a source of rotational energy) of the endoscopic tool 5100 to the flexible torque delivery assembly of the endoscopic tool 5100. In some implementations, the proximal connector 5110 includes a first connector end 5114 at which the drive assembly 5150 is coupled, and a second connector end 5118 at which the flexible torque delivery assembly 5200 is coupled. As shown in FIGS. 51A and 51C, the first connector end 5114 includes an inner wall 5116 defining an opening in which the drive assembly 5150 can be received. For example, in some implementations, the proximal connector 5110 can be used to connect the drive assembly 5150 to a drive shaft of a surgical console (see, e.g., console drive assembly 6150 of console 6000 shown in FIGS. 55A-55D and 57A-57C, etc.). The proximal connector 5110 includes a drive transfer assembly 5122. The drive transfer assembly 5122 is configured to be operatively coupled to the drive assembly 5150, receive torque from the drive assembly 5150 when the drive assembly 5150 rotates, and transfer the torque to the flexible torque delivery assembly 5200 in order to rotate the flexible torque delivery assembly 5200. In some implementations, the drive assembly 5150, drive transfer assembly 5122, and at least a portion of the flexible torque delivery assembly 5200 are coaxial. For example, the drive transfer assembly 5122 can be engaged to the drive assembly 5150 along a drive axis 5102, and the drive transfer assembly 5122 can also be engaged to the flexible torque delivery assembly 5200 at a proximal end 5204 of the flexible torque delivery assembly 5200 along the drive axis 5102. It should be appreciated that rotating the flexible torque delivery assembly may include causing the flexible torque delivery assembly to rotate a component (such as an inner cannula) at one of the flexible torque delivery assembly.

In some implementations, the drive transfer assembly 5122 includes gears, belts, or other drive components to control the direction and/or torque transferred from the drive assembly 5150 to the flexible torque delivery assembly 5200. For example, such drive components can be positioned at an angle to one another to change an axis of rotation of the flexible torque delivery assembly 5200, or offset from one another to shift an axis of rotation of the flexible torque delivery assembly 5200 relative to the drive axis 5102.

In some implementations, the drive assembly 5150 includes a drive engagement member 5152. The drive engagement member 5152 is configured to engage the drive assembly 5150 to a source of rotational energy (e.g., a drive rotated by a motor, such as console drive assembly 6150 of console 6000, etc.). The drive engagement member 5152 can be configured to be fixedly and/or rigidly connected to the console drive assembly 6150, such that the drive engagement member 5152 rotates in unison with the console drive assembly 6150. For example, as shown in FIG. 51A, the drive engagement member 5152 includes a proximal drive end 5154 including a fitting (e.g., hex fitting, pin fitting, etc.) configured to engage (e.g., lock with, mate with, fixedly engage, frictionally engage, etc.) an engagement receiver member 6158 of the console drive assembly 6150 of the console 6000. As such, rotation of the console drive assembly 6150 causes rotation of the drive engagement member 5152.

In some implementations, the drive assembly 5150 includes one or more shaft components 5154 configured to transfer rotation of the drive engagement member 5150 to the drive transfer assembly 5122. In some implementations, the drive transfer assembly 5122 includes the one or more shaft components 5156. The shaft components 5156 can include an insulator member 5156a (e.g., a heat sheath, heat shrink, etc.) configured to insulate components of the drive assembly 5150 from heat generated by rotation of the drive assembly or components thereof. The shaft components 5156 can include a cutter 5156b. The shaft components 5156 can include a shaft torque coil 5156c which may be similar to other torque coils described herein. In some implementations, the shaft components 5156 can include a shaft torque rope. The shaft components 5156 can include a shaft tube 5156d. The shaft tube 5156d can include a radius that is less than a relatively greater radius of the drive engagement member 5152 (e.g., a relatively greater radius that may facilitate receiving rotational energy from a drive shaft or other rotational energy source, such as by engaging the drive engagement member 5152 to the engagement receiver member 6158 of the console drive assembly 6150). For example, the shaft tribe 5156d can include a relatively lesser smaller corresponding more closely to a radius of the drive transfer assembly 5122 and/or the flexible torque delivery assembly 5200. In such implementations, the torque received at the drive transfer assembly 5122 and/or the flexible torque delivery assembly 5200 can be modified (e.g., increased) in a manner corresponding to the change in radius between the radius of the drive engagement member 5152 and the radius of the shaft tube 5156d.

The distal portion of the endoscopic tool 5100 (e.g., the distal portion including the cutting assembly 5201) can be similar to other distal portions of endoscopic tools described herein (e.g., cutting assembly 4010 shown in FIG. 42, etc.). In some implementations, the cutting assembly 5201 can include an outer cannula and an inner cannula disposed within the outer cannula. The outer cannula can define an opening 5208 through which material to be resected can enter the cutting assembly 5201. In some implementations, the opening 5208 is defined through a portion of the radial wall of the outer cannula. In some implementations, the opening 5208 may extend around only a portion of the radius of the outer cannula, for example, up to one third of the circumference of the radial wall. As the aspiration channel extends between a vacuum port (e.g., vacuum port 5126) and the opening 5208, any suction applied at the vacuum port causes a suction force to be exerted at the opening 5208. The suction force causes material to be introduced into the opening or cutting window of the outer cannula, which can then be cut by the inner cannula of the cutting assembly 5201.

The inner cannula can include a cutting section that is configured to be positioned adjacent to the opening 5208 such that material to be resected that enters the cutting assembly 5201 via the opening 5208 can be resected by the cutting section of the inner cannula. The inner cannula may be hollow and an inner wall of the inner cannula may define a portion of an aspiration channel that may extend through the length of the endoscopic tool. A distal end of the inner cannula can include the cutting section while a proximal end of the inner cannula can be open such that material entering the distal end of the inner cannula via the cutting section can pass through the proximal end of the inner cannula. In some implementations, the distal end of the inner cannula can come into contact with an inner surface of a distal end of the outer cannula. In some implementations, this can allow the inner cannula to rotate relative to the outer cannula along a generally longitudinal axis, providing more stability to the inner cannula while the inner cannula is rotating. In some implementations, the size of the opening can dictate the size of the materials being cut or resected by the inner cannula. As such, the size of the opening may be determined based in part on the size of the aspiration channel defined by the inner circumference of the flexible torque coil.

The endoscopic tool 5100 can include a flexible torque coil 5212 that is configured to couple to the proximal end of the inner cannula at a distal end of the flexible torque coil 5212. The flexible torque coil can include a fine coil with multiple threads and multiple layers, which can transmit the rotation of one end of the flexible torque coil to an opposite end of the flexible torque coil. Each of the layers of thread of the flexible torque coil can be wound in a direction opposite to a direction in which each of the layers of thread adjacent to the layer of thread is wound. In some implementations, the flexible torque coil can include a first layer of thread wound in a clockwise direction, a second layer of thread wound in a counter-clockwise direction and a third layer of thread wound in a clockwise direction. In some implementations, the first layer of thread is separated from the third layer of thread by the second layer of thread. In some implementations, each of the layers of thread can include one or more threads. In some implementations, the layers of thread can be made from different materials or have different characteristics, such as thickness, length, among others.

The flexibility of the torque coil 5212 allows the coil to maintain performance even in sections of the torque coil 5212 that are bent. Examples of the flexible torque coil 5212 include torque coils made by ASAHI INTECC USA, INC located in Santa Ana, Calif., USA. In some implementations, the flexible torque coil 5212 can be surrounded by a sheath or lining (e.g., sheath 5214) to avoid frictional contact between the outer surface of the flexible torque coil 5212 and other surfaces. In some implementations, the flexible torque coil 5212 can be coated with Polytetrafluoroethylene (PFTE) to reduce frictional contact between the outer surface of the flexible torque coil 5212 and other surfaces. The flexible torque coil 5212 can be sized, shaped or configured to have an outer diameter that is smaller than the diameter of the instrument channel of the endoscope in which the endoscopic tool is to be inserted. For example, in some implementations, the outer diameter of the flexible torque coil can be within the range of 1-4 millimeters. The length of the flexible torque coil can be sized to exceed the length of the endoscope. In some implementations, the inner wall of the flexible torque coil 5212 can be configured to define another portion of the aspiration channel that is fluidly coupled to the portion of the aspiration channel defined by the inner wall of the inner cannula of the cutting assembly 5201. A proximal end of the flexible torque coil 5212 can be coupled to the proximal connector 5110 (e.g., to the drive transfer assembly 5122 of the proximal connector 5110, etc.).

The endoscopic tool 5100 can include a flexible outer tubing 5206 that can be coupled to the proximal end of the outer cannula. In some implementations, a distal end of the flexible outer tubing 5206 can be coupled to the proximal end of the outer cannula using a coupling component. In some implementations, the outer cannula can be configured to rotate responsive to rotating the flexible outer tubing. In some implementations, the flexible outer tubing 5206 can be a hollow, braided tubing that has an outer diameter that is smaller than the instrument channel of the endoscope in which the endoscopic tool 5100 is to be inserted. In some implementations, the length of the flexible outer tubing 5206 can be sized to exceed the length of the endoscope. The flexible outer tubing 5206 can define a bore through which a portion of the flexible outer tubing 5206 extends. The flexible outer tubing 5206 can include braids, threads, or other features that facilitate the rotation of the flexible outer tubing 5206 relative to the flexible torque coil, which is partially disposed within the flexible outer tubing 5206. The flexible outer tubing can define a portion of an irrigation channel for outputting fluid to a site within a subject.

The endoscopic tool 5100 can include a rotational coupler 5216 configured to be coupled to a proximal end of the flexible outer tubing 5206. The rotational coupler 5216 may be configured to allow an operator of the endoscopic tool to rotate the flexible outer tubing 5206 via a rotational tab 5218 coupled to or being an integral part of the rotational coupler 5216. By rotating the rotational tab 5218, the operator can rotate the flexible outer tubing and the outer cannula along a longitudinal axis of the endoscope and relative to the endoscope and the inner cannula of the cutting assembly 5201. In some implementations, the operator may want to rotate the outer cannula while the endoscopic instrument is inserted within the endoscope while the endoscope is within the patient. The operator may desire to rotate the outer cannula to position the opening of the outer cannula to a position where the portion of the radial wall of the outer cannula within which the opening is defined may aligned with the camera of the endoscope such that the operator can view the material entering the endoscopic instrument for resection via the opening. This is possible in part because the opening is defined along a radial wall extending on a side of the outer cannula as opposed to an opening formed on the axial wall of the outer cannula.

In some implementations, a proximal end 5220 of the rotational coupler 5216 can be fluidly coupled to the proximal connector 5110, such that the irrigation channel of the endoscopic tool 5100 passes from an irrigation port 5134 through the flexible outer tubing 5206 into the rotational coupler 5216. Irrigation fluid entering the proximal connector 5110 at the irrigation port 5134 can thus pass through the rotational coupler 5216 in order to be outputted at a site within a subject. In some implementations, the rotational coupler 5216 can be a rotating luer component that allows a distal end 5222 of the rotational coupler 5216 to rotate relative to the proximal end 5220 of the rotational coupler 5216. In this way, when the flexible outer tubing 5206 is rotated, the component to which the proximal end of the rotational coupler 5216 is coupled, is not caused to rotate. The rotational coupler 5216 can define a bore along a central portion of the rotational coupler 5216 through which a portion of the flexible torque coil 5212 extends. In some implementations, the rotational coupler 5216 can be a male to male rotating luer connector. In some implementations, the rotational coupler can be configured to handle pressures up to 1200 psi.

In some implementations, the flexible torque delivery assembly 5200 is configured to be fluidly coupled to a vacuum source to apply a suction force to the aspiration channel. The aspiration channel allows for fluid and material (e.g., a sample to be obtained) to be drawn into the distal end 5204 of the flexible torque delivery assembly 5200 in order to flow to the proximal end 5202 of the flexible torque delivery assembly 5200. For example, after the cutting assembly 5201 has been used to resect material from a site within a subject, vacuum pressure can be applied through the aspiration channel to draw (e.g., transfer by suction, etc.) fluid and material into the flexible torque delivery assembly 5200.

In some implementations, the proximal connector 5110 is configured to be coupled to a vacuum source to provide a suction force for aspiration. For example, as shown in FIGS. 51A and 51C, the proximal connector 5110 includes a vacuum port 5126 (e.g., aspiration port). The vacuum port/aspiration port 5126 can be similar to other aspiration ports disclosed herein. The vacuum port 5126 is configured to fluidly couple an aspiration channel of the endoscopic tool 5100 to a vacuum source (e.g., to a vacuum source with a specimen receiver positioned between the vacuum source and the endoscopic tool). The vacuum port 5126 is configured to transmit a suction force applied to the vacuum port 5126 to the aspiration channel, in order to draw fluid and material entering the distal end 5204 of the endoscopic tool 5100 through the aspiration channel towards the vacuum source. In some implementations, such as shown in FIGS. 51A and 51C, the vacuum port 5126 includes a vacuum port channel 5130 oriented transverse to the drive axis 5102 (and thus the aspiration channel). This may facilitate coupling tubing to the vacuum port 5126 that extends to a specimen receiver or vacuum source without interfering with manipulation of the proximal connector 5110 and the endoscopic tool 5100. In various implementations, the vacuum port channel 5130 can be oriented at varying angles relative to the drive axis 5102. In some implementations, vacuum tubing 5132 can be coupled to the vacuum port 5126.

In some implementations, the proximal connector 5110 is configured to be coupled to a fluid source to provide fluid to be outputted by the endoscopic tool 5100 to a site within a subject. As shown in FIGS. 51A-51C, the proximal connector 5110 includes an irrigation port 5134, including an irrigation port channel 5136, configured to receive fluid from a fluid source. The irrigation port 5134 is configured to be fluidly coupled to an irrigation channel of the flexible torque delivery assembly 5200 (e.g., an irrigation channel defined between the flexible outer tubing 5206 and the flexible torque coil 5212 and extending to an opening at the distal end 5204 of the flexible torque delivery assembly 5200), such that fluid can flow from the proximal connector 5110 through flexible torque delivery assembly 5200 to be outputted at a site within a subject. In some implementations, the fluid (e.g., irrigation fluid) can be used to cool the flexible torque delivery assembly 5200, which may generate heat due to friction caused by rotation or other movements.

In some implementations, the fluid can be used to wash a site within a subject. In some implementations, the fluid provides lubrication to facilitate rotation or other movement of components of the endoscopic tool 5100 relative to one another. In some implementations, the irrigation port 5134 is configured to be coupled to a fluid transfer device or irrigation pump (e.g., fluid transfer device 6200 as shown in FIGS. 52A-52F, etc.). The irrigation port 5134 receives a flow of irrigation fluid from the irrigation pump and transfers the fluid into the irrigation channel. In some implementations, the irrigation channel is defined to include the irrigation port 5134 and/or tubing connecting the irrigation port 5134 to the fluid source. In some implementations, the irrigation port 5134 can be coupled to a fluid source by fluid tubing 5140. The fluid tubing 5140 can be coupled to a fitting 5144 (e.g., vented spike fitting, non-vented spike fitting, etc.) configured to interface the fluid tubing 5140 to a fluid source.

Console for Endoscopic Tool

Figure 64:
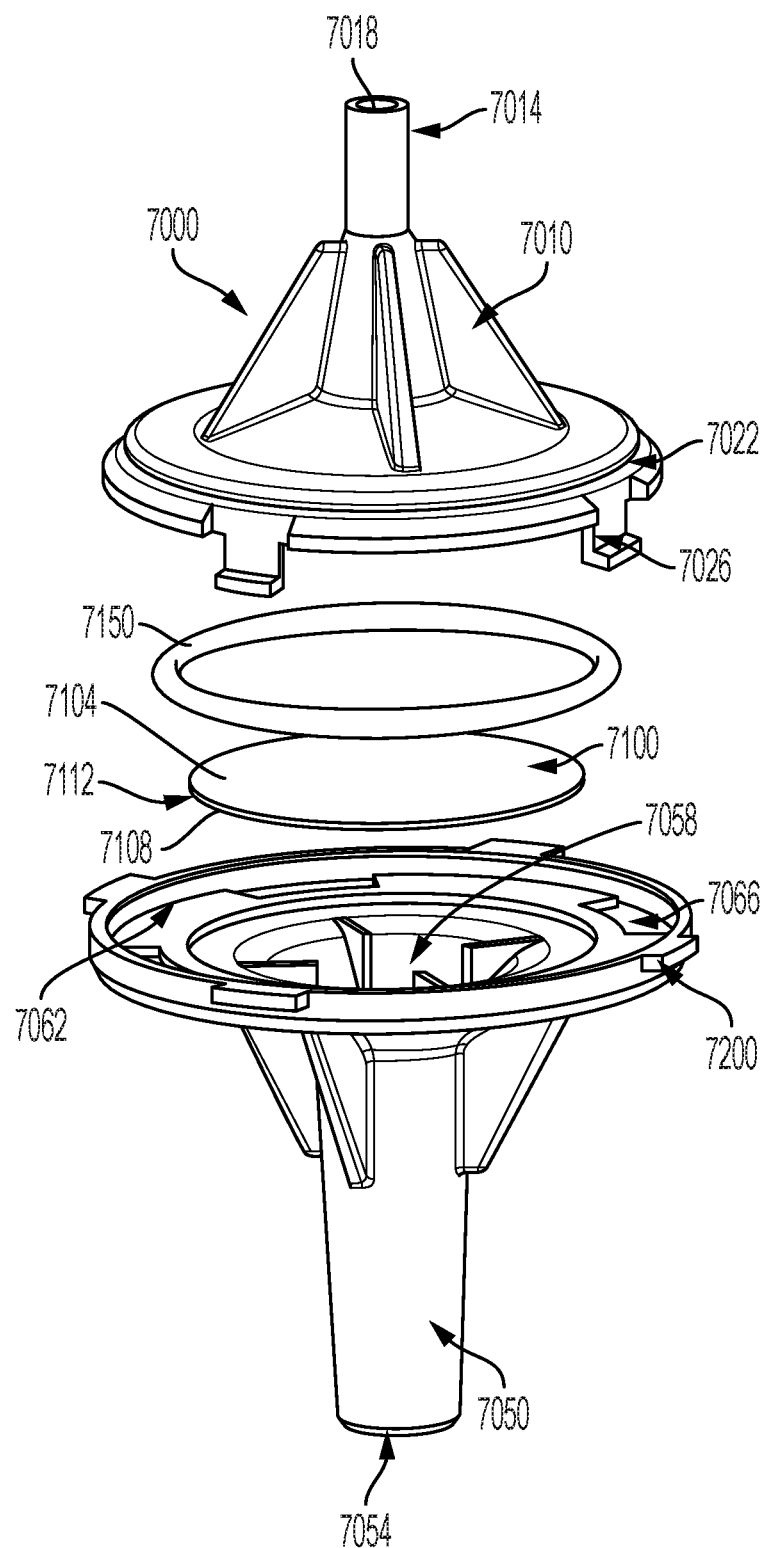
FIG. 64 is an exploded view of a specimen receiver configured for operation with a console and an endoscopic tool according to embodiments of the present disclosure.

Referring now to FIGS. 52A-56D, a console 6000 for an endoscopic tool is illustrated. The console 6000 is configured to receive control commands (e.g., user inputs) for controlling operation of an endoscopic tool (e.g., endoscopic tool 5100), such as the various endoscopic tools disclosed herein, including an endoscopic tool 5100 as illustrated in FIGS. 51A-51C, etc. The console 6000 is configured to interface with devices such as the endoscopic tool 5100, a specimen receiver (e.g., a specimen receiver 7000 as illustrated in FIG. 64), a vacuum source, an aspiration source, etc. As such, the console 6000 is configured to interface devices coupled to the console 5100 with each other. The console 6000 can interface devices using mechanical connections as well as electronic connections.

In some implementations, the console 6000 includes a user interface 6010. The user interface 6010 is configured to receive user input (e.g., user input from an operator of the console 6000, a user performing a procedure using the console and/or the endoscopic tool 5100, etc.). The console 6000 is configured to perform operations based on the received user input. For example, the console 6000 can include processing electronics (e.g., a processing circuit/processor, memory, etc.) configured to process user input in order to generate outputs (e.g., control signals) configured to cause devices to perform operations associated with the user input. A processor may be, or may include, one or more microprocessors, application specific integrated circuits (ASICs), circuits containing one or more processing components, a group of distributed processing components, circuitry for supporting a microprocessor, or other hardware configured for processing. A processor may be configured for executing computer code. The computer code may be stored in memory to complete and facilitate the activities described herein. In some implementations, the computer code may be retrieved and provided to a processor from a hard disk storage or communications interface (e.g., the computer code may be provided from a source external to the console 6000). A memory can be any volatile or non-volatile computer-readable storage medium capable of storing data or computer code relating to activities described herein. For example, a memory can include modules which are computer code modules (e.g., executable code, object code, source code, script code, machine code, etc.) configured for execution by a processor. A memory can include computer executable code related to functions including motor control, processing user inputs, controlling devices such as the endoscopic tools disclosed herein, receiving and transmitting data, etc. In some implementations, processing electronics can represent a collection of multiple processing devices.

Figure 52A:
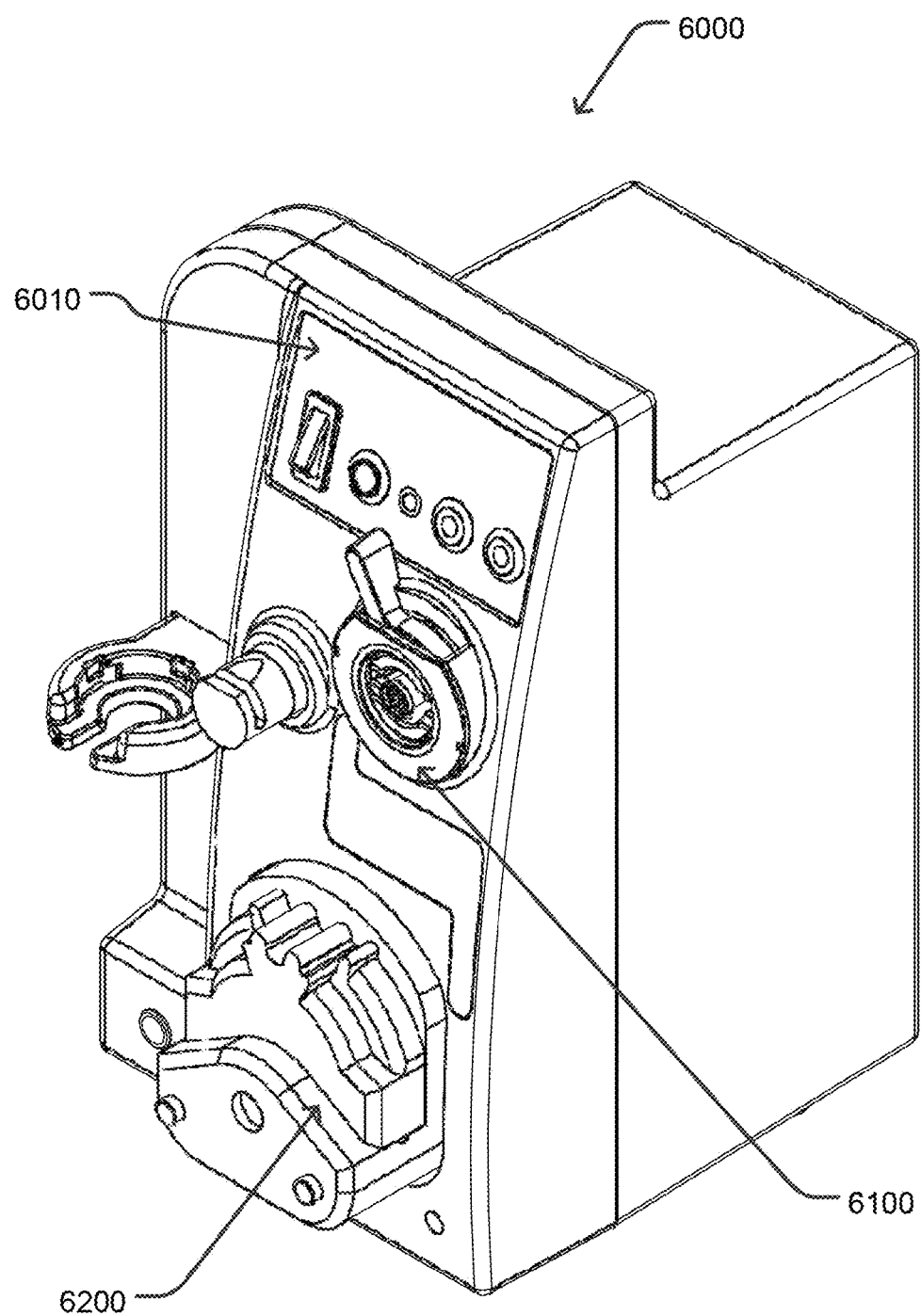
FIGS. 52A-52F illustrate aspects of a console configured for operation with an endoscopic tool according to embodiments of the present disclosure.
Figure 52B:
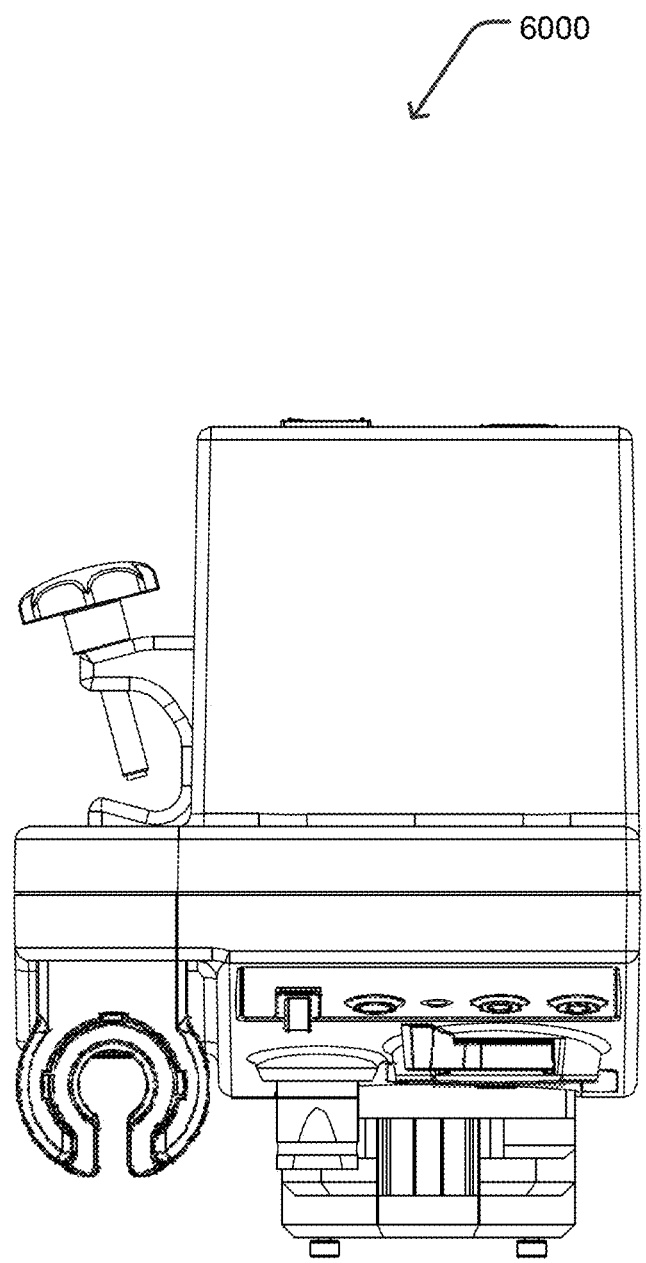
Figure 52C:
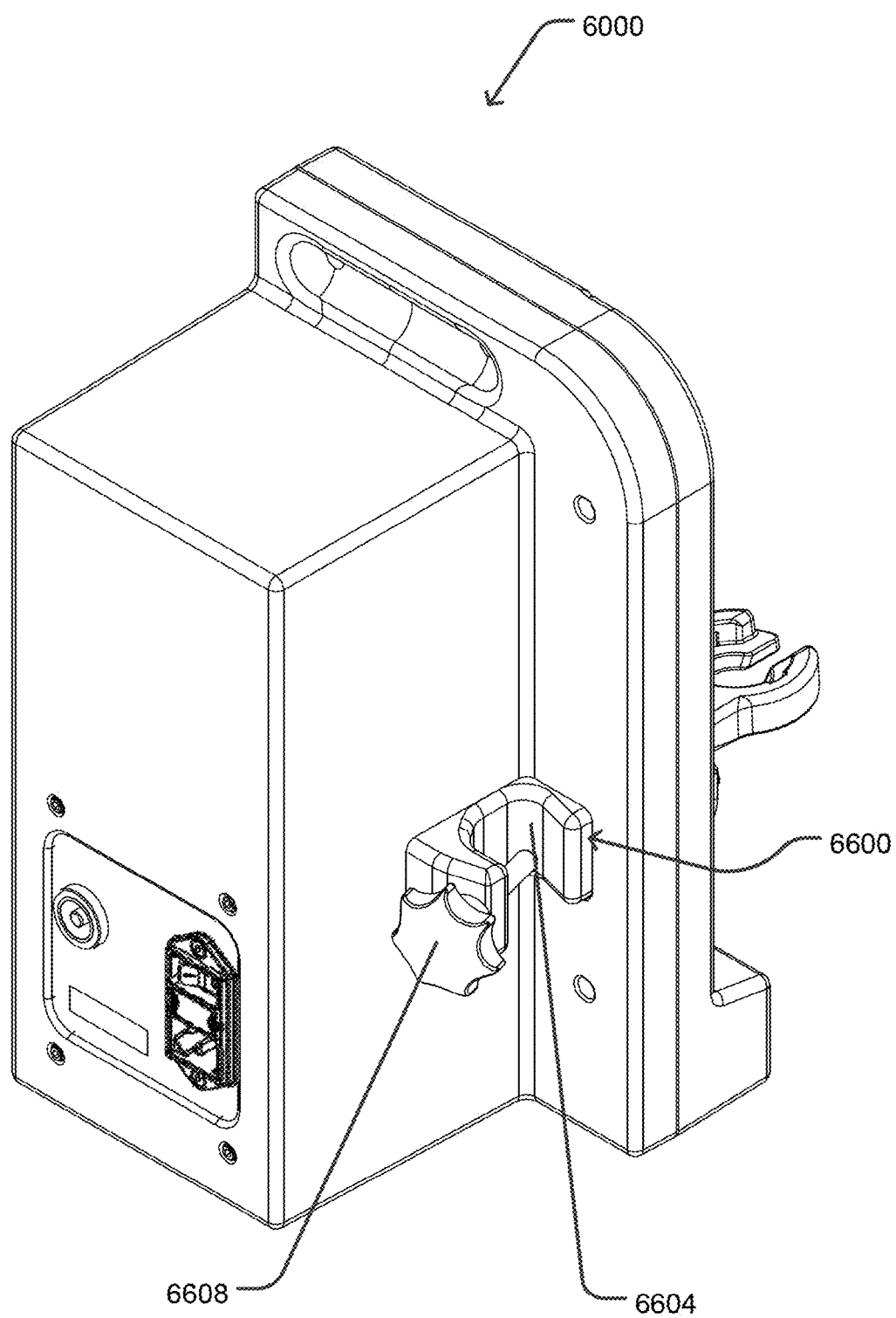
Figure 52D:
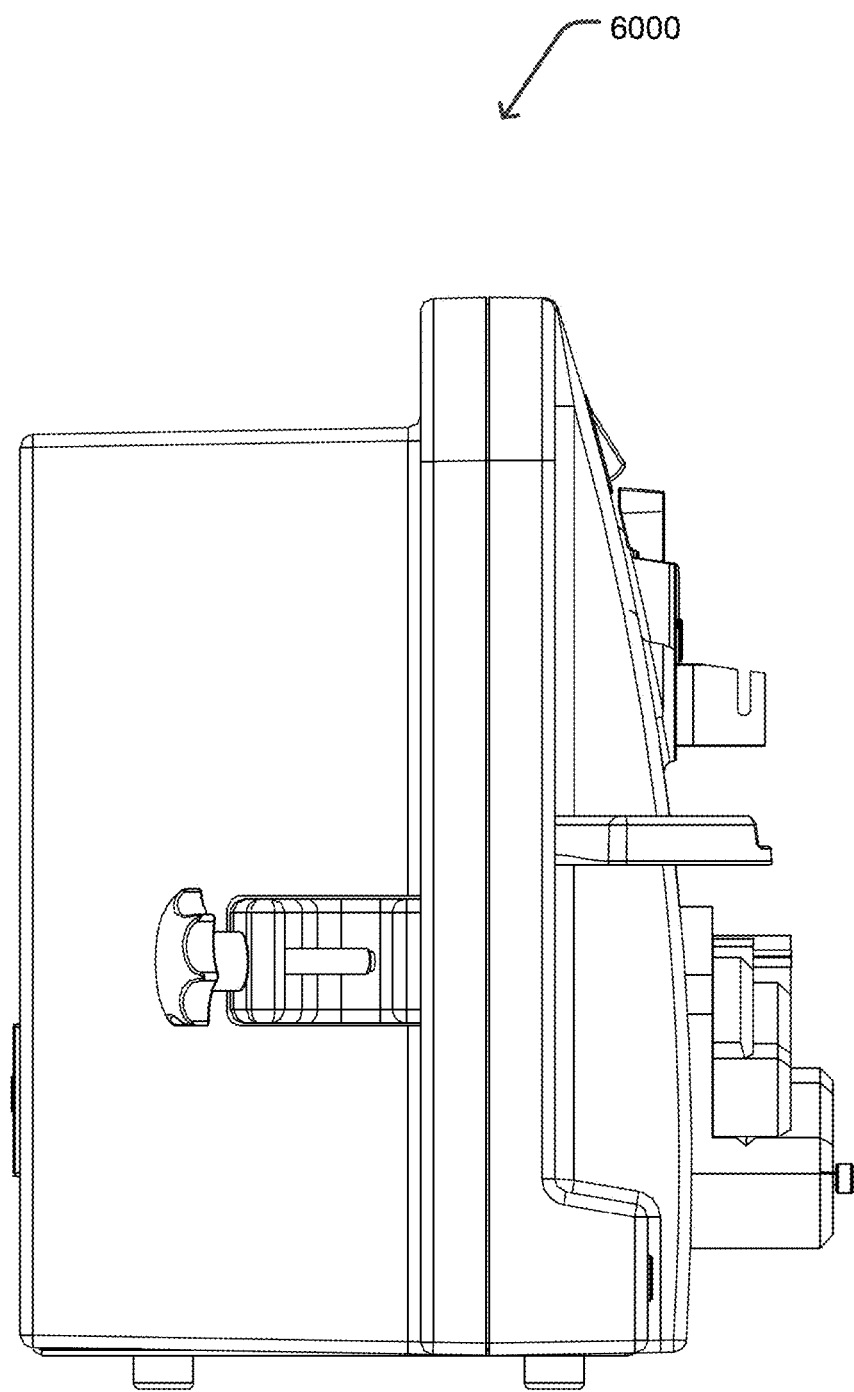
Figure 52E:
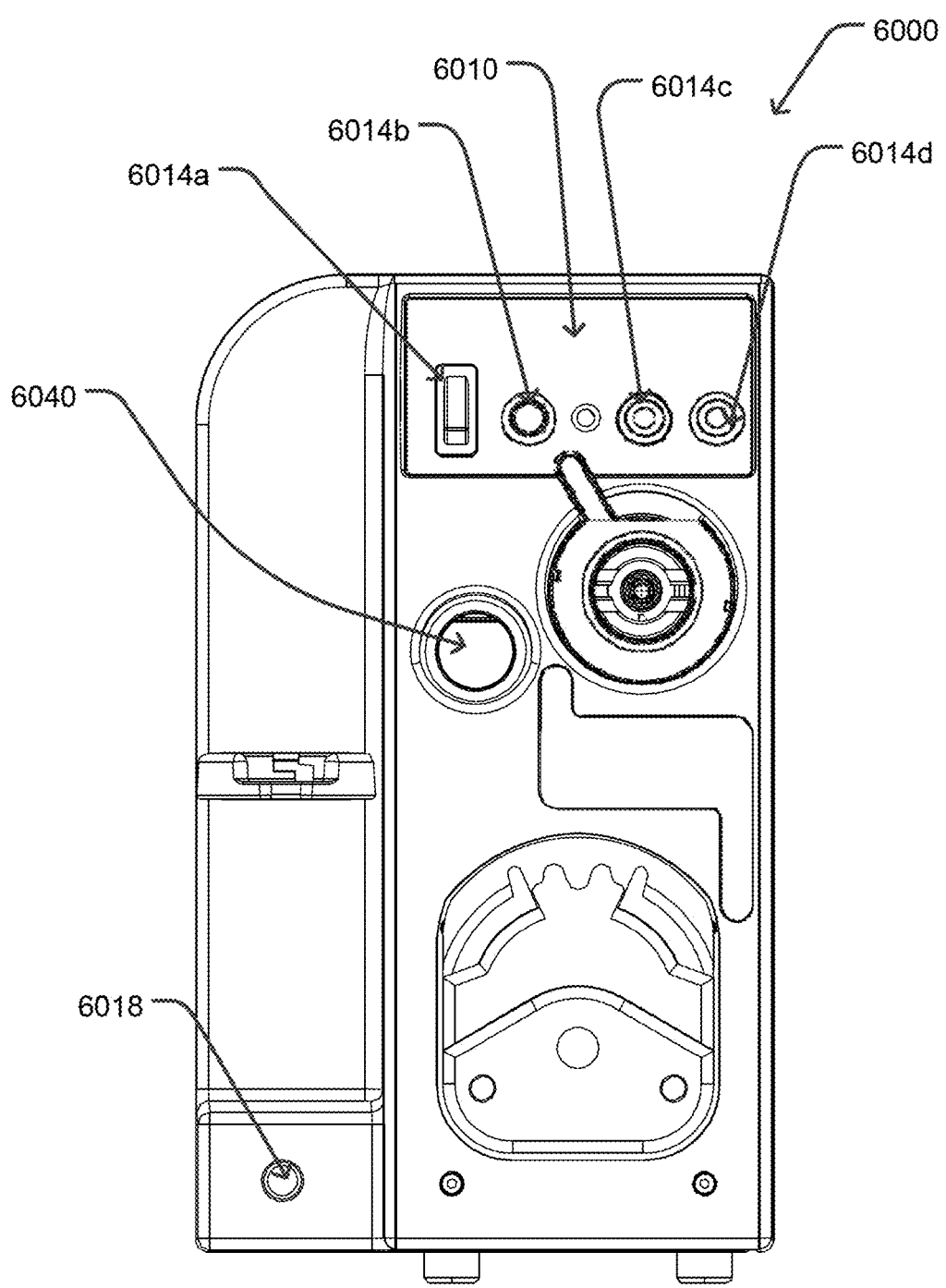
Figure 52F:
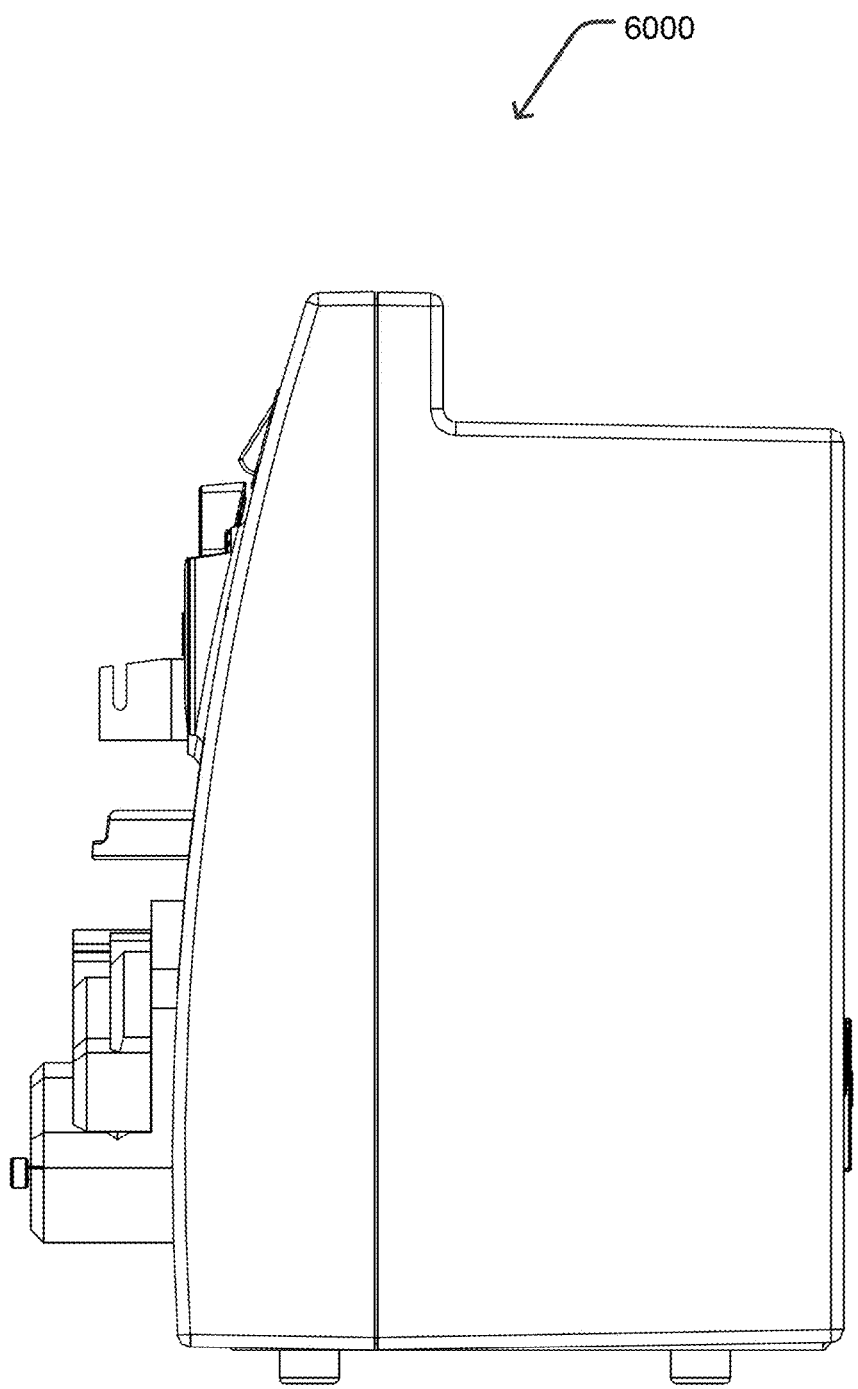

In some implementations, the user interface 6010 includes user input devices 6014 (e.g., buttons, knob, switches, foot pedals etc.) configured to receive user input for controlling operation of the console 6000, as well as for controlling devices operatively coupled to the console 6000 such as endoscopic tool 5100, etc. For example, as shown in FIGS. 52A and 52E, the user interface 6010 can include a speed control 6014*a* (e.g., to control a speed of rotation of a drive of the console, etc.), a power button 6014*b*, a vacuum control release 6014*c* configured to receive user input for controlling a vacuum control device 6040 (e.g., user input indicating instructions to open the vacuum control device 6040 so that a vacuum source, the endoscopic tool 5100, a specimen receiver 7000, etc., can be fluidly coupled via the vacuum control device 6040), and a primer input 6014*d* configured to prime and/or flush irrigation tubing (e.g., to prime and/or flush tubing configured to fluidly couple a fluid transfer device 6200 to an endoscopic tool, etc.).

In some implementations, the user interface 6010 includes an auxiliary control interface 6018. For example, the auxiliary control interface 6018 can be configured to receive user inputs for rotation (for example, the inner cannula) of an endoscopic tool 5100, for vacuum control, for irrigation control, etc. In some implementations, the auxiliary control interface 6018 is configured to receive user inputs or other control signals from a remote input device (e.g., foot pedal, hand control, portable electronic device, etc.). The auxiliary control interface 6018 can be configured to communicate with the remote input device via a wired connection or wireless signals (e.g., radio frequency, infrared, Bluetooth, internet protocol, etc.). For example, a foot pedal can be configured to receive user inputs for rotation, vacuum control, and or/irrigation control, and transmit control signals based on the user inputs for reception by the auxiliary control interface 6018. In some implementations, the auxiliary control interface 6018 is configured to receive the control signals from the foot pedal for processing in order to control operation of the endoscopic tool 5100, including for applying vacuum to an aspiration channel of the endoscopic tool 5100, for rotating components of the endoscopic tool 5100, and/or for flowing irrigation fluid through an irrigation channel of the endoscopic tool 5100 to a site within a subject. In some implementations, the foot pedal includes a pedal input configured to receive an input corresponding to each function of the foot pedal (e.g., rotation, vacuum, irrigation, etc.). In some implementations, a first pedal input is configured to receive an input corresponding to activation of multiple functions (e.g., rotation and suction/vacuum), and a second pedal input is configured to receive an input corresponding to activation of other functions (e.g., irrigation). In some implementations, a first pedal input is configured to receive an input corresponding to activation of multiple functions (e.g., rotation and irrigation), and a second pedal input is configured to receive an input corresponding to activation of other functions (e.g., suction/vacuum). For example, the second pedal input can be configured for vacuum control or irrigation, but only within a predetermined period of time after activation of the first pedal input (e.g., 5 seconds, 10 seconds, 12 seconds, 15 seconds, etc.). In some implementations, the predetermined period of time is determined based on preventing heat buildup in the endoscopic tool or ensuring that the vacuum draws the tissue towards the cutting window for resection by the rotating cutting window. In some implementations, the predetermined period of time is determined based on preventing inadvertent activation of suction force. In some implementations, when the first foot pedal is actuated, a suction force is applied and after a predetermined time, the drive motor for causing rotation of the inner cannula is actuated. In this way, the material to be resected can be suctioned into the cutting window of the outer cannula before rotation of the inner cannula. Furthermore, by applying suction prior to actuation of the cutter, any materials trapped within the aspiration channel can be removed prior to the cutting of additional material.

In some implementations, the console 6000 includes a vacuum control device 6040 (e.g., a vacuum control valve). The vacuum control device 6040 is configured to couple a vacuum source to the endoscopic tool 5100. For example, the vacuum control device 6040 can be configured to fluidly couple tubing to the vacuum port 5126 of the proximal connector 5110 of the endoscopic tool 5100, and also fluidly couple tubing to a specimen receiver (e.g., specimen receiver 7000) and/or a vacuum source. In some implementations, the vacuum control device 6040 mechanically engages (e.g., grips, locks, holds, etc.) vacuum tubing that fluidly couples the endoscopic tool 5100 to the specimen receiver 7000. In some embodiments, the vacuum control device 6040 includes a manifold configured to be fluidly coupled the endoscopic tool 5100 to a plurality of specimen receivers 7000. The user interface 6010 can include a manifold/valve control configured to control fluid flow through exiting the endoscopic tool 5100 to one or more of the plurality of specimen receivers 7000.

In some implementations, the vacuum control device 6040 is configured to be opened in response to user input received at the vacuum control release 6014*c*. For example, in response to actuation of the vacuum control release 6014*c*, processing electronics of the console 6000 can receive a vacuum release signal and cause the vacuum control device 6040 to open, allowing vacuum tubing to be positioned in the vacuum control device 6040. In some implementations, the vacuum control device 6040 can be configured to be mechanically coupled to the vacuum control release 6014*c*, such that actuation of the vacuum control release 6014*c* mechanically actuates the vacuum control device 6040 to open the vacuum control device 6040. In some implementations, the vacuum control device 6040 is configured to be opened for a predetermined amount of time. For example, the vacuum control device 6040 can be actuated to an open position for a predetermined amount of time in response to input received at the vacuum control release 6014*c*, and then automatically close after the predetermined amount of time.

In some implementations, processing electronics of the console 6000 are configured to receive control signals from the foot pedal, and performing at least one of controlling rotation of the endoscopic tool 5100, controlling a fluid source for delivering irrigation fluid through the endoscopic tool 5100 (e.g., control operation of a fluid transfer device 6200 to output fluid from the fluid transfer device 6200 into the endoscopic tool 5100), or controlling application of a vacuum pressure to the endoscopic tool 5100 (e.g., enabling a vacuum source to apply a suction force to the endoscopic tool 5100). For example, the processing electronics can be configured to receive a first signal from a first pedal input and a second signal from a second pedal input, cause a motor 6300 to rotate the endoscopic tool 5100 in response to receiving the first signal, cause a fluid transfer device 6200 to output fluid into the endoscopic tool 5100 in response to receiving the first signal, and cause the vacuum control device 6040 to enable vacuum pressure to be applied to the endoscopic tool 5100 in response to receiving the second signal (e.g., in response to receiving the second signal within a predetermined time of receiving the first signal).

In some implementations, the console 6000 includes an endoscopic tool interface 6100. The endoscopic tool interface 6100 is configured to engage the endoscopic tool 5100. In some implementations, the endoscopic tool interface 6100 is configured to mechanically engage the drive assembly 5150 of the endoscopic tool 5100 (e.g., fixedly engage, rigidly engage, etc.), in order to rotate the drive assembly 5150. For example, the endoscopic tool interface 6100 can act as an interface between the endoscopic tool 5100 and a drive mechanism of the console 6000.

Figure 56A:
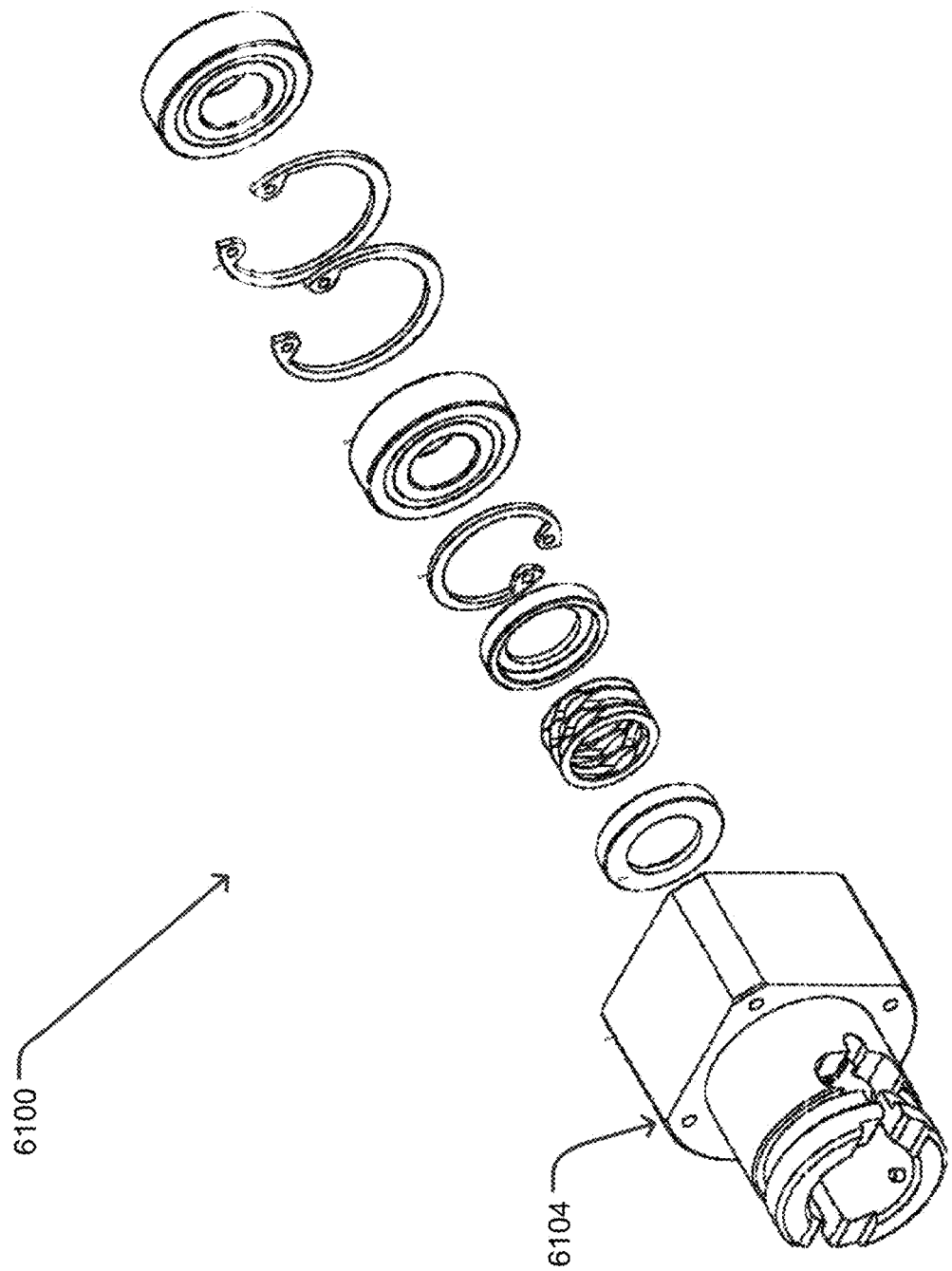
FIG. 56A is an exploded perspective view of an interface of a console configured for operation with an endoscopic tool according to embodiments of the present disclosure.
Figure 56B:
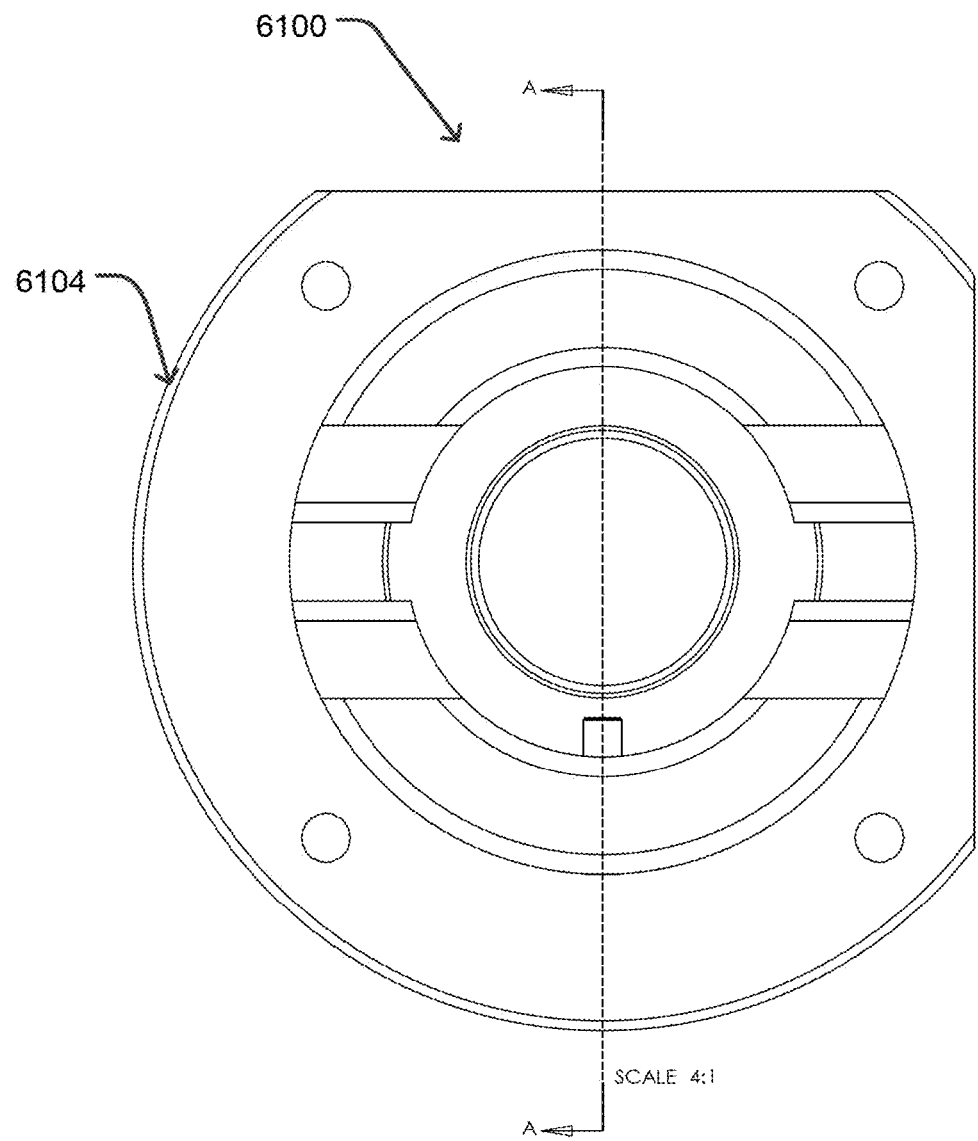
FIG. 56B is an end view of the interface shown in FIG. 56A according to embodiments of the present disclosure.
Figure 56C:
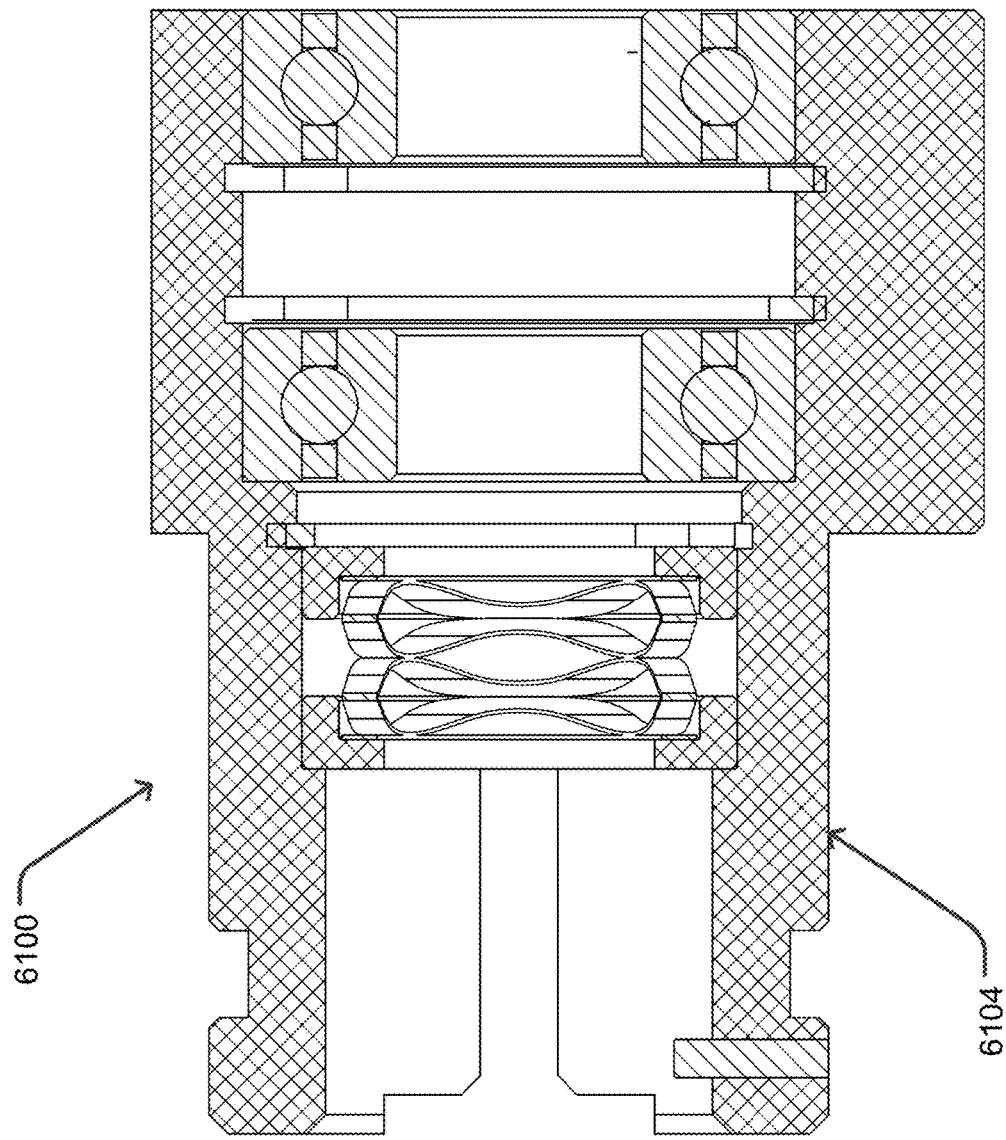
FIG. 56C is a cross-sectional view taken along section A-A of the interface shown in FIGS. 56A-56B according to embodiments of the present disclosure.

FIGS. 56A-56C show an implementation of the endoscopic tool interface 6100 in further detail. The endoscopic tool interface is configured to be attached to the console 6000 coaxially with a console drive assembly (e.g., console drive assembly 6150). The endoscopic tool interface includes an interface receiver 6104 configured to be coupled to the proximal connector 5110 of the endoscopic tool 5100, facilitating alignment and coupling of the console drive assembly 6150 to the proximal connector 5110 such that the console drive assembly 6150 can rotate the drive assembly 5150 of the endoscopic tool 5100.

Referring back to FIGS. 52A-54C, in some implementations, the console 6000 includes a fluid transfer device 6200 (e.g., an irrigation pump). The fluid transfer device 6200 is configured to flow fluid (e.g., irrigation fluid) through the endoscopic tool 5100 to be output by the endoscopic tool 5100 at the distal end 5104 of the endoscopic tool 5100. In some implementations, the irrigation fluid is received from a fluid source in a procedure room (e.g., water container, saline/IV bag, etc). The fluid transfer device 6200 can be configured to output fluid at a pressure sufficient to drive the fluid to an outlet at the distal end 5104 of the endoscopic tool 5100.

In some implementations, the console 6000 includes a motor 6300. The motor 6300 is configured to provide rotational energy in order to rotate the endoscopic tool 5100. In some implementations, the motor 6300 is an electric motor. In some implementations, the motor 6300 is a variable speed motor. In some implementations, the motor 6300 is a fixed speed motor; if variable rotation rates are desired from the fixed speed motor 6300, then a speed change device (e.g., gears, etc.) can be used to step from a rotation rate of the motor 6300 to a desired rotation rate. In some implementations, the speed control 6014a of the console 6000 is configured to receive a speed control input (e.g., a speed control input corresponding to an absolute rotation rate of the motor 6300 or the console drive assembly 6150, a relative rotation rate based on a percentage of a maximum rotation rate of the motor 6300 or the console drive assembly 6150, etc.). In such implementations, user input can be received indicating a desired rotation rate of the endoscopic tool 5100, and the motor 6300 and the console drive assembly 6150 (including any gears, etc., coupled between an output shaft of the motor 6300 and the console drive assembly 6150) can be configured to output a torque to the endoscopic tool 5100 based on the desired rotation rate indicated by the user input.

Referring further to FIGS. 55A-55D, mechanical engagements are shown between various components of the console 6000, including the endoscopic tool interface 6100, the console drive assembly 6150, the vacuum control device 6040, and the motor 6300. In some implementations, an output shaft of the motor 6300 is engaged to and coaxial with the console drive assembly 6150. In other implementations, as shown in FIGS. 55A-55D, an output shaft 6304 of the motor 6300 is parallel to and offset from a drive axis of the console drive assembly 6150. In such implementations, an intermediate drive assembly 6350 can be configured to be coupled to the output shaft 6304 and to the console drive assembly 6150, such as to transfer the rotational output of the output shaft 6304 to the drive assembly 6150. For example, as shown in FIGS. 55A-55D, the intermediate drive assembly 6350 includes a first rotation member (e.g., a pulley) 6354 that is configured to be engaged to the output shaft 6304, a second rotation member (e.g., a pulley) 6358 that is configured to be engaged to the console drive assembly 6150, and a rotation transfer device (e.g., a belt) 6362 configured to transfer rotation from the first rotation member 6354 to the second rotation member 6358. For example, the rotation transfer device 6362 can frictionally engaged both the first rotation member 6354 and the second rotation member 6358, so that when the output shaft 6304 of the motor 6300 causes the first rotation member 6354 to rotate, the rotation transfer device 6362 and thus the console drive assembly 6150 are also rotated.

FIGS. 57A-57C show an implementation of the console drive assembly 6150 in further detail. The console drive assembly 6150 is configured to transfer rotation of a rotational energy source (e.g., the motor 6300) to rotation of an endoscopic tool (e.g., the endoscopic tool 5100). In some implementations, the console drive assembly 6150 includes an input shaft 6154. The input shaft 6154 can be configured to be coupled to the output shaft 6304 of the motor 6300. For example, the input shaft 6154 can be coupled to the output shaft 6304 via intermediate shafts, gears, a two-sided coupling member (e.g., a coupling member having a first receiving surface configured to engage the input shaft 6154 and a second receiving surface configured to engage the output shaft 6304). In some embodiments, the input shaft 6154 is configured to be coupled to the intermediate drive assembly 6350. For example, the input shaft 6154 can be configured to engage the second rotation member 6358, such that rotation of the second rotation member 6358, caused by rotation of the output shaft 6304, causes rotation of the input shaft 6154.

In some implementations, the console drive assembly 6150 includes an engagement receiving member 6158. The engagement receiver member 6158 is configured to engage the console drive assembly 6150 to the endoscopic tool 5100, such as to engage drive engagement member 5152. For example, the engagement receiver member 6158 can include a receiving surface 6162 shape to engage (e.g., frictionally engage) the drive engagement member 5152 (e.g., a hex fitting shaped to match a hex head of the drive engagement member 5152, etc.). As the console drive assembly 6150 is rotated by the motor 6300, the rotational energy is transferred through the input shaft 6154 to the engagement receiver member 6158 to the drive engagement member 5152, thus rotating the endoscopic tool 5100.

In some implementations, the console drive assembly 6150 includes a drive torque coil 6400. FIGS. 58A-58C show an implementation of the drive torque coil 6400 in further detail. The drive torque coil 6400 is configured to be positioned within the console drive assembly 6150 between the engagement receiving member 6158 and the input shaft 6154. The drive torque coil 6400 can be similar to other torque coils disclosed herein. The drive torque coil 6400 can be configured to compensate for torque forces that could disrupt an orientation of the endoscopic tool 5100, and can complement compensation by the flexible torque coil 5212.

The drive torque coil 6400 can include friction reduction members 6404 positioned on ends of the drive torque coil 6400, the friction reduction members being configured to reduce friction and wear between the drive torque coil 6400 and other components of the console drive assembly 6150. The drive torque coil 6400 can complement action of the flexible torque coil 5212. The drive torque coil 6400 can be configured to rotate freely in the console drive assembly 6150 using the friction reduction members 6404 while compressing or expanding to compensate for compression or expansion forces applied to the console drive assembly 6150.

Figure 59B:
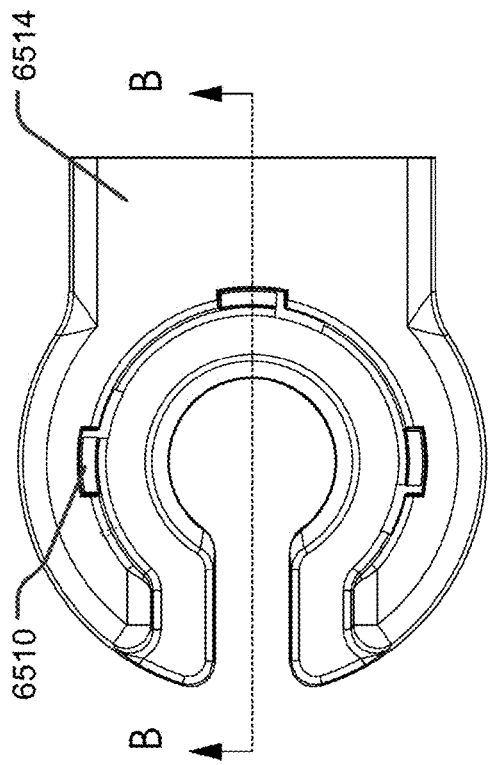
FIGS. 59A-59C illustrate aspects of a bracket assembly for holding a specimen receiver for a console configured for operation with an endoscopic tool according to embodiments of the present disclosure.
Figure 59C:
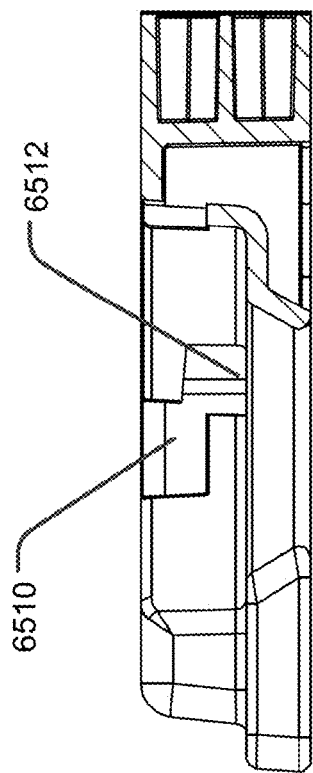
Figure 59A:
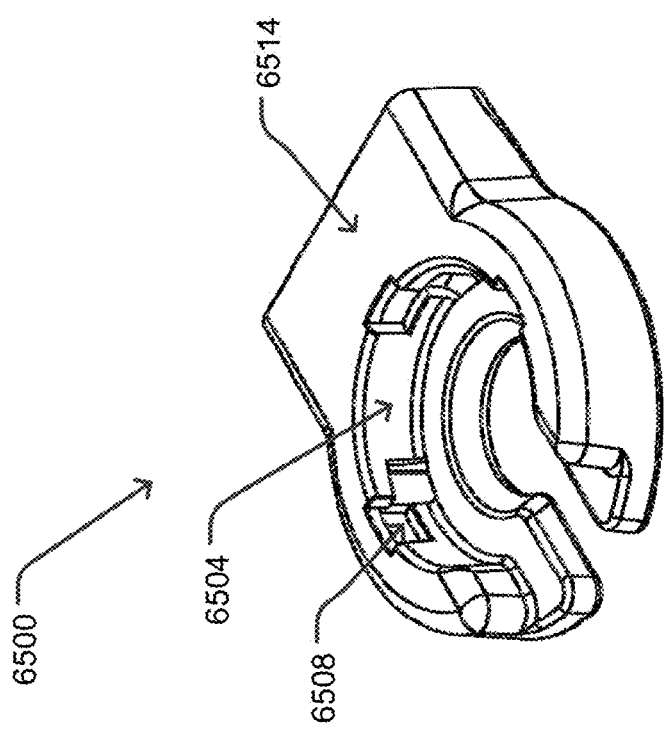

In some implementations, the console 6000 includes one or more bracket assemblies 6500. FIGS. 59A-59C show an implementation of the bracket assembly 6500 in further detail. The bracket assembly 6500 can be configured to hold (e.g., support, engage) a device configured to be fluidly coupled to the console 6000 and/or the endoscopic tool 5100. For example, the bracket assembly 6500 can be configured to hold a specimen receiver (e.g., specimen receiver 7000 as shown in FIG. 64). In some implementations, the bracket assembly 6500 includes a bracket receiver surface 6504. The bracket receiver surface 6504 can be configured to receive and engage the specimen receiver 7000. For example, the bracket receiver surface 6504 can include features configured to frictionally and/or mechanically engage the specimen receiver 7000. As shown in FIGS. 59A-59C, the bracket assembly 6500 can include one or more specimen engagement receiving members 6508 extending into a bracket body 6514 of the bracket assembly 6500. The specimen engagement receiving, members 6508 are configured to reciprocally engage engagement features of the specimen receiver 7000. In some implementations, the specimen engagement receiving members 6508 include a first receiving portion 6510 continuous with and offset from a second receiving portion 6512. As such, an engagement feature of the specimen receiver 7000 can be positioned in the first receiving portion 6510. As the specimen receiver 7000 is rotated, the engagement feature can be translated (e.g., slid) along the first receiver portion 6510 and then vertically repositioned into the second receiving portion 6512. The specimen engagement receiving members 6508 are thus configured to prevent rotation of the specimen receiver 7000 unless the specimen receiver 7000 is also translated in a direction perpendicular to the plane of rotation. In other words, while a user can insert or remove the specimen receiver 7000 by both rotating and shifting the specimen receiver 7000, unintentional forces applied to the specimen receiver 7000 (e.g., during a procedure) will not cause the specimen receiver 7000 to be removed from the bracket assembly 6500. In some implementations, the bracket assembly 6500 is configured to be fluidly coupled to the specimen receiver 7000. For example, if the console 6000 includes fluid connections for coupling to the specimen receiver 7000 (e.g., for coupling a vacuum source to the specimen receiver 7000), the fluid connections can be fluidly coupled to the specimen receiver 7000 via the bracket assembly 6500.

Referring back to FIGS. 52A-52F, in some implementations, the console 6000 includes a holder assembly 6600. The holder assembly 6600 can include a holding receiver 6604 configured to hold (e.g., support) components configured to be used with the console 6000. For example, the holding receiver 6604 can be configured to hold control devices for controlling operation of an endoscopic tool. The holder assembly 6600 can include a fastening member (e.g., screw, bolt, etc.) 6608 configured to fasten a component to the holding receiver 6604.

Figure 53A:
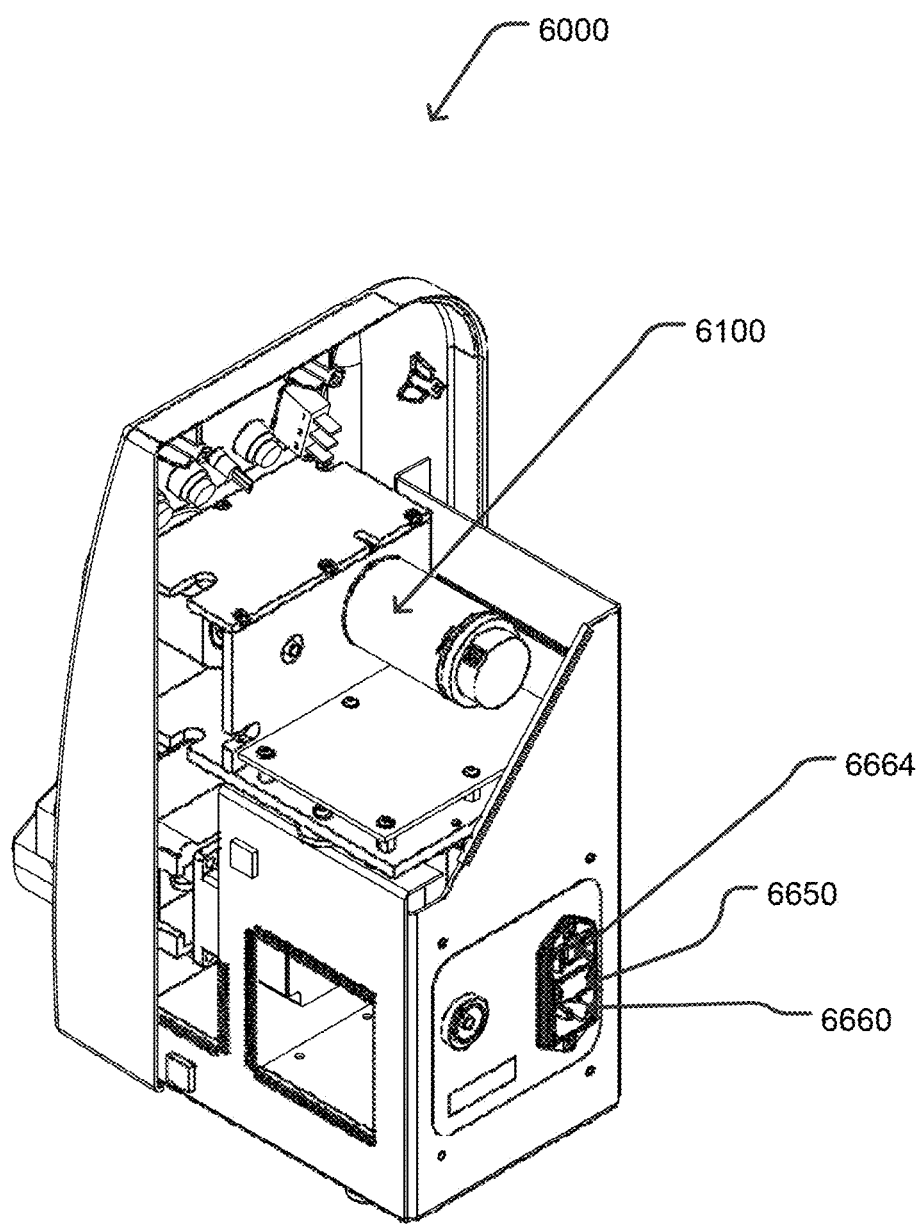
FIG. 53A is a rear perspective view of components of a console configured for operation with an endoscopic tool according to embodiments of the present disclosure.
Figure 53B:
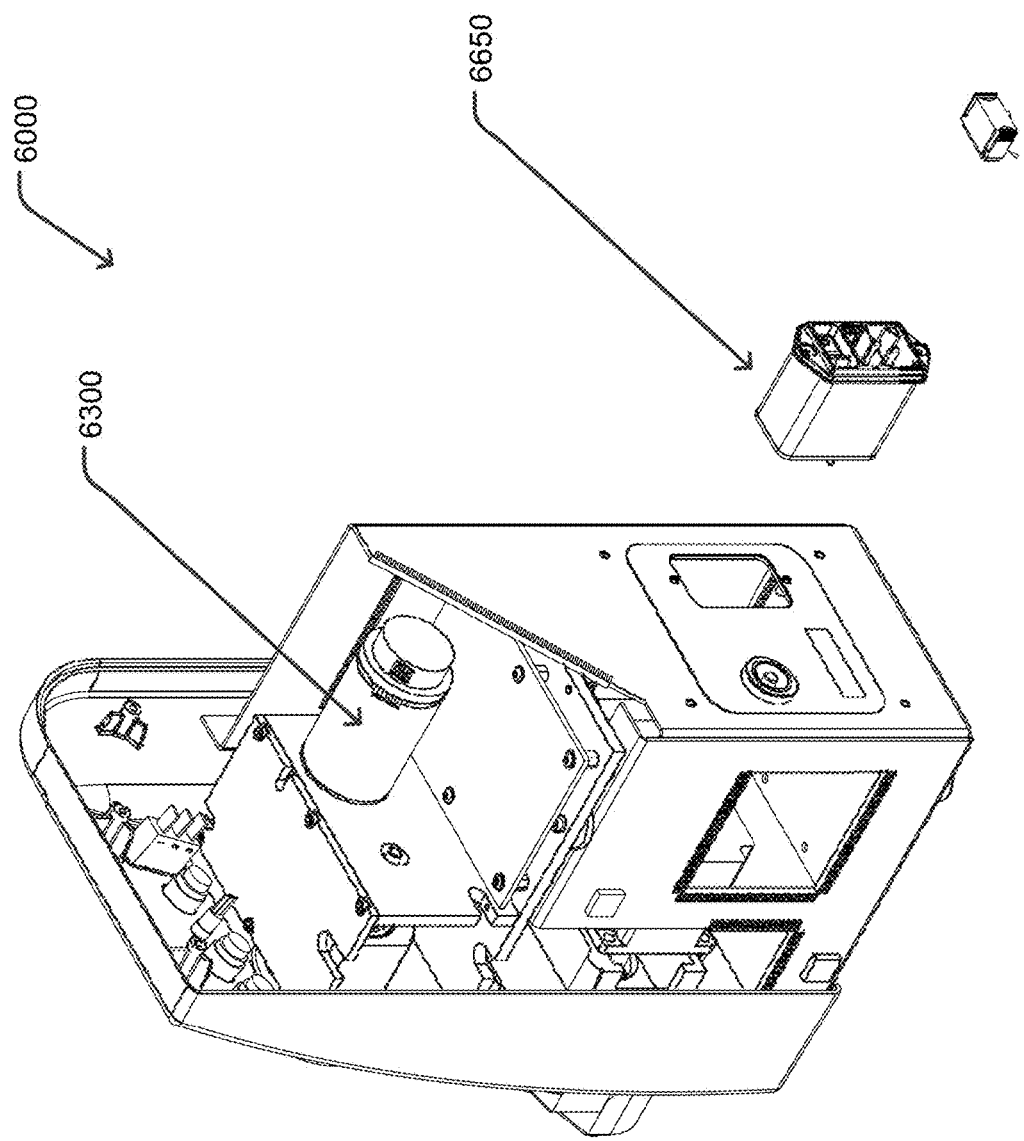
FIG. 53B is an exploded perspective view of the components of the console shown in FIG. 53A according to embodiments of the present disclosure.
Figure 54A:
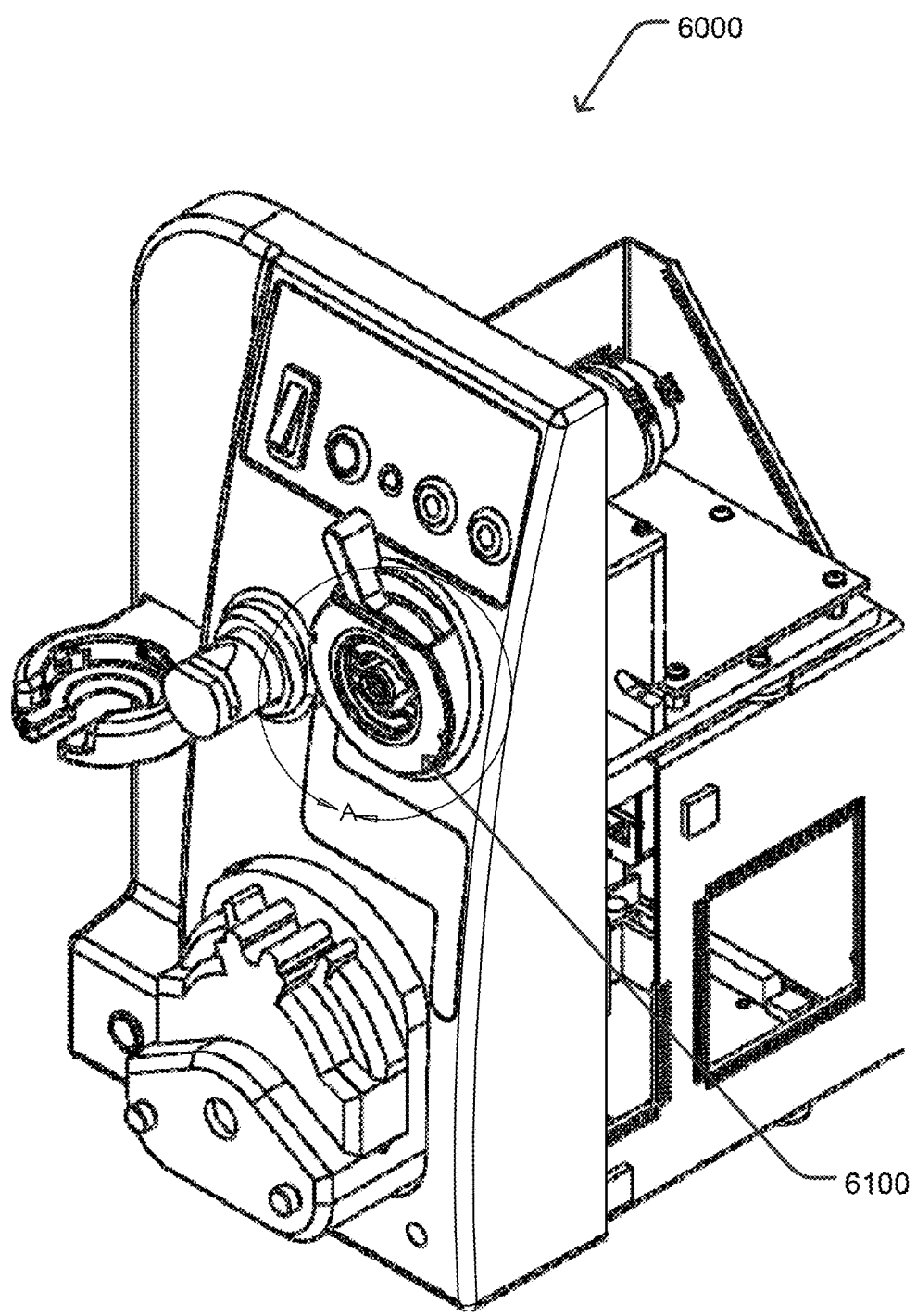
FIG. 54A is a perspective view of components of a console configured for operation with an endoscopic tool according to embodiments of the present disclosure.
Figure 54B:
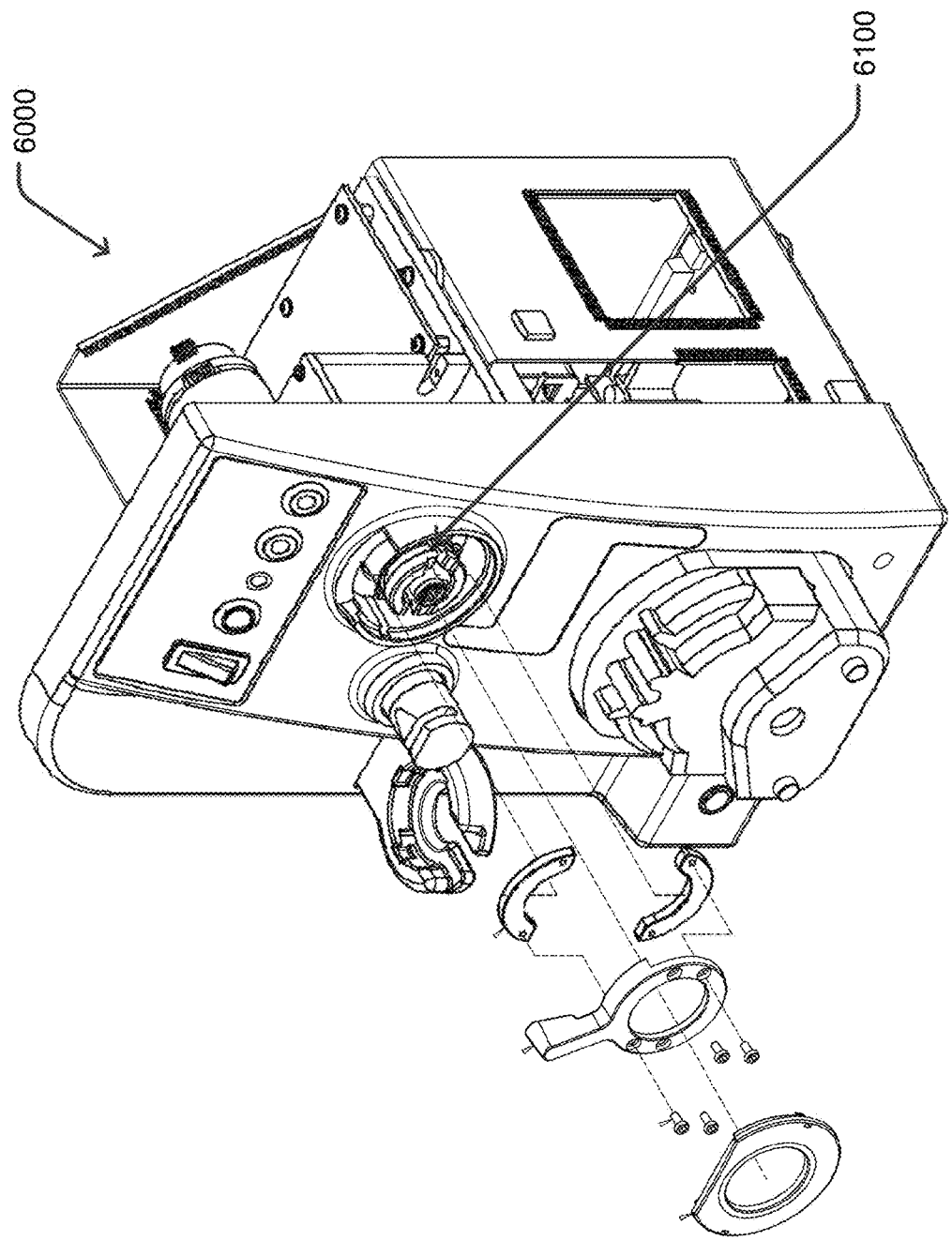
FIG. 54B is an exploded perspective view of the components of the console shown in FIG. 54A according to embodiments of the present disclosure.
Figure 54C:
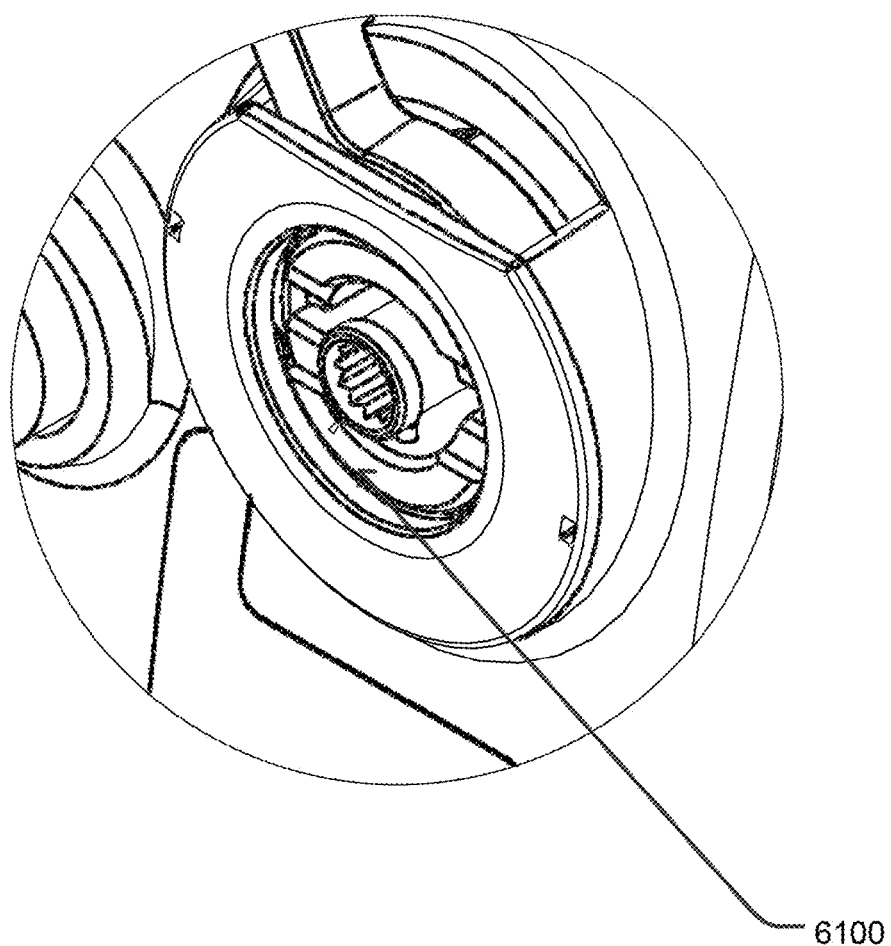
FIG. 54C is a detail view of an interface of the console shown in FIG. 54A according to embodiments of the present disclosure.
Figure 55A:
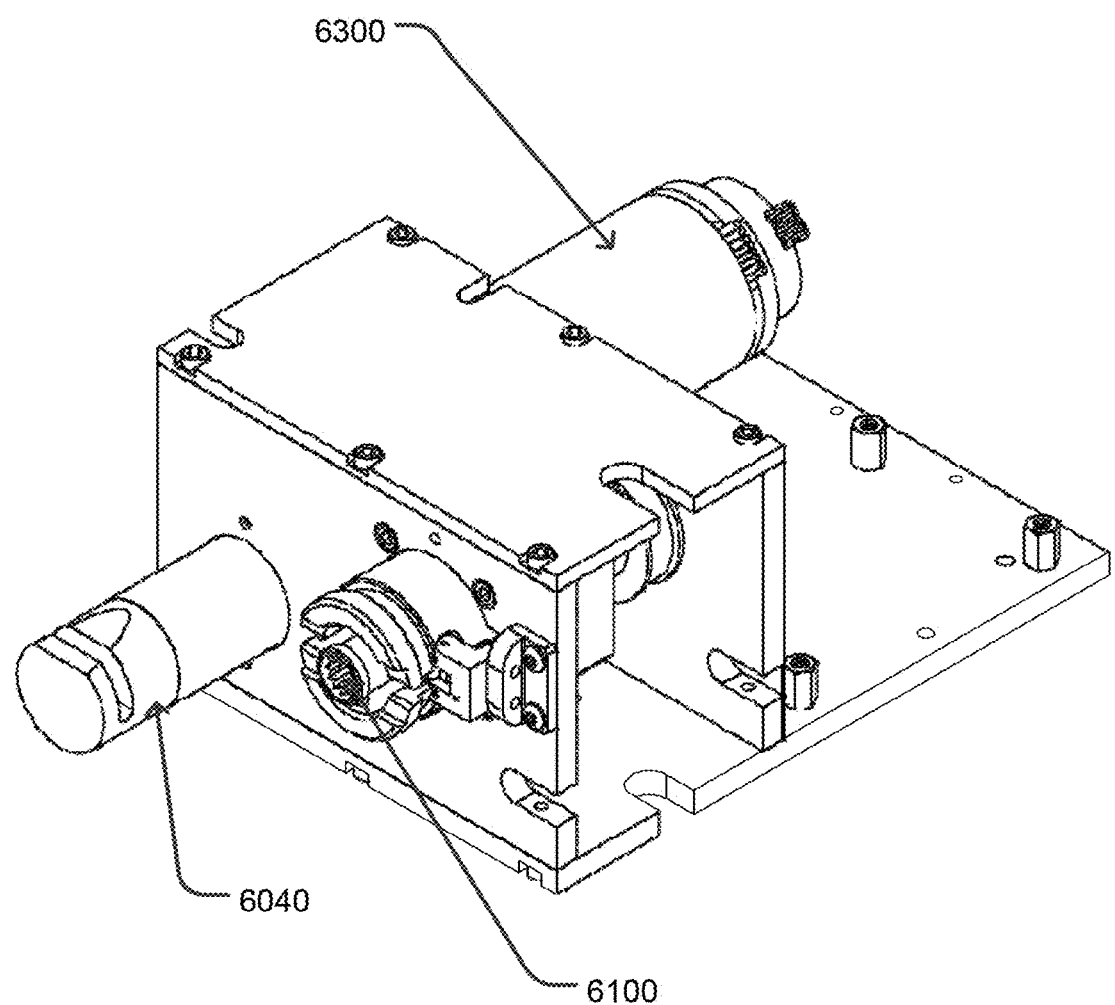
FIG. 55A is a perspective view of components of a console configured for operation with an endoscopic tool according to embodiments of the present disclosure.
Figure 55B:
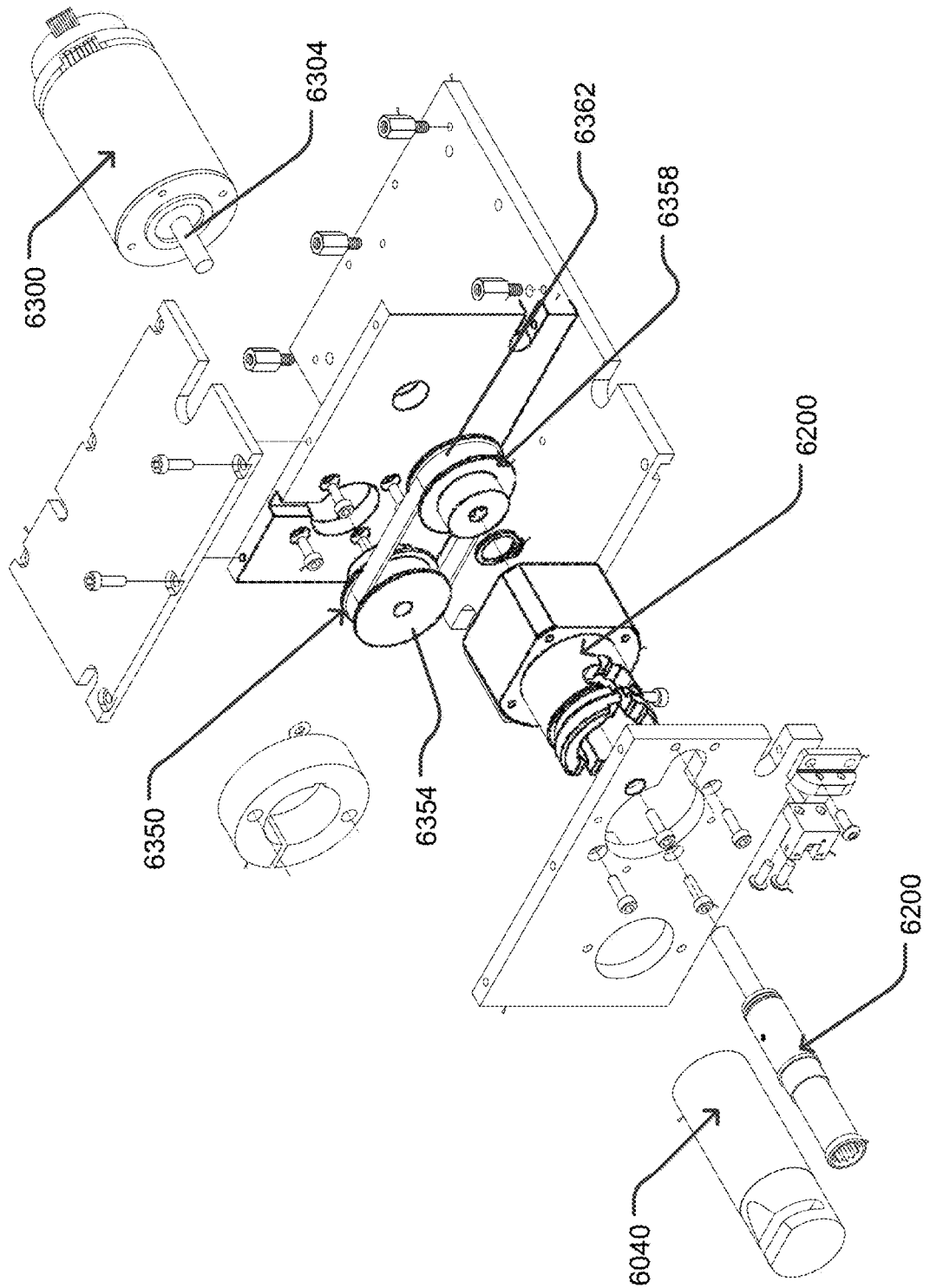
FIG. 55B is an exploded perspective view of the components of the console shown in FIG. 55A according to embodiments of the present disclosure.
Figure 55C:
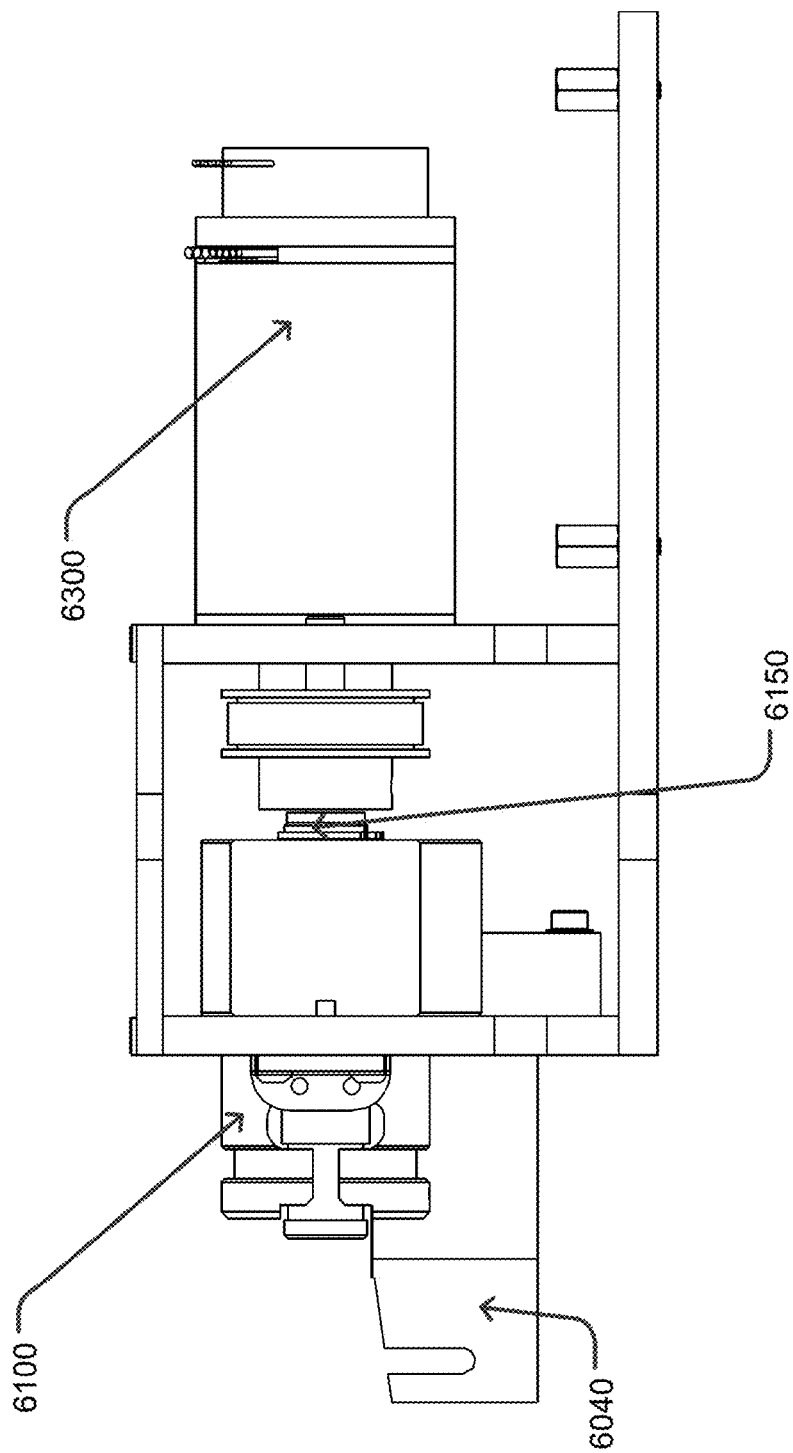
FIG. 55C is a side view of the components of the console shown in FIG. 55A according to embodiments of the present disclosure.
Figure 55D:
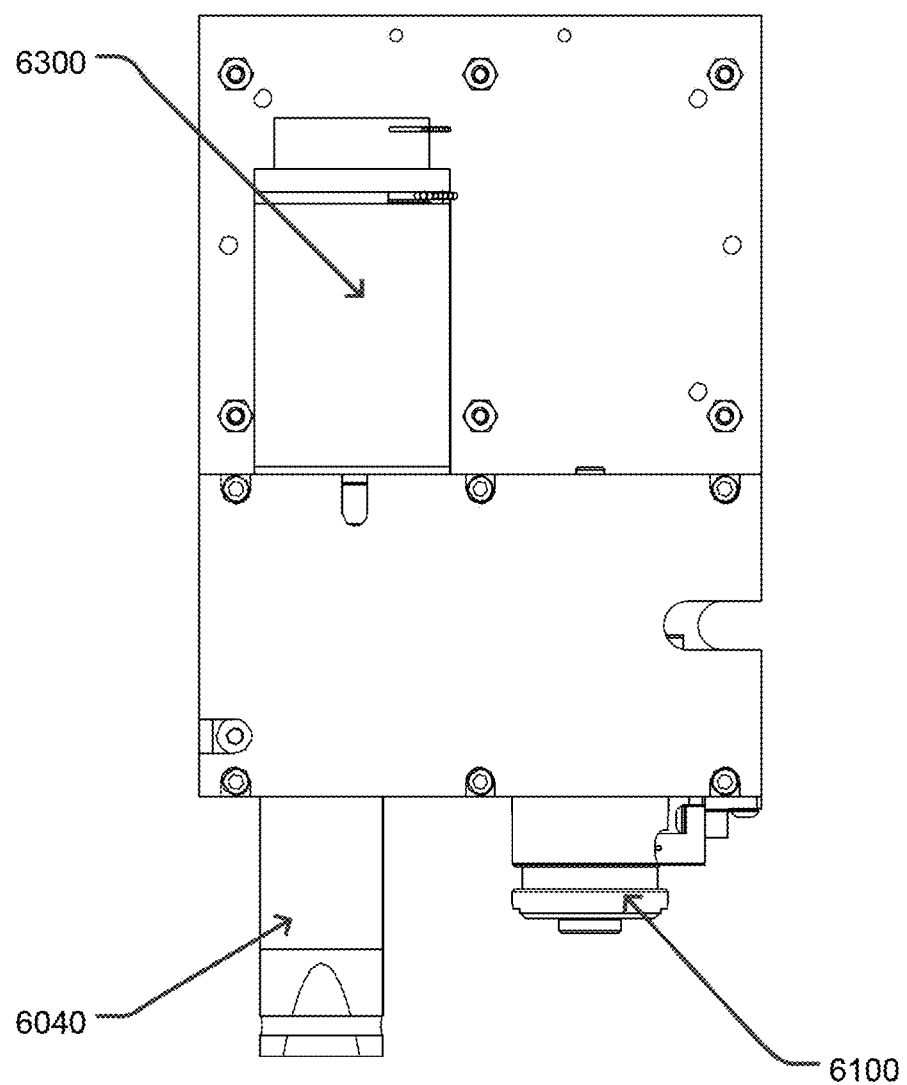
FIG. 55D is a top view of the components of the console shown in FIG. 55A according to embodiments of the present disclosure.

Referring further to FIGS. 53A-53B, in some implementations, the console 6000 includes a power input assembly 6650. The power input assembly 6650 can include a power cable receiver 6660 configured to receive electrical power from a remote power source. The power input assembly 6650 can include an input (e.g., switch, button, etc.) 6664 configured to turn power to the console 6000 on/off. The power input assembly 6650 can be configured to deliver energy to components of the console 6000 (e.g., motor 6300, user interface 6010, processing electronics, etc.). In some implementations, the power input assembly 6650 can include a local power source (e.g., a battery). The local power source can be configured to supply all power to the console 6000, backup power to the console 6000, and or local power to certain components of the console 6000. For example, a battery can be configured to supply power to processing electronics, while a remote power source can be configured to provide power to the motor 6300.

Figure 60B:
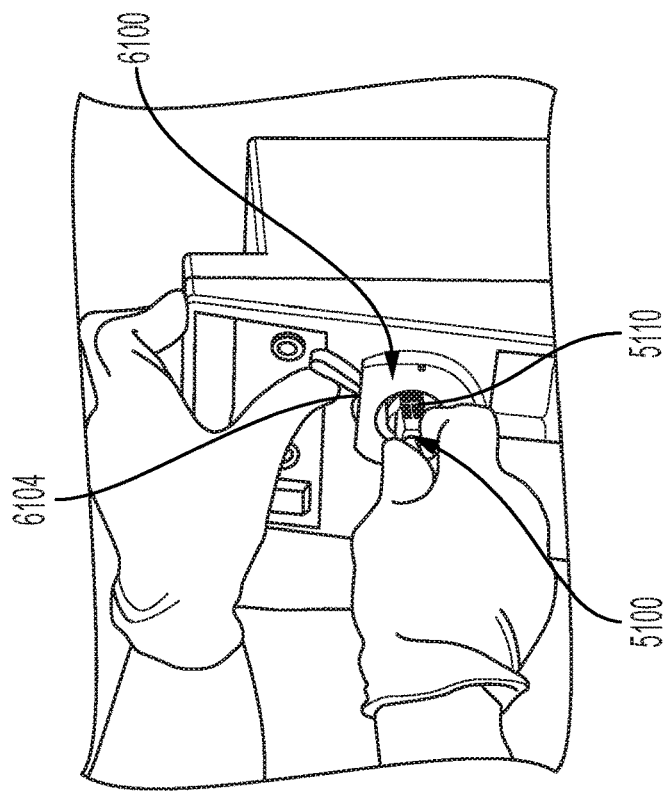
FIGS. 60A-60B illustrate aspects of engagement of an endoscopic tool to a console according to embodiments of the present disclosure.
Figure 60A:
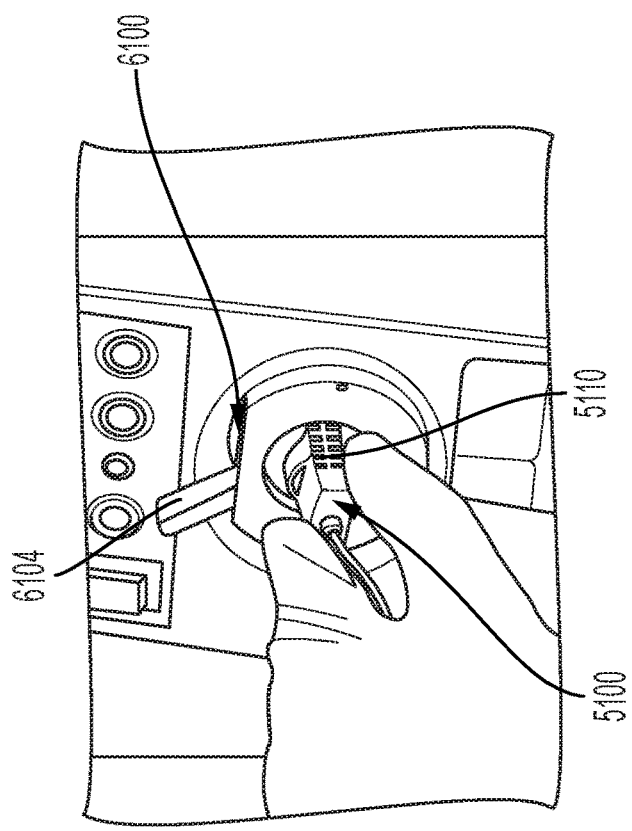
Figure 62:
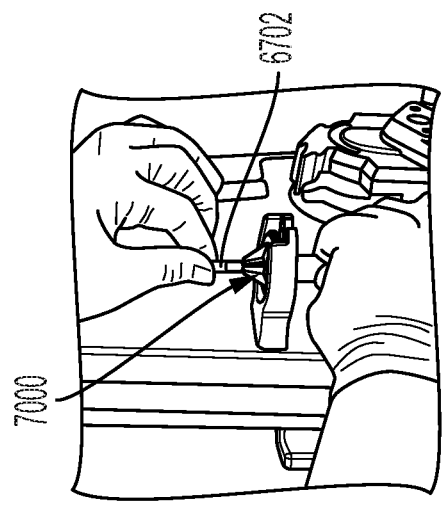
FIG. 62 illustrates aspects of coupling tubing to an outlet of a specimen receiver according to embodiments of the present disclosure.

FIGS. 60A-63 show various views of operating and connecting the console 6000 with the endoscopic tool 5100 and other components described herein. Referring now to FIGS. 60A-60B, the endoscopic tool 5100 is shown being coupled to the console 6000 at the endoscopic tool 6100. The proximal connector 5110 is configured to be positioned adjacent to the endoscopic tool interface 6100 in order to engage the endoscopic tool 5100 to the console drive assembly 6150. In some implementations, the endoscopic tool interface 6100 includes an engagement actuator 6104 configured to engage the endoscopic tool 5100 to the console 6000. In some implementations, the engagement actuator 6104 can be configured to be positioned in a first, unlocked position (shown in FIG. 60A), and a second, locked position (shown in FIG. 60B), such that movement of the engagement actuator 6104 moves the engagement actuator 6104 between the first and second positions. For example, an operator of the console 6000 can move the engagement actuator 6104 between the positions in order to lock or unlock the endoscopic tool 5100 from the console 6000.

Figure 61:
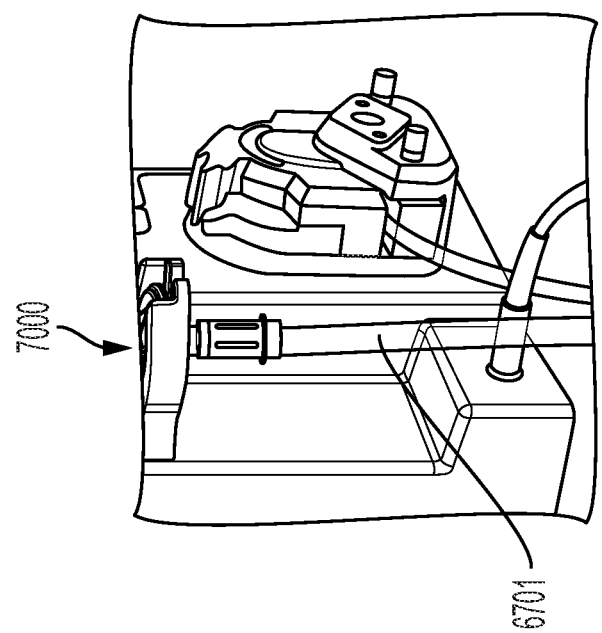
FIG. 61 illustrates aspects of coupling tubing to an inlet of a specimen receiver according to embodiments of the present disclosure.
Figure 63A:
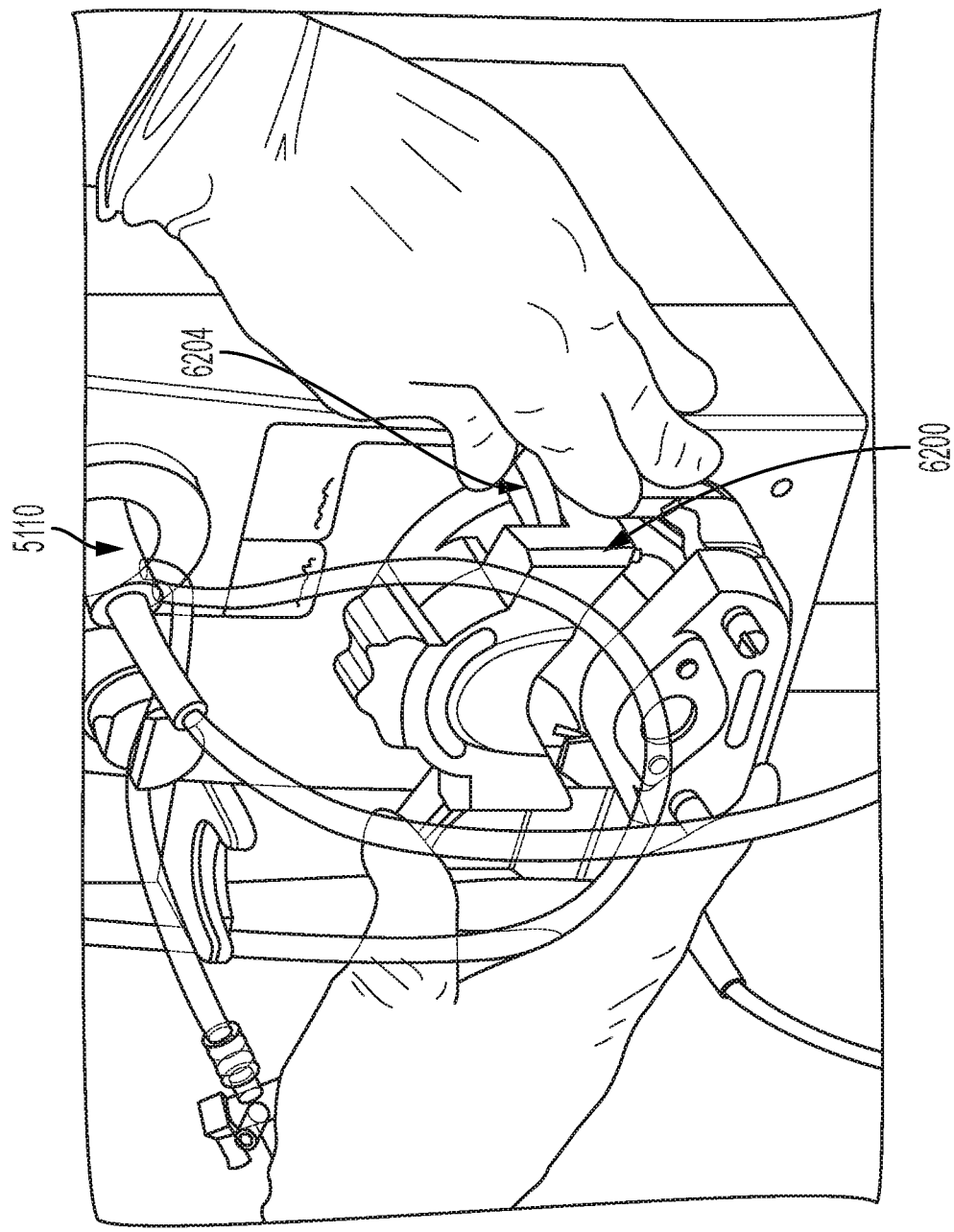
FIGS. 63A-63B illustrate aspects of coupling a fluid transfer device to an endoscopic tool according to embodiments of the present disclosure.
Figure 63B:
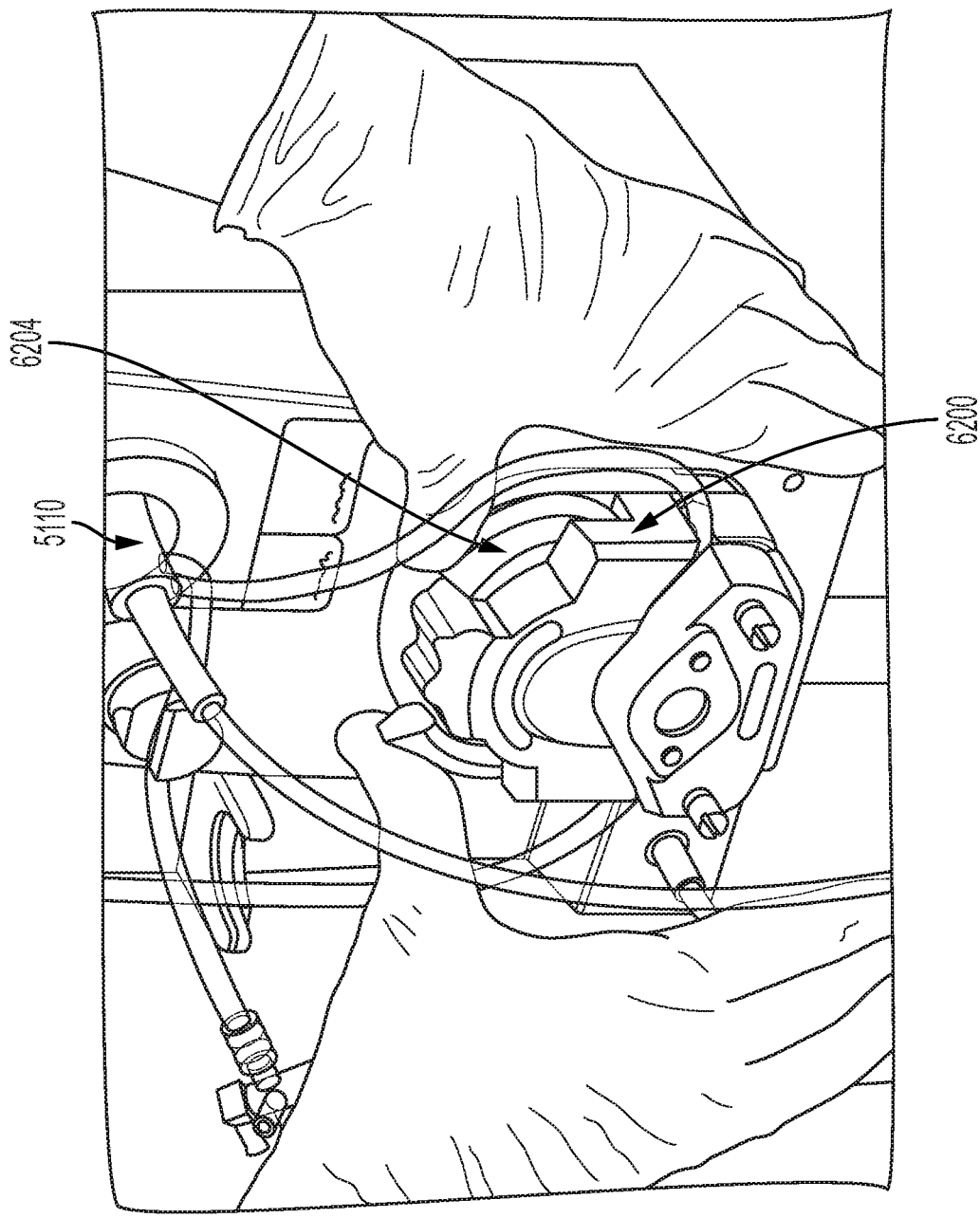

Referring now to FIG. 61, a specimen receiver (e.g., specimen receiver 7000 shown in FIG. 64) can be fluidly coupled to a vacuum source. For example, tubing (e.g., vacuum tubing, suction tubing, etc.) can be fluidly coupled to an outlet of the specimen receiver (e.g., second receiver port 7018). The tubing can be used to apply a suction force to the specimen receiver 7000, in order to draw fluid out of the endoscopic tool 5100 (e.g., via an aspiration channel) through the specimen receiver 7000 towards the vacuum source. In some implementations, the tubing can be configured to remove excess fluids exiting the specimen receiver 7000. In some implementations, the tubing is clear, allowing an operator to view the fluid exiting the specimen receiver 7000 to determine the content of the fluid. In some implementations, the console 6000 is positioned on a fluid pathway between the vacuum source and the specimen receiver.

In some implementations, the irrigation channel includes the irrigation port 5134, the irrigation port channel 5136, a portion defined between the flexible outer tubing 5206 and the flexible torque coil 5212 (e.g., a portion defined between an inner wall of the flexible outer tubing 5206 and an exterior of the flexible torque coil 5212), and extending to an opening at the distal end 5204 of the torque delivery assembly 5200. In some implementations, the irrigation channel includes a portion defined between the rotational coupler 5216 and the flexible torque coil 5212. In some implementations, the irrigation channel includes a portion defined by an interface of the proximal connector 5110 between the irrigation port channel 5136 and the portion defined between the flexible outer tubing 5206 and the flexible torque coil 5212. In some implementations, the irrigation channel extends from the irrigation port 5134 to the opening at the distal end 5204 of the torque delivery assembly 5200. In some implementations, the irrigation channel extends out of the endoscopic tool 5100 to a fluid source. For example, the irrigation channel can extend through tubing that fluidly couples the irrigation port 5134 to a fluid source (e.g., to fluid transfer device 6200). In some implementations, the irrigation channel includes the fluid source.

Referring now to FIG. 62 and FIGS. 51A-51C, a specimen receiver (e.g., specimen receiver 7000) can be fluidly coupled to the endoscopic tool 5100. For example, tubing 6702 (e.g., vacuum tubing, suction tubing, etc.) can be fluidly coupled between the vacuum port 5126 of the proximal connector 5110 and an inlet of the specimen receiver 7000 (e.g., first receiver port 7014). The tubing can be used to apply a suction force to the endoscopic tool 5100, in order to draw fluid out of the endoscopic tool 5100 (e.g., via an aspiration channel), such as for obtaining a sample in the specimen receiver 7000.

In some implementations, the aspiration channel includes the vacuum port 5126, the vacuum port channel 5130, and a portion defined by an inner wall of the flexible torque coil 5212. The aspiration channel be partially defined by a portion defined by an inner wall of the inner cannula of the cutting assembly 5201, extending to the opening 5208. In some implementations, the aspiration channel includes (or is partially defined by) an interface of the proximal connector 5110 between the vacuum port channel 5130 and the portion defined by the flexible torque coil 5212. In some implementations, the aspiration channel extends from the vacuum port 5126 to the opening 5208.

In some implementations, the aspiration channel extends out of the endoscopic tool 5100 to a vacuum source. For example, the aspiration channel can be partially defined by tubing fluidly coupling the vacuum port 5126 to a vacuum source. In some implementations, the aspiration channel includes a specimen receiver (e.g., specimen receiver 7000). The aspiration channel can include (or partially be defined by) tubing fluidly coupling the endoscopic tool 5100 to the specimen receiver (e.g., tubing 6702 shown in FIG. 62), a channel extending through the specimen receiver, and tubing fluidly coupling the specimen receiver to a vacuum source (e.g., tubing 6701 shown in FIG. 61). In some implementations, the aspiration channel extends from the vacuum source through the specimen receiver through the endoscopic tool 5100 to the opening 5208, such as when the distal end 5204 of the torque delivery assembly 5200 is positioned at a site within a subject.

Referring now to FIGS. 63A-63B and 51A-51C, the fluid transfer device 6200 (e.g., irrigation pump) can be fluidly coupled to the irrigation port 5134 of the proximal connector 5110. In some implementations, the fluid transfer device 6200 includes actuation members 6204 configured to open the fluid transfer device 6200 in order to expose an outlet of the fluid transfer device 6200. An operator of the console 6000 can couple tubing to the outlet of the fluid transfer device 6200 and to the irrigation port in order to fluidly couple the fluid transfer device 6200 to the irrigation channel of the endoscopic tool 5100. In some embodiments, the actuation members 6204 are configured to be positioned in a first, closed position (see FIG. 63B), and shifted to a second, open position (see FIG. 63A). In some embodiments, the console 6000 includes a user input configured to receive a fluid transfer device control command. Processing electronics of the console 6000 can be configured to receive the fluid transfer device control command and cause the fluid transfer device 6200 to open or close (e.g., cause the actuation members 6204 to actuate) based on the fluid transfer device control command.

Specimen Receiver

FIG. 64 shows an exploded perspective view of a specimen receiver 7000. The specimen receiver 7000 is configured to receive fluid flow and obtain samples of a material (e.g., tissue from a patient, a polyp resected from a colon of a patient, etc.) from the fluid flow. The specimen receiver 7000 can be fluidly coupled to the endoscopic tool 5100. The specimen receiver 7000 can be fluidly coupled to a vacuum source. The vacuum source can be used to provide a suction force through the specimen receiver 7000 to draw fluid flow from the endoscopic tool 5100 through the specimen receiver 7000 and out of the specimen receiver 7000. The fluid flow can thus be drawn through a sample obtaining member for capturing a sample from the fluid flow.

The specimen receiver 7000 includes a first receiver member 7010, a second receiver member 7050, and a specimen capture member 7100. The first receiver member 7010 is configured to be positioned upstream relative to fluid flow through the specimen receiver 7000. The second receiver member 7050 is configured to be positioned downstream relative to fluid flow through the specimen receiver 7000. The first receiver member 7010 and second receiver member 7050 are configured to be engaged to one another with the specimen capture member 7100 positioned inside the first receiver member 7010 and second receiver member 7050.

For example, as shown in FIG. 64, the first receiver member 7010 includes a first receiver port 7014 configured to receive fluid flow and pass the fluid flow to an interior of the specimen receiver 7000 via a first receiver channel 7018 fluidly coupled to the first receiver port 7014. The second receiver member 7050 includes a second receiver port 7054 configured to receive fluid flow via a second receiver channel 7058 fluidly coupled to the second receiver port 7054. The second receiver port 7054 is configured to be coupled to a vacuum source (e.g., a vacuum source positioned downstream of the specimen receiver 7000) to provide a suction force to draw the fluid flow out of the specimen receiver 7000.

In some implementations, the first receiver member 7010 is configured to engage the second receiver member 7050. For example, the first receiver member 7010 can include features configured to reciprocally mate with and engage (e.g., lock, attach to, couple, connect, etc.) features of the second receiver member 7050. As shown in FIG. 64, the first receiver member 7010 includes an outer rim 7022 having receiver engagement members 7026 extending from the outer rim 7022. The receiver engagement members 7026 are configured to be positioned in corresponding receiver engaging members 7066 located on an inner rim 7062 of the second receiver member 7050. For example, the receiver engaging members 7066 can include tracks configured to receive the receiver engagement members 7026, such that when the first receiver member 7010 is rotated relative to the second receiver member 7050, the receiving engagement members 7026 slide within the tracks of the receiver engaging members 7066. In various implementations, the inclusion of such engagement members can be interchanged between the first receiver member 7010 and the second receiver member 7050.

In some implementations, the first receiver port 7014 (and/or the first receiver channel 7018) includes an inner diameter that is less than an inner diameter of the second receiver port 7054 (and/or the second receiver channel 7058). This may facilitate fluid flow through the specimen receiver 7100 by facilitating a pressure gradient that decreases in the direction of the fluid flow.

In some implementations, the specimen receiver 7000 is configured to be engaged to the console 6000. For example, the specimen receiver 7000 can be engaged to the bracket assembly 6500 of the console 6000. Referring further to FIG. 64 and back to FIGS. 59A-59C, in some implementations, the specimen receiver 7000 includes console engagement members 7200 configured to engage to specimen receiver engaging members 6508 of the bracket assembly 6500. For example, the specimen receiver engaging members 6508 can include tracks configured to receive the console engagement members 7200 when the specimen receiver 7000 is positioned in the bracket assembly 6500. In some implementations, a first receiving portion 6510 is offset from a second receiving portion 6512, facilitating locking the specimen receiver 7000 in the bracket assembly 6500. This may help hold the specimen receiver 7000 in place if angular forces are applied to the specimen receiver 7000, such as angular forces resulting from fluid flow through the specimen receiver 7000, action of the motor 6300, or from objects contacting the specimen receiver 7000.

The specimen capture member 7100 is configured to obtain a sample of material from the fluid flow passing through the specimen receiver 7000. In some implementations, the specimen capture member 7100 is configured to filter the fluid flow to obtain the sample of material. For example, the specimen capture member 7100 can be a size filter (e.g., mesh filter, paper filter, etc.) configured to separate material in the fluid flow by size. The specimen capture member 7100 can be selected based on a known or expected size of material to be obtained from the fluid flow, so as to separate samples to be obtained from other material having a similar size (e.g., sized within an order of magnitude of the samples to be captured). For example, prior to a procedure to be performed, an operator can select the specimen capture member 7100 to have a filter size (e.g., mesh size, etc.) configured based on a known or expected size of material. The specimen capture member 7100 can include a bulk size (e.g., surface area, circumference, etc.) configured to fit within a receiving surface of the first receiver member 7010 and/or the second receiver member 7050.

For example, as shown in FIG. 64, the specimen capture member 7100 includes a first specimen capture surface (e.g., upstream surface) 7104, a second specimen capture surface (e.g., downstream surface) 7108, a specimen capture body 7112 extending between the first specimen capture surface 7104 and the second specimen capture surface 7108, and a specimen capture rim 7112. Fluid flow having entered the specimen receiver 7000 via the first receiver port 7014 flows through the first receiver channel 7018, contacts the first specimen capture surface 7104, flows through the specimen capture body 7112, and exits the specimen capture member 7100 via the second specimen capture surface 7108 to flow into the second receiver channel 7058. The specimen capture member 7100 selectively transmits fluid through the specimen capture body 7112, such as by blocking material that is too large to pass through specimen capture body 7112. For example, if the specimen capture member 7100 includes a mesh filter, the mesh can be sized such that samples to be obtained are too large to pass through the mesh, while blood and other fluids in the fluid flow pass through gaps in the mesh.

In some implementations, after a procedure is complete (e.g., after a specimen is obtained), the specimen receiver 7000 can be opened to remove the sample. For example, the first receiver member 7010 can be rotated relative to the second receiver member 7050 to open the specimen receiver 7000, thus exposing the specimen capture member 7100 and the sample.

In some implementations, if the size of material to be captured is not known or expected, the specimen capture member 7100 can be selected intraoperatively. For example, based on information acquired by the endoscopic tool 5100 regarding the sample to be obtained, an operator can determine an expected size of the sample and select the specimen capture member 7100. In some implementations, the specimen receiver 7000 can be decoupled from the endoscopic tool 5100 to allow the specimen capture member 7100 and/or the specimen receiver 7000 to be replaced. In some implementations, if the specimen receiver 7000 is fluidly coupled to the endoscopic tool 5100 via the console 6000, the specimen receiver 7000 can be decoupled from the console 6000. In some implementations, if the console 6000 is fluidly coupled to multiple specimen receivers 7000, a fluid output control can be used to redirect fluid flow exiting the endoscopic tool 5100 to a specimen receiver 7000 having an appropriately sized specimen capture member 7100.

In some implementations, the specimen receiver 7000 includes a fluid seal member 7150. The fluid seal member is configured to be positioned inside the specimen receiver 7000 and against surfaces of the first receiver member 7010 and/or second receiver member 7050, so as to prevent fluid flow from exiting the specimen receiver 7000 at an interface between the first receiver member 7010 and the second receiver member 7050. In some implementations, the fluid seal member 7150 is configured to surround the specimen capture member 7100 to support the specimen capture member 7100. In some implementations, one or more surfaces of the first receiver member 7010 and/or the second receiver member 7050 are configured to support the specimen capture member 7100, such as by applying tension and/or compression to the specimen capture member 7100 to support the specimen capture member 7100 against a pressure different caused by fluid flow through the specimen capture member 7100.

In some implementations, the specimen receiver 7000 includes an indicator configured to provide a visual indication of whether material has been obtained by the specimen receiver 7000. The indicator can include a transparent or translucent portion configured to allow an operator to see inside the specimen receiver 7000. The indicator can be coupled to a pressure sensor disposed within the specimen receiver 7000, and provide an output indicating a pressure within the specimen receiver 7000. In some implementations, fluid exiting the specimen receiver 7000 to the vacuum source can provide the indication of whether material has been obtained by the specimen receiver 7000.

In some implementations, the specimen receiver 7000 is directly coupled to the vacuum port 5126 of the endoscopic tool 5100, such as by using tubing to connect the vacuum port 5126 to the first receiver port 7014 of the specimen receiver 7000. In some implementations, the specimen receiver 7000 is fluidly coupled to the endoscopic tool 5100 via the console 6000. For example, the console 6000 can include a valve and/or manifold system configured to be fluidly coupled to the endoscopic tool 5100 and transfer fluids in or out of the endoscopic tool 5100, including a manifold configured to fluidly couple the specimen receiver to the endoscopic tool 5100. In some implementations, the specimen receiver 7000 defines a length from an opening of the first receiver port 7014 (e.g., an opening at which the fluid is received) to an opening of the second receiver port 7054 (e.g., an opening at which a vacuum source may be coupled; an opening at which fluid exits the second receiver port 7054). The length may be greater than or equal to 1 inch and less than or equal to 5 inches. The length may be greater than or equal to 2 inches and less than or equal to 4 inches. The length may be 2 inches. In some implementations, the specimen receiver 7000 defines a diameter or width of the outer rim 7022. The diameter may be greater than or equal to 0.5 inches and less than or equal to 4 inches. The diameter may be greater than or equal to 1 inch and less than or equal to 3 inches. The diameter may be 1.5 inches. The dimensions of the specimen receiver 7000 such as the length of the specimen receiver 7000 and/or the diameter of the outer rim 7022 may be configured to facilitate a pressure gradient through the specimen receiver 7000 enabling effective specimen capture by the specimen capture member 7100. For example, given a known vacuum pressure or range of vacuum pressures to be applied via the second receiver port 7054, the dimensions of the specimen receiver 7000 may be configured to facilitate a pressure gradient through the specimen receiver 7000 that is greater than a first threshold sufficient to draw fluid through the specimen capture member 7100 and less than a second threshold above which the specimen capture member 7100 is expected to collapse into the second receiver channel 7058.

Figure 65:
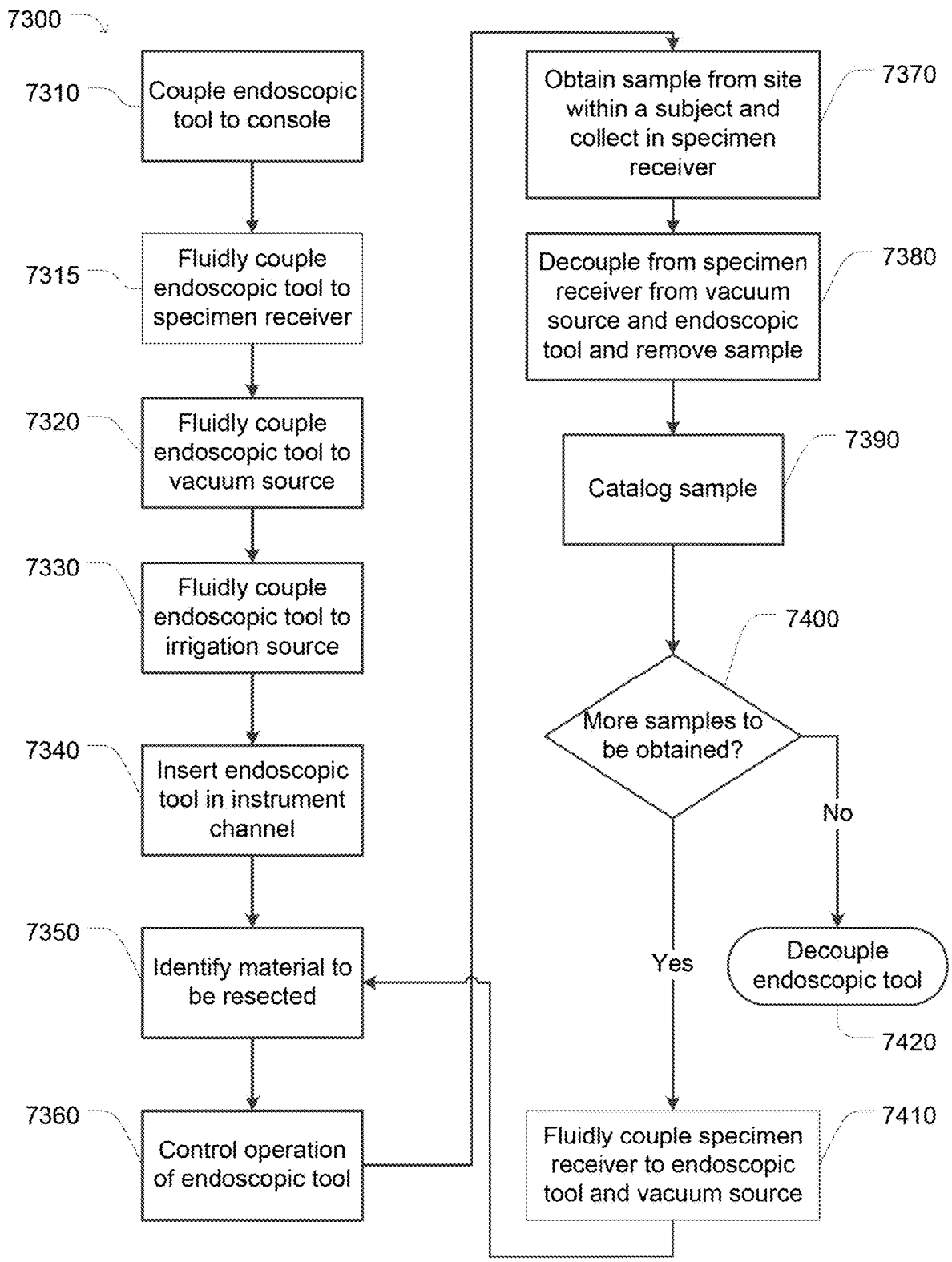
FIG. 65 illustrates a flow diagram of a method of operating an endoscopic tool with a console according to embodiments of the present disclosure.

FIG. 65 shows a flow diagram of a method 7300 for operation of a console configured to operate with an endoscopic tool. The method 7300 may be performed using various systems and apparatuses disclosed herein, including the endoscopic tool 5100, the console 6000, and the specimen receiver 7000. The method 7300 may be performed by a surgeon, medical assistant, or other operator, such as in a procedure room. The method 7300 may include or be performed as part of a procedure for obtaining samples of polyps and neoplasms from a patient; a procedure using a gastroscope, such as a colonoscope, a laryngoscope, or any other flexible endoscope; a minimally invasive surgical procedure; etc. In some implementations, the method 7300 includes positioning an instrument channel at a site within a patient. In some implementations, the method 7300 can start with identifying material to be resected (e.g., as discussed with regards to step 7350).

At 7310, an endoscopic tool is coupled to a console. For example, the endoscopic tool can include a proximal connector including an engagement member configured to engage an engagement receiving member of an interface of the console. The proximal connector can be positioned adjacent to the interface to align the engagement member with the engagement receiving member and to engage the engagement member with the engagement receiving member. In some implementations, the console includes an actuation member configured to be actuated in order to lock or unlock the engagement between the endoscopic tool and the console. In some implementations, engaging the engagement member to the engagement receiving member operatively couples a motor of the console to the endoscopic tool, such that rotation of the motor can cause rotation of the endoscopic tool. In some implementations, a surgeon or other operator couples the endoscopic tool to the console.

In some implementations, at 7315, the endoscopic tool is fluidly coupled to a specimen receiver (e.g., a specimen receiver configured to filter fluid from the endoscopic tool to separate a sample of material from the fluid). For example, the endoscopic tool can include a vacuum port (e.g., a vacuum port of a proximal connector of the endoscopic tool) that is fluidly coupled via tubing to an inlet of the specimen receiver. In some implementations, a surgeon or other operator can fluidly couple the endoscopic tool to the specimen receiver.

In some implementations, at 7320, the endoscopic tool is fluidly coupled to a vacuum source. For example, the endoscopic tool can include a vacuum port (e.g., a vacuum port positioned on the proximal connector of the endoscopic tool) configured to be fluidly coupled to a vacuum source by tubing. The tubing can be coupled to the vacuum port, such as by sliding the tubing around the vacuum port to form a fluid seal, or by positioning the tubing adjacent to the vacuum port and engaging the tubing to the vacuum port using an engagement fitting or other device. In some implementations, coupling the endoscopic tool to the vacuum source at the vacuum port fluidly couples an aspiration channel of the endoscopic tool (e.g., an aspiration channel extending from the vacuum port to an opening at a distal end of the endoscopic tool) to the vacuum source. In some implementations, the endoscopic tool is fluidly coupled to the vacuum source via a specimen receiver configured to obtain a sample of material that is drawn through the aspiration channel from the opening at the distal end of the endoscopic tool to the vacuum port. For example, tubing can be fluidly coupled to the vacuum port and to an inlet (e.g., a first receiver port) of the specimen receiver, and tubing can also be fluidly coupled between an outlet (e.g., a second receiver port) of the specimen receiver and the vacuum source, such that a vacuum applied to the outlet of the specimen receiver is applied through an aspiration channel extending through an interior of the specimen receiver through the endoscopic tool to the opening at the distal end of the endoscopic tool, in order to draw a sample of material through the opening through the endoscopic tool into the specimen receiver. In some implementations, the tubing between the endoscopic tool and the specimen receiver is coupled via a vacuum control device. The console may receive a vacuum control release instruction at a user interface, process the vacuum control release instruction, and actuate, release, or open the vacuum control device to allow tubing to be coupled via the vacuum control device. In some implementations, a surgeon or other operator can fluidly couple the endoscopic tool to the vacuum source, such as by fluidly coupling tubing from a vacuum port of the endoscopic tool to a specimen receiver and fluidly coupling tubing from the specimen receiver to the vacuum source.

In some implementations, at 7330, the endoscopic tool is fluidly coupled to a fluid source. For example, the endoscopic tool can be fluidly coupled to a fluid transfer device, such as an irrigation pump, including a fluid transfer device included in the console. In some implementations, tubing can be fluidly coupled between an irrigation port of the endoscopic tool, such as an irrigation port positioned on the proximal connector of the endoscopic tool, and the fluid transfer device. In some implementations, fluidly coupling the fluid transfer device to the endoscopic tool fluidly couples the fluid transfer device to an irrigation channel extending through the endoscopic tool from the irrigation port through tubing of the endoscopic tool to an opening at the distal end of the endoscopic tool, such that irrigation fluid can be outputted at the distal end (e.g., at a site within a subject) by action of the fluid transfer device. In some implementations, the console can receive a prime or flush instruction at a user interface, process the instruction, and cause the fluid transfer device to prime or flush the fluid transfer device and/or prime or flush the irrigation channel. In some implementations, a surgeon or other operator can fluidly couple the endoscopic tool to the fluid source, such that fluid from the fluid source can pass through the irrigation channel defined by the endoscopic tool to a distal end of the cutting assembly.

In some implementations, at 7340, the endoscopic tool is inserted in an instrument channel of an endoscope. For example, the endoscopic tool can be inserted in an instrument channel, such that the distal end of the endoscopic tool is positioned at the site within the subject in order to interact with the site (e.g., resect material, obtain a sample of material, etc.). In other implementations, the endoscopic tool is inserted in the instrument channel prior to coupling the endoscopic tool to the console. In some implementations, a surgeon or other operator can insert the endoscopic tool in the instrument channel.

In some implementations, at 7350, material to be resected at the site within the subject is identified. For example, image information e.g., image information received from an image capture device of the instrument channel, etc.) can be used to determine a location of the material and/or properties of the material. In some implementations, a surgeon or operator can identify material to be resected. In some implementations, the surgeon or operator can move or orient the cutting window defined within the outer cannula of the endoscopic tool by rotating a rotational coupler that is positioned outside of the subject. As described herein, the rotational coupler is configured to control the orientation of the cutting window. In some implementations, upon identifying the material to be resected, the surgeon or operator can orient the cutting window to be adjacent to the material to be resected, such that when a suction force is applied to the endoscopic tool, the material is resected.

In some implementations, at 7360, operation of the endoscopic tool can be controlled. For example, commands can be received at the console to be processed for controlling the endoscopic tool or other components operatively coupled to the console. In some implementation, commands are received as user inputs at a user interface of the console. In some implementations, processing electronics of the console receive the user inputs from the user interface, and process the inputs to determine how to control operation of the endoscopic tool or other components. For example, one or more user inputs can be received (e.g., at a foot pedal) indication instructions to perform operations such as rotating the endoscopic tool, applying a vacuum to the endoscopic tool (e.g., to an aspiration channel of the endoscopic tool), and/or flowing irrigation fluid through the endoscopic tool to be outputted by the endoscopic tool (e.g., flowing irrigation fluid through an irrigation channel of the endoscopic tool). The processing electronics can receive the user inputs, and process the user inputs to determine operations indicated by the inputs in order to cause the operations to occur. For example, in response to receiving an input indicating an instruction to rotate the endoscopic tool, the processing electronics can cause a motor of the console to rotate in order to rotate the endoscopic tool, in some implementations, the processing electronics can receive multiple user inputs and process the multiple user inputs to coordinate operation of the endoscopic tool or other devices. For example, the processing electronics can receive a first input indicating instructions to rotate the endoscopic tool and a second input indicating instructions to apply a vacuum to the endoscopic tool (e.g., by controlling operation of a vacuum control device), and control operation of the vacuum control device based on whether the second input was received within a predetermined time of the first input. In some implementations, controlling operation of the endoscopic tool includes using the endoscopic tool to resect material from the site within the subject, including by rotating a cutting window at the distal end of the endoscopic tool against the material. In some implementations, operation of the endoscopic tool can be controlled by a surgeon or other operator, such as by providing user inputs to the user interface.

In some implementations, at 7370, a sample of the material is obtained. For example, after material has been resected, a suction force can be applied to the material via an aspiration channel of the endoscopic tool (e.g., by controlling operation of a vacuum control device to apply a suction force from a vacuum source to the endoscopic tool) in order to apply a suction force at an opening of the endoscopic tool to draw in the sample through the aspiration channel of the endoscopic tool. The sample can be drawn into a specimen receiver fluidly coupled to the aspiration channel, such as a specimen receiver configured to filter fluid exiting the endoscopic tool and entering the specimen receiver in order to separate the sample from the remainder of the fluid. In some implementations, a surgeon or other operator obtains the sample of material by controlling operation of the console to apply the suction force.

In some implementations, at 7380, a sample is removed from the specimen receiver. For example, a sample can be captured in a specimen receiver and removed from the specimen receiver. In some implementations, removing the sample includes decoupling the specimen receiver from the endoscopic tool. In some implementations, removing the sample includes opening the specimen receiver in order to access the sample. In some implementations, the specimen receiver is a one-time use specimen receiver, such that the entire specimen receiver is removed as part of removing the sample. In some implementations, a specimen capture device (e.g., a filter) of the specimen receiver is a one-time use filter, such that the filter can be replaced while the specimen receiver is reused. In some implementations, the sample is removed by a surgeon or other operator.

In some implementations, at 7390, the sample is cataloged. For example, the sample can be cataloged based on properties of the sample (e.g., chemical properties, medical properties, etc.), and/or based on a location of the site within the subject from which the sample was obtained. For example, samples can be associated with different locations within a subject, such as different locations within a colon, larynx, lung, or other region of the subject. In some implementations, the sample can be cataloged by a surgeon or other operator. In some implementations, the sample is stored for transport and sent to a remote facility (e.g., a testing laboratory remote from a procedure room in which the procedure to obtain the sample is performed) for cataloging or other analysis.

In some implementations, at 7400, it is determined whether more samples are to be obtained. For example, more samples can be obtained based on whether more polyps, neoplasms, or other materials have been identified for resection and/or analysis. More samples can be obtained based on a pre-operative plan or an intraoperative decision.

In some implementations, a surgeon or other operator can determine whether more samples are to be obtained.

In some implementations, if it is determined that more samples are to be obtained, then at step 7410, a specimen receiver is fluidly coupled to the endoscopic tool and to the vacuum source, such that the endoscopic tool can be controlled to obtain additional samples in the specimen receiver. In some implementations, if the previous specimen receiver was a one-time use specimen receiver, then a new specimen receiver can be used. In some implementations, if the previous specimen receiver included a one-time use filter, then the filter can be replaced. In some implementations, a surgeon or other operator can fluidly couple the specimen receiver to the endoscopic tool and to the vacuum source. The method can then return to step 7350, such as for identifying additional material to be resected. The endoscopic tool can be controlled to obtain additional samples as disclosed herein. For example, the endoscopic tool can be repositioned, rotated, or otherwise controlled to be able to obtain additional samples. In some implementations, a surgeon or other operator can repeat steps of the method, such as by repeating control of the endoscopic tool, etc.

In some implementations, if it is determined that more samples are not to be obtained, then at 7420, the procedure can end. In some implementations, ending the procedure includes decoupling the endoscopic tool from the console and/or from other components coupled to the endoscopic tool, such as a vacuum source, a specimen receiver, and/or a fluid transfer device. In some implementations, a sample is not removed from a specimen receiver until the endoscopic tool is decoupled from the specimen receiver.

It should be appreciated that one or more steps of the method shown in FIG. 65 do not have to be performed in the order shown. For example, step 7340 can be performed prior to steps 7310 through 7330.

What is claimed is:

1. A specimen receiver, comprising:
   a first receiver member including a first receiver port configured to receive a fluid flow including a material, the first receiver member defining a first portion of an interior of the specimen receiver and at least one receiver engagement member extending from the first receiver member;
   a specimen capture member in fluid communication with the first portion of the interior, the specimen capture member configured to obtain a sample of the material from the fluid flow, the specimen capture member disposed between the first portion of the interior and a second portion of the interior, the specimen capture member configured to filter the fluid flow to obtain the sample of the material; and
   a second receiver member having at least one track configured to receive the at least one receiver engagement member such that the at least one receiver engagement member from the second receiver member slides within the at least one track of the first receiver member while the first receiver member rotates relative the second receiver member, the second receiver member defining the second portion of the interior of the specimen receiver, the second portion downstream of the first portion, the second receiver member including a second receiver port configured to be coupled to a vacuum source, the vacuum source applying a predetermined vacuum pressure through the second receiver port, wherein a first inner diameter of the first receiver port is less than a second inner diameter of the second receiver port to cause a pressure gradient in the direction of fluid flow from the first receiver port to the second receiver port to decrease, the pressure gradient greater than the predetermined vacuum pressure sufficient to draw fluid through the specimen receiver and less than a predetermined threshold above which the specimen capture member is expected to collapse into a second receiver channel of the second receiver member.

2. The specimen receiver of claim 1, wherein the second receiver channel is in fluid communication with the second receiver port, the second receiver channel defining a channel diameter that is less than a diameter of the specimen capture member.

3. The specimen receiver of claim 1, wherein the specimen capture member is a size filter configured to separate material in the fluid flow by size by blocking material greater than a mesh size of the filter from passing through the specimen capture member to the second portion of the interior.

4. The specimen receiver of claim 3, wherein the mesh size of the specimen capture member is less than an expected size of the sample of the material.

5. The specimen receiver of claim 1, further comprising a fluid seal member configured to be positioned around the specimen capture member and adjacent to a boundary at which the first receiver member is coupled to the second receiver member to seal the boundary.

6. The specimen receiver of claim 1, further comprising an indicator configured to provide a visual indication of whether material has been obtained by the specimen capture member, the indicator including a translucent or transparent portion.

7. The specimen receiver of claim 1, wherein the first receiver member includes an outer rim having the at least one receiver engagement member extending from the outer rim, and the second receiver member includes an inner rim defining the at least one track.

8. The specimen receiver of claim 1, wherein the second receiver member defines an inner opening opposite the second receiver port and an inner rim surface surrounding the inner opening, the inner opening in fluid communication with the second portion of the interior, the inner rim surface shaped to receive the specimen capture member while the specimen capture member covers the inner opening.

9. The specimen receiver of claim 1, wherein a length of the specimen receiver from an opening of the first receiver port to an opening of the second receiver port is greater than 1 inch and less than 5 inches.

10. A method of obtaining a sample of material from an endoscopic tool in a specimen receiver, comprising:
    positioning a specimen capture member between a first receiver member and a second receiver member;
    receiving a fluid flow including the material at a first receiver port of the first receiver member, the first receiver port having a first inner diameter, the first receiver member defining a first portion of an interior of the specimen receiver in which the specimen capture member is positioned;
    coupling the second receiver member to the first receiver member by positioning at least one receiver engagement member extending from the second receiver member within at least one track of the first receiver member, the second receiver member defining a second portion of the interior of the specimen receiver;
    rotating the first receiver member relative the second receiver member such that the at least one receiver engagement member from the second receiver member slides within the at least one track of the first receiver member;

coupling a vacuum source to a second receiver port of the second receiver member to flow the fluid flow through the specimen receiver, the vacuum source applying a predetermined vacuum pressure through the second receiver port, the second receiver port having a second inner diameter greater than the first inner diameter such that a pressure gradient by which the fluid flows through the specimen receiver is greater than the predetermined vacuum pressure sufficient to draw fluid through the specimen receiver and less than a predetermined threshold above which the specimen capture member is expected to collapse into a second receiver channel of the second receiver member; and obtaining a sample of the material by filtering the fluid flow using the specimen capture member.

11. The method of claim 10, wherein the second receiver channel is in fluid communication with the second receiver port, the second receiver channel defining a channel diameter that is less than a diameter of the specimen capture member.

12. The method of claim 10, wherein the specimen capture member is a size filter configured to separate material in the fluid flow by size, the method further comprising blocking material less than a mesh size of the size filter from passing through the specimen capture member to the second portion of the interior.

13. The method of claim 12, further comprising selecting the mesh size of the specimen capture member based on an expected size of the sample of the material.

14. The method of claim 10, further comprising positioning a fluid seal member configured to be positioned around the specimen capture member and adjacent to a boundary at which the first receiver member is coupled to the second receiver member to seal the boundary.

15. The method of claim 10, further comprising providing a visual indication of whether material has been obtained by the specimen capture member via an indicator including a translucent or transparent portion.

16. The method of claim 10, wherein the first receiver member includes an outer rim having the at least one receiver engagement member extending from the outer rim, and the second receiver member includes an inner rim defining at least one track.

17. The method of claim 10, further comprising positioning the specimen capture member on an inner rim surface of the second receiver member surrounding an inner opening of the second receiver member, the inner opening in fluid communication with the second portion of the interior, and covering the inner opening with the specimen capture member.

18. The method of claim 10, wherein a length of the specimen receiver from an opening of the first receiver port to an opening of the second receiver port is greater than 1 inch and less than 5 inches.

\* \* \* \* \*

UNITED STATES PATENT AND TRADEMARK OFFICE
CERTIFICATE OF CORRECTION

PATENT NO. : 11,076,840 B2  
APPLICATION NO. : 15/459870  
DATED : August 3, 2021  
INVENTOR(S) : Cosme Furlong et al.

Page 1 of 1

It is certified that error appears in the above-identified patent and that said Letters Patent is hereby corrected as shown below:

In the Claims

Claim 1, at Column 73, Line 55, delete "from the second" and insert -- extending from the first --;

Claim 1, at Column 73, Line 56, delete "first" and insert -- second --;

Claim 10, at Column 74, Line 62, delete "second" and insert -- first --;

Claim 10, at Column 74, Line 63, delete "first" and insert -- second --;

Claim 10, at Column 75, Line 1, delete "from the second" and insert -- extending from the first --;

Claim 10, at Column 75, Line 2, delete "first" and insert -- second --; and

Claim 16, at Column 76, Line 17, insert -- the -- between "defining" and "at least one track".

Signed and Sealed this  
Twenty-first Day of December, 2021

Drew Hirshfeld  
*Performing the Functions and Duties of the*  
*Under Secretary of Commerce for Intellectual Property and*  
*Director of the United States Patent and Trademark Office*